US012760036B2

(12) United States Patent
Ding et al.

(10) Patent No.: US 12,760,036 B2
(45) Date of Patent: Oct. 13, 2026

(54) INHIBITORS OF KIF18A AND USES THEREOF

(71) Applicant: Insilico Medicine IP Limited, Hong Kong (CN)

(72) Inventors: Xiao Ding, Shanghai (CN); Xiaoyu Ding, Shanghai (CN); Feng Gao, Shanghai (CN); Feng Ren, Shanghai (CN); Min Zheng, Shanghai (CN); Wei Zhu, Shanghai (CN)

(73) Assignee: INSILICO MEDICINE IP LIMITED, Hong Kong (CN)

( * ) Notice: Subject to any disclaimer, the term of this patent is extended or adjusted under 35 U.S.C. 154(b) by 0 days.

(21) Appl. No.: 19/272,410

(22) Filed: Jul. 17, 2025

(65) Prior Publication Data

US 2025/0340569 A1 Nov. 6, 2025

Related U.S. Application Data

(63) Continuation of application No. PCT/CN2024/073202, filed on Jan. 19, 2024.

(30) Foreign Application Priority Data

Jan. 20, 2023 (WO) ................ PCT/CN2023/073384
May 24, 2023 (WO) ................ PCT/CN2023/096044
Sep. 19, 2023 (WO) ................ PCT/CN2023/119748
Dec. 21, 2023 (WO) ................ PCT/CN2023/140730

(51) Int. Cl.

| | |
|---|---|
| ***C07D 498/18*** | (2006.01) |
| ***A61K 31/439*** | (2006.01) |
| ***A61K 31/4995*** | (2006.01) |
| ***A61K 31/504*** | (2006.01) |
| ***A61K 31/529*** | (2006.01) |
| ***A61K 31/537*** | (2006.01) |
| ***A61K 31/5386*** | (2006.01) |
| ***A61K 31/553*** | (2006.01) |
| ***A61K 31/675*** | (2006.01) |
| ***C07D 471/18*** | (2006.01) |
| ***C07D 471/22*** | (2006.01) |
| ***C07D 491/22*** | (2006.01) |
| ***C07D 498/08*** | (2006.01) |
| ***C07D 498/22*** | (2006.01) |
| ***C07D 513/22*** | (2006.01) |

(52) U.S. Cl.

CPC .......... *C07D 498/18* (2013.01); *A61K 31/439* (2013.01); *A61K 31/4995* (2013.01); *A61K 31/504* (2013.01); *A61K 31/529* (2013.01); *A61K 31/537* (2013.01); *A61K 31/5386* (2013.01); *A61K 31/553* (2013.01); *A61K 31/675* (2013.01); *C07D 471/18* (2013.01); *C07D 471/22* (2013.01); *C07D 491/22* (2013.01); *C07D 498/08* (2013.01); *C07D 498/22* (2013.01); *C07D 513/22* (2013.01)

(58) Field of Classification Search

CPC ............................ C07D 498/18; A61K 31/439

See application file for complete search history.

(56) References Cited

U.S. PATENT DOCUMENTS

| | | | | |
|---|---|---|---|---|
| 11,034,671 | B2 | 6/2021 | Jin et al. | |
| 11,168,095 | B2 | 11/2021 | Gonzalez Lopez De Turiso et al. | |
| 11,236,069 | B2 | 2/2022 | Tamayo et al. | |
| 2012/0277249 | A1* | 11/2012 | Andersson ........... | A61K 9/1075 514/517 |
| 2020/0239441 | A1* | 7/2020 | Tamayo ............... | C07D 413/14 |
| 2022/0056015 | A1 | 2/2022 | Tamayo et al. | |
| 2022/0073504 | A1 | 3/2022 | Tamayo et al. | |
| 2023/0151432 | A1 | 5/2023 | Payton | |
| 2023/0233565 | A1 | 7/2023 | Stumpff | |

FOREIGN PATENT DOCUMENTS

| | | | |
|---|---|---|---|
| CN | 113226473 | A | 8/2021 |
| CN | 115594664 | A | 1/2023 |
| CN | 115947717 | B | 5/2023 |
| CN | 116903605 | A | 10/2023 |
| WO | WO-2020132648 | A1 | 6/2020 |
| WO | WO-2020132649 | A1 | 6/2020 |
| WO | WO-2020132651 | A1 | 6/2020 |
| WO | WO-2021026100 | A1 | 2/2021 |
| WO | WO-2023148129 | A1 | 8/2023 |
| WO | WO-2023212714 | A1 | 11/2023 |
| WO | WO-2023217232 | A1 | 11/2023 |
| WO | WO-2024067675 | A1 | 4/2024 |
| WO | WO-2024108765 | A1 | 5/2024 |
| WO | WO-2024140799 | A1 | 7/2024 |
| WO | WO-2024153217 | A1 | 7/2024 |
| WO | WO-2025026392 | A1 | 2/2025 |
| WO | WO-2025067239 | A1 | 4/2025 |
| WO | WO-2025081019 | A1 | 4/2025 |
| WO | WO-2025109540 | A1 | 5/2025 |
| WO | WO-2026021411 | A1 | 1/2026 |

OTHER PUBLICATIONS

CAS Number Citation: Chemical Abstracts Service. CAS Registry: 129946-88-9. 5-(Trifluoromethyl)dibenzothiophenium trifluoromethanesulfonate: pp. 1-19. STN Entry Date Jul. 19, 2005. Retrieved Jul. 18, 2025. Retrieved from:https://pubchem.ncbi.nlm.nih.gov/compound/2777507.

Co-pending U.S. Appl. No. 19/132,308, inventors Ding; Xiao et al., filed on May 22, 2025.

Co-pending U.S. Appl. No. 19/140,581, inventors Ding; Xiao et al., filed on Jun. 18, 2025.

(Continued)

*Primary Examiner* — James H Alstrum-Acevedo
*Assistant Examiner* — Chris E Simmons
(74) *Attorney, Agent, or Firm* — WILSON SONSINI GOODRICH & ROSATI

(57) ABSTRACT

Described herein are KIF18A inhibitors and pharmaceutical compositions comprising said inhibitors. The subject compounds and compositions are useful for the treatment of a disease or disorder associated with KIF18A.

26 Claims, No Drawings

(56) References Cited

OTHER PUBLICATIONS

Mayr, Monika I. et al. The human kinesin Kif18A is a motile microtubule depolymerase essential for chromosome congression. Curr Biol 17(6):488-498 (2007).
PCT/CN2024/073202 International Search Report and Written Opinion dated Apr. 19, 2024.
PCT/CN2025/109733 International Search Report and Written Opinion dated Oct. 22, 2025.

* cited by examiner

INHIBITORS OF KIF18A AND USES THEREOF

CROSS REFERENCE TO RELATED APPLICATIONS

This patent application is a continuation application of International Application No. PCT/CN2024/073202, filed Jan. 19, 2024, which claims the benefit of International Application No. PCT/CN2023/073384, filed Jan. 20, 2023, International Application No. PCT/CN2023/096044, filed May 24, 2023, International Application No. PCT/CN2023/119748, filed Sep. 19, 2023, and International Application No. PCT/CN2023/140730, filed Dec. 21, 2023, each of which is incorporated herein by reference in its entirety.

BACKGROUND

The KIF18A gene belongs to the kinesin-8 subfamily and is a plus-end-directed motor. KIF18A is believed to influence dynamics at the plus end of kinetochore microtubules to control correct chromosome positioning and spindle tension. Depletion of human KIF18A leads to longer spindles, increased chromosome oscillation at metaphase, and activation of the mitotic spindle assembly checkpoint in HeLa cervical cancer cells (MI Mayr et al, Current Biology 17, 488-98, 2007). KIF18A is a viable target for the treatment of cancer. KIF18A is overexpressed in various types of cancers, including but not limited to colon, breast, lung, pancreas, prostate, bladder, head, neck, cervix, and ovarian cancers. Further, genetic deletion or knockdown, or inhibition of KIF18A affects mitotic spindle apparatus in cancer cell lines. Particularly, inhibition of KIF18A has been found to induce mitotic cell arrest, a known vulnerability that can promotes cell death in mitosis via apoptosis, mitotic catastrophe, or multipolarity driven lethality or death after mitotic slippage in interphase. Accordingly, there has been a strong interest in finding inhibitors of KIF18A proteins.

Thus, the inhibition of KIF18A activity is a promising approach for the development of novel anti-cancer agents.

SUMMARY

One embodiment provides a compound of Formula (I), or a pharmaceutically acceptable salt thereof:

Formula (I)

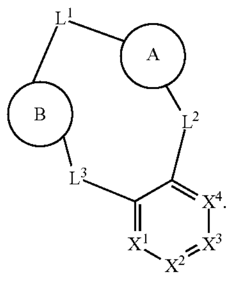

as described herein

In some embodiments, a compound of Formula (I), or a pharmaceutically acceptable salt thereof, has the structure of Formula (Ia), (Ia-1), (Ib), or (Ic):

Formula (Ia)

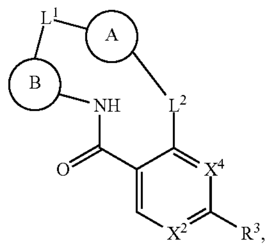

Formula (Ia-1)

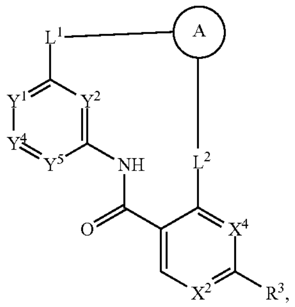

Formula (Ib)

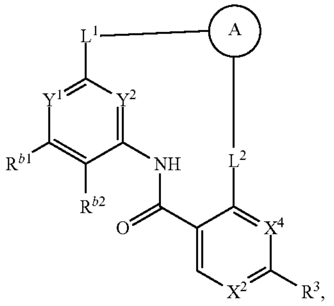

Formula (Ic)

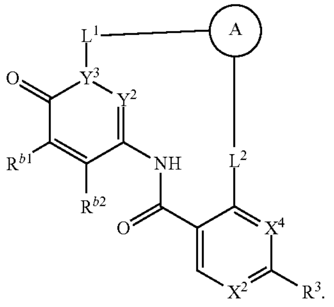

In some embodiments, provided herein is a compound of Formula (III), or a pharmaceutically acceptable salt thereof:

Formula (III)

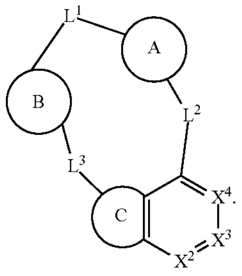

as described herein

In some embodiments, provided herein is a compound of Formula (IV), or a pharmaceutically acceptable salt thereof:

Formula (IV)

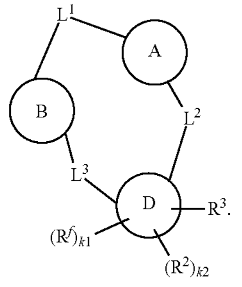

as described herein

In some embodiments, disclosed herein is a pharmaceutical composition comprising a compound of Formula (III), (IIIa), (IV), (IVa), (I), (Ia), (Ia-1), (Ib), (Id), (Ie), or (Ic), or a pharmaceutically acceptable salt thereof, and at least one pharmaceutically acceptable excipient.

In some embodiments, disclosed herein is a method of modulating kinase-like protein 18A (KIF18A) in a subject in need thereof, comprising administering to the subject a compound of Formula (III), (IIIa), (IV), (IVa), (I), (Ia), (Ia-1), (Ib), (Id), (Ie), or (Ic), or a pharmaceutically acceptable salt thereof. In some embodiments, disclosed herein is a method of inhibiting kinase-like protein 18A (KIF18A) in a subject in need thereof, comprising administering to the subject a compound of Formula (III), (IIIa), (IV), (IVa), (I), (Ia), (Ia-1), (Ib), (Id), (Ie), or (Ic), or a pharmaceutically acceptable salt thereof.

In some embodiments, disclosed herein is a method of treating cancer in a mammal in need thereof, comprising administering to the mammal a compound of Formula (IV), (IVa), (III), (IIIa), (I), (Ia), (Ia-1), (Ib), (Id), (Ie), or (Ic), or a pharmaceutically acceptable salt thereof. In some embodiments, disclosed herein is a method of treating cancer in a mammal in need thereof, comprising administering to the mammal a compound of Formula (IV), (IVa), (III), (IIIa), (I), (Ia), (Ia-1), (Ib), (Id), (Ie), or (Ic), or a pharmaceutically acceptable salt thereof, wherein the cancer is selected from the group consisting of: (a) a solid or hematologically derived tumor selected from cancer of the bladder, endometrial, lung squamous cell, breast, colon, kidney, liver, lung, small cell lung cancer, esophagus, gallbladder, brain, head and neck, ovary, pancreas, stomach, cervix, thyroid, prostate, and skin; (b) a hematopoietic tumor of lymphoid lineage selected from leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, and Burkett's lymphoma; (c) a hematopoietic tumor of myeloid lineage selected from acute and chronic myelogenous leukemias, myelodysplastic syndrome and promyelocytic leukemia; (d) a tumor of mesenchymal origin selected from fibrosarcoma and rhabdomyosarcoma; (e) a tumor of the central and peripheral nervous system selected from astrocytoma, neuroblastoma, glioma, and schwannoma; and (f) a melanoma, seminoma, teratocarcinoma, osteosarcoma, xenoderoma pigmentosum, keratoctanthoma, thyroid follicular cancer or Karposi's sarcoma.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise.

"oxo" refers to C═O.

"Carboxyl" refers to —COOH.

"Cyano" refers to —CN.

"Alkyl" refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-6}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —$NH_2$, or —$NO_2$. In some embodiments, the alkyl is optionally substituted with halogen, —CN, —OH, or —OMe. In some embodiments, the alkyl is optionally substituted with halogen.

"Alkenyl" refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" or "$C_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —$NH_2$, or —$NO_2$. In some embodiments, the alkenyl is optionally substituted with halogen, —CN, —OH, or —OMe. In some embodiments, the alkenyl is optionally substituted with halogen. As used here, "alkenylene" refers to a divalent alkenyl. Unless stated otherwise specifically in the specification, an alkenylene group may be optionally substituted.

"Heteroalkenylene" refers to an alkenylene group in which one or more skeletal atoms of the alkenylene are selected from an atom other than carbon, e.g., oxygen, nitrogen (e.g., —NH—, —N(alkyl)-), sulfur, phosphorus, or combinations thereof. Unless stated otherwise specifically in the specification, a heteroalkenylene group may be optionally substituted.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —$NH_2$, or —$NO_2$. In some embodiments, the alkynyl is optionally substituted with halogen, —CN, —OH, or —OMe. In some embodiments, the alkynyl is optionally substituted with halogen. As used here, "alkynylene" refers to a divalent alkynyl. Unless stated otherwise specifically in the specification, an alkynylene group may be optionally substituted.

"Heteroalkynylene" refers to an alkynylene group in which one or more skeletal atoms of the alkynylene are selected from an atom other than carbon, e.g., oxygen, nitrogen (e.g., —NH—, —N(alkyl)-), sulfur, phosphorus, or combinations thereof. Unless stated otherwise specifically in the specification, a heteroalkynylene group may be optionally substituted.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —$NH_2$, or —$NO_2$. In some embodiments, the alkylene is optionally substituted with halogen, —CN, —OH, or —OMe. In some embodiments, the alkylene is optionally substituted with halogen.

"Alkoxy" refers to a radical of the formula —$OR_a$ where $R_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —$NH_2$, or —$NO_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —$CF_3$, —OH, —OMe, —$NH_2$, or —$NO_2$. In some embodiments, the aryl is optionally substituted with halogen, methyl, ethyl, —CN, —$CF_3$, —OH, or —OMe. In some embodiments, the aryl is optionally substituted with halogen. As used here, "arylene" refers to a divalent aryl. Unless stated otherwise specifically in the specification, an arylene group may be optionally substituted.

"Cycloalkyl" refers to a partially or fully saturated, monocyclic or polycyclic carbocyclic ring, which may include fused (when fused with an aryl or a heteroaryl ring, the cycloalkyl is bonded through a non-aromatic ring atom), spiro, or bridged ring systems. In some embodiments, the cycloalkyl is fully saturated. Representative cycloalkyls include, but are not limited to, cycloalkyls having from three to fifteen carbon atoms (e.g., $C_3$-$C_{15}$ fully saturated cycloalkyl or $C_3$-$C_{15}$ cycloalkenyl), from three to ten carbon atoms (e.g., $C_3$-$C_{10}$ fully saturated cycloalkyl or $C_3$-$C_{10}$ cycloalkenyl), from three to eight carbon atoms (e.g., $C_3$-$C_8$ fully saturated cycloalkyl or $C_3$-$C_8$ cycloalkenyl), from three to six carbon atoms (e.g., $C_3$-$C_6$ fully saturated cycloalkyl or $C_3$-$C_6$ cycloalkenyl), from three to five carbon atoms (e.g., $C_3$-$C_5$ fully saturated cycloalkyl or $C_3$-$C_5$ cycloalkenyl), or three to four carbon atoms (e.g., $C_3$-$C_4$ fully saturated cycloalkyl or $C_3$-$C_4$ cycloalkenyl). In some embodiments, the cycloalkyl is a 3- to 10-membered fully saturated cycloalkyl or a 3- to 10-membered cycloalkenyl. In some embodiments, the cycloalkyl is a 3- to 6-membered fully saturated cycloalkyl or a 3- to 6-membered cycloalkenyl. In some embodiments, the cycloalkyl is a 5- to 6-membered fully saturated cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —$CF_3$, —OH, —OMe, —$NH_2$, or —$NO_2$. In some embodiments, a cycloalkyl is optionally substituted with oxo, halogen, methyl, ethyl, —CN, —$CF_3$, —OH, or —OMe. In some embodiments, the cycloalkyl is optionally substituted with halogen. As used herein, a "cycloalkylene" refers to a divalent cycloalkyl. Unless stated otherwise specifically in the specification, a cycloalkylene is optionally substituted.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —$CH_2OCH_3$, —$CH_2CH_2OCH_3$, —$CH_2CH_2OCH_2CH_2OCH_3$, —$CH(CH_3)OCH_3$, —$CH_2NHCH_3$, —$CH_2N(CH_3)_2$, —$CH_2CH_2NHCH_3$, or —$CH_2CH_2N(CH_3)_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —$CF_3$, —OH, —OMe, —$NH_2$, or —$NO_2$. In some embodiments, a heteroalkyl is optionally substituted with oxo, halogen, methyl, ethyl, —CN, —$CF_3$, —OH, or —OMe. In some embodiments, the heteroalkyl is optionally substituted with halogen. As used herein, "heteroalkylene" refers to a divalent heteroalkyl. Unless stated otherwise specifically in the specification, a heteroalkylene is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous, silicon, and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom), spiro, or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms (e.g., $C_2$-$C_{15}$ fully saturated heterocycloalkyl or $C_2$-$C_{15}$ heterocycloalkenyl), from two to ten carbon atoms (e.g., $C_2$-$C_{10}$ fully saturated heterocycloalkyl or $C_2$-$C_{10}$ heterocycloalkenyl), from two to eight carbon atoms (e.g., $C_2$-$C_8$ fully saturated heterocycloalkyl or $C_2$-$C_8$ heterocycloalkenyl), from two to seven carbon atoms (e.g., $C_2$-$C_7$ fully saturated heterocycloalkyl or $C_2$-$C_7$ heterocycloalkenyl), from two to six carbon atoms (e.g., $C_2$-$C_6$ fully saturated heterocycloalkyl or $C_2$-$C_7$ heterocycloalkenyl), from two to five carbon atoms (e.g., $C_2$-$C_8$ fully saturated heterocycloalkyl or $C_2$-$C_8$ heterocycloalkenyl), or two to four carbon atoms (e.g., $C_2$-$C_4$ fully saturated heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. In some embodiments, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, —$CF_3$, —OH, —OMe, —$NH_2$, or —$NO_2$. In some embodiments, the heterocycloalkyl is optionally substituted with halogen, methyl, ethyl, —CN, —$CF_3$, —OH, or —OMe. In some embodiments, the heterocycloalkyl is optionally substituted with halogen. As used herein, a "heterocycloalkylene" refers to a divalent heterocycloalkyl. Unless stated otherwise specifically in the specification, a heterocycloalkylene is optionally substituted.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —$CF_3$, —OH, —OMe, —$NH_2$, or —$NO_2$. In some embodiments, the heteroaryl is optionally substituted with halogen, methyl, ethyl, —CN, —$CF_3$, —OH, or —OMe. In some embodiments, the heteroaryl is optionally substituted with halogen. As used here, "heteroarylene" refers to a divalent heteroaryl. Unless stated otherwise specifically in the specification, a heteroarylene group may be optionally substituted.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —$CH_2CH_3$), fully substituted (e.g., —$CF_2CF_3$), mono-substituted (e.g., —$CH_2CH_2F$) or substituted at a level anywhere in-between fully substituted and mono-substituted (e.g., $—CH_2CHF_2$, $—CH_2CF_3$, $—CF_2CH_3$, $—CFHCHF_2$, etc.). It will be understood by those skilled in the art with respect to any group containing one or more substituents that such groups are not intended to introduce any substitution or substitution patterns that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition.

The terms "treat," "treating" or "treatment," as used herein, include alleviating, abating, or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition.

Compounds

In one aspect, provided herein are inhibitors of kinase-like protein 18A (KIF18A).

In some embodiments, provided herein is a compound of Formula (I), or a pharmaceutically acceptable salt thereof:

Formula (I)

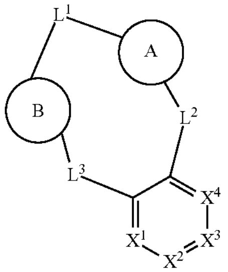

wherein,

- ring A is $C_3$-$C_7$cycloalkyl, 4- to 12-membered heterocycloalkyl, phenyl, or 5- to 10-membered heteroaryl, each of which is optionally substituted with one or more $R^a$;
- ring B is phenyl, 5- to 10-membered heteroaryl, $C_3$-$C_{12}$cycloalkyl, or 5- to 12-membered heterocycloalkyl, each of which is optionally substituted with one or more $R^b$;
- $L^1$ is a bond or a linker moiety connecting ring A and ring B, wherein the linker moiety comprises a linear sequence ranging from 1 to 20 non-hydrogen atoms, optionally substituted with one or more $R^c$;
- $L^2$ is a bond, —O—, —S—, —N(R)—, —N(R)CO—, $—CON(R^8)—$, $C_1$-$C_6$alkylene, or $C_1$-$C_6$heteroalkylene, wherein the alkylene and heteroalkylene is optionally substituted with one or more R;
- $L^3$ is a bond, —O—, —S—, $—N(R^8)CO—$, $—CON(R^8)—$, $—N(R^8)—$, $C_1$-$C_6$alkylene, or $C_1$-$C_6$heteroalkylene, wherein the alkylene and heteroalkylene is optionally substituted with one or more R;
- $X^1$ is N or $CR^1$;
- $X^2$ is N or $CR^2$;
- $X^3$ is N or $CR^3$;
- $X^4$ is N or $CR^4$;
- $R^1$, $R^2$ and $R^4$ are each independently selected from hydrogen, —CN, —OH, —SH, halogen, amino, $C_1$-$C_6$alkyl, $C_1$-$C_6$alkoxyl, $C_1$-$C_6$heteroalkyl, $C_2$-$C_6$alkenyl and $C_2$-$C_6$alkynyl, wherein the alkyl, alkoxyl, heteroalkyl, alkenyl and alkynyl are each optionally substituted with one or more $R^6$;
- each $R^6$ is independently selected from halogen, —CN, $—NO_2$, —OH, oxo, $—OR^7$, $—OC(=O)R^7$, $—OC(=O)OR^7$, $—OC(=O)NR^8R^8$, —SH, $—SR^7$, $—S(=O)R^7$, $—S(=O)_2R^7$, $—S(=O)_2NR^8R^8$, $—S(=O)(=NR^8)R^7$, $—NR^8R^8$, $—NR^8C(=O)NR^8R^8$, $—NR^8C(=O)R^8$, $—NR^8C(=O)OR^7$, $—NR^8S(=O)_2R^7$, $—N=S(=O)(R^7)_2$, $—C(=O)R^7$, $—C(=O)OR^8$, $—C(=O)NR^8R^8$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, and $C_2$-$C_6$alkynyl;
- $R^3$ is —CN or a group $—Z—R^5$;
- or $R^4$ and $R^3$ are taken together to form a cycloalkyl, heterocycloalkyl, aryl, or heteroaryl, each of which is optionally substituted with $—Z—R^5$ and one or more $R^d$;
- or $R^3$ and $R^2$ are taken together to form a cycloalkyl, heterocycloalkyl, aryl, or heteroaryl, each of which is optionally substituted with $—Z—R^5$ and one or more $R^d$;
- or $R^2$ and $R^1$ are taken together to form a cycloalkyl, heterocycloalkyl, aryl, or heteroaryl, each of which is optionally substituted with one or more $R^d$;
- Z is a bond, $C_1$-$C_8$alkylene, $C_1$-$C_8$heteroalkylene, —NR—, $—S(=O)C_0$-$C_6$alkylene-, $—NR^8SO_2—(C_0$-$C_6$alkylene)-, $—SO_2NR^8—(C_0$-$C_6$alkylene)-, $—NR^8O_2NR^8—$, $—NR^8SO_2NR^8C(=O)O—$, $—(C_0$-$C_6$alkylene)-S(=O)(=NH)—, $—(C_0$-$C_6$alkylene)-$NR^8$—S(=O)(=NH)—, $—(C_0$-$C_6$alkylene)-S—, $—(C_0$-$C_6$alkylene)-S(=O)—, $—(C_0$-$C_6$alkylene)-$SO_2$—, —O—, —P(=O)—, $—P(=O)_2—$, $—P(=O)(OR^8)—$, —(C=O)—, $—(C=O)NR^8—$, or $—NR^8(C=O)—$, wherein the alkylene or heteroalkylene is optionally substituted with one or more R;
- $R^5$ is selected from the group consisting of hydrogen, halogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, and heteroaryl, wherein the alkyl, haloalkyl, hydroxyalkyl, aminoalkyl, heteroalkyl, alkenyl, alkynyl, cycloalkyl, heterocycloalkyl, aryl, or heteroaryl is optionally substituted with one or more $R^e$; or
- the group $—Z—R^5$ is $—N=S(=O)—(R^5)_2$, wherein the two $R^5$ can alternatively combine with the sulfur atom to which they are attached to form a heterocycloalkyl, which is optionally substituted with one or more $R^e$;
- $R^a$, $R^b$, $R^c$, and $R^d$ are each independently selected from halogen, oxo, —CN, $—NO_2$, —OH, $—OR^7$, —OC (=O)$R^7$, —OC(=O)$OR^7$, —OC(=O)$NR^8R^8$, —SH, —$SR^7$, —S(=O)$R^7$, —$S(=O)_2R^7$, —$S(=O)_2NR^8R^8$, —S(=O)(=$NR^8$)$R^7$, —$NR^8R^8$, —$NR^8C$(=O)$NR^8R^8$, —$NR^8C$(=O)$R^7$, —$NR^8C$(=O)$OR^7$, —$NR^8S(=O)_2R^7$, —N=S(=O)$(R^7)_2$, —C(=O)$R^7$, —C(=O)$OR^8$, —C(=O)$NR^8R^8$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, and heteroaryl, wherein the alkyl, haloalkyl, hydroxyalkyl, aminoalkyl, heteroalkyl, alkenyl, alkynyl, cycloalkyl, heterocycloalkyl, aryl, or heteroaryl is optionally substituted with one or more R;

or two $R^c$ are taken together with the atom they are attached to form a cycloalkyl or heterocycloalkyl, each of which is optionally substituted with one or more R;

each $R^e$ is independently selected from halogen, oxo, —CN, —$NO_2$, OH, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl —$OR^7$, —$OC_1$-$C_4$haloalkyl, —CN, —C(=O)$R^7$, —C(=O)$OR^8$, —C(=O)$N(R^8)_2$, —C(=$NR^8$)$N(R^8)_2$, —OC(=O)$R^7$, —OC(=O)$N(R^8)_2$, —S(=O)(=$NR^8$)$R^7$, —$NR^8R^8$, —$OC_2$-$C_6$alkylene)$N(R^8)_2$, —$OC_2$-$C_6$alkyleneOR$^8$, —SH, —$SR^7$, —S(=O)$R^7$, —$S(=O)_2R^7$, —$S(=O)_2N(R^8)_2$, —$N(R^8)C$(=O)$R^7$, —$NR^8C$(=O)$OR^7$, —$N(R^8)C$(=O)$N(R^8)_2$, —$N(R^8)C$(=$NR^8$)$N(R^8)_2$, —N=S(=O)$(R^7)_2$, —$N(R^8)S(=O)_2R^7$, —$N(R^8)S(=O)_2N(R^8)_2$, —$NR^8C_2$-$C_6$alkyleneN$(R^8)_2$, —$NR^8C_2$-$C_6$alkyleneOR$^8$, —$C_1$-$C_6$alkyleneN$(R^8)_2$, —$C_1$-$C_6$alkyleneOR$^8$, —$C_1$-$C_6$alkyleneN$(R^8)$C(=O)$R^7$, —$C_1$-$C_6$alkyleneOC(=O)$R^8$, —$C_1$-$C_6$alkyleneC(=O)$N(R^8)_2$, and —$C_1$-$C_6$alkyleneC(=O)$OR^7$, wherein the alkyl, haloalkyl, hydroxyalkyl, aminoalkyl, heteroalkyl, alkenyl, alkynyl, cycloalkyl, or heterocycloalkyl is optionally substituted with one or more R;

$R^7$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl, each of which is optionally substituted with one or more R;

each $R^8$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), or $C_1$-$C_6$alkylene(heterocycloalkyl), wherein the alkyl, haloalkyl, hydroxyalkyl, aminoalkyl, heteroalkyl, alkenyl, alkynyl, cycloalkyl, heterocycloalkyl, aryl, heteroaryl, or alkylene is optionally substituted with one or more R; or two $R^8$ on the same atom are taken together with the atom to which they are attached to form a heterocycloalkyl optionally substituted with one or more R; and each R is independently halogen, —CN, —OH, oxo, —$SF_5$, —SH, —S(=O)$C_1$-$C_3$alkyl, —$S(=O)_2C_1$-$C_3$alkyl, —$S(=O)_2NH_2$, —$S(=O)_2NHC_1$-$C_3$alkyl, —$S(=O)_2N(C_1$-$C_3$alkyl$)_2$, —S(=O)(=$NC_1$-$C_3$alkyl)($C_1$-$C_3$alkyl), —$NH_2$, —$NHC_1$-$C_3$alkyl, —N($C_1$-$C_3$alkyl$)_2$, —N=S(=O)($C_1$-$C_3$alkyl$)_2$, —C(=O)$C_1$-$C_3$alkyl, —C(=O)OH, —C(=O)$OC_1$-$C_3$alkyl, —C(=O)$NH_2$, —C(=O)$NHC_1$-$C_3$alkyl, —C(=O)N($C_1$-$C_3$alkyl$)_2$, —P(=O)($C_1$-$C_3$alkyl$)_2$, $C_1$-$C_3$alkyl, $C_1$-$C_3$alkoxy, $C_1$-$C_3$haloalkyl, $C_1$-$C_3$haloalkoxy, $C_1$-$C_3$hydroxyalkyl, $C_1$-$C_3$aminoalkyl, $C_1$-$C_3$heteroalkyl, or $C_3$-$C_6$cycloalkyl.

In some embodiments, a compound of Formula (I), or a pharmaceutically acceptable salt thereof, has the structure of Formula (Ia):

Formula (Ia)

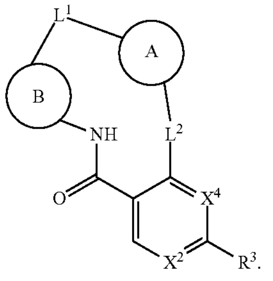

In some embodiments, a compound of Formula (I), or a pharmaceutically acceptable salt thereof, has the structure of Formula (Ia-1):

Formula (Ia-1)

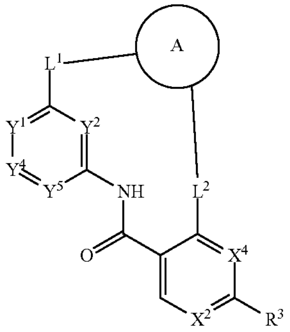

wherein, $Y^1$ is N, CH, or $CR^b$;

$Y^2$ is N, CH, or $CR^b$;

$Y^5$ is N or $CR^{b2}$;

$Y^4$ is N or $CR^{b1}$;

$R^{b2}$ is H or $R^b$; and $R^{b1}$ is H or $R^b$.

In some embodiments, a compound of Formula (I), or a pharmaceutically acceptable salt thereof, has the structure of Formula (Ib):

Formula (Ib)

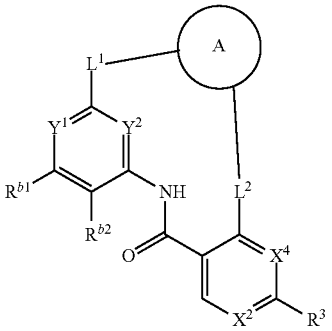

wherein, $Y^1$ is N, CH, or $CR^b$;

$Y^2$ is N, CH, or $CR^b$;

$R^{b1}$ is H or $R^b$; and $R^{b2}$ is H or R.

In some embodiments, a compound of Formula (I), or a pharmaceutically acceptable salt thereof, has the structure of Formula (Ic):

Formula (Ic)

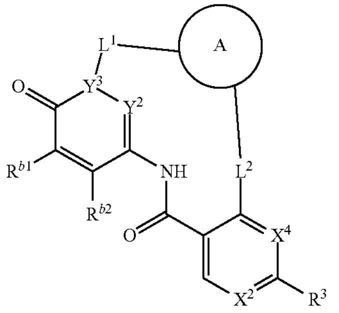

wherein, $Y^2$ is N, CH, or $CR^b$;

$Y^3$ is N, CH, or $CR^b$;

$R^{b1}$ is H or $R^b$; and $R^{b2}$ is H or $R^b$.

In some embodiments, a compound of Formula (I), or a pharmaceutically acceptable salt thereof, has the structure of Formula (Id):

Formula (Id)

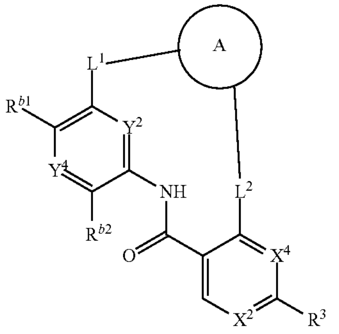

wherein, $Y^2$ is N, CH, or $CR^b$;

$Y^4$ is N, CH, or $CR^b$;

$R^1$ is H or $R^b$; and $R^{b2}$ is H or $R^b$.

In some embodiments, a compound of Formula (I), or a pharmaceutically acceptable salt thereof, has the structure of Formula (Ie):

Formula (Ie)

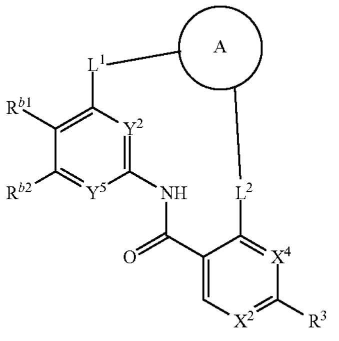

wherein, $Y^2$ is N, CH, or $CR^b$;

$Y^5$ is N, CH, or $CR^b$;

$R^{b1}$ is H or $R^b$; and $R^{b2}$ is H or $R^b$.

In some embodiments, provided herein is a compound of Formula (III), or a pharmaceutically acceptable salt thereof:

Formula (III)

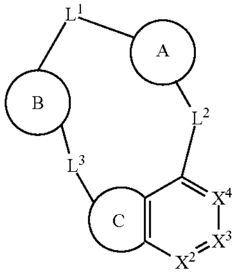

wherein, ring A is $C_3$-$C_7$cycloalkyl, 4- to 12-membered heterocycloalkyl, phenyl, or 5- to 10-membered heteroaryl, each of which is optionally substituted with one or more $R^a$;

ring B is phenyl, 5- to 10-membered heteroaryl, $C_3$-$C_{12}$cycloalkyl, or 5- to 12-membered heterocycloalkyl, each of which is optionally substituted with one or more $R^b$; ring C is phenyl, 5- to 6-membered heteroaryl, $C_3$-$C_7$cycloalkyl, 5- to 7-membered heterocycloalkyl, each of which is optionally substituted with one or more $R^f$;

$L^1$ is a bond or a linker moiety connecting ring A and ring B, wherein the linker moiety comprises a linear sequence ranging from 1 to 20 non-hydrogen atoms, optionally substituted with one or more $R^c$;

$L^2$ is a bond, —O—, —S—, —$N(R^8)$—, —$N(R^8)CO$—, —$CON(R^8)$—, $C_1$-$C_6$alkylene, or $C_1$-$C_6$heteroalkylene, wherein the alkylene and heteroalkylene is optionally substituted with one or more R;

$L^3$ is a bond, —O—, —S—, —$N(R^8)CO$—, —$CON(R^8)$—, —$N(R^8)$—, $C_1$-$C_6$alkylene, or $C_1$-$C_6$heteroalkylene, wherein the alkylene and heteroalkylene is optionally substituted with one or more R;

$X^2$ is N or $CR^2$;

$X^3$ is N or $CR^3$;

$X^4$ is N or $CR^4$;

$R^2$ and $R^4$ are each independently selected from hydrogen, —CN, —OH, —SH, halogen, amino, $C_1$-$C_6$alkyl, $C_1$-$C_6$alkoxyl, $C_1$-$C_6$heteroalkyl, $C_2$-$C_6$alkenyl and $C_2$-$C_6$alkynyl, wherein the alkyl, alkoxyl, heteroalkyl, alkenyl and alkynyl are each optionally substituted with one or more $R^6$;

each $R^6$ is independently selected from halogen, —CN, —$NO_2$, —OH, oxo, —$OR^7$, —$OC(=O)R^7$, —$OC(=O)OR^7$, —$OC(=O)NR^8R^8$, —SH, —$SR^7$, —$S(=O)R^7$, —$S(=O)_2R^7$, —$S(=O)_2NR^8R^8$, —$S(=O)(=NR^8)R^7$, —$NR^8R^8$, —$NR^8C(=O)NR^8R^8$, —$NR^8C(=O)R^8$, —$NR^8C(=O)OR^7$, —$NR^8S(=O)_2R^7$, —$N=S(=O)(R^7)_2$, —$C(=O)R^7$, —$C(=O)OR^8$, —$C(=O)NR^8R^8$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, and $C_2$-$C_6$alkynyl;

$R^3$ is —CN or a group —Z—$R^5$;

Z is a bond, $C_1$-$C_8$alkylene, $C_1$-$C_8$heteroalkylene, —NR—, —$S(=O)C_0$-$C_6$alkylene-, —$NR^8SO_2$—($C_0$-$C_6$alkylene)-, —$SO_2NR^8$—($C_0$-$C_6$alkylene)-, —$NR^8SO_2NR^8$—, —$NR^8SO_2NR^8C(=O)O$—, —($C_0$-

$C_6$alkylene)-S(=O)(=NH)—, —($C_0$-$C_6$alkylene)-$NR^8$—S(=O)(=NH)—, —($C_0$-$C_6$alkylene)-S—, —($C_0$-$C_6$alkylene)-S(=O)—, —($C_0$-$C_6$alkylene)-$SO_2$—, —O—, —P(=O)—, —P(=O)$_2$—, —P(=O)($OR^8$)—, —(C=O)—, —(C=O)$NR^8$—, or —$NR^8$(C=O)—, wherein the alkylene or heteroalkylene is optionally substituted with one or more R;

$R^5$ is selected from the group consisting of hydrogen, halogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, and heteroaryl, wherein the alkyl, haloalkyl, hydroxyalkyl, aminoalkyl, heteroalkyl, alkenyl, alkynyl, cycloalkyl, heterocycloalkyl, aryl, or heteroaryl is optionally substituted with one or more $R^e$; or the group —Z—$R^5$ is —N=S(=O)—($R^5$)$_2$, wherein the two R can alternatively combine with the sulfur atom to which they are attached to form a heterocycloalkyl, which is optionally substituted with one or more $R^e$;

$R^a$, $R^b$, $R^c$, $R^d$, and R are each independently selected from halogen, oxo, —CN, —$NO_2$, —OH, —$OR^7$, —OC(=O)$R^7$, —OC(=O)$OR^7$, —OC(=O)$NR^8R^8$, —SH, —$SR^7$, —S(=O)$R^7$, —S(=O)$_2R^7$, —S(=O)$_2NR^8R^8$, —S(=O)(=$NR^8$)$R^7$, —$NR^8R^8$, —$NR^8$C(=O)$NR^8R^8$, —$NR^8$C(=O)$R^7$, —$NR^8$C(=O)$OR^7$, —$NR^8$S(=O)$_2R^7$, —N=S(=O)($R^7$)$_2$, —C(=O)$R^7$, —C(=O)$OR^8$, —C(=O)$NR^8R^8$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, and heteroaryl, wherein the alkyl, haloalkyl, hydroxyalkyl, aminoalkyl, heteroalkyl, alkenyl, alkynyl, cycloalkyl, heterocycloalkyl, aryl, or heteroaryl is optionally substituted with one or more R;

or two $R^c$ are taken together with the atom they are attached to form a cycloalkyl or heterocycloalkyl, each of which is optionally substituted with one or more R;

each $R^e$ is independently selected from halogen, oxo, —CN, —$NO_2$, OH, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl —$OR^7$, —O$C_1$-$C_4$haloalkyl, —CN, —C(=O)$R^7$, —C(=O)$OR^8$, —C(=O)N(R)$_2$, —C(=$NR^8$)N($R^8$)$_2$, —OC(=O)$R^7$, —OC(=O)N($R^8$)$_2$, —S(=O)(=$NR^8$)$R^7$, —$NR^8R^8$, —O$C_2$-$C_6$alkylene)N($R^8$)$_2$, —O$C_2$-$C_6$alkylene$OR^8$, —SH, —$SR^7$, —S(=O)$R^7$, —S(=O)$_2R^7$, —S(=O)$_2$N($R^8$)$_2$, —N($R^8$)C(=O)$R^7$, —$NR^8$C(=O)$OR^7$, —N($R^8$)C(=O)N($R^8$)$_2$, —N($R^8$)C(=$NR^8$)N($R^8$)$_2$, —N=S(=O)($R^7$)$_2$, —N($R^8$)S(=O)$_2R^7$, —N($R^8$)S(=O)$_2$N($R^8$)$_2$, —$NR^8C_2$-$C_6$alkyleneN($R^8$)$_2$, —$NR^8C_2$-$C_6$alkylene$OR^8$, —$C_1$-$C_6$alkyleneN($R^8$)$_2$, —$C_1$-$C_6$alkylene$OR^8$, —$C_1$-$C_6$alkyleneN($R^8$)C(=O)$R^7$, —$C_1$-$C_6$alkyleneOC(=O)$R^8$, —$C_1$-$C_6$alkyleneC(=O)N($R^8$)$_2$, and —$C_1$-$C_6$alkyleneC(=O)$OR^7$, wherein the alkyl, haloalkyl, hydroxyalkyl, aminoalkyl, heteroalkyl, alkenyl, alkynyl, cycloalkyl, or heterocycloalkyl is optionally substituted with one or more R;

$R^7$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl, each of which is optionally substituted with one or more R;

each $R^8$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), or $C_1$-$C_6$alkylene(heterocycloalkyl), wherein the alkyl, haloalkyl, hydroxyalkyl, aminoalkyl, heteroalkyl, alkenyl, alkynyl, cycloalkyl, heterocycloalkyl, aryl, heteroaryl, or alkylene is optionally substituted with one or more R; or two $R^8$ on the same atom are taken together with the atom to which they are attached to form a heterocycloalkyl optionally substituted with one or more R; and each R is independently halogen, —CN, —OH, oxo, —$SF_5$, —SH, —S(=O)$C_1$-$C_3$alkyl, —S(=O)$_2C_1$-$C_3$alkyl, —S(=O)$_2NH_2$, —S(=O)$_2NHC_1$-$C_3$alkyl, —S(=O)$_2$N($C_1$-$C_3$alkyl)$_2$, —S(=O)(=N$C_1$-$C_3$alkyl)($C_1$-$C_3$alkyl), —$NH_2$, —NH$C_1$-$C_3$alkyl, —N($C_1$-$C_3$alkyl)$_2$, —N=S(=O)($C_1$-$C_3$alkyl)$_2$, —C(=O)$C_1$-$C_3$alkyl, —C(=O)OH, —C(=O)O$C_1$-$C_3$alkyl, —C(=O)$NH_2$, —C(=O)NH$C_1$-$C_3$alkyl, —C(=O)N($C_1$-$C_3$alkyl)$_2$, —P(=O)($C_1$-$C_3$alkyl)$_2$, $C_1$-$C_3$alkyl, $C_1$-$C_3$alkoxy, $C_1$-$C_3$haloalkyl, $C_1$-$C_3$haloalkoxy, $C_1$-$C_3$hydroxyalkyl, $C_1$-$C_3$aminoalkyl, $C_1$-$C_3$heteroalkyl, or $C_3$-$C_6$cycloalkyl.

In some embodiments, a compound of Formula (III), or a pharmaceutically acceptable salt thereof, has the structure of Formula (IIIa):

Formula (IIIa)

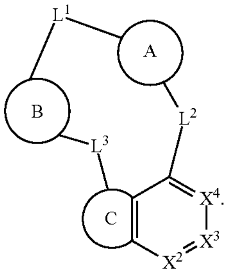

In some embodiments, provided herein is a compound of Formula (IV), or a pharmaceutically acceptable salt thereof:

Formula (IV)

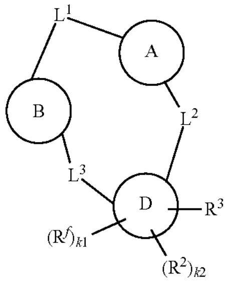

wherein, ring A is $C_3$-$C_7$cycloalkyl, 4- to 12-membered heterocycloalkyl, phenyl, or 5- to 10-membered heteroaryl, each of which is optionally substituted with one or more $R^a$;

ring B is phenyl, 5- to 10-membered heteroaryl, $C_3$-$C_{12}$cycloalkyl, or 5- to 12-membered heterocycloalkyl, each of which is optionally substituted with one or more $R^b$;

ring D is cycloalkyl, heterocycloalkyl, aryl, or heteroaryl;

$L^1$ is a bond or a linker moiety connecting ring A and ring B, wherein the linker moiety comprises a linear sequence ranging from 1 to 20 non-hydrogen atoms, optionally substituted with one or more $R^c$;

$L^2$ is a bond, —O—, —S—, —$N(R^8)$—, —$N(R^8)CO$—, —$CON(R^8)$—, $C_1$-$C_6$alkylene, or $C_1$-$C_6$heteroalkylene, wherein the alkylene and heteroalkylene is optionally substituted with one or more R;

$L^3$ is a bond, —O—, —S—, —$N(R^8)CO$—, —$CON(R^8)$—, —$N(R^8)$—, $C_1$-$C_6$alkylene, or $C_1$-$C_6$heteroalkylene, wherein the alkylene and heteroalkylene is optionally substituted with one or more R;

each $R^2$ is independently selected from hydrogen, —CN, —OH, —SH, halogen, amino, $C_1$-$C_6$alkyl, $C_1$-$C_6$alkoxyl, $C_1$-$C_6$heteroalkyl, $C_2$-$C_6$alkenyl and $C_2$-$C_6$alkynyl, wherein the alkyl, alkoxyl, heteroalkyl, alkenyl and alkynyl are each optionally substituted with one or more $R^6$;

each $R^6$ is independently selected from halogen, —CN, —$NO_2$, —OH, oxo, —$OR^7$, —$OC(=O)R^7$, —$OC(=O)OR^7$, —$OC(=O)NR^8R^8$, —SH, —$SR^7$, —$S(=O)R^7$, —$S(=O)_2R^7$, —$S(=O)_2NR^8R^8$, —$S(=O)(=NR^8)R^7$, —$NR^8R^8$, —$NR^8C(=O)NR^8R^8$, —$NR^8C(=O)R^8$, —$NR^8C(=O)OR^7$, —$NR^8S(=O)_2R^7$, —$N=S(=O)(R^7)_2$, —$C(=O)R^7$, —$C(=O)OR^8$, —$C(=O)NR^8R^8$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, and $C_2$-$C_6$alkynyl;

k2 is 0, 1, 2, or 3;

$R^3$ is —CN or a group —Z—$R^5$;

k1 is 0, 1, 2, or 3;

Z is a bond, $C_1$-$C_8$alkylene, $C_1$-$C_8$heteroalkylene, —NR—, —$S(=O)C_0$-$C_6$alkylene-, —$NR^8SO_2$—($C_0$-$C_6$alkylene)-, —$SO_2NR^8$—($C_0$-$C_6$alkylene)-, —$NR^8SO_2NR^8$—, —$NR^8SO_2NR^8C(=O)O$—, —($C_0$-$C_6$alkylene)-$S(=O)(=NH)$—, —($C_0$-$C_6$alkylene)-$NR^8$—$S(=O)(=NH)$—, —($C_0$-$C_6$alkylene)-S—, —($C_0$-$C_6$alkylene)-$S(=O)$—, —($C_0$-$C_6$alkylene)-$SO_2$—, —O—, —$P(=O)$—, —$P(=O)_2$—, —$P(=O)(OR^8)$—, —$(C=O)$—, —$(C=O)NR^8$—, or —$NR^8(C=O)$—, wherein the alkylene or heteroalkylene is optionally substituted with one or more R;

$R^5$ is selected from the group consisting of hydrogen, halogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, and heteroaryl, wherein the alkyl, haloalkyl, hydroxyalkyl, aminoalkyl, heteroalkyl, alkenyl, alkynyl, cycloalkyl, heterocycloalkyl, aryl, or heteroaryl is optionally substituted with one or more $R^e$; or the group —Z—$R^5$ is —$N=S(=O)$—$(R^5)_2$, wherein the two $R^5$ can alternatively combine with the sulfur atom to which they are attached to form a heterocycloalkyl, which is optionally substituted with one or more $R^e$;

$R^a$, $R^b$, $R^c$, $R^d$, and R are each independently selected from halogen, oxo, —CN, —$NO_2$, —OH, —$OR^7$, —$OC(=O)R^7$, —$OC(=O)OR^7$, —$OC(=O)NR^8R^8$, —SH, —$SR^7$, —$S(=O)R^7$, —$S(=O)_2R^7$, —$S(=O)_2NR^8R^8$, —$S(=O)(=NR^8)R^7$, —$NR^8R^8$, —$NR^8C(=O)NR^8R^8$, —$NR^8C(=O)R^7$, —$NR^8C(=O)OR^7$, —$NR^8S(=O)_2R^7$, —$N=S(=O)(R^7)_2$, —$C(=O)R^7$, —$C(=O)OR^8$, —$C(=O)NR^8R^8$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, and heterocycloalkyl, wherein the alkyl, haloalkyl, hydroxyalkyl, aminoalkyl, heteroalkyl, alkenyl, alkynyl, cycloalkyl, or heterocycloalkyl is optionally substituted with one or more R;

or two $R^c$ are taken together with the atom they are attached to form a cycloalkyl or heterocycloalkyl, each of which is optionally substituted with one or more R;

each $R^e$ is independently selected from halogen, oxo, —CN, —$NO_2$, OH, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl —$OR^7$, —$OC_1$-$C_4$haloalkyl, —CN, —$C(=O)R^7$, —$C(=O)OR^8$, —$C(=O)N(R^8)_2$, —$C(=NR^8)N(R^8)_2$, —$OC(=O)R^7$, —$OC(=O)N(R^8)_2$, —$S(=O)(=NR^8)R^7$, —$NR^8R^8$, —$OC_2$-$C_6$alkylene)$N(R^8)_2$, —$OC_2$-$C_6$alkylene$OR^8$, —SH, —$SR^7$, —$S(=O)R^7$, —$S(=O)_2R^7$, —$S(=O)_2N(R^8)_2$, —$N(R^8)C(=O)R^7$, —$NR^8C(=O)OR^7$, —$N(R^8)C(=O)N(R^8)_2$, —$N(R^8)C(=NR^8)N(R^8)_2$, —$N=S(=O)(R^7)_2$, —$N(R^8)S(=O)_2R^7$, —$N(R^8)S(=O)_2N(R^8)_2$, —$NR^8C_2$-$C_6$alkylene$N(R^8)_2$, —$NR^8C_2$-$C_6$alkylene$OR^8$, —$C_1$-$C_6$alkylene$N(R^8)_2$, —$C_1$-$C_6$alkylene$OR^8$, —$C_1$-$C_6$alkylene$N(R^8)C(=O)R^7$, —$C_1$-$C_6$alkylene$OC(=O)R^8$, —$C_1$-$C_6$alkylene$C(=O)N(R^8)_2$, and —$C_1$-$C_6$alkylene$C(=O)OR^7$, wherein the alkyl, haloalkyl, hydroxyalkyl, aminoalkyl, heteroalkyl, alkenyl, alkynyl, cycloalkyl, or heterocycloalkyl is optionally substituted with one or more R;

$R^7$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl, each of which is optionally substituted with one or more R;

each $R^8$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), or $C_1$-$C_6$alkylene(heterocycloalkyl), wherein the alkyl, haloalkyl, hydroxyalkyl, aminoalkyl, heteroalkyl, alkenyl, alkynyl, cycloalkyl, heterocycloalkyl, aryl, heteroaryl, or alkylene is optionally substituted with one or more R; or two $R^8$ on the same atom are taken together with the atom to which they are attached to form a heterocycloalkyl optionally substituted with one or more R; and each R is independently halogen, —CN, —OH, oxo, —$SF_5$, —SH, —$S(=O)C_1$-$C_3$alkyl, —$S(=O)_2C_1$-$C_3$alkyl, —$S(=O)_2NH_2$, —$S(=O)_2NHC_1$-$C_3$alkyl, —$S(=O)_2N(C_1$-$C_3$alkyl$)_2$, —$S(=O)(=NC_1$-$C_3$alkyl)($C_1$-$C_3$alkyl), —$NH_2$, —$NHC_1$-$C_3$alkyl, —$N(C_1$-$C_3$alkyl$)_2$, —$N=S(=O)(C_1$-$C_3$alkyl$)_2$, —$C(=O)C_1$-$C_3$alkyl, —$C(=O)OH$, —$C(=O)OC_1$-$C_3$alkyl, —$C(=O)NH_2$, —$C(=O)NHC_1$-$C_3$alkyl, —$C(=O)N(C_1$-$C_3$alkyl$)_2$, —$P(=O)(C_1$-$C_3$alkyl$)_2$, $C_1$-$C_3$alkyl, $C_1$-$C_3$alkoxy, $C_1$-$C_3$haloalkyl, $C_1$-$C_3$haloalkoxy, $C_1$-$C_3$hydroxyalkyl, $C_1$-$C_3$aminoalkyl, $C_1$-$C_3$heteroalkyl, or $C_3$-$C_6$cycloalkyl.

In some embodiments, a compound of Formula (IV) has the structure of Formula (III). In some embodiments, a compound of Formula (IV) has the structure of Formula (IIIa). In some embodiments, a compound of Formula (IV) has the structure of Formula (I), (Ia), (Ia-1), (Ib), (Id), (Ie), or (Ic). In some embodiments,

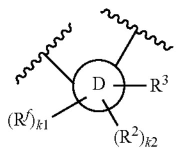 is 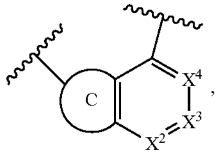, wherein ring C, $X^2$, $X^3$, and $X^4$ are defined in Formula (III). In some embodiments,

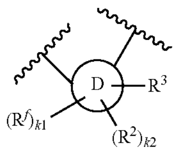 is. 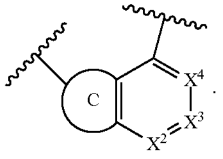.

In some embodiments,

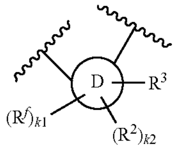 is 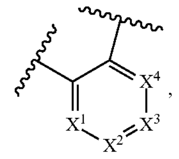, wherein $X^1$, $X^2$, $X^3$, and $X^4$ are defined in Formula (I). In some embodiments, k1 is 0. In some embodiments, k1 is 1. In some embodiments, k1 is 2. In some embodiments, k1 is 3. In some embodiments, k2 is 0. In some embodiments, k2 is 1. In some embodiments, k2 is 2. In some embodiments, k2 is 3. In some embodiment, $R^3$ is in a para position to the attachment point of $L^3$. In some embodiment, $R^3$ is in a meta position to the attachment point of $L^2$. In some embodiment, $R^3$ is in an ortho position to the attachment point of $L^2$.

In some embodiments, a compound of Formula (IV) has a structure of Formula (IVa), Formula (IVa)

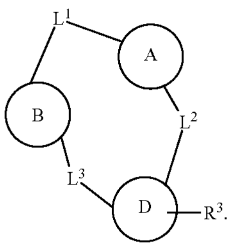

In some embodiments of a compound of Formula (IV) or (IVa), or a pharmaceutically acceptable salt thereof, ring D is aryl. In some embodiments, ring D is phenyl. In some embodiments, ring D is phenyl fused with a cycloalkyl. In some embodiments, ring D is phenyl fused with a 5-6 membered cycloalkyl. In some embodiments,

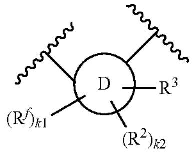 (or 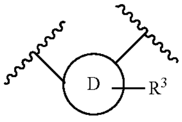) is

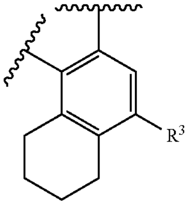 or 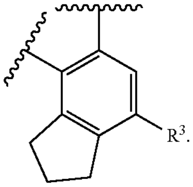

In some embodiments, ring D is phenyl fused with a heterocycloalkyl. In some embodiments, ring D is phenyl fused with a 5-6 membered heterocycloalkyl. In some embodiments,

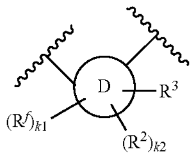 (or 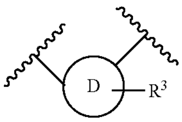) is

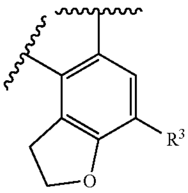 or 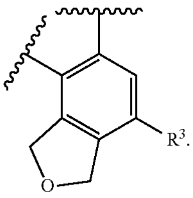

In some embodiments,

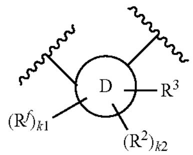 (or 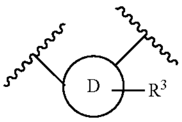) is

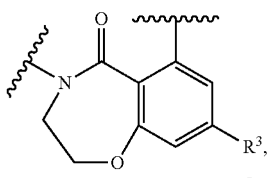, 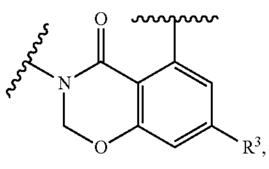, or

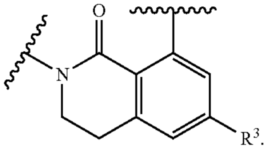

In some embodiments of a compound of Formula (IV) or (IVa), or a pharmaceutically acceptable salt thereof, ring D is naphthyl. In some embodiments,

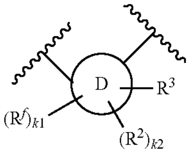

(or 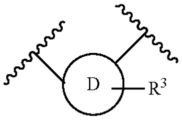 ) is

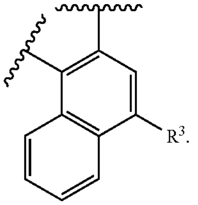

In some embodiments, ring D is heterocycloalkyl. In some embodiments, ring D is cycloalkyl.

In some embodiments of a compound of Formula (IV) or (IVa), or a pharmaceutically acceptable salt thereof, ring D is heteroaryl. In some embodiments, ring D is monocyclic heteroaryl. In some embodiments, ring D is bicyclic heteroaryl. In some embodiments, ring D is 5-6, 6-6, or 6-5 fused bicyclic heteroaryl. In some embodiments, ring D is 6-5 fused bicyclic heteroaryl. In some embodiments, ring D contains 1-3 nitrogen, 0-1 sulfur and 0-1 oxgen. In some embodiments, ring D contains 1-3 nitrogen. In some embodiments, ring D contains 0-2 nitrogen and 1 oxgen. In some embodiments,

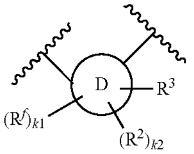

(or 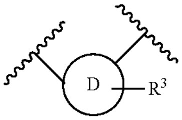 ) is

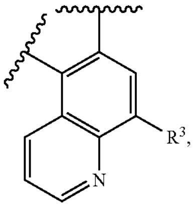 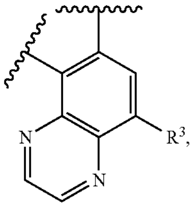

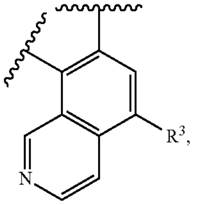 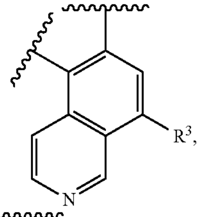 or

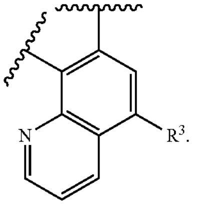

In some embodiments,

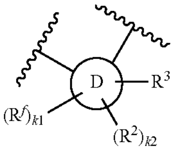

(or 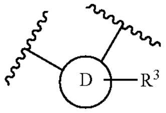 ) is

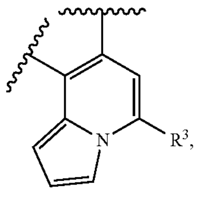 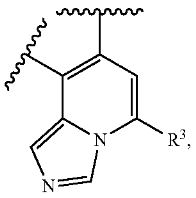

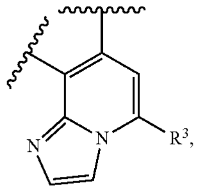 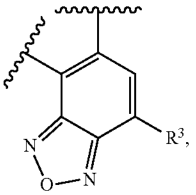

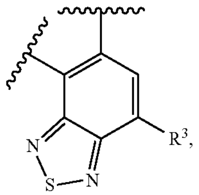 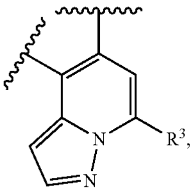

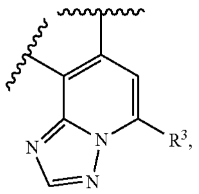 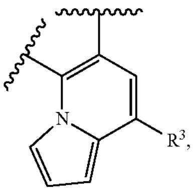

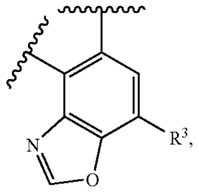 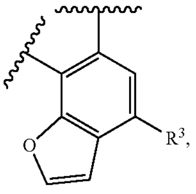

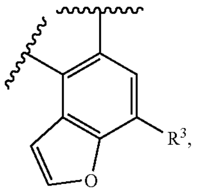 or 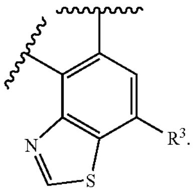

In some embodiments,

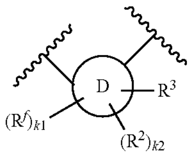

(or 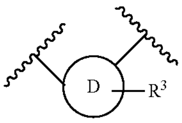 ) is

-continued

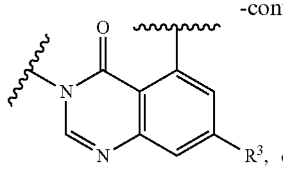

or

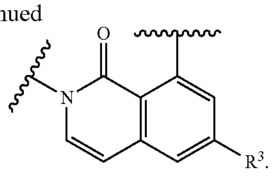

In some embodiment, $R^3$ is in a para position to the attachment point of $L^3$. In some embodiment, $R^3$ is in a meta position to the attachment point of $L^2$. In some embodiments,

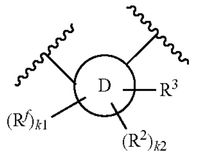

(or

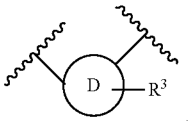

) is

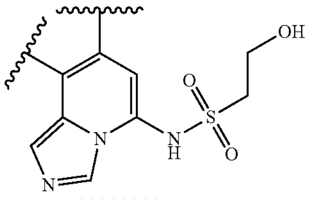

or

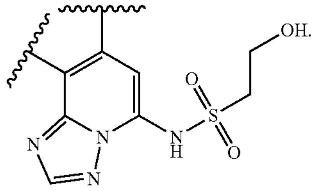

In some embodiments of a compound of Formula (I), or a pharmaceutically acceptable salt thereof, $X^1$ is N.

In some embodiments of a compound of Formula (I), or a pharmaceutically acceptable salt thereof, $X^1$ is $CR^1$. In some embodiments of the compound, or a pharmaceutically acceptable salt thereof, $R^1$ is hydrogen or $C_1$-$C_3$alkyl. In some embodiments of the compound, or a pharmaceutically acceptable salt thereof, $R^1$ is hydrogen.

In some embodiments of a compound of Formula (III), (IIIa), or (I), or a pharmaceutically acceptable salt thereof, $X^3$ is N.

In some embodiments of a compound of Formula (III), (IIIa), or (I), or a pharmaceutically acceptable salt thereof, $X^3$ is $CR^3$.

In some embodiments of a compound of Formula (IV), (IVa), (III), (IIIa), (I), (Ia), (Ia-1), (Ib), (Id), (Ie), or (Ic), $R^3$ is CN.

In some embodiments of a compound of Formula (IV), (IVa), (III), (IIIa), (I), (Ia), (Ia-1), (Ib), (Id), (Ie), or (Ic), $R^3$ is —Z—$R^5$. In some embodiments, Z is selected from the group consisting of a bond, $C_1$-$C_8$alkylene, —NR—, —$NR^8SO_2$—($C_0$-$C_6$alkylene)-, —$SO_2NR^8$—($C_0$-$C_6$alkylene)-, —$NR^8SO_2NR^8$—, and —($C_0$-$C_6$alkylene)-$SO_2$—. In some embodiments, Z is —$NHSO_2$—, —$CH_2SO_2$—, —NH—, or —$SO_2$NH—. In some embodiments, Z is —$NHSO_2$—. In some embodiments, Z is —$CH_2SO_2$—. In some embodiments, Z is —NH—. In some embodiments, Z is —$SO_2$NH—. In some embodiments, Z is —$NR^8SO_2$—. In some embodiments, Z is —$NR^8SO_2$—($C_0$-$C_6$alkylene)-. In some embodiments, Z is $C_1$-$C_8$heteroalkylene, which is optionally substituted with one or more R. In some embodiments, the $C_1$-$C_8$heteroalkylene is

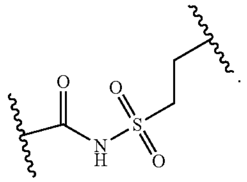 [SMILES: *CCS(=O)(=O)NC(*)=O]

In some embodiments of a compound of Formula (IV), (IVa), (III), (IIIa), (I), (Ia), (Ia-1), (Ib), (Id), (Ie), or (Ic), or a pharmaceutically acceptable salt thereof, the group —Z—$R^5$ is —N═S(═O)—$(R^5)_2$, wherein the two $R^5$ can alternatively combine with the sulfur atom to which they are attached to form a saturated or partially-saturated 3-, 4-, 5-, or 6-membered monocyclic ring containing 0, 1, 2 or 3 N atoms and 0, 1 or 2 atoms selected from O and S.

In some embodiments of a compound of Formula (IV), (IVa), (III), (IIIa), (I), (Ia), (Ia-1), (Ib), (Id), (Ie), or (Ic), or a pharmaceutically acceptable salt thereof, $R^5$ is selected from the group consisting of hydrogen, $C_1$-$C_6$alkyl, $C_1$-$C_4$haloalkyl, and $C_1$-$C_6$hydroxyalkyl.

In some embodiments of a compound of Formula (IV), (IVa), (III), (IIIa), (I), (Ia), (Ia-1), (Ib), (Id), (Ie), or (Ic), or a pharmaceutically acceptable salt thereof, —Z—$R^5$ is selected from the group consisting of: —$NHSO_2CH_2CH_2OH$, —$NHSO_2CH_2CH_3$, —$NHSO_2CH_3$, —$NHC(CH_3)_2CH_2OH$, and

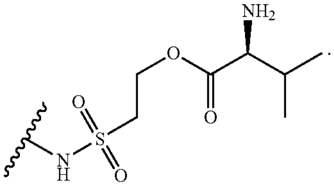 [SMILES: *NS(=O)(=O)CCOC(=O)[C@@H](N)C(C)C]

In some embodiments of a compound of Formula (IV), (IVa), (III), (IIIa), (I), (Ia), (Ia-1), (Ib), (Id), (Ie), or (Ic), or a pharmaceutically acceptable salt thereof, —Z—$R^5$ is selected from the group consisting of: —$SO_2NHCH_2CH_2OH$, —$SO_2NHC(CH_3)_3$, —$SO_2NHCH_3$, and —$SO_2NH_2$.

In some embodiments of a compound of Formula (IV), (IVa), (III), (IIIa), (I), (Ia), (Ia-1), (Ib), (Id), (Ie), or (Ic), or a pharmaceutically acceptable salt thereof, —Z—$R^5$ is —$CH_2SO_2CH_2CH_2OH$.

In some embodiments of a compound of Formula (IV), (IVa), (III), (IIIa), (I), (Ia), (Ia-1), (Ib), (Id), (Ie), or (Ic), or a pharmaceutically acceptable salt thereof, $R^3$ is

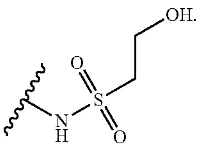 [SMILES: *NS(=O)(=O)CCO]

In some embodiments, $R^3$ is

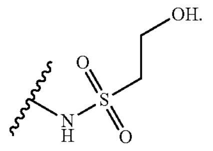 [SMILES: *NS(=O)(=O)CCO]

In some embodiments, $R^3$ is

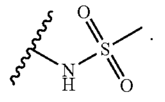 [SMILES: *NS(C)(=O)=O]

In some embodiments, $R^3$ is

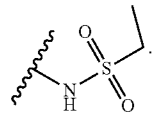 [SMILES: *NS(=O)(=O)CC]

In some embodiments, $R^3$ is

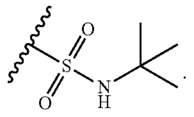 [SMILES: *S(=O)(=O)NC(C)(C)C]

In some embodiments, $R^3$ is

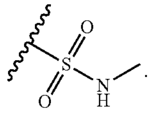 [SMILES: *S(=O)(=O)NC]

In some embodiments, $R^3$ is

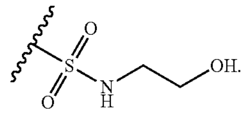 [SMILES: *S(=O)(=O)NCCO]

In some embodiments, $R^3$ is

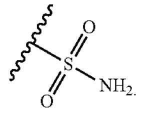 [SMILES: *S(N)(=O)=O]

In some embodiments, $R^3$ is

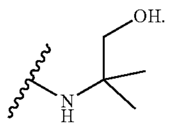 [SMILES: *NC(C)(C)CO]

In some embodiments, $R^3$ is

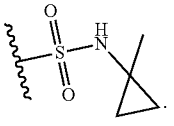 [SMILES: *S(=O)(=O)NC1(C)CC1]

In some embodiments, $R^3$ is

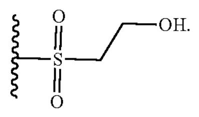 [SMILES: *S(=O)(=O)CCO]

In some embodiments of a compound of Formula (I), or a pharmaceutically acceptable salt thereof,

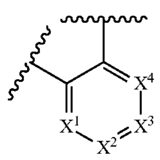
is
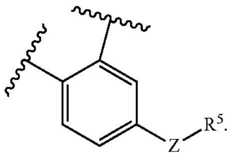

In some embodiments of a compound of Formula (III), (IIIa), (I), (Ia), (Ia-1), (Ib), (Id), (Ie), or (Ic), or a pharmaceutically acceptable salt thereof, $X^2$ is N.

In some embodiments of a compound of Formula (III), (IIIa), (I), (Ia), (Ia-1), (Ib), (Id), (Ie), or (Ic), or a pharmaceutically acceptable salt thereof, $X^2$ is $CR^2$. In some embodiments of the compound, or a pharmaceutically acceptable salt thereof, $R^2$ is hydrogen or $C_1$-$C_3$alkyl. In some embodiments, $R^2$ is hydrogen. In some embodiments, $R^2$ is halogen. In some embodiments, $R^2$ is F.

In some embodiments of a compound of Formula (III), (IIIa), (I), (Ia), (Ia-1), (Ib), (Id), (Ie), or (Ic), or a pharmaceutically acceptable salt thereof, $X^4$ is N.

In some embodiments of a compound of Formula (III), (IIIa), (I), (Ia), (Ia-1), (Ib), (Id), (Ie), or (Ic), or a pharmaceutically acceptable salt thereof, $X^4$ is $CR^4$. In some embodiments of the compound, or a pharmaceutically acceptable salt thereof, $R^4$ is hydrogen or $C_1$-$C_3$alkyl. In some embodiments of the compound, or a pharmaceutically acceptable salt thereof, $R^4$ is hydrogen.

In some embodiments of a compound of Formula (I), (Ia), (Ia-1), (Ib), (Id), (Ie), or (Ic), or a pharmaceutically acceptable salt thereof, $R^4$ and $R^3$ are taken together to form a cycloalkyl, heterocycloalkyl, aryl, or heteroaryl, each of which is optionally substituted with one or more $R^d$. In some embodiments, $R^4$ and $R^3$ are taken together to form a cycloalkyl, heterocycloalkyl, aryl, or heteroaryl, each of which is substituted with —Z—$R^5$ and optionally one or more $R^d$. In some embodiments, $R^4$ and $R^3$ are taken together to form an optionally substituted heteroaryl. In some embodiments,

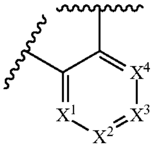 is 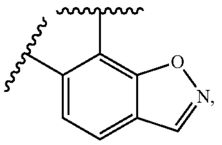

which is substituted with —Z—$R^5$ and optionally one or more $R^d$. In some embodiments,

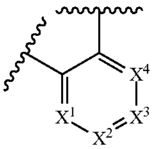 is 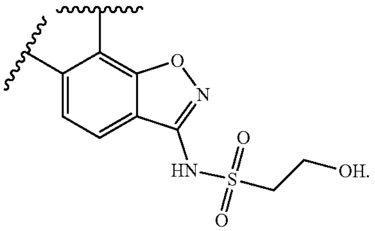

In some embodiments of a compound of Formula (I), (Ia), (Ia-1), (Ib), (Id), (Ie), or (Ic), or a pharmaceutically acceptable salt thereof, $R^3$ and $R^2$ are taken together to form a cycloalkyl, heterocycloalkyl, aryl, or heteroaryl, each of which is optionally substituted with one or more $R^d$.

In some embodiments of a compound of Formula (I), (Ia), (Ia-1), (Ib), (Id), (Ie), or (Ic), or a pharmaceutically acceptable salt thereof, $R^4$ and $R^3$ are taken together to form a cycloalkyl, heterocycloalkyl, aryl, or heteroaryl, each of which is optionally substituted with one or more $R^d$.

In some embodiments of a compound of Formula (I), (Ia), (Ia-1), (Ib), (Id), (Ie), or (Ic), or a pharmaceutically acceptable salt thereof, $R^3$ and $R^2$ are taken together to form a cycloalkyl, heterocycloalkyl, aryl, or heteroaryl, each of which is optionally substituted with one or more $R^d$.

In some embodiments of a compound of Formula (I), (Ia), (Ia-1), (Ib), (Id), (Ie), or (Ic), or a pharmaceutically acceptable salt thereof, $R^3$ and $R^2$ are taken together to form a cycloalkyl, heterocycloalkyl, aryl, or heteroaryl, each of which is optionally substituted with —Z—$R^5$ and one or more $R^d$. In some embodiments of a compound of Formula (I), (Ia), (Ia-1), (Ib), (Id), (Ie), or (Ic), or a pharmaceutically acceptable salt thereof, $R^3$ and $R^2$ are taken together to form a heterocycloalkyl or heteroaryl, each of which is substituted with —Z—$R^5$ and optionally substituted with one or more $R^d$. In some embodiments, $R^3$ and $R^2$ are taken together to form a 5-6 membered heterocycloalkyl or 5-6 membered heteroaryl, each of which is substituted with —Z—$R^5$ and optionally substituted with one or more $R^d$. In some embodiments,

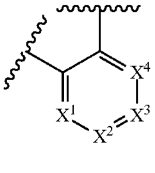 is 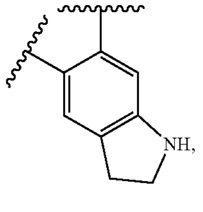

-continued

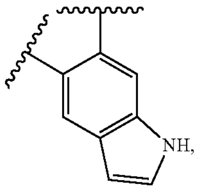 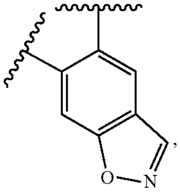 , or

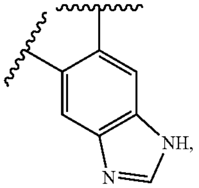

each of which is substituted with —Z—$R^5$ and optionally substituted with one or more $R^d$. In some embodiments,

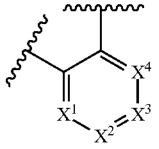 is 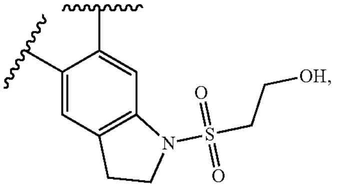

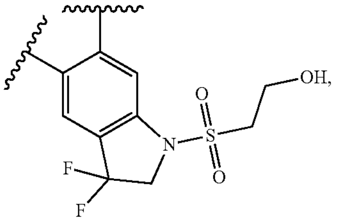

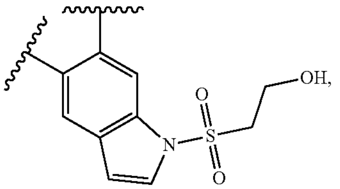

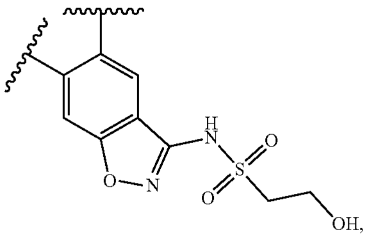 or

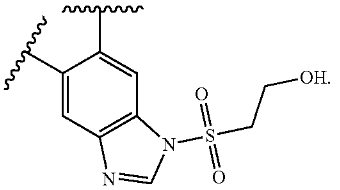

In some embodiments,

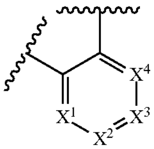
is
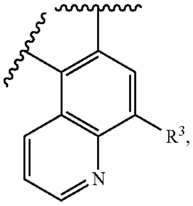
,
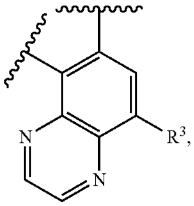
,
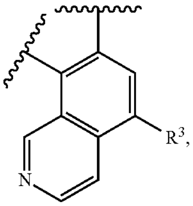
,
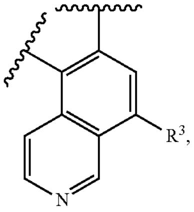
, or
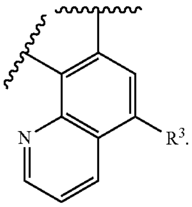
.

In some embodiments,

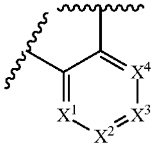
is
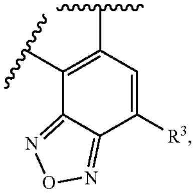
,
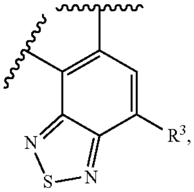
,
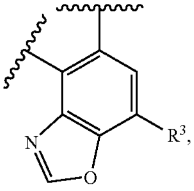
,
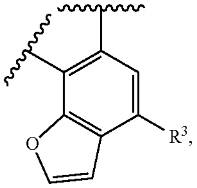
,
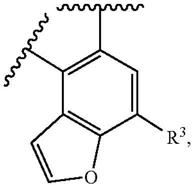
, or
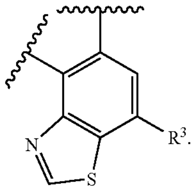
.

In some embodiments,

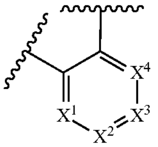
is
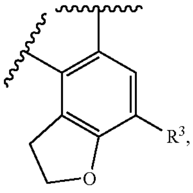
,
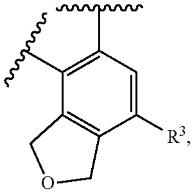
,
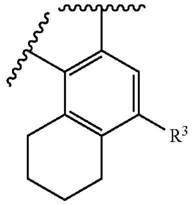
or
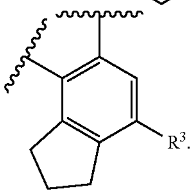
.

In some embodiments,

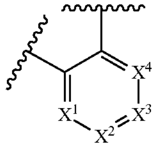
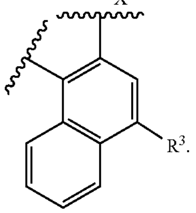
.

In some embodiments of a compound of Formula (I), or a pharmaceutically acceptable salt thereof, $R^2$ and $R^1$ are taken together to form a cycloalkyl, heterocycloalkyl, aryl, or heteroaryl, each of which is optionally substituted with one or more $R^d$. In some embodiments, $R^2$ and $R^1$ are taken together to form a cycloalkyl, which is optionally substituted with one or more $R^d$. In some embodiments, $R^2$ and $R^1$ are taken together to form a heterocycloalkyl, which is optionally substituted with one or more $R^d$. In some embodiments, $R^2$ and $R^1$ are taken together to form a 5 membered heterocycloalkyl, which is optionally substituted with one or more $R^d$. In some embodiments, $R^2$ and $R^1$ are taken together to form a 5 membered heterocycloalkyl comprising one oxygen, which is optionally substituted with one or more $R^d$. In some embodiments, $R^2$ and $R^1$ are taken together to form an aryl, which is optionally substituted with one or more $R^d$. In some embodiments, $R^2$ and $R^1$ are taken together to form a heteroaryl, which is optionally substituted with one or more $R^d$.

In some embodiments of a compound of Formula (Ia-1), or (Ib), or a pharmaceutically acceptable salt thereof, $Y^1$ is N, CH, or $CR^b$. In some embodiments, $Y^1$ is N. In some embodiments, $Y^1$ is CH. In some embodiments, $Y^1$ is $CR^b$.

In some embodiments of a compound of Formula (Ia-1), (Ib), (Ic), (Id), or (Ie), or a pharmaceutically acceptable salt thereof, $Y^2$ is N, CH, or $CR^b$. In some embodiments, $Y^2$ is N. In some embodiments, $Y^2$ is CH. In some embodiments, $Y^2$ is $CR^b$.

In some embodiments of a compound of Formula (Ic), or a pharmaceutically acceptable salt thereof, $Y^3$ is N, CH, or $CR^b$. In some embodiments, $Y^3$ is N. In some embodiments, $Y^3$ is CH. In some embodiments, $Y^3$ is $CR^b$.

In some embodiments of a compound of Formula (Ia-1), or a pharmaceutically acceptable salt thereof, $Y^4$ is N or $CR^{b1}$. In some embodiments, $Y^4$ is N. In some embodiments, $Y^4$ is $CR^{b1}$. In some embodiments of a compound of Formula (Ia-1), or a pharmaceutically acceptable salt thereof, $Y^5$ is N or $CR^{b2}$. In some embodiments, $Y^5$ is N. In some embodiments, $Y^5$ is $CR^{b2}$.

In some embodiments of a compound of Formula (Id), or a pharmaceutically acceptable salt thereof, $Y^4$ is N, CH, or $CR^b$. In some embodiments, $Y^4$ is N. In some embodiments, $Y^4$ is CH. In some embodiments, $Y^4$ is $CR^b$.

In some embodiments of a compound of Formula (Ie), or a pharmaceutically acceptable salt thereof, $Y^5$ is N, CH, or $CR^b$. In some embodiments, $Y^5$ is N. In some embodiments, $Y^5$ is CH. In some embodiments, $Y^5$ is $CR^b$.

In some embodiments of a compound of Formula (III) or (IIIa), or a pharmaceutically acceptable salt thereof, ring C is phenyl, 5- to 6-membered heteroaryl, $C_5$-$C_6$cycloalkyl, 5- to 7-membered heterocycloalkyl, each of which is optionally substituted with one or more R. In some embodiments of a compound of Formula (III) or (IIIa), or a pharmaceutically acceptable salt thereof, ring C is phenyl, 5- to 6-membered heteroaryl, $C_5$-$C_6$cycloalkyl, 5- to 6-membered heterocycloalkyl, each of which is optionally substituted. In some embodiments, ring C is optionally substituted phenyl. In some embodiments, ring C is optionally substituted $C_5$-$C_6$cycloalkyl or 5- to 6-membered heterocycloalkyl. In some embodiments, ring C is optionally substituted 5- to 6-membered heterocycloalkyl. In some embodiments, ring C is optionally substituted heteroaryl. In some embodiments, ring C is optionally substituted 5- to 7-membered heterocycloalkyl. In some embodiments, ring C is optionally substituted 5-membered heterocycloalkyl. In some embodiments, ring C is optionally substituted 6-membered heterocycloalkyl. In some embodiments, ring C is optionally substituted 7-membered heterocycloalkyl. In some embodiments, ring C is 6-membered heterocycloalkyl, which is optionally substituted with one or more R. In some embodiments, ring C is 7-membered heterocycloalkyl, which is optionally substituted with one or more R.

In some embodiments of a compound of Formula (III) or (IIIa), or a pharmaceutically acceptable salt thereof, ring C is a 6 membered heteroaryl, which is optionally substituted with one or more $R^f$. In some embodiments,

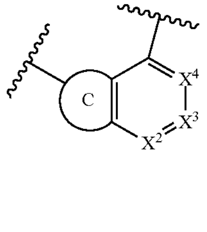

or

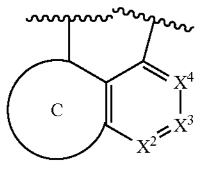

is

-continued

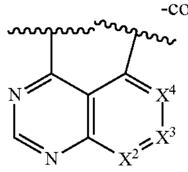

or

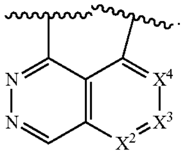

In some embodiments of a compound of Formula (III) or (IIIa), or a pharmaceutically acceptable salt thereof, ring C is a 5 membered heteroaryl, which is optionally substituted with one or more $R^f$. In some embodiments,

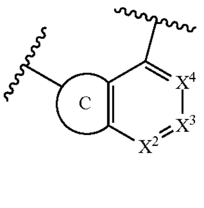

or

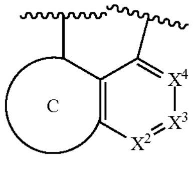

is

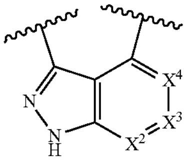

or

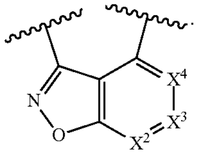

In some embodiments of a compound of Formula (III),

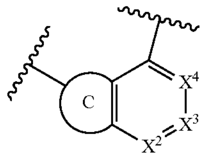

is

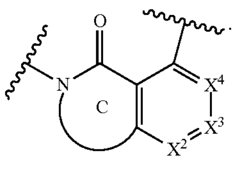

In some embodiments,

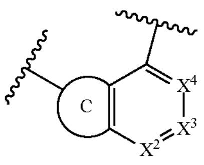

is

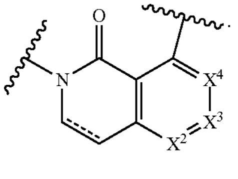

wherein wherein ---- represents a double bond or a single bond. In some embodiments, ---- represents a double bond.

In some embodiments, ---- represents a single bond. In some embodiments of a compound of Formula (III),

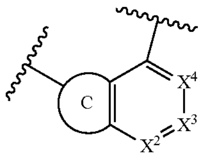
is
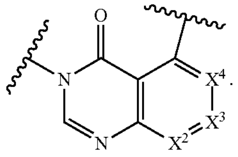

In some embodiments,

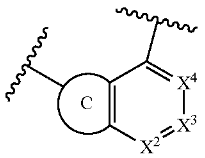
is
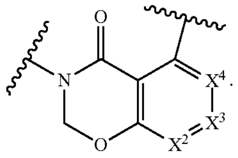

In some embodiments,

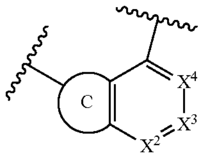
is
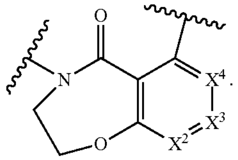

In some embodiments of a compound of Formula (IV), (IVa), (III), (IIIa), (I), (Ia), (Ia-1), (Ib), (Id), (Ie), or (Ic), or a pharmaceutically acceptable salt thereof, $L^1$ comprises the structure of Formula (II):

Formula (II)

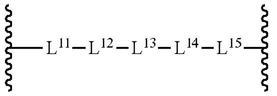

wherein, each of $L^{11}$, $L^{12}$, $L^{13}$, $L^{14}$, and $L^{15}$ is independently selected from substituted or unsubstituted $C_1$-$C_{20}$alkylene, substituted or unsubstituted $C_1$-$C_{19}$heteroalkylene, substituted or unsubstituted $C_2$-$C_{20}$heteroalkenylene, substituted or unsubstituted $C_2$-$C_{20}$heteroalkynylene, substituted or unsubstituted $C_2$-$C_{20}$alkenylene, substituted or unsubstituted $C_2$-$C_{20}$alkynylene, substituted or unsubstituted cycloalkylene, substituted or unsubstituted heterocycloalkylene, substituted or unsubstituted arylene, substituted or unsubstituted heteroarylene, —$(CH_2CH_2O)_p$—, —$(OCH_2CH_2)_p$—, —O—, —S—, —S(=O)—, —S(=O)$_2$—, —S(=O)(=NR$^{LK}$)—, —C(=O)—, —C(=O)O—, —OC(=O)—, —C(=O)C(=O)—, —C(=O)NR$^{LK}$—, —NR$^{LK}$C(=O)—, —OC(=O)NR$^{LK}$—, —NR$^{LK}$C(=O)O—, —NR$^{LK}$C(=O)NR$^{LK}$, —C(=O)NR C(=O)—, —S(=O)$_2$NR$^{LK}$—, —NR$^{LK}$S(=O)$_2$—, —NR$^{LK}$—, —N(OR$^{LK}$)—, and a bond;

each $R^{LK}$ is independently hydrogen or substituted or unsubstituted $C_1$-$C_6$ alkyl; and p is an integer selected from 1 to 6.

In some embodiments, each of $L^{11}$, $L^{12}$, $L^{13}$, $L^{14}$, and $L^{15}$ is independently selected from substituted or unsubstituted $C_1$-$C_{20}$alkylene, substituted or unsubstituted $C_1$-$C_{19}$heteroalkylene, substituted or unsubstituted $C_2$-$C_{20}$alkenylene, substituted or unsubstituted $C_2$-$C_{20}$alkynylene, substituted or unsubstituted cycloalkylene, substituted or unsubstituted heterocycloalkylene, substituted or unsubstituted arylene, substituted or unsubstituted heteroarylene, —$(CH_2CH_2O)_p$—, —$(OCH_2CH_2)_p$—, —O—, —S—, —S(=O)—, —S(=O)$_2$—, —S(=O)(=NR$^{LK}$)—, —C(=O)—, —C(=O)O—, —OC(=O)—, —C(=O)C(=O)—, —C(=O)NR$^{K}$, —NR$^{LK}$C(=O)—, —OC(=O)NR$^{LK}$—, —NR$^{LK}$C(=O)O—, —NR$^{LK}$C(=O)NR$^{LK}$—, —C(=O)NR$^{LK}$C(=O)—, —S(=O)$_2$NR$^{LK}$—, —NR$^{LK}$S(=O)$_2$—, —NR$^{LK}$—, —N(OR$^{LK}$)—, and a bond.

In some embodiments of a compound of Formula (IV), (IVa), (III), (IIIa), (I), (Ia), (Ia-1), (Ib), (Id), (Ie), or (Ic), or a pharmaceutically acceptable salt thereof, $L^1$ comprises the structure of Formula (II):

Formula (II)

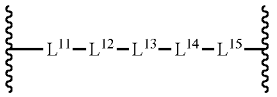

wherein, each of $L^{11}$, $L^{12}$, $L^{13}$, $L^{14}$, and $L^{15}$ is independently selected from substituted or unsubstituted $C_1$-$C_{20}$alkylene, substituted or unsubstituted $C_1$-$C_{19}$heteroalkylene, substituted or unsubstituted $C_2$-$C_{20}$alkenylene, substituted or unsubstituted $C_2$-$C_{20}$alkynylene, substituted or unsubstituted cycloalkylene, substituted or unsubstituted heterocycloalkylene, substituted or unsubstituted arylene, substituted or unsubstituted heteroarylene, —$(CH_2CH_2O)_p$—, —$(OCH_2CH_2)_p$—, —O—, —S—, —S(=O)—, —S(=O)$_2$—, —S(=O)(=NR$^{LK}$)—, —C(=O)—, —C(=O)O—, —OC(=O)—, —C(=O)C(=O)—, —C(=O)NR$^{LK}$, —NR$^{LK}$C(=O)—, —OC(=O)NR$^{LK}$—, —NR$^{LK}$C(=O)O—, —NR$^{LK}$C(=O)NR$^{LK}$—, —C(=O)NR$^{LK}$C(=O)—, —S(=O)$_2$NR$^{LK}$—, —NR$^{LK}$S(=O)$_2$—, —NR$^{LK}$—, —N(OR$^{LK}$)—, and a bond, wherein if the alkylene, heteroalkylene, alkenylene, cycloalkylene, heterocycloalkylene, arylene, and heteroarylene are substituted, then they are substituted with one or more $R^c$;

each $R^c$ is independently selected from hydrogen, halogen, —CN, —$NO_2$, —OR, —SR, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_8$cycloalkyl, $C_2$-$C_9$heterocycloalkyl, aryl, and heteroaryl;

each $R^{LK}$ is independently hydrogen or substituted or unsubstituted $C_1$-$C_6$ alkyl; and p is an integer selected from 1 to 6.

In some embodiments, $R^{LK}$ is substituted with one or more $R^c$.

In some embodiments, the linker $L^1$ comprises the structure of Formula (II):

Formula (II)

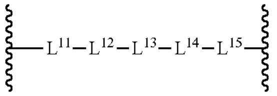

wherein, each of $L^{11}$, $L^{12}$, $L^{13}$, $L^{14}$, and $L^{15}$ is independently selected from substituted or unsubstituted $C_1$-$C_{20}$alkylene, substituted or unsubstituted $C_1$-$C_{19}$heteroalkylene, substituted or unsubstituted $C_2$-$C_{20}$alkenylene, substituted or unsubstituted $C_2$-$C_{20}$alkynylene, substituted or unsubstituted cycloalkylene, substituted or unsubstituted heterocycloalkylene, substituted or unsubstituted arylene, substituted or unsubstituted heteroarylene, $-(CH_2CH_2O)_p-$, $-(OCH_2CH_2)_p-$, —O—, —S—, —S(═O)—, $-S(=O)_2-$, $-S(=O)(=NR^{LK})-$, —C(O)—, —C(═O)O—, —OC(═O)—, —C(═O)C(═O)—, $-C(=O)NR^{LK}-$, $-NR^{LK}C(=O)-$, $-OC(=O)NR^{LK}-$, $-NR^{LK}C(=O)O-$, $-NR^{LK}C(=O)NR^{LK}-$, $-C(=O)NR^{LK}C(=O)-$, $-S(=O)_2NR^{LK}-$, $-NR^{LK}S(=O)_2-$, $-NR^{LK}-$, $-N(OR^{LK})-$, and a bond;

each $R^{LK}$ is independently hydrogen, —CN, $-C(=O)R^7$, $-C(=O)OR^7$, $-C(=O)NR^8R^8$ $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl, wherein each of the alkyl, heteroalkyl, alkenyl, alkynyl, cycloalkyl, heterocycloalkyl, aryl, or heteroaryl is optionally substituted;

p is an integer selected from 1 to 6.

In some embodiments, $L^{11}$ is attaching to Ring B. In some embodiments, $L^{11}$ is attaching to Ring A. In some embodiments, at least one of $L^{11}$, $L^{12}$, $L^{13}$, $L^{14}$, and $L^{15}$ is not a bond. In some embodiments, one of $L^{11}$, $L^{12}$, $L^{13}$, $L^{14}$, and $L^{15}$ is a bond. In some embodiments, two of $L^{11}$, $L^{12}$, $L^{13}$, $L^{14}$, and $L^{15}$ are bonds. In some embodiments, three of $L^{11}$, $L^{12}$, $L^{13}$, $L^{14}$, and $L^{15}$ are bonds. In some embodiments, four of $L^{11}$, $L^{12}$, $L^{13}$, $L^{14}$, and $L^{15}$ are bonds. In some embodiments, the linker $L^1$ has a structure of $-L^{11}-L^{12}-$, $-L^{11}-L^{12}-L^{13}-$, $-L^{11}-L^{12}-L^{13}-L^{14}-$, $-L^{11}-L^{12}-L^{13}-L^{14}-L^{15}-$, $-L^{13}-L^{14}-L^{15}-$, or $-L^{11}-L^{15}-$. In some embodiments, the linker $L^1$ has a structure of $-L^{11}-L^{12}-$.

In some embodiments, $L^{11}$ is selected from a bond, —O—, $-NR^{LK}-$, $-C(=O)NR^{LK}-$, $C_1$-$C_{20}$alkylene, $C_2$-$C_{19}$heteroalkylene, and heterocycloalkylene. In some embodiments, $L^{11}$ is —NH—. In some embodiments, $L^{11}$ is substituted or unsubstituted heterocycloalkylene. In some embodiments, the heterocycloalkylene is a 4-6 membered ring. In some embodiments, the heterocycloalkylene is a 6 membered ring.

In some embodiments, $L^{12}$ is selected from a bond, —O—, $C_1$-$C_{20}$alkylene, $C_1$-$C_{19}$heteroalkylene, $C_1$-$C_6$alkylene(cycloalkyl), and cycloalkylene. In some embodiments, $L^{12}$ is $C_3$-$C_6$ cycloalkylene. In some embodiments, $L^{12}$ is substituted or unsubstituted $C_1$-$C_{20}$alkylene. In some embodiments, $L^{12}$ is substituted or unsubstituted $C_1$-$C_6$alkylene. In some embodiments, $L^{12}$ is substituted or unsubstituted $C_1$-$C_{19}$heteroalkylene. In some embodiments, $L^{12}$ is substituted or unsubstituted $C_1$-$C_6$heteroalkylene. In some embodiments, $L^{12}$ is substituted or unsubstituted $C_1$-$C_3$heteroalkylene.

In some embodiments, $L^{13}$ is selected from a bond, —O—, $C_1$-$C_{20}$alkylene, $C_1$-$C_{19}$heteroalkylene, $C_1$-$C_6$alkylene(cycloalkyl), and cycloalkylene. In some embodiments, $L^{13}$ is $C_1$-$C_6$alkylene or $C_1$-$C_6$heteroalkylene. In some embodiments, $L^{13}$ is $C_1$-$C_3$alkylene or $C_1$-$C_3$heteroalkylene.

In some embodiments, $L^{14}$ is selected from a bond, —O—, $C_1$-$C_{20}$alkylene, and $C_1$-$C_{19}$heteroalkylene. In some embodiments, $L^{14}$ is a bond.

In some embodiments, $L^{15}$ is selected from a bond, O—, and $C_1$-$C_{20}$alkylene. In some embodiments, $L^{15}$ is a bond.

In some embodiments, each of $L^{11}$, $L^{12}$, $L^{13}$, $L^{14}$, and $L^{15}$ is independently selected from a bond, —O—, $-CH_2-$, $-CH_2CH_2-$, —CH═CH—, $-CH_2CH_2CH_2-$, —NH—, —C(═O)—,

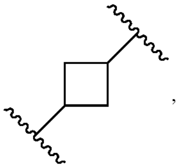, 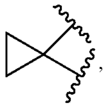, 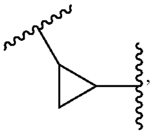, 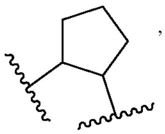, 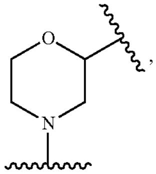, 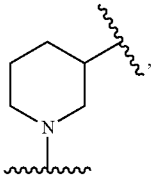, and 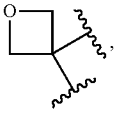, wherein each of the $-CH_2-$, $-CH_2CH_2-$, $-CH_2CH_2CH_2-$, —NH—,

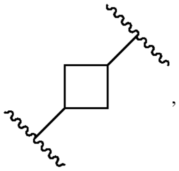, 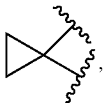, 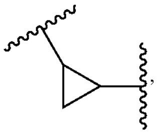, 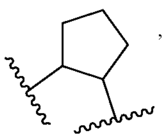, 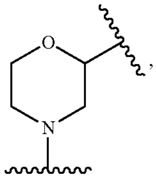, 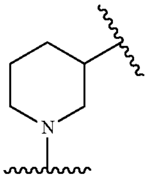 or 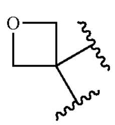

is optionally substituted with one or two or three $CH_3$ (eg., $CD_3$), halogen, $-CH_2CF_3$, $-OCH_3$, $-CF_3$, —OH or

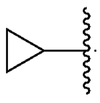.

In some embodiments, each $R^{LK}$ is independently $C_1$-$C_6$ alkyl optionally substituted with one or more R, wherein each R is independently halogen, oxo, —CN, —OH, $-OCH_3$, $-S(=O)CH_3$, $-S(=O)_2CH_3$, $-S(=O)_2NH_2$, —$S(=O)_2NHCH_3$, —$S(=O)_2N(CH_3)_2$, —$NH_2$, —$NHCH_3$, —$N(CH_3)_2$, —$C(=O)CH_3$, —$C(=O)OH$, —$C(=O)OCH_3$, $C_1$-$C_6$alkyl, $C_1$-$C_6$haloalkyl, $C_1$-$C_6$hydroxyalkyl, $C_1$-$C_6$aminoalkyl, and $C_1$-$C_6$heteroalkyl; or two R are taken together to form an oxo.

In some embodiments of a compound of Formula (IV), (IVa), (III), (IIIa), (I), (Ia), (Ia-1), (Ib), (Id), (Ie), or (Ic), or a pharmaceutically acceptable salt thereof, $L^1$ is -heterocycloalkyl-$C_1$-$C_6$alkylene-, -heterocycloalkyl-$C_1$-$C_6$heteroalkylene-, -cycloalkyl-$C_1$-$C_6$alkylene-, -cycloalkyl-$C_1$-$C_6$heteroalkylene, —$C_1$-$C_6$alkylene-heterocycloalkyl-, —$C_1$-$C_6$heteroalkylene-heterocycloalkyl-, —$C_1$-$C_6$alkylene-cycloalkyl-, —$C_1$-$C_6$heteroalkylene-cycloalkyl-, —$C_1$-$C_6$heteroalkylene-cycloalkyl-$C_1$-$C_6$heteroalkylene, —$C_1$-$C_6$alkylene-cycloalkyl-$C_1$-$C_6$alkylene, $C_1$-$C_6$heteroalkylene-cycloalkyl-$C_1$-$C_6$alkylene, $C_1$-$C_6$alkylene-cycloalkyl-$C_1$-$C_6$heteroalkylene, —$C_1$-$C_6$heteroalkylene-heterocycloalkyl —$C_1$-$C_6$heteroalkylene, —$C_1$-$C_6$heteroalkylene-heterocycloalkyl —$C_1$-$C_6$alkylene, —$C_1$-$C_6$alkylene-heterocycloalkyl —$C_1$-$C_6$heteroalkylene, or —$C_1$-$C_6$alkylene-heterocycloalkyl —$C_1$-$C_6$alkylene, wherein each of the cycloalkyl, heterocycloalkyl, alkylene and heteroalkylene is optionally substituted with one or more $R^c$.

In some embodiments of a compound of Formula (IV), (IVa), (III), (IIIa), (I), (Ia), (Ia-1), (Ib), (Id), (Ie), or (Ic), or a pharmaceutically acceptable salt thereof, $L^1$ is -heterocycloalkyl-$C_1$-$C_6$heteroalkylene-, wherein each of the heterocycloalkyl and heteroalkylene is optionally substituted with one or more $R^c$. In some embodiments, the heterocycloalkyl is a 4-6 membered heterocycloalkyl. In some embodiments, the heterocycloalkyl is a 6 membered heterocycloalkyl. In some embodiments, the $C_1$-$C_6$heteroalkylene contains 1-2 oxygen. In some embodiments, the $C_1$-$C_6$heteroalkylene is $C_1$-$C_4$heteroalkylene. In some embodiments, $L^1$ is

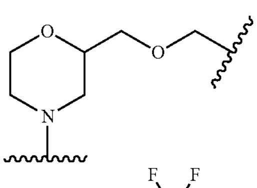
,
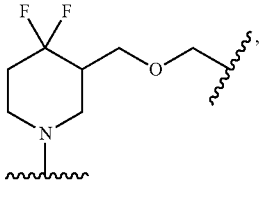
,
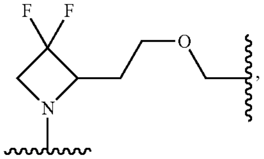
, or
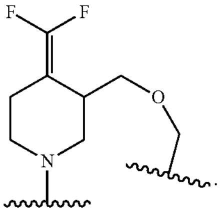
.

In some embodiments of a compound of Formula (IV), (IVa), (III), (IIIa), (I), (Ia), (Ia-1), (Ib), (Id), (Ie), or (Ic), or a pharmaceutically acceptable salt thereof, $L^1$ is a linker moiety comprising cyclic moieties, wherein each cyclic moiety is optionally substituted with one or more $R^c$.

In some embodiments of a compound of Formula (IV), (IVa), (III), (IIIa), (I), (Ia), (Ia-1), (Ib), (Id), (Ie), or (Ic), or a pharmaceutically acceptable salt thereof, $L^1$ is a linker moiety comprising noncyclic moieties, wherein each noncyclic moiety is optionally substituted with one or more $R^c$.

In some embodiments of a compound of Formula (IV), (IVa), (III), (IIIa), (I), (Ia), (Ia-1), (Ib), (Id), (Ie), or (Ic), or a pharmaceutically acceptable salt thereof, $L^1$ is a linker moiety comprising aromatic moieties, wherein each aromatic moiety is optionally substituted with one or more $R^c$.

In some embodiments of a compound of Formula (IV), (IVa), (III), (IIIa), (I), (Ia), (Ia-1), (Ib), (Id), (Ie), or (Ic), or a pharmaceutically acceptable salt thereof, $L^1$ is a linker moiety comprising non-aromatic moieties, wherein each non-aromatic moiety is optionally substituted with one or more $R^c$.

In some embodiments of a compound of Formula (IV), (IVa), (III), (IIIa), (I), (Ia), (Ia-1), (Ib), (Id), (Ie), or (Ic), or a pharmaceutically acceptable salt thereof, $L^1$ is a linker moiety consisting of a linear sequence ranging from 1 to 20 non-hydrogen atoms.

In some embodiments of a compound of Formula (IV), (IVa), (III), (IIIa), (I), (Ia), (Ia-1), (Ib), (Id), (Ie), or (Ic), or a pharmaceutically acceptable salt thereof, $L^1$ is a linker moiety consisting of a linear sequence ranging from 1 to 8 non-hydrogen atoms.

In some embodiments of a compound of Formula (IV), (IVa), (III), (IIIa), (I), (Ia), (Ia-1), (Ib), (Id), (Ie), or (Ic), or a pharmaceutically acceptable salt thereof, $L^1$ is $C_1$-$C_6$alkylene or $C_1$-$C_6$heteroalkylene, each of which is optionally substituted with one or more $R^c$. In some embodiments, $L^1$ is $C_1$-$C_8$alkylene or $C_1$-$C_8$heteroalkylene, each of which is optionally substituted with one or more $R^c$.

In some embodiments of a compound of Formula (IV), (IVa), (III), (IIIa), (I), (Ia), (Ia-1), (Ib), (Id), (Ie), or (Ic), or a pharmaceutically acceptable salt thereof, $L^1$ is $C_1$-$C_6$alkylene, which is optionally substituted with one or more $R^c$. In some embodiments, $L^1$ is —$(CH_2)_3$—, —$(CH_2)_4$—, —$(CH_2)_5$—, or —$(CH_2)_6$—. In some embodiments, $L^1$ is —$(CH_2)_3$—. In some embodiments, $L^1$ is —$(CH_2)_4$—. In some embodiments, $L^1$ is —$(CH_2)_5$—. In some embodiments, $L^1$ is —$(CH_2)_6$—.

In some embodiments of a compound of Formula (IV), (IVa), (III), (IIIa), (I), (Ia), (Ia-1), (Ib), (Id), (Ie), or (Ic), or a pharmaceutically acceptable salt thereof, $L^1$ is $C_1$-$C_6$heteroalkylene, which is optionally substituted with one or more $R^c$. In some embodiments, the $C_1$-$C_6$heteroalkylene comprises 1, 2, or 3 heteroatoms selected from N, O, and S, which is optionally substituted with one or more $R^c$. In some embodiments, the $C_1$-$C_6$heteroalkylene comprises 1 or 2 heteroatoms selected from N and O, which is optionally substituted with one or more $R^c$. In some embodiments, the $C_1$-$C_6$heteroalkylene comprises 1 N. In some embodiments, the $C_1$-$C_6$heteroalkylene comprises 2 N atoms. In some embodiments, the $C_1$-$C_6$heteroalkylene comprises 1 O atom. In some embodiments, the $C_1$-$C_6$heteroalkylene comprises 2 O atoms. In some embodiments, the $C_1$-$C_6$heteroalkylene comprises 1 N and 1 O. In some embodiments, the $C_1$-$C_6$heteroalkylene comprises 1 N and 2 O atoms.

In some embodiments of Formula (IV), (IVa), (III), (IIIa), (I), (Ia), (Ia-1), (Ib), (Id), (Ie), (Ic), or (II), each $R^c$ is independently selected from halogen, oxo, —CN, —$NO_2$, —OH, —$OR^7$, —$OC(=O)R^7$, —$OC(=O)OR^7$, —$OC(=O)NR^8R^8$, —SH, —$SR^7$, —$S(=O)R^7$, —$S(=O)_2R^7$, —$S(=O)_2NR^8R^8$, —$S(=O)(=NR^8)R^7$, —$NR^8R^8$, —$NR^8C(=O)NR^8R^8$, —$NR^8C(=O)R^7$, —$NR^8C(=O)OR^7$, —$NR^8S(=O)_2R^7$, —$N{=}S(=O)(R^7)_2$, —$C(=O)R^7$, —$C(=O)OR^8$, —$C(=O)NR^8R^8$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, and heterocycloalkyl, wherein the alkyl, haloalkyl, hydroxyalkyl, aminoalkyl, heteroalkyl, alkenyl, alkynyl, cycloalkyl, or heterocycloalkyl is optionally substituted with one or more R; or two $R^c$ are taken together with the atom they are attached to form a cycloalkyl or heterocycloalkyl, each of which is optionally substituted with one or more R. In some embodiments, two $R^c$ are taken together to form

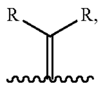 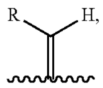 or 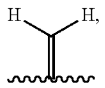

wherein R is defined herein. In some embodiments, two $R^c$ are taken together to form

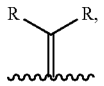

wherein each R is independently halogen, —$C_1$-$C_3$alkyl, —$C_1$-$C_3$haloalkyl, or $C_3$-$C_6$cycloalkyl. In some embodiments, two $R^c$ are taken together to form

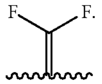

In some embodiments of Formula (IV), (IVa), (III), (IIIa), (I), (Ia), (Ia-1), (Ib), (Id), (Ie), (Ic), or (II), each $R^c$ is independently selected from hydrogen, halogen, —CN, —$NO_2$, —$OR^b$, —$SR^b$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_8$cycloalkyl, $C_2$-$C_9$heterocycloalkyl, aryl, and heteroaryl. In some embodiments, each $R^c$ is independently selected from hydrogen, halogen, —CN, —$NO_2$, $C_1$-$C_6$alkyl, $C_1$-$C_6$alkoxyl, $C_1$-$C_6$haloalkyl, $C_1$-$C_6$hydroxyalkyl, $C_1$-$C_6$aminoalkyl, and $C_1$-$C_6$heteroalkyl.

In some embodiments of Formula (IV), (IVa), (III), (IIIa), (I), (Ia), (Ia-1), (Ib), (Id), (Ie), (Ic), or (II), each $R^c$ is independently selected from halogen, oxo, —OH, —$OR^7$, $C_1$-$C_6$haloalkyl, $C_1$-$C_6$alkyl, and cycloalkyl, wherein the alkyl or cycloalkyl is optionally substituted with one or more R.

In some embodiments of Formula (IV), (IVa), (III), (IIIa), (I), (Ia), (Ia-1), (Ib), (Id), (Ie), (Ic), or (II), $R^c$ is halogen. In some embodiments, $R^c$ is F.

In some embodiments of Formula (IV), (IVa), (III), (IIIa), (I), (Ia), (Ia-1), (Ib), (Id), (Ie), (Ic), or (II), $R^c$ is oxo.

In some embodiments of Formula (IV), (IVa), (III), (IIIa), (I), (Ia), (Ia-1), (Ib), (Id), (Ie), (Ic), or (II), $R^c$ is —OH.

In some embodiments of Formula (IV), (IVa), (III), (IIIa), (I), (Ia), (Ia-1), (Ib), (Id), (Ie), (Ic), or (II), $R^c$ is —$OR^7$. In some embodiments, $R^c$ is —$OCH_3$.

In some embodiments of Formula (IV), (IVa), (III), (IIIa), (I), (Ia), (Ia-1), (Ib), (Id), (Ie), (Ic), or (II), $R^c$ is $C_1$-$C_6$haloalkyl. In some embodiments, $R^c$ is —$CF_3$. In some embodiments, $R^c$ is —$CH_2CF_3$, In some embodiments of Formula (IV), (IVa), (III), (IIIa), (I), (Ia), (Ia-1), (Ib), (Id), (Ie), (Ic), or (II), $R^c$ is $C_1$-$C_6$alkyl, wherein the alkyl is optionally substituted with one or more R. In some embodiments, $R^c$ is —$CH_3$. In some embodiments, $R^c$ is —$CD_3$.

In some embodiments of Formula (IV), (IVa), (III), (IIIa), (I), (Ia), (Ia-1), (Ib), (Id), (Ie), (Ic), or (II), at least one $R^c$ is cycloalkyl, wherein the cycloalkyl is optionally substituted with one or more R. In some embodiments, $R^c$ is $C_3$-$C_6$cycloalkyl, wherein the cycloalkyl is optionally substituted with one or more R. In some embodiments, $R^c$ is

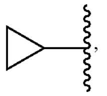, which is optionally substituted with one or more R.

In some embodiments of Formula (IV), (IVa), (III), (IIIa), (I), (Ia), (Ia-1), (Ib), (Id), (Ie), (Ic), or (II), $L^1$ is selected from the group consisting of: —$OCH_2CH_2OCH_2$—, —$OCH_2CH_2CH_2OCH_2$—, —$OCH_2CH_2CH_2CH_2CH_2$—, —$OCH(CH_3)CH_2CH_2OCH_2$—, —$OCH_2CH(CH_3)CH_2OCH_2$—, —$OCH_2CH(CH_3)OCH_2CH_2$—, —$OCH(CH_3)CH_2OCH_2CH_2$—, —$CH_2CH_2OCH_2$—, —$CH_2CH_2CH_2CH_2OCH_2$—, —$CH_2OCH(CH_3)CH_2OCH_2$—, —$CH_2OCH_2CH_2$—, —$N(CH_3)CH_2CH_2OCH_2$—, —N(cyclopropyl)$CH_2CH_2CH_2OCH_2$—, —$N(CH_3)CH_2CH_2CH_2OCH_2$—, —$NHCH_2CH_2OCH_2$—, —$NHCH_2CH_2CH_2OCH_2$—, —$NHCH_2CH(CH_3)CH_2OCH_2$—, —$N(CH_3)CH_2CH_2OCH_2CH_2$—, —$NHCH_2CH_2OCH_2CH_2$—, —$NH(CH_2)_4$—, —$NH(CH_2)_5$—, —$NHCH_2CH(CH_3)(CH_2)_3$—, —$N(CH_3)(CH_2)_4$—, —$N(CH_3)(CH_2)_5$—, —$NHCH_2CH_2CH_2CH_2O$—, —$NHCH_2C(=O)N(CH_3)CH_2CH_2$—, —$NHCH_2CH_2CH_2NHCH_2$—, —$NHCH(CH_3)CH_2OCH_2CH_2$—, —$NHCH_2CH(CH_3)OCH_2CH_2$—, —$N(CH_3)CH_2CH(CH_3)OCH_2CH_2$—, —$NHCH_2CF_2CH_2OCH_2$—, —$N(CH_3)CH_2CF_2CH_2OCH_2$—, —$NHCH_2CH(CH_3)CH_2OCH_2$—, —$N(CH_3)CH_2CH(CH_3)CH_2OCH_2$—, —$NHCH(CH_3)CH_2CH_2OCH_2$—, —$NHCH_2CH_2CH(CH_3)OCH_2$—, —$NHCH_2CH(CH_3)CH_2OCH_2$—, —$NHCH_2CHFCH_2OCH_2$—, —$NHCH_2CH(OCH_3)CH_2OCH_2$—, —$NHCH_2CH(CF_3)CH_2OCH_2$—, —$NHCH_2CF_2CH_2OCH_2$—, —$NHCH_2CH(OH)CH_2OCH_2$—, —$N(CH_3)CH_2CH(CH_3)CH_2OCH_2$—, —$N(CH_3)CH_2CHFCH_2OCH_2$—, —$N(CH_3)CH_2CH(OCH_3)CH_2OCH_2$—, —$N(CH_3)CH_2CH(CF_3)CH_2OCH_2$—, —$N(CH_3)CH_2CF_2CH_2OCH_2$—, —$N(CH_3)CH_2CH(OH)CH_2OCH_2$—, —$C(=O)N(CH_3)CH_2CH_2OCH_2$—, —$C(=O)N(CH_3)CH_2CH_2CH_2OCH_2$—, and —$C(=O)N(CH_3)CH_2CH_2CH_2CH_2$—. In some embodiments, $L^1$ is —$N(CH_3)(CH_2)_5$— or —$N(CH_3)(CH_2)_6$—. In some embodiments, —$N(CH_3)(CH_2)_5$— is —$N(CD_3)(CH_2)_5$—. In some embodiments, —$N(CH_3)(CH_2)_6$— is —$N(CD_3)(CH_2)_6$—

In some embodiments of a compound of Formula (IV), (IVa), (III), (IIIa), (I), (Ia), (Ia-1), (Ib), (Id), (Ie), (Ic), or (II), or a pharmaceutically acceptable salt thereof, $L^1$ is selected from the group consisting of: —$OCH_2CH_2OCH_2$—, —$OCH_2CH_2CH_2OCH_2$—, —$OCH_2CH_2CH_2CH_2CH_2$—, —$OCH(CH_3)CH_2CH_2OCH_2$—, —$OCH_2CH(CH_3)CH_2OCH_2$—, —$OCH_2CH(CH_3)OCH_2CH_2$—, and —$OCH(CH_3)CH_2OCH_2CH_2$—.

In some embodiments of a compound of Formula (IV), (IVa), (III), (IIIa), (I), (Ia), (Ia-1), (Ib), (Id), (Ie), (Ic), or (II), or a pharmaceutically acceptable salt thereof, $L^1$ is selected from the group consisting of: $—CH_2OCH_2—$, $—CH_2CH_2OCH_2—$, $—CH_2CH_2CH_2CH_2OCH_2—$, and $—CH_2OCH_2CH_2—$.

In some embodiments of a compound of Formula (IV), (IVa), (III), (IIIa), (I), (Ia), (Ia-1), (Ib), (Id), (Ie), (Ic), or (II), or a pharmaceutically acceptable salt thereof, $L^1$ is selected from the group consisting of: $—N(CH_3)CH_2CH_2OCH_2—$, $—N(CH_3)CH_2CH_2CH_2OCH_2—$, $—NHCH_2CH_2OCH_2—$, or $—NHCH_2CH_2CH_2OCH_2—$.

In some embodiments of a compound of Formula (IV), (IVa), (III), (IIIa), (I), (Ia), (Ia-1), (Ib), (Id), (Ie), (Ic), or (II), or a pharmaceutically acceptable salt thereof, $L^1$ is selected from the group consisting of: $—N(CH_3)CH_2CH_2OCH_2CH_2—$, $—NHCH_2CH_2OCH_2CH_2—$, $—NH(CH_2)_4—$, $—NH(CH_2)_5—$, $—NHCH_2CH_2CH_2CH_2O—$, and $—NHCH_2CH_2CH_2NHCH_2—$.

In some embodiments of a compound of Formula (IV), (IVa), (III), (IIIa), (I), (Ia), (Ia-1), (Ib), (Id), (Ie), (Ic), or (II), or a pharmaceutically acceptable salt thereof, $L^1$ is selected from the group consisting of: $—NHCH(CH_3)CH_2OCH_2CH_2—$, $—NHCH_2CH(CH_3)OCH_2CH_2—$, and $—N(CH_3)CH_2CH(CH_3)OCH_2CH_2—$.

In some embodiments of a compound of Formula (IV), (IVa), (III), (IIIa), (I), (Ia), (Ia-1), (Ib), (Id), (Ie), (Ic), or (II), or a pharmaceutically acceptable salt thereof, $L^1$ is selected from the group consisting of: $—NHCH_2CF_2CH_2OCH_2—$, $—N(CH_3)CH_2CF_2CH_2OCH_2—$, $—N(CH_3)CH_2CH(CH_3)CH_2OCH_2—$, $—NHCH(CH_3)CH_2CH_2OCH_2—$, and $—NHCH_2CH_2CH(CH_3)OCH_2—$.

In some embodiments of a compound of Formula (IV), (IVa), (III), (IIIa), (I), (Ia), (Ia-1), (Ib), (Id), (Ie), (Ic), or (II), or a pharmaceutically acceptable salt thereof, $L^1$ is selected from the group consisting of: $—NHCH_2CH(CH_3)CH_2OCH_2—$, $—NHCH_2CHFCH_2OCH_2—$, $—NHCH_2CH(OCH_3)CH_2OCH_2—$, $—NHCH_2CH(CF_3)CH_2OCH_2—$, $—NHCH_2CF_2CH_2OCH_2—$, $—NHCH_2CH(OH)CH_2OCH_2—$, $—N(CH_3)CH_2CH(CH_3)CH_2OCH_2—$, $—N(CH_3)CH_2CHFCH_2OCH_2—$, $—N(CH_3)CH_2CH(OCH_3)CH_2OCH_2—$, $—N(CH_3)CH_2CH(CF_3)CH_2OCH_2—$, $—N(CH_3)CH_2CF_2CH_2OCH_2—$, and $—N(CH_3)CH_2CH(OH)CH_2OCH_2—$.

In some embodiments of a compound of Formula (IV), (IVa), (III), (IIIa), (I), (Ia), (Ia-1), (Ib), (Id), (Ie), (Ic), or (II), or a pharmaceutically acceptable salt thereof, $L^1$ is selected from the group consisting of: $—C(=O)N(CH_3)CH_2CH_2OCH_2—$, $—C(=O)N(CH_3)CH_2CH_2CH_2OCH_2—$, and $—C(=O)N(CH_3)CH_2CH_2CH_2CH_2—$.

In some embodiments of Formula (IV), (IVa), (III), (IIIa), (I), (Ia), (Ia-1), (Ib), (Id), (Ie), (Ic), or (II), two $R^c$ are taken together with the atom they are attached to form a cycloalkyl or heterocycloalkyl, each of which is optionally substituted with one or more R.

In some embodiments of Formula (IV), (IVa), (III), (IIIa), (I), (Ia), (Ia-1), (Ib), (Id), (Ie), (Ic), or (II), or a pharmaceutically acceptable salt thereof, two $R^c$ are taken together with the atom they are attached to form a cycloalkyl, which is optionally substituted with one or more R. In some embodiments, two $R^c$ are taken together with the atom they are attached to form a $C_3$-$C_6$ cycloalkyl, each of which is optionally substituted with one or more R. In some embodiments, two $R^c$ are taken together with the atom they are attached to form a

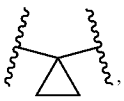

, which is optionally substituted with one or more R. In some embodiments, $L^1$ is

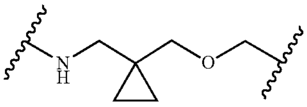

.

In some embodiments of Formula (IV), (IVa), (III), (IIIa), (I), (Ia), (Ia-1), (Ib), (Id), (Ie), (Ic), or (II), or a pharmaceutically acceptable salt thereof, two $R^c$ are taken together with the atom they are attached to form a heterocycloalkyl, which is optionally substituted with one or more R (e.g., $L^1$ is

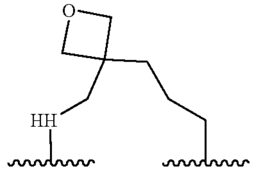

).

In some embodiments of Formula (IV), (IVa), (III), (IIIa), (I), (Ia), (Ia-1), (Ib), (Id), (Ie), (Ic), or (II), two $R^c$ are taken together with the intervening atoms to form a cycloalkyl or heterocycloalkyl, each of which is optionally substituted. In some embodiments, two $R^c$ are taken together with the intervening atoms to form a cycloalkyl or heterocycloalkyl, each of which is optionally substituted with one or more R. In some embodiments, the intervening atoms comprise two or more carbons. In some embodiments, the intervening atoms comprise two carbons. In some embodiments, the intervening atoms comprise three carbons. In some embodiments, the intervening atoms comprise at least one carbon and at least one heteroatom. In some embodiments, the hteroatom is nitrogen. In some embodiments, the intervening atoms comprise one carbon and one nitrogen. In some embodiments, the intervening atoms comprise two carbons and one nitrogen.

In some embodiments of Formula (IV), (IVa), (III), (IIIa), (I), (Ia), (Ia-1), (Ib), (Id), (Ie), (Ic), or (II), $L^1$ is $C_1$-$C_6$heteroalkylene, which is optionally substituted with one or more $R^c$, wherein two $R^c$ are taken together with the intervening atoms to form a ring (e.g., $L^1$ is

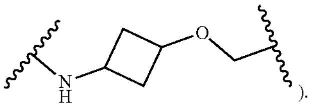 [SMILES: *COC1CC(N*)C1]

).

In some embodiments, $L^1$ is $C_1$-$C_6$heteroalkylene, which is optionally substituted with one or more R, wherein two $R^c$ attached to adjacent atoms are taken together to form a bond (e.g., $L^1$ is

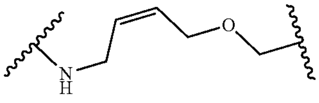

).

In some embodiments of Formula (IV), (IVa), (III), (IIIa), (I), (Ia), (Ia-1), (Ib), (Id), (Ie), (Ic), or (II), two $R^c$ are taken together with the intervening atoms to form a cycloalkyl, which is optionally substituted with one or more R. In some embodiments, two $R^c$ are taken together with the intervening atoms to form a $C_3$-$C_6$ cycloalkyl, which is optionally substituted with one or more R. In some embodiments, two $R^c$ are taken together with the intervening atoms to form

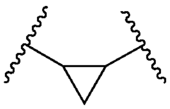 or 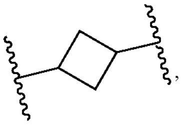, each of which is optionally substituted with one or more R. In some embodiments, two $R^c$ are taken together with the intervening atoms to form

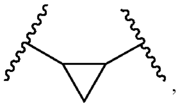 [SMILES: *C1CC1*], which is optionally substituted with one or more R. In some embodiments, two $R^c$ are taken together with the intervening atoms to form

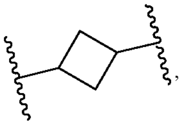 [SMILES: *C1CC(*)C1], which is optionally substituted with one or more R. In some embodiments, $L^1$ is

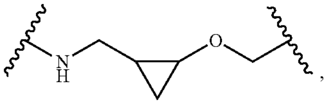, or

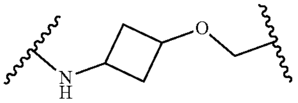.

In some embodiments, $L^1$ is

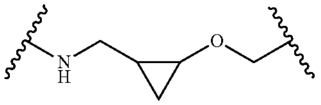.

In some embodiments, $L^1$ is

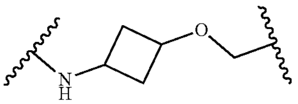.

In some embodiments, $L^1$ is

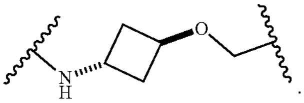.

In some embodiments, $L^1$ is

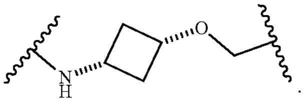.

In some embodiments of Formula (IV), (IVa), (III), (IIIa), (I), (Ia), (Ia-1), (Ib), (Id), (Ie), (Ic), or (II), two $R^c$ are taken together with the intervening atoms to form a heterocycloalkyl, which is optionally substituted with one or more R. In some embodiments, two $R^c$ are taken together with the intervening atoms to form a 4- to 6-membered heterocycloalkyl comprising 1 or 2 heteroatoms selected from N and O, which is optionally substituted with one or more R. In some embodiments, two $R^c$ are taken together with the intervening atoms to form

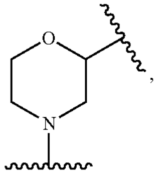 [SMILES: *C1CN(*)CCO1], 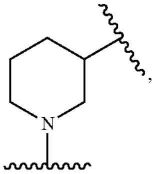 [SMILES: *C1CCCN(*)C1], or 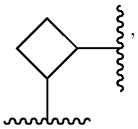, each of which is optionally substituted with one or more R. In some embodiments, two $R^c$ are taken together with the intervening atoms to form

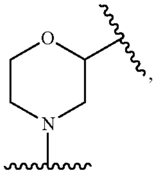, which is optionally substituted with one or more R. In some embodiments, two $R^c$ are taken together with the intervening atoms to form

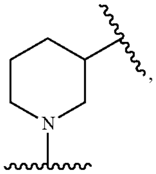, which is optionally substituted with one or more R. In some embodiments, two $R^c$ are taken together with the intervening atoms to form

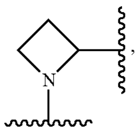

which is optionally substituted with one or more R. In some embodiments, $L^1$ is

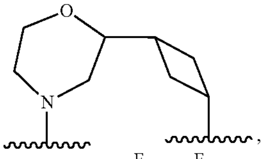

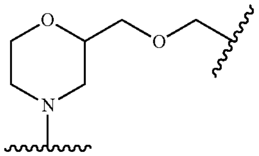

,

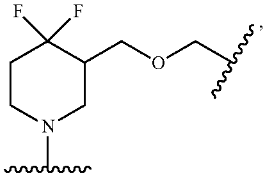

or

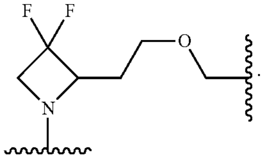

In some embodiments, $L^1$ is

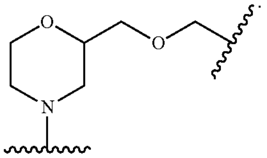 [SMILES: *COCC1CN(*)CCO1]

In some embodiments, $L^1$ is

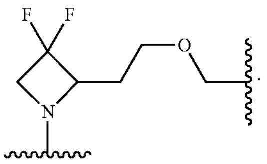 [SMILES: *COCCC1N(*)CC1(F)F]

In some embodiments, $L^1$ is

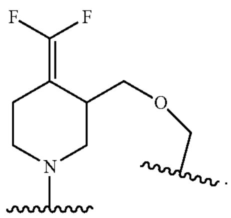 [SMILES: *COCC1CN(*)CCC1=C(F)F]

In some embodiments of Formula (IV), (IVa), (III), (IIIa), (I), (Ia), (Ia-1), (Ib), (Id), (Ie), (Ic), or (II), two $R^c$ attached to adjacent atoms are taken together to form a bond. In some embodiments, $L^1$ is selected from the group consisting of:

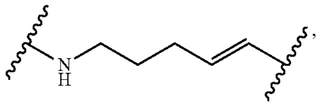 [SMILES: */C=C/CCCN*]

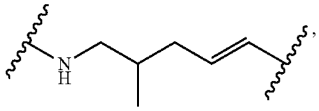 [SMILES: */C=C/CC(C)CN*]

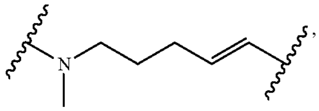

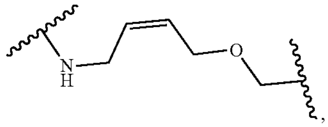

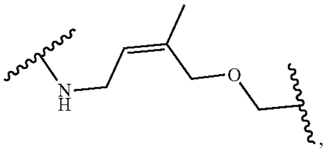

and

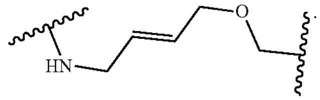

In some embodiments, $L^1$ is

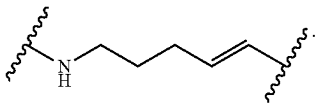

In some embodiments, $L^1$ is

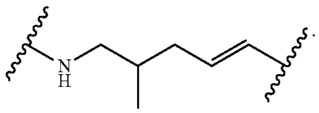

In some embodiments, $L^1$ is

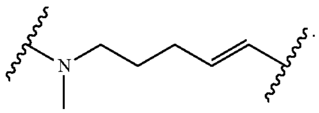 [SMILES: */C=C/CCCN(*)C]

In some embodiments, $L^1$ is

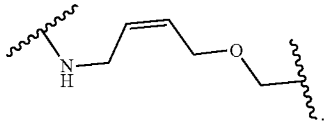 [SMILES: *COC/C=C\CN*]

In some embodiments, $L^1$ is
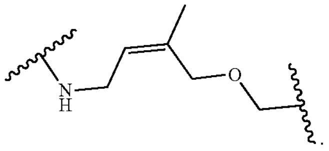 [SMILES: *COC/C(C)=C\CN*]
In some embodiments, $L^1$ is
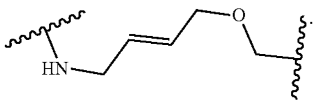 [SMILES: *COC/C=C/CN*]
In some embodiments of a compound of Formula (IV), (IVa), (III), (IIIa), (I), (Ia), (Ia-1), (Ib), (Id), (Ie), or (Ic), or a pharmaceutically acceptable salt thereof, wherein $L^1$ is selected from the group consisting of:
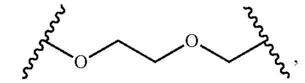
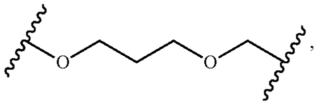
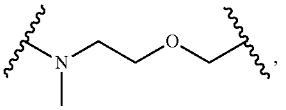
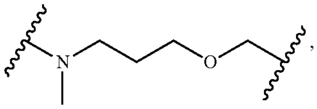
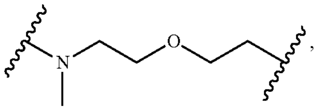
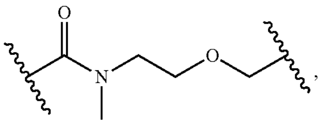
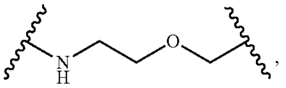
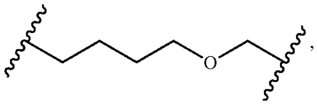
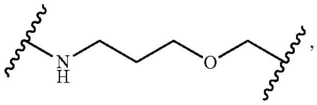
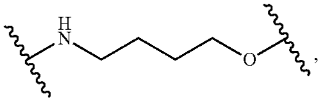
-continued
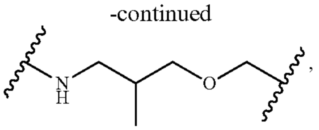
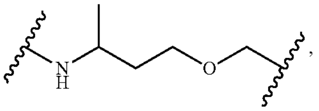
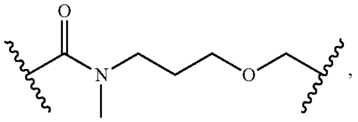
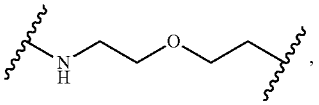
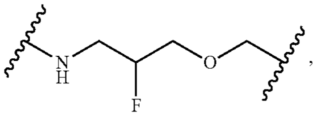
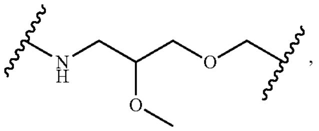
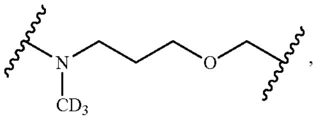
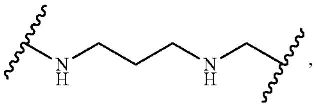
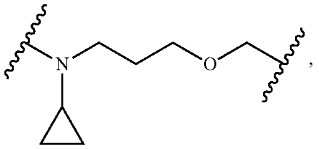
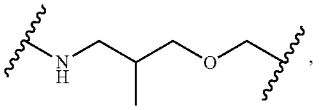
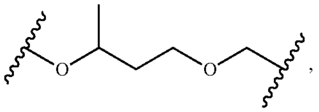
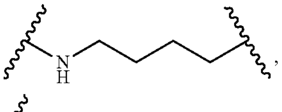
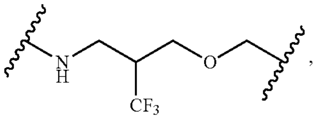
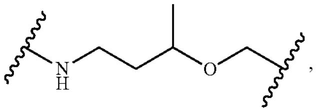
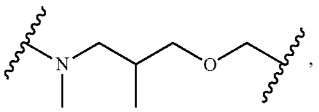

-continued
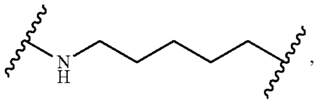
,
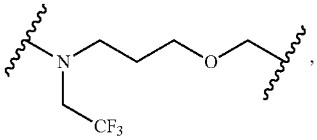
,
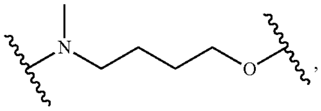
,
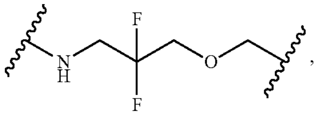
,
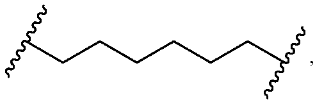
,
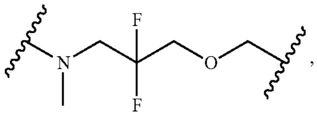
,
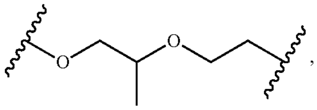
,
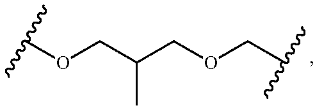
,
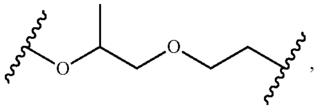
,
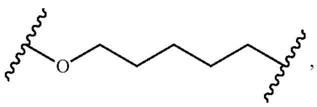
,
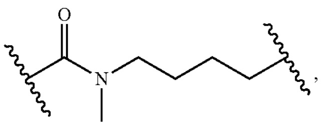
,
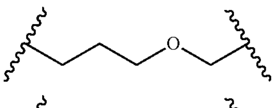
,
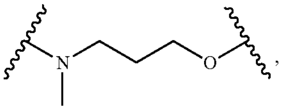
,
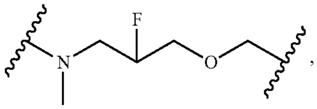
,
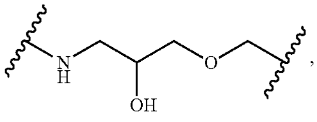
,
-continued
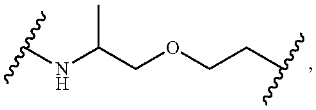
,
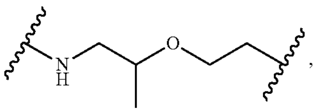
,
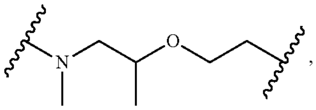
,
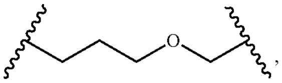
,
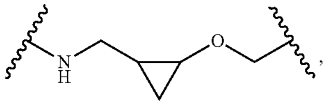
,
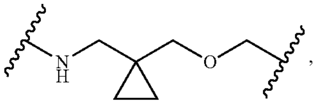
,
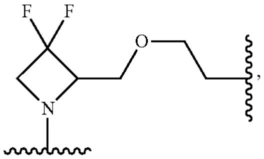
, and
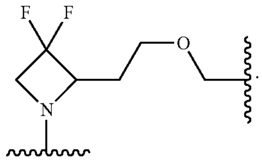
.
In some embodiments, $L^1$ is connecting ring B and ring A from left to right, for example, when $L^1$ is $-OCH_2CH_2OCH_2-$, the motiey of
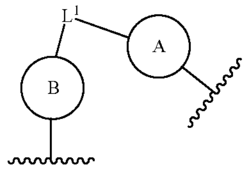
is
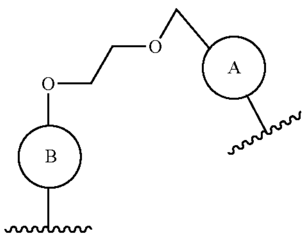
.
In some embodiments, $L^1$ is connecting ring B and right A from right to left, or example, when $L^1$ is $-OCH_2CH_2OCH_2-$, the motiey of

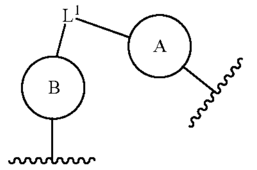

is

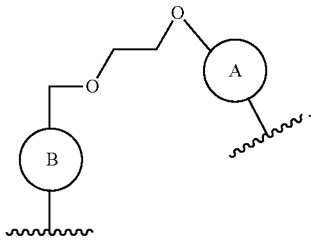

In some embodiments of a compound of Formula (IV), (IVa), (III), (IIIa), (I), (Ia), (Ia-1), (Ib), (Id), (Ie), or (Ic), or a pharmaceutically acceptable salt thereof, $L^2$ is a bond, —N($R^8$)CO—, —CON($R^8$)—, $C_1$-$C_6$alkylene, or $C_1$-$C_6$heteroalkylene, wherein the alkylene and heteroalkylene is optionally substituted with one or more R. In some embodiments, $L^2$ is a $C_1$-$C_3$alkylene or $C_1$-$C_3$heteroalkylene, each of which is optionally substituted. In some embodiments of a compound of Formula (IV), (IVa), (III), (IIIa), (I), (Ia), (Ia-1), (Ib), (Id), (Ie), or (Ic), or a pharmaceutically acceptable salt thereof, $L^2$ is selected from a bond, —$OCH_2$—, or —$CH_2O$—. In some embodiments, $L^2$ is a bond. In some embodiments, $L^2$ is —$OCH_2$—. In some embodiments, $L^2$ is $CH_2O$—.

In some embodiments of a compound of Formula (IV), (IVa), (III), (IIIa), or (I), (or a pharmaceutically acceptable salt thereof, $L^3$ is a bond, —N(R)CO—, —CON($R^8$)—, $C_1$-$C_6$alkylene, or $C_1$-$C_6$heteroalkylene, wherein the alkylene and heteroalkylene is optionally substituted with one or more R. In some embodiments of a compound of Formula (IV), (IVa), (III), (IIIa), (I), (Ia), (Ia-1), (Ib), (Id), (Ie), or (Ic), or a pharmaceutically acceptable salt thereof, $L^3$ is —NHCO—. In some embodiments, $L^3$ is —NHCO— or —C(═O)O—. In some embodiments, $L^3$ is $C_1$-$C_3$heteroalkylene (e.g., —C(═O)O—). In some embodiments, $L^3$ is —N(R)CO—, wherein the —N($R^8$)— is attached to ring B and the —CO— is attached to

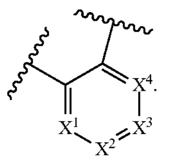

In some embodiments, $L^3$ is —N(R)CO—, wherein the —CO— is attached to ring B and the —N($R^8$)— is attached to

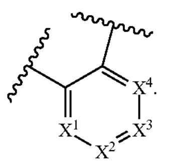

In some embodiments, $L^3$ is —NHCO—, wherein the —NH— is attached to ring B. In some embodiments, $L^3$ is —NHCO—, wherein the —CO— is attached to ring B. In some embodiments, $L^3$ is —N($R^8$)—. In some embodiments, $L^3$ is —NH—

In some embodiments of the compound of Formula (IV), (IVa), (III), (IIIa), (I), (Ia), (Ia-1), (Ib), (Id), (Ie), or (Ic), or a pharmaceutically acceptable salt thereof, ring A is $C_4$-$C_7$cycloalkyl, monocyclic 4- to 7-membered heterocycloalkyl, or bicyclic 6- to 10-membered heterocycloalkyl, each of which is optionally substituted with one or more $R^a$. In some embodiments, ring A is $C_3$-$C_6$cycloalkyl, which is optionally substituted with one or more $R^a$. In some embodiments, ring A is 4- to 6-membered heterocycloalkyl, which is optionally substituted with one or more $R^a$. In some embodiments, ring A is 4- to 6-membered heterocycloalkyl, which is optionally substituted with one or more $R^a$, and wherein the heterocycloalkyl contains 1-3 nitrogens, 0-1 oxygen, and 0-1 sulfur. In some embodiments, ring A is 6-membered heterocycloalkyl, which is optionally substituted with one or more $R^a$, and wherein the heterocycloalkyl contains 1-3 nitrogens, 0-1 oxygen, and 0-1 sulfur.

In some embodiments of a compound of Formula (IV), (IVa), (III), (IIIa), (I), (Ia), (Ia-1), (Ib), (Id), (Ie), or (Ic), or a pharmaceutically acceptable salt thereof, ring A is

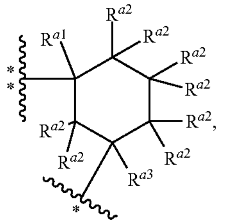

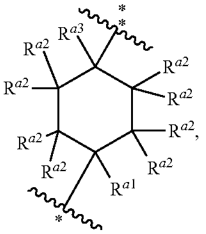

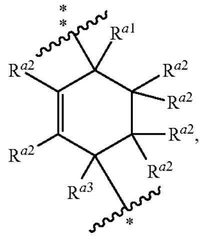

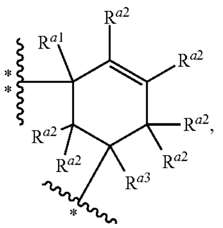

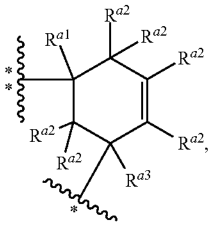

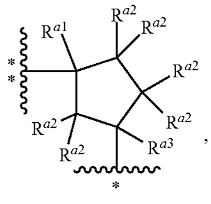

,

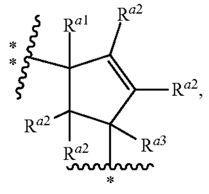

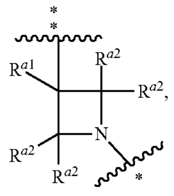

-continued

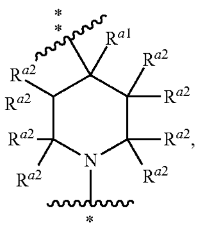
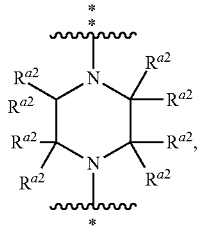
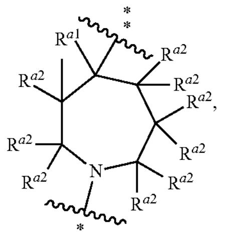
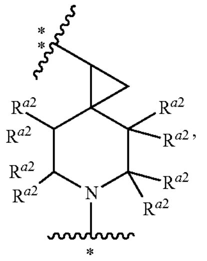
or
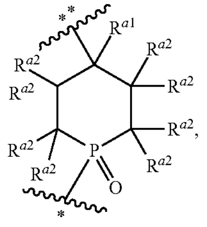

wherein * indicates the attachment point to $L^2$, and ** indicates the attachment point to $L^1$, and wherein each $R^{a1}$, $R^{a2}$, and $R^{a3}$ are each independently selected from hydrogen, halogen, oxo, —CN, —$NO_2$, —OH, —$OR^7$, —OC(=O)$R^7$, —OC(=O)$OR^7$, —OC(=O)$NR^8R^8$, —SH, —$SR^7$, —S(=O)$R^7$, —S(=O)$_2R^7$, —S(=O)$_2NR^8R^8$, —S(=O)(=$NR^8$)$R^7$, —$NR^8R^8$, —$NR^8$C(=O)$NR^8R^8$, —$NR^8$C(=O)$R^7$, —$NR^8$C(=O)$OR^7$, —$NR^8$S(=O)$_2R^7$, —N=S(=O)$(R^7)_2$, —C(=O)$R^7$, —C(=O)$OR^8$, —C(=O)$NR^8R^8$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, 3- to 9-membered cycloalkyl, and 3- to 9-membered heterocycloalkyl, wherein the alkyl, haloalkyl, hydroxyalkyl, aminoalkyl, heteroalkyl, alkenyl, alkynyl, cycloalkyl, or heterocycloalkyl is optionally substituted with one or more R.

In some embodiments of a compound of Formula (IV), (IVa), (III), (IIIa), (I), (Ia), (Ia-1), (Ib), (Id), (Ie), or (Ic), or a pharmaceutically acceptable salt thereof, $R^{a1}$, $R^{a2}$, and $R^{a3}$ are each independently selected from hydrogen, halogen, oxo, —CN, —$NO_2$, —OH, $C_1$-$C_3$alkyl, $C_1$-$C_3$haloalkyl, 3- to 6-membered cycloalkyl, and 5- to 6-membered heterocycloalkyl. In some embodiments, $R^{a1}$, $R^{a2}$, and $R^{a3}$ are each independently selected from hydrogen, halogen, oxo, —CN, —$NO_2$, —OH, $C_1$-$C_3$alkyl, and $C_1$-$C_3$haloalkyl.

In some embodiments of a compound of Formula (IV), (IVa), (III), (IIIa), (I), (Ia), (Ia-1), (Ib), (Id), (Ie), (Ic), or a pharmaceutically acceptable salt thereof, ring A is monocyclic 4- to 7-membered heterocycloalkyl, which is optionally substituted with one or more $R^a$. In some embodiments, ring A is monocyclic 5- to 6-membered heterocycloalkyl containing 1 or 2 nitrogens, which is optionally substituted with one or more $R^a$. In some embodiments, ring A is optionally substituted piperidine. In some embodiments, ring A is selected from the group consisting of:

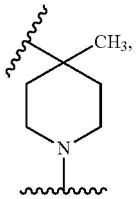
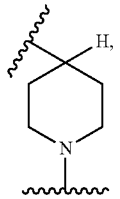
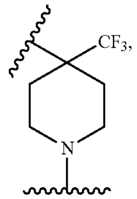
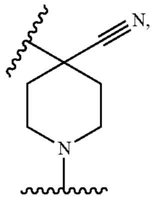
and
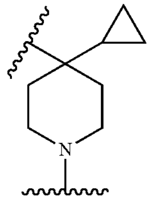

In some embodiments, the hetero ring atom of ring A is attached to $L^2$. In some embodiments, ring A is optionally substituted piperidine, wherein the nitrogen of the piperidine is directly attached to $L^2$. In some embodiments, ring A is

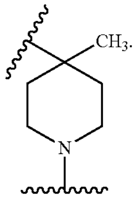 [SMILES: *N1CCC(*)(C)CC1]

In some embodiments, ring A is

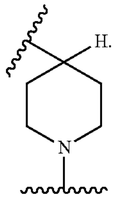

In some embodiments, ring A is

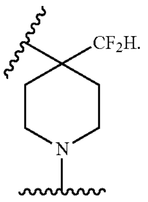

In some embodiments, ring A is

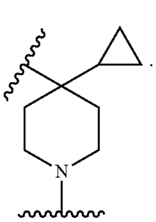 [SMILES: *N1CCC(*)(C2CC2)CC1]

In some embodiments, ring A is

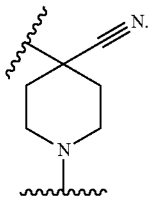 [SMILES: *N1CCC(*)(C#N)CC1]

In some embodiments, ring A is

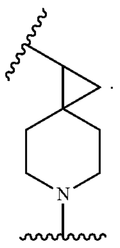 [SMILES: *C1CC12CCN(*)CC2]

In some embodiments, ring A is

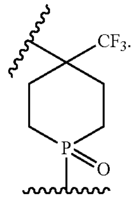 [SMILES: *C1(C(F)(F)F)CCP(*)(=O)CC1]

In some embodiments of a compound of Formula (IV), (IVa), (III), (IIIa), (I), (Ia), (Ia-1), (Ib), (Id), (Ie), or (Ic), or a pharmaceutically acceptable salt thereof, ring A is bicyclic 6- to 10-membered heterocycloalkyl, which is optionally substituted with one or more $R^a$. The bicyclic ring can be a fused, bridged or spirocyclic ring. In some embodiments, the bicyclic ring is a spirocyclic ring. In some embodiments, ring A is

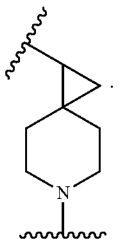 [SMILES: *C1CC12CCN(*)CC2]

In some embodiments of a compound of Formula (IV), (IVa), (III), (IIIa), (I), (Ia), (Ia-1), (Ib), (Id), (Ie), or (Ic), or a pharmaceutically acceptable salt thereof, each of $R^a$ is independently selected from halogen, oxo, —CN, —$NO_2$, —OH, —$OR^7$, —OC(═O)$R^7$, —OC(═O)$OR^7$, —OC(═O)$NR^8R^8$, —SH, —$SR^7$, —S(═O)$R^7$, —S(═O)$_2R^7$, —S(═O)$_2NR^8R^8$, —S(═O)(═$NR^8$)$R^7$, —$NR^8R^8$, —$NR^8$C(═O)$NR^8R^8$, —$NR^8$C(═O)$R^7$, —$NR^8$C(═O)$OR^7$, —$NR^8$S(═O)$_2R^7$, —N═S(═O)$(R^7)_2$, —C(═O)$R^7$, —C(═O)$OR^8$, —C(═O)$NR^8R^8$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, and heterocycloalkyl, wherein the alkyl, haloalkyl, hydroxyalkyl, aminoalkyl, heteroalkyl, alkenyl, alkynyl, cycloalkyl, or heterocycloalkyl is optionally substituted with one or more R. In some embodiments, each of $R^a$ is independently selected from halogen, —CN, —$NO_2$, —OH, —$OR^7$, —SH, —$SR^7$, —$NR^8R^8$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, and heterocycloalkyl, wherein the alkyl, haloalkyl, hydroxyalkyl, aminoalkyl, heteroalkyl, alkenyl, alkynyl, cycloalkyl, or heterocycloalkyl is optionally substituted with one or more R. In some embodiments, each of $R^a$ is independently selected from halogen, —CN, —$NO_2$, —OH, amino, $C_1$-$C_6$alkyl, $C_1$-$C_6$alkoxyl, $C_1$-$C_6$haloalkoxyl, $C_1$-$C_6$haloalkyl, $C_1$-$C_6$hydroxyalkyl, $C_1$-$C_6$aminoalkyl, $C_1$-$C_6$heteroalkyl, and $C_3$-$C_6$cycloalkyl, wherein the cycloalkyl is optionally substituted with one or more R. In some embodiments, each of $R^a$ is independently selected from halogen, —CN, —$NO_2$, $C_1$-$C_6$alkyl, $C_1$-$C_6$haloalkyl, and cycloalkyl, wherein the alkyl, haloalkyl, or cycloalkyl is optionally substituted with one or more R. In some embodiments, each of $R^a$ is independently selected from —CN, —$C_1$-$C_6$alkyl, $C_1$-$C_6$haloalkyl, and cycloalkyl, wherein the alkyl, haloalkyl, or cycloalkyl is optionally substituted with one or more R. In some embodiments, $R^a$ is —CN. In some embodiments, $R^a$ is —$C_1$-$C_6$alkyl. In some embodiments, $R^a$ is —$C_1$-$C_3$alkyl. In some embodiments, $R^a$ is —$CH_3$. In some embodiments, $R^a$ is $C_1$-$C_6$haloalkyl. In some embodiments, $R^a$ is $C_1$-$C_3$haloalkyl. In some embodiments, $R^a$ is —$CF_3$. In some embodiments, $R^a$ is —$CF_2H$. In some embodiments, $R^a$ is cycloalkyl. In some embodiments, $R^a$ is $C_3$-$C_6$cycloalkyl. In some embodiments, $R^a$ is

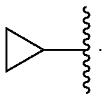

In some embodiments of a compound of Formula (IV), (IVa), (III), (IIIa), (I), (Ia), (Ia-1), (Ib), (Id), (Ie), or (Ic), or a pharmaceutically acceptable salt thereof, ring A is selected from the group consisting of:

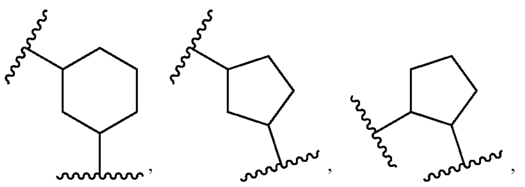

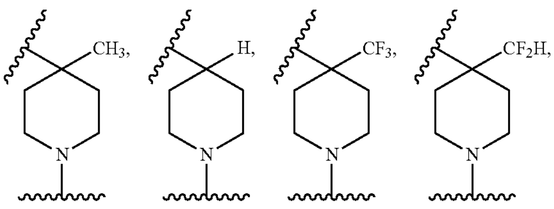

-continued

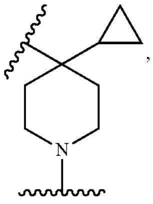
,
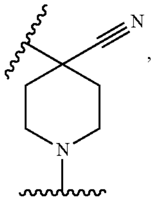
,
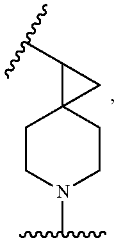
, and

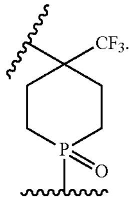

In some embodiments, ring A is connecting $L^1$ and $L^2$ from top to bottom, for example, when ring A is

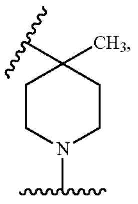 [SMILES: *N1CCC(*)(C)CC1]

the motiey of

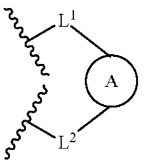
is
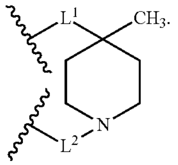

In some embodiments of a compound of Formula (IV), (IVa), (III), (IIIa), (I), (Ia), (Ia-1), (Ib), (Id), (Ie), or (Ic), or a pharmaceutically acceptable salt thereof, ring A is $C_4$-$C_7$cycloalkyl which is optionally substituted with one or more $R^a$. In some embodiments, ring A is $C_5$-$C_6$ cycloalkyl, which is optionally substituted with one or more $R^a$. In some embodiments, ring A is optionally substituted cyclopentyl or cyclohexyl. In some embodiments, ring A is

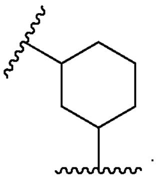 [SMILES: *C1CCCC(*)C1]

In some embodiments, ring A is

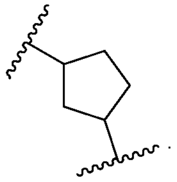 [SMILES: *C1CCC(*)C1]

In some embodiments, ring A is

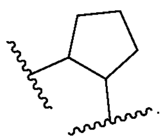 [SMILES: *C1CCCC1*]

In some embodiments of a compound of Formula (IV), (IVa), (III), (IIIa), (I) or (Ia), or a pharmaceutically acceptable salt thereof, ring B is phenyl, 5- to 10-membered heteroaryl, or 5- to 12-membered heterocycloalkyl, each of which is optionally substituted with one or more R.

In some embodiments of a compound of Formula (IV), (IVa), (III), (IIIa), (I) or (Ia), or a pharmaceutically acceptable salt thereof, ring B is 5- to 12-membered heterocycloalkyl, which is optionally substituted with one or more R. In some embodiments, ring B is optionally substituted monocyclic heterocycloalkyl. In some embodiments, ring B is optionally substituted bicyclic heterocycloalkyl. In some embodiments of a compound of Formula (IV), (IVa), (III), (IIIa), (I) or (Ia), or a pharmaceutically acceptable salt thereof, ring B is $C_3$-$C_{12}$cycloalkyl, which is optionally substituted with one or more $R^b$. In some embodiments, ring B is optionally substituted $C_5$-$C_6$cycloalkyl. In some embodiments, ring B is optionally substituted bicyclic cycloalkyl.

In some embodiments of a compound of Formula (IV), (IVa), (III), (IIIa), (I) or (Ia), or a pharmaceutically acceptable salt thereof, ring B is phenyl, 5- to 6-membered heteroaryl, or 9- to 10-membered heterocycloalkyl, each of which is optionally substituted with one or more $R^b$.

In some embodiments of a compound of Formula (IV), (IVa), (III), (IIIa), (I) or (Ia), or a pharmaceutically acceptable salt thereof, ring B is phenyl or 6-membered heteroaryl, each of which is optionally substituted with one or more $R^b$. In some embodiments, ring B is optionally substituted phenyl. In some embodiments, Ring B is

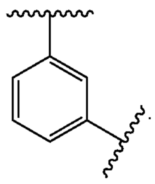 [SMILES: *c1cccc(*)c1]

In some embodiments of a compound of Formula (IV), (IVa), (III), (IIIa), (I) or (Ia), or a pharmaceutically acceptable salt thereof, ring B is 5 or 6-membered heteroaryl, which is optionally substituted with one or more $R^b$. In some embodiments, ring B is optionally substituted 6-membered heteroaryl. In some embodiments, ring B is optionally substituted 5-membered heteroaryl. In some embodiments, ring B is pyridine, pyrimidine, pyrazine, pyridazine, or triazine, each of which is optionally substituted. In some embodiments, ring B is pyridine, which is optionally substituted. In some embodiments, ring B is pyrimidine, which is optionally substituted. In some embodiments, ring B is optionally substituted imidazole, optionally substituted pyrazole, or optionally substituted triazole. In some embodiments, ring B is

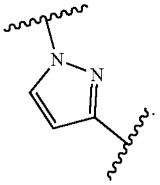 [SMILES: *c1ccn(*)n1]

In some embodiments, Ring B is

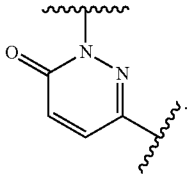 [SMILES: *c1ccc(=O)n(*)n1]

In some embodiments, ring B is

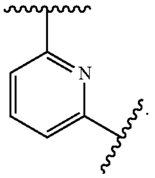

In some embodiments, Ring B is

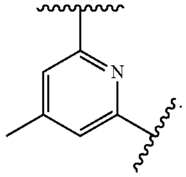 [SMILES: *c1cc(C)cc(*)n1]

In some embodiments, Ring B is

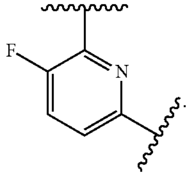 [SMILES: *c1ccc(F)c(*)n1]

In some embodiments, Ring B is

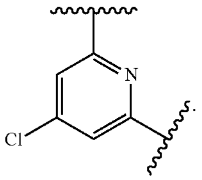 [SMILES: *c1cc(Cl)cc(*)n1]

In some embodiments, Ring B is

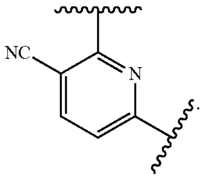 [SMILES: *c1ccc(C#N)c(*)n1]

In some embodiments, Ring B is

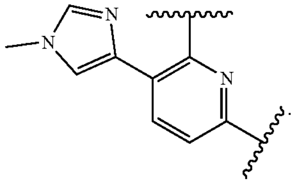 [SMILES: *c1ccc(-c2cn(C)cn2)c(*)n1]

In some embodiments, Ring B is

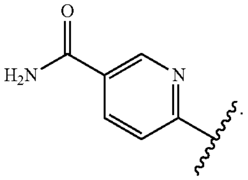 [SMILES: *c1ccc(C(N)=O)cn1]

In some embodiments, Ring B is

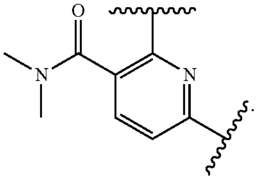 [SMILES: *c1ccc(C(=O)N(C)C)c(*)n1]

In some embodiments, Ring B is

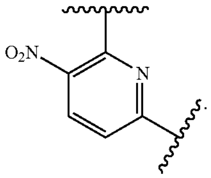 [SMILES: *c1ccc([N+](=O)[O-])c(*)n1]

In some embodiments, Ring B is
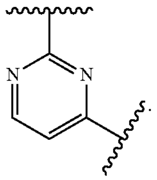 [SMILES: *c1ccnc(*)n1]
In some embodiments, ring B is
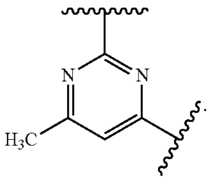 [SMILES: *c1cc(C)nc(*)n1]
In some embodiments, ring B is
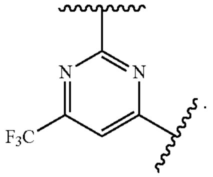 [SMILES: *c1cc(C(F)(F)F)nc(*)n1]
In some embodiments, ring B is
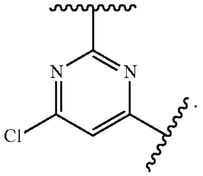 [SMILES: *c1cc(Cl)nc(*)n1]
In some embodiments, ring B is
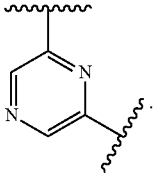 [SMILES: *c1cncc(*)n1]
In some embodiments, ring B is
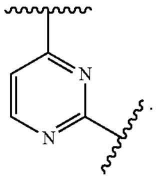 [SMILES: *c1ccnc(*)n1]
In some embodiments, Ring B is
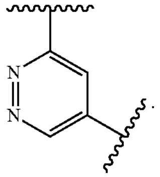 [SMILES: *c1cnnc(*)c1]
In some embodiments of a compound of Formula (IV), (IVa), (III), (IIIa), (I), (Ia), (Ia-1), (Ib), (Id), (Ie), or (Ic), or a pharmaceutically acceptable salt thereof, ring B
(or 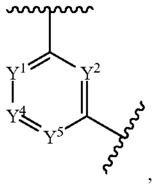, 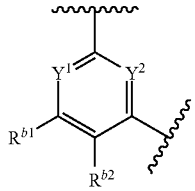, 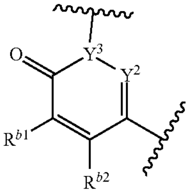, 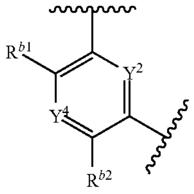, or 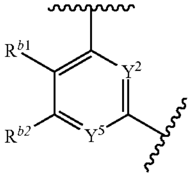 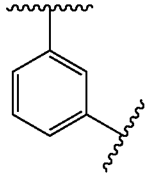) is
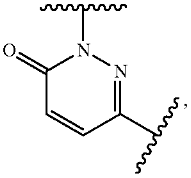, 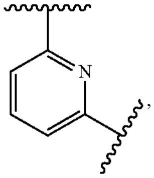, 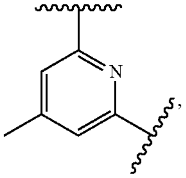, 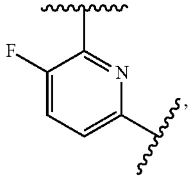, 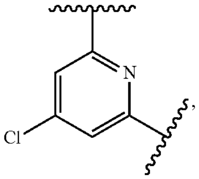, 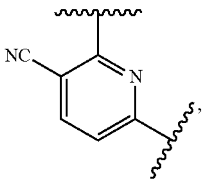, 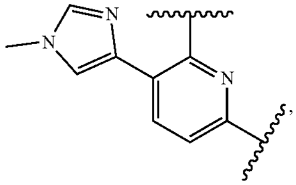, 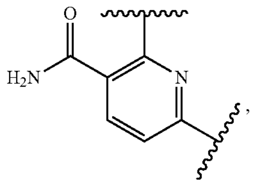, 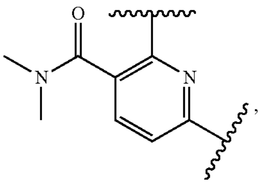, -continued

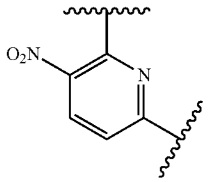
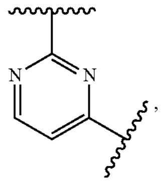
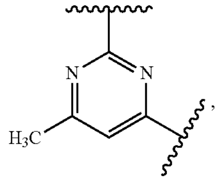
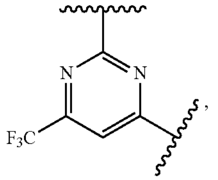
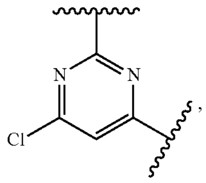
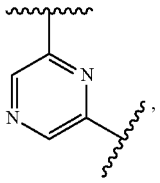
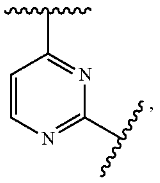
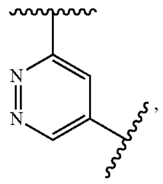
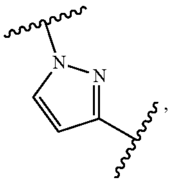
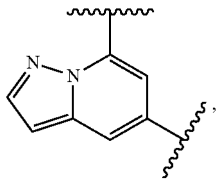
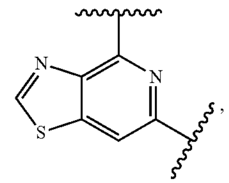
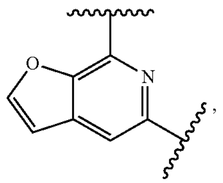
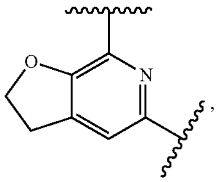
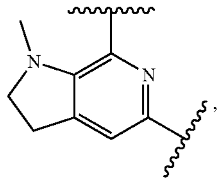
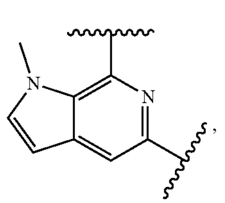
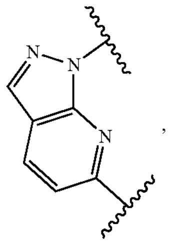
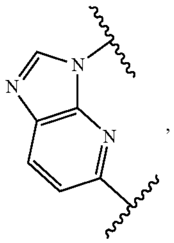
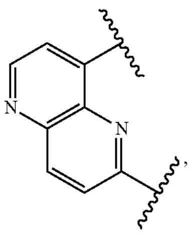

and

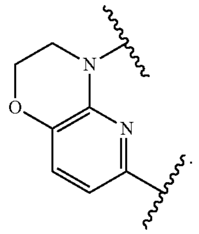

In some embodiments, ring B is connecting $L^1$ and $L^3$ from top to bottom, for example, when ring B is

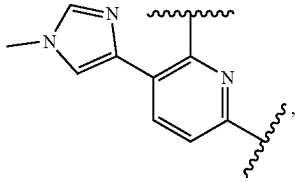 [SMILES: *c1ccc(-c2cn(C)cn2)c(*)n1]

the motiey of

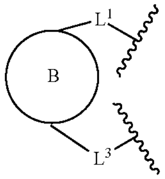

is

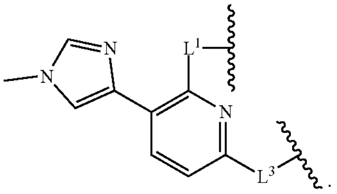

In some embodiments, ring B is connecting $L^1$ and $L^3$ from top to bottom, for example, when ring B is

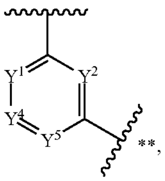
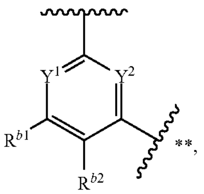
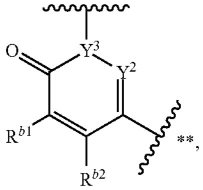
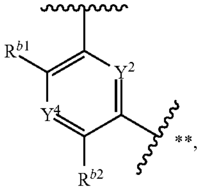

or

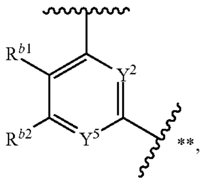

then * represents the attachment point to $L^1$ and ** represents the attachment point to $L^3$.

In some embodiments of a compound of Formula (IV), (IVa), (III), (IIIa), (I) or (Ia), or a pharmaceutically acceptable salt thereof, ring B is 9- to 10-membered heteroaryl, which is optionally substituted with one or more R. In some embodiments, ring B is 9- to 10-membered heteroaryl, which is optionally substituted with one or more $R^b$, and wherein the heteroaryl contains 1-3 nitrogens, 0-1 oxygen, and 0-1 sulfur. In some embodiments, ring B is

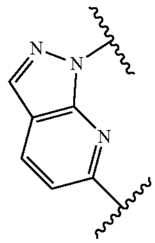, 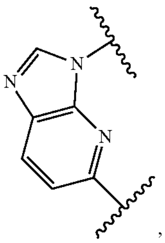, or 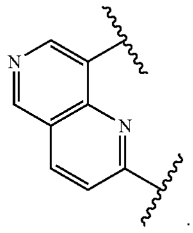.

In some embodiments, ring B is

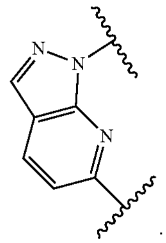 [SMILES: *c1ccc2cnn(*)c2n1].

In some embodiments, ring B is

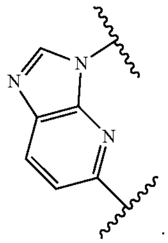 [SMILES: *c1ccc2ncn(*)c2n1].

In some embodiments, ring B is

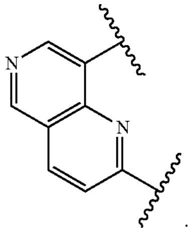 [SMILES: *c1ccc2cncc(*)c2n1].

In some embodiments, Ring B is

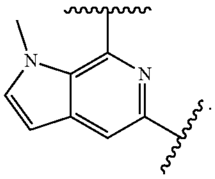 [SMILES: *c1cc2ccn(C)c2c(*)n1].

In some embodiments, Ring B is

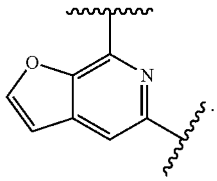 [SMILES: *c1cc2ccoc2c(*)n1].

In some embodiments, Ring B is

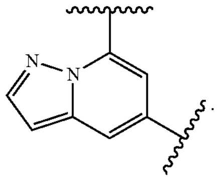 [SMILES: *c1cc(*)n2nccc2c1].

In some embodiments, Ring B is

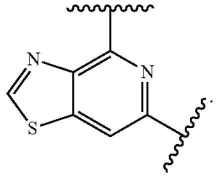 [SMILES: *c1cc2scnc2c(*)n1].

In some embodiments, ring B is optionally substituted 9- to 10-membered heteroaryl, comprising a heteroaryl fused with a heterocycloalkyl. In some embodiments, Ring B is

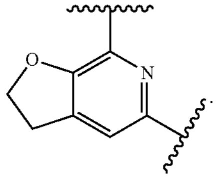 [SMILES: *c1cc2c(c(*)n1)OCC2].

In some embodiments, Ring B is

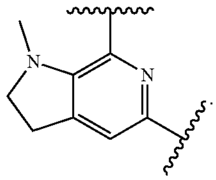 [SMILES: *c1cc2c(c(*)n1)N(C)CC2].

In some embodiments of a compound of Formula (IV), (IVa), (III), (IIIa), (I) or (Ia), or a pharmaceutically acceptable salt thereof, Ring B is 9- to 10-membered heterocycloalkyl, which is optionally substituted with one or more R. In some embodiments, Ring B is 5- to 6-membered heterocycloalkyl, which is optionally substituted with one or more $R^b$. In some embodiments, the heterocycloalkyl is

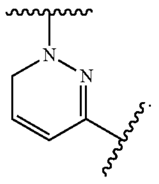 [SMILES: *C1=NN(*)CC=C1]

In some embodiments of a compound of Formula (IV), (IVa), (III), (IIIa), (I), (Ia), (Ia-1), or (Ib), or a pharmaceutically acceptable salt thereof, ring B (or 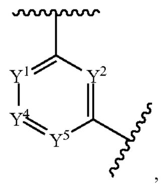 , or 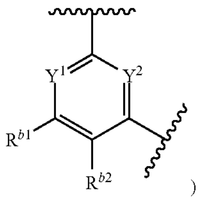 )

is selected from the group consisting of:

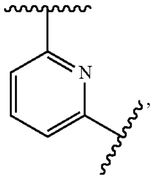 , 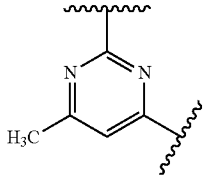 and

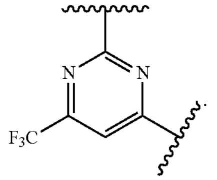

In some embodiments of a compound of Formula (IV), (IVa), (III), (IIIa), (I), (Ia), (Ia-1), (Ib), (Id), (Ie), or (Ic), or a pharmaceutically acceptable salt thereof, each of R is independently selected from halogen, oxo, —CN, —$NO_2$, —OH, —$OR^7$, —OC(═O)$R^7$, —OC(═O)$OR^7$, —OC(═O)$NR^8R^8$, —SH, —$SR^7$, —S(═O)$R^7$, —S(═O)$_2R^7$, —S(═O)$_2NR^8R^8$, —S(═O)(═$NR^8$)$R^7$, —$NR^8R^8$, —$NR^8$C(═O)$NR^8R^8$, —$NR^8$C(═O)$R^7$, —$NR^8$C(═O)$OR^7$, —$NR^8$S(═O)$_2R^7$, —N═S(═O)$(R^7)_2$, —C(═O)$R^7$, —C(═O)$OR^8$, —C(═O)$NR^8R^8$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, and heteroaryl, wherein the alkyl, haloalkyl, hydroxyalkyl, aminoalkyl, heteroalkyl, alkenyl, alkynyl, cycloalkyl, heterocycloalkyl, aryl, or heteroaryl is optionally substituted with one or more R. In some embodiments, each of $R^a$, $R^b$, $R^c$, $R^d$, and R are each independently selected from halogen, oxo, —CN, —$NO_2$, —OH, —$OR^7$, —OC(═O)$R^7$, —OC(═O)$OR^7$, —OC(═O)$NR^8R^8$, —SH, —$SR^7$, —S(═O)$R^7$, —S(═O)$_2R^7$, —S(═O)$_2NR^8R^8$, —S(═O)(═$NR^8$)$R^7$, —$NR^8R^8$, —$NR^8$C(═O)$NR^8R^8$, —$NR^8$C(═O)$R^7$, —$NR^8$C(═O)$OR^7$, —$NR^8$S(═O)$_2R^7$, —N═S(═O)$(R^7)_2$, —C(═O)$R^7$, —C(═O)$OR^8$, —C(═O)$NR^8R^8$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, and heterocycloalkyl, wherein the alkyl, haloalkyl, hydroxyalkyl, aminoalkyl, heteroalkyl, alkenyl, alkynyl, cycloalkyl, or heterocycloalkyl is optionally substituted with one or more R.

In some embodiments, each of R is independently selected from halogen, oxo, —CN, —$NO_2$, —OH, —$OR^7$, —SH, —$SR^7$, —$NR^8R^8$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, and heterocycloalkyl, wherein the alkyl, haloalkyl, hydroxyalkyl, aminoalkyl, heteroalkyl, cycloalkyl, or heterocycloalkyl is optionally substituted with one or more R. In some embodiments, each of R is independently selected from halogen, oxo, —CN, —$NO_2$, —OH, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, and heterocycloalkyl, wherein the alkyl, haloalkyl, hydroxyalkyl, aminoalkyl, heteroalkyl, alkenyl, alkynyl, cycloalkyl, or heterocycloalkyl is optionally substituted with one or more R. In some embodiments, each of R is independently selected from halogen, —OH, oxo, —CN, $C_1$-$C_6$alkyl, and $C_1$-$C_6$haloalkyl. In some embodiments, $R^b$ is halogen (e.g., F and Cl). In some embodiments, $R^b$ is OH or oxo. In some embodiments, $R^b$ is OH. In some embodiments, $R^b$ is oxo. In some embodiments, $R^b$ is —$NR^8R^8$. In some embodiments, $R^b$ is $NH_2$, —NH($C_1$-$C_6$alkyl), or —N($C_1$-$C_6$alkyl)$_2$. In some embodiments, $R^b$ is —CN. In some embodiments, $R^b$ is $C_1$-$C_6$alkyl. In some embodiments, $R^b$ is $C_1$-$C_3$alkyl. In some embodiments, $R^b$ is —$CH_3$. In some embodiments, $R^b$ is $C_1$-$C_6$haloalkyl. In some embodiments, $R^b$ is $C_1$-$C_3$haloalkyl. In some embodiments, $R^b$ is —$CF_3$. In some embodiments, $R^b$ is 5-6 membered heteroaryl.

In some embodiments of a compound of Formula (Ia-1), (Ib), (Id), (Ie), or (Ic), or a pharmaceutically acceptable salt thereof, $R^{b1}$ is hydrogen, $C_1$-$C_6$alkyl or $C_1$-$C_6$haloalkyl. In some embodiments, $R^{b1}$ is hydrogen. In some embodiments, $R^{b1}$ is $C_1$-$C_3$alkyl or $C_1$-$C_3$haloalkyl. In some embodiments, $R^{b1}$ is methyl. In some embodiments, $R^{b1}$ is hydrogen, halogen, —CN, —$NO_2$, —OH, —$OR^7$, —SH, —$SR^7$, —$NR^8R^8$, $C_1$-$C_6$alkyl, $C_1$-$C_6$haloalkyl. $C_1$-$C_6$hydroxyalkyl, $C_1$-$C_6$aminoalkyl, $C_1$-$C_6$heteroalkyl, cycloalkyl, and heterocycloalkyl, wherein the alkyl, haloalkyl, hydroxyalkyl, aminoalkyl, heteroalkyl, cycloalkyl, or heterocycloalkyl is optionally substituted with one or more R. In some embodiments, $R^{b1}$ is hydrogen, halogen, —CN, —$NO_2$, —OH, —SH, $NH_2$, —NH($C_1$-$C_6$alkyl), —N($C_1$-$C_6$alkyl)$_2$, —O—$C_1$-$C_6$alkyl, $C_1$-$C_6$alkyl, $C_1$-$C_6$haloalkyl. $C_1$-$C_6$hydroxyalkyl, $C_1$-$C_6$aminoalkyl, $C_1$-$C_6$heteroalkyl, cycloalkyl, and heterocycloalkyl, wherein the alkyl, haloalkyl, hydroxyalkyl, aminoalkyl, heteroalkyl, cycloalkyl, or heterocycloalkyl is optionally substituted with one or more R. In some embodiments, $R^{b1}$ is hydrogen, halogen, —CN, $C_1$-$C_3$alkyl, or $C_1$-$C_3$haloalkyl. In some embodiments, $R^{b1}$ is heteroaryl. In some embodiments, $R^{b1}$ is 5-6 membered heteroaryl.

In some embodiments of a compound of Formula (Ia-1), (Ib), (Id), (Ie), or (Ic), or a pharmaceutically acceptable salt thereof, $R^{b2}$ is hydrogen, $C_1$-$C_6$alkyl or $C_1$-$C_6$haloalkyl. In some embodiments, $R^{b2}$ is hydrogen. In some embodiments, $R^{b2}$ is $C_1$-$C_3$alkyl or $C_1$-$C_3$haloalkyl. In some embodiments, $R^{b2}$ is methyl. In some embodiments of a compound of Formula (Ia-1), (Ib), (Id), (Ie), or (Ic), or a pharmaceutically acceptable salt thereof, $R^{b2}$ is hydrogen, halogen, —CN, —$NO_2$, —OH, —$OR^7$, —SH, —$SR^7$, —$NR^8R^8$, $C_1$-$C_6$alkyl, $C_1$-$C_6$haloalkyl. $C_1$-$C_6$hydroxyalkyl, $C_1$-$C_6$aminoalkyl, $C_1$-$C_6$heteroalkyl, cycloalkyl, and heterocycloalkyl, wherein the alkyl, haloalkyl, hydroxyalkyl, aminoalkyl, heteroalkyl, cycloalkyl, or heterocycloalkyl is optionally substituted with one or more R. In some embodiments, $R^2$ is hydrogen, halogen, —CN, —$NO_2$, —OH, —SH, $NH_2$, —NH($C_1$-$C_6$alkyl), —N($C_1$-$C_6$alkyl)$_2$, —O—$C_1$-$C_6$alkyl, $C_1$-$C_6$alkyl, $C_1$-$C_6$haloalkyl. $C_1$-$C_6$hydroxyalkyl, $C_1$-$C_6$aminoalkyl, $C_1$-$C_6$heteroalkyl, cycloalkyl, and heterocycloalkyl, wherein the alkyl, haloalkyl, hydroxyalkyl, aminoalkyl, heteroalkyl, cycloalkyl, or heterocycloalkyl is optionally substituted with one or more R. In some embodiments, $R^{b2}$ is hydrogen, halogen, —CN, $C_1$-$C_3$alkyl, or $C_1$-$C_3$haloalkyl. In some embodiments, provided herein a compound of Formula (Ib), or a pharmaceutically acceptable salt thereof, wherein $X^1$ is CH, $X^2$ is CH, $X^3$ is —Z—$R^5$, $X^4$ is CH, $Y^1$ is N, $Y^2$ is N, and ring A is a optionally substituted 6 membered heteroalkyl. In some embodiments, $L^1$ is $C_1$-$C_6$alkylene or $C_1$-$C_6$heteroalkylene, each of which is optionally substituted with one or more $R^c$. In some embodiments, each $R^c$ is independently selected from hydrogen, halogen, —CN, —$NO_2$, —OR, —SR, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, $C_3$-$C_8$cycloalkyl, $C_2$-$C_9$heterocycloalkyl, aryl, and heteroaryl; or wo $R^c$ are taken together with the intervening atoms to form a heterocycloalkyl or cycloalkyl, which is optionally substituted with one or more R.

In any of the above embodiments, each $R^6$ is independently selected from halogen, —CN, —$NO_2$, —OH, oxo, —$OR^7$, —OC(═O)$R^7$, —OC(═O)$OR^7$, —OC(═O)$NR^8R^8$, —SH, —$SR^7$, —S(═O)$R^7$, —S(═O)$_2R^7$, —S(═O)$_2NR^8R^8$, —S(═O)(═$NR^8$)$R^7$, —$NR^8R^8$, —$NR^8$C(═O)$NR^8R^8$, —$NR^8$C(═O)$R^8$, —$NR^8$C(═O)$OR^7$, —$NR^8$S(═O)$_2R^7$, —N═S(═O)($R^7$)$_2$, —C(═O)$R^7$, —C(═O)$OR^8$, —C(═O)$NR^8R^8$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, and $C_2$-$C_6$alkynyl. In some embodiments, $R^6$ is selected from halogen, $C_1$-$C_6$alkyl, and $C_1$-$C_6$haloalkyl.

In any of the above embodiments, each $R^d$ is independently selected from halogen, oxo, —CN, —$NO_2$, —OH, —$OR^7$, —OC(═O)$R^7$, —OC(═O)$OR^7$, —OC(═O)$NR^8R^8$, —SH, —$SR^7$, —S(═O)$R^7$, —S(═O)$_2R^7$, —S(═O)$_2NR^8R^8$, —S(═O)(═$NR^8$)$R^7$, —$NR^8R^8$, —$NR^8$C(═O)$NR^8R^8$, —$NR^8$C(═O)$R^7$, —$NR^8$C(═O)$OR^7$, —$NR^8$S(═O)$_2R^7$, —N═S(═O)($R^7$)$_2$, —C(═O)$R^7$, —C(═O)$OR^8$, —C(═O)$NR^8R^8$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, and heterocycloalkyl, wherein the alkyl, haloalkyl, hydroxyalkyl, aminoalkyl, heteroalkyl, alkenyl, alkynyl, cycloalkyl, or heterocycloalkyl is optionally substituted with one or more R. In some embodiments, $R^d$ is selected from halogen, $C_1$-$C_6$alkyl, and $C_1$-$C_6$haloalkyl.

In any of the above embodiments, each $R^e$ is independently selected from halogen, oxo, —CN, —$NO_2$, OH, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl —$OR^7$, —$OC_1$-$C_4$haloalkyl, —CN, —C(═O)$R^7$, —C(═O)$OR^8$, —C(═O)N($R^8$)$_2$, —C(═$NR^8$)N($R^8$)$_2$, —OC(═O)$R^7$, —OC(═O)N($R^8$)$_2$, —S(═O)(═$NR^8$)$R^7$, —$NR^8R^8$, —$OC_2$-$C_6$alkylene)N($R^8$)$_2$, —$OC_2$-$C_6$alkyleneO$R^8$, —SH, —$SR^7$, —S(═O)$R^7$, —S(═O)$_2R^7$, —S(═O)$_2$N($R^8$)$_2$, —N($R^8$)C(═O)$R^7$, —$NR^8$C(═O)$OR^7$, —N($R^8$)C(═O)N($R^8$)$_2$, —N($R^8$)C(═$NR^8$)N($R^8$)$_2$, —N═S(═O)($R^7$)$_2$, —N($R^8$)S(═O)$_2R^7$, —N($R^8$)S(═O)$_2$N($R^8$)$_2$, —$NR^8C_2$-$C_6$alkyleneN($R^8$)$_2$, —$NR^8C_2$-$C_6$alkyleneO$R^8$, —$C_1$-$C_6$alkyleneN($R^8$)$_2$, —$C_1$-$C_6$alkyleneO$R^8$, —$C_1$-$C_6$alkyleneN($R^8$)C(═O)$R^7$, —$C_1$-$C_6$alkyleneOC(═O)$R^8$, —$C_1$-$C_6$alkyleneC(═O)N($R^8$)$_2$, and —$C_1$-$C_6$alkyleneC(═O)$OR^7$, wherein the alkyl, haloalkyl, hydroxyalkyl, aminoalkyl, heteroalkyl, alkenyl, alkynyl, cycloalkyl, or heterocycloalkyl is optionally substituted with one or more R. In some embodiments, $R^c$ is selected from halogen, $C_1$-$C_6$alkyl, and $C_1$-$C_6$haloalkyl.

In any of the above embodiments, $R^7$ is $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, or heterocycloalkyl, each of which is optionally substituted with one or more R. In some embodiments, $R^7$ is $C_1$-$C_6$alkyl, $C_1$-$C_6$haloalkyl, and cycloalkyl, each of which is optionally substituted with one or more R. In some embodiments, $R^7$ is $C_1$-$C_6$alkyl. In some embodiments, $R^7$ is $C_1$-$C_3$alkyl.

In any of the above embodiments, each $R^8$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), or $C_1$-$C_6$alkylene(heterocycloalkyl), wherein the alkyl, haloalkyl, hydroxyalkyl, aminoalkyl, heteroalkyl, alkenyl, alkynyl, cycloalkyl, heterocycloalkyl, aryl, heteroaryl, or alkylene is optionally substituted with one or more R. In some embodiments, $R^8$ is hydrogen or $C_1$-$C_6$alkyl. Alternatively, in any of the above embodiments, two $R^8$ on the same atom are taken together with the atom to which they are attached to form a heterocycloalkyl optionally substituted with one or more R.

In any of the above embodiments, each R is independently halogen, —CN, —OH, oxo, —$SF_5$, —SH, —S(═O)$C_1$-$C_3$alkyl, —S(═O)$_2C_1$-$C_3$alkyl, —S(═O)$_2NH_2$, —S(═O)$_2$$NHC_1$-$C_3$alkyl, —S(═O)$_2$N($C_1$-$C_3$alkyl)$_2$, —S(═O)(═$NC_1$-$C_3$alkyl)($C_1$-$C_3$alkyl), —$NH_2$, —$NHC_1$-$C_3$alkyl, —N($C_1$-$C_3$alkyl)$_2$, —N═S(═O)($C_1$-$C_3$alkyl)$_2$, —C(═O)$C_1$-$C_3$alkyl, —C(═O)OH, —C(═O)$OC_1$-$C_3$alkyl, —C(═O)$NH_2$, —C(═O)$NHC_1$-$C_3$alkyl, —C(═O)N($C_1$-$C_3$alkyl)$_2$, —P(═O)($C_1$-$C_3$alkyl)$_2$, $C_1$-$C_3$alkyl, $C_1$-$C_3$alkoxy, $C_1$-$C_3$haloalkyl, $C_1$-$C_3$haloalkoxy, $C_1$-$C_3$hydroxyalkyl, $C_1$-$C_3$aminoalkyl, $C_1$-$C_3$heteroalkyl, or $C_3$-$C_6$cycloalkyl. In some embodiments, R is halogen, —CN, —OH, oxo, —$SF_5$, —SH, —$NH_2$, —$NHC_1$-$C_3$alkyl, —N($C_1$-$C_3$alkyl)$_2$, $C_1$-$C_3$alkyl, $C_1$-$C_3$alkoxy, $C_1$-$C_3$haloalkyl, $C_1$-$C_3$haloalkoxy, $C_1$-$C_3$hydroxyalkyl, $C_1$-$C_3$aminoalkyl, $C_1$-$C_3$heteroalkyl, or $C_3$-$C_6$cycloalkyl. In some embodiments, R is halogen, —CN, —OH, oxo, —$NH_2$, —$NHC_1$-$C_3$alkyl, —N($C_1$-$C_3$alkyl)$_2$, $C_1$-$C_3$alkyl, $C_1$-$C_3$alkoxy, $C_1$-$C_3$haloalkyl, $C_1$-$C_3$haloalkoxy, $C_1$-$C_3$hydroxyalkyl, $C_1$-$C_3$aminoalkyl, $C_1$-$C_3$heteroalkyl, or $C_3$-$C_6$cycloalkyl. In some embodiments, R is halogen, —CN, $C_1$-$C_3$alkyl, or $C_3$-$C_6$cycloalkyl. In some embodiments, R is halogen, $C_1$-$C_3$alkyl, or $C_3$-$C_6$cycloalkyl. In some embodiments, R is halogen or —$C_1$-$C_3$alkyl.

Any combination of the groups described above for the various variables is contemplated herein. Throughout the specification, groups and substituents thereof are chosen by one skilled in the field to provide stable moieties and compounds.

In some embodiments, disclosed herein is a compound, or a pharmaceutically acceptable salt thereof, selected from the compound provided in Table 1.

TABLE 1
| No. | Structure |
| --- | --- |
| EX01 | 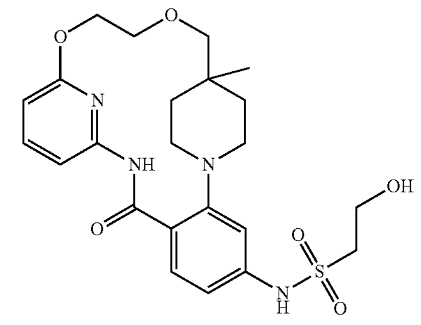 [SMILES: CC12CCN(CC1)c1cc(NS(=O)(=O)CCO)ccc1C(=O)Nc1cccc(n1)OCCOC2] |
| EX02 | 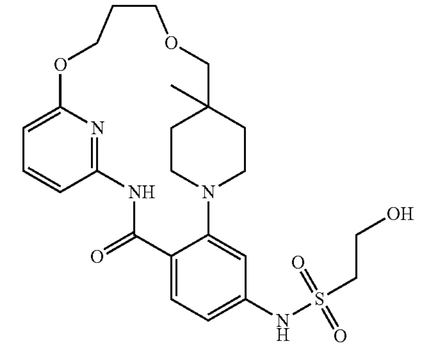 [SMILES: CC12CCN(CC1)c1cc(NS(=O)(=O)CCO)ccc1C(=O)Nc1cccc(n1)OCCCOC2] |
| EX03 | 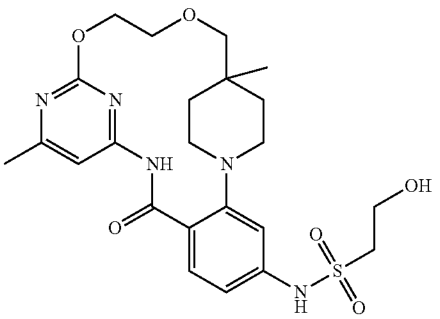 [SMILES: Cc1cc2nc(n1)OCCOCC1(C)CCN(CC1)c1cc(NS(=O)(=O)CCO)ccc1C(=O)N2] |
| EX04 | 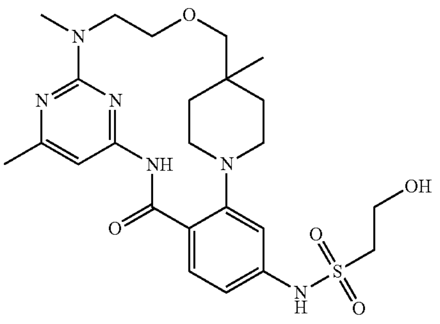 [SMILES: Cc1cc2nc(n1)N(C)CCOCC1(C)CCN(CC1)c1cc(NS(=O)(=O)CCO)ccc1C(=O)N2] |
TABLE 1-continued
| No. | Structure |
| --- | --- |
| EX05 | 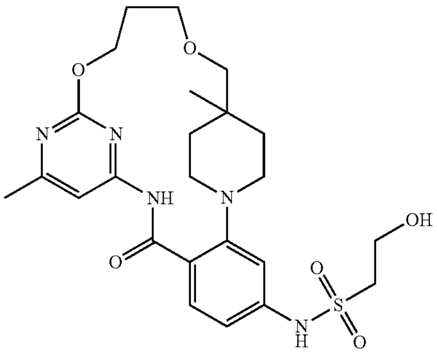 [SMILES: Cc1cc2nc(n1)OCCCOCC1(C)CCN(CC1)c1cc(NS(=O)(=O)CCO)ccc1C(=O)N2] |
| EX06 | 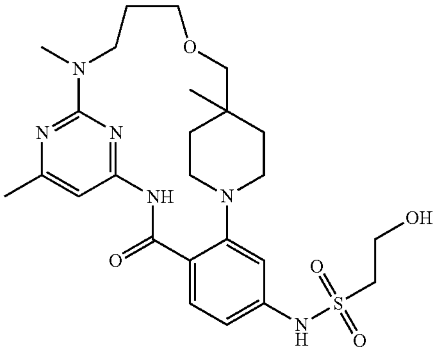 [SMILES: Cc1cc2nc(n1)N(C)CCCOCC1(C)CCN(CC1)c1cc(NS(=O)(=O)CCO)ccc1C(=O)N2] |
| EX07 | 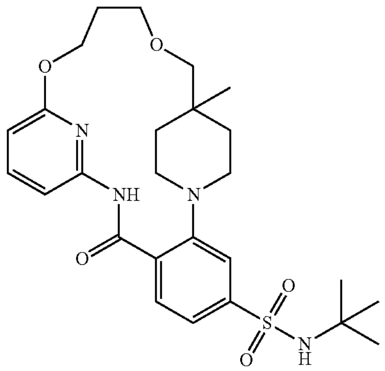 [SMILES: CC12CCN(CC1)c1cc(S(=O)(=O)NC(C)(C)C)ccc1C(=O)Nc1cccc(n1)OCCCOC2] |
| EX08 | 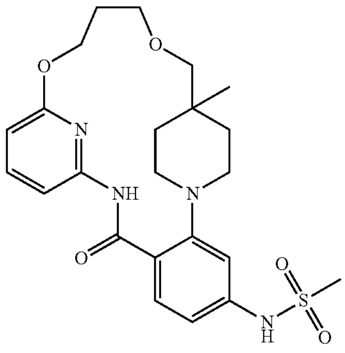 [SMILES: CC12CCN(CC1)c1cc(NS(C)(=O)=O)ccc1C(=O)Nc1cccc(n1)OCCCOC2] |

TABLE 1-continued
| No. | Structure |
|---|---|
| EX09 | 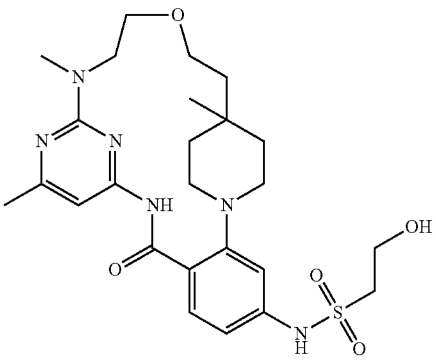 [SMILES: Cc1cc2nc(n1)N(C)CCOCCC1(C)CCN(CC1)c1cc(NS(=O)(=O)CCO)ccc1C(=O)N2] |
| EX10 | 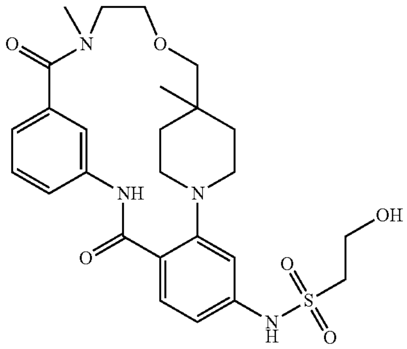 [SMILES: CN1CCOCC2(C)CCN(CC2)c2cc(NS(=O)(=O)CCO)ccc2C(=O)Nc2cccc(c2)C1=O] |
| EX11 | 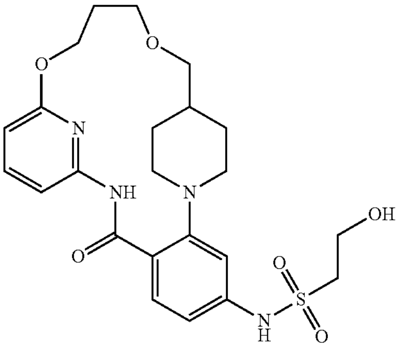 [SMILES: O=C1Nc2cccc(n2)OCCCOCC2CCN(CC2)c2cc(NS(=O)(=O)CCO)ccc21] |
| EX12 | 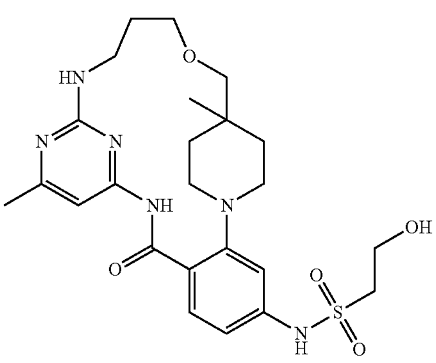 [SMILES: Cc1cc2nc(n1)NCCCOCC1(C)CCN(CC1)c1cc(NS(=O)(=O)CCO)ccc1C(=O)N2] |
TABLE 1-continued
| No. | Structure |
|---|---|
| EX13 | 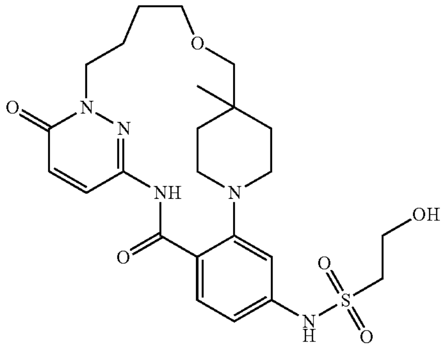 [SMILES: CC12CCN(CC1)c1cc(NS(=O)(=O)CCO)ccc1C(=O)Nc1ccc(=O)n(n1)CCCCOC2] |
| EX14 | 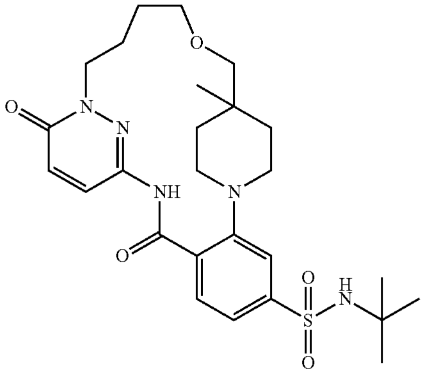 [SMILES: CC12CCN(CC1)c1cc(S(=O)(=O)NC(C)(C)C)ccc1C(=O)Nc1ccc(=O)n(n1)CCCCOC2] |
| EX15 | 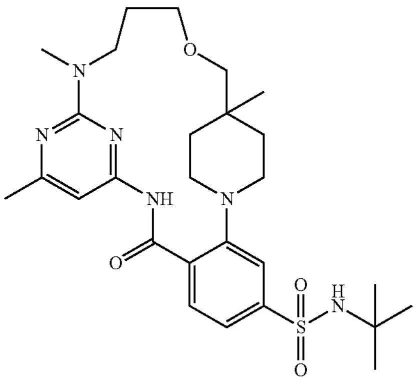 [SMILES: Cc1cc2nc(n1)N(C)CCCOCC1(C)CCN(CC1)c1cc(S(=O)(=O)NC(C)(C)C)ccc1C(=O)N2] |
| EX16 | 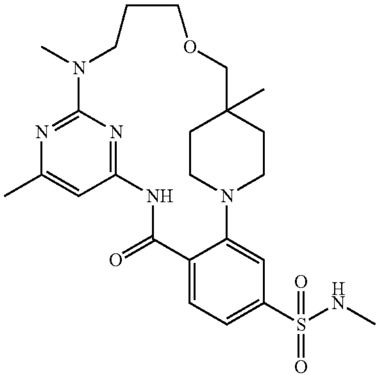 |

TABLE 1-continued
| No. | Structure |
|---|---|
| EX17 | 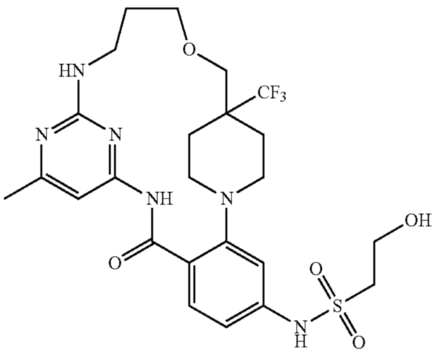 [SMILES: Cc1cc2nc(n1)NCCCOCC1(C(F)(F)F)CCN(CC1)c1cc(NS(=O)(=O)CCO)ccc1C(=O)N2] |
| EX18 | 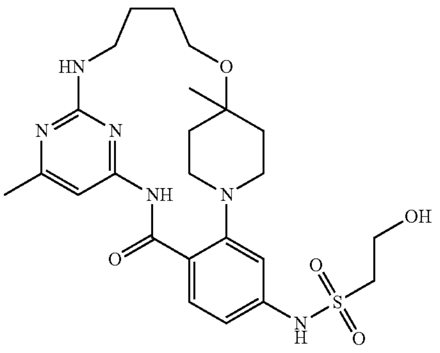 [SMILES: Cc1cc2nc(n1)NCCCCOC1(C)CCN(CC1)c1cc(NS(=O)(=O)CCO)ccc1C(=O)N2] |
| EX19 | 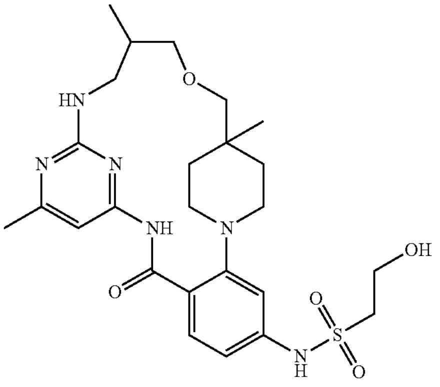 [SMILES: Cc1cc2nc(n1)NCC(C)COCC1(C)CCN(CC1)c1cc(NS(=O)(=O)CCO)ccc1C(=O)N2] |
| EX20 | 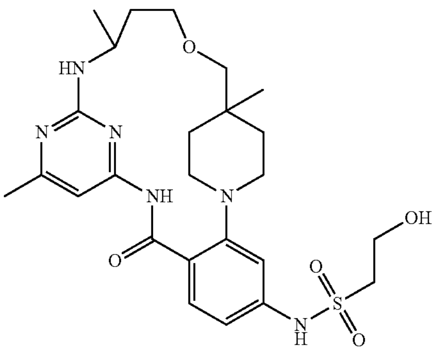 [SMILES: Cc1cc2nc(n1)NC(C)CCOCC1(C)CCN(CC1)c1cc(NS(=O)(=O)CCO)ccc1C(=O)N2] |
TABLE 1-continued
| No. | Structure |
|---|---|
| EX21 | 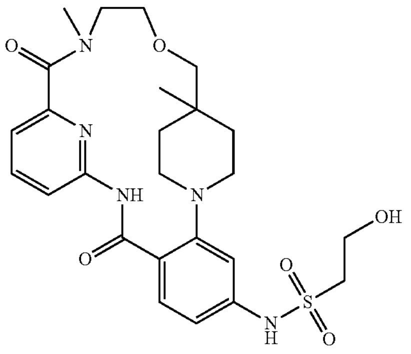 [SMILES: CN1CCOCC2(C)CCN(CC2)c2cc(NS(=O)(=O)CCO)ccc2C(=O)Nc2cccc(n2)C1=O] |
| EX22 | 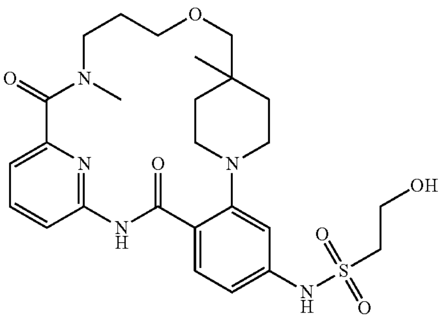 [SMILES: CN1CCCOCC2(C)CCN(CC2)c2cc(NS(=O)(=O)CCO)ccc2C(=O)Nc2cccc(n2)C1=O] |
| EX23 | 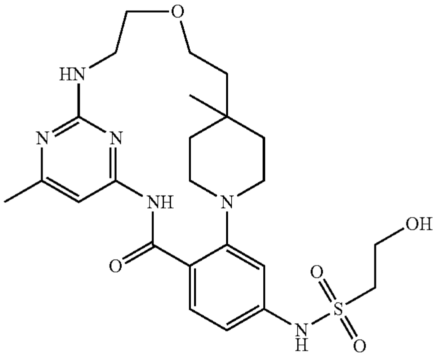 [SMILES: Cc1cc2nc(n1)NCCOCCC1(C)CCN(CC1)c1cc(NS(=O)(=O)CCO)ccc1C(=O)N2] |
| EX24 | 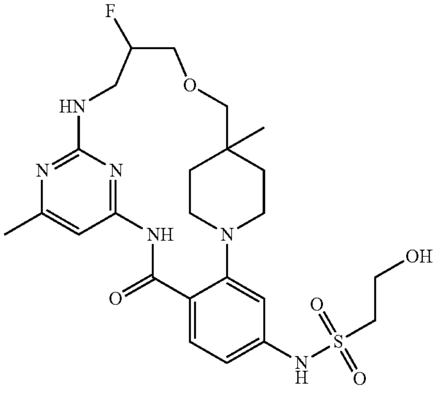 [SMILES: Cc1cc2nc(n1)NCC(F)COCC1(C)CCN(CC1)c1cc(NS(=O)(=O)CCO)ccc1C(=O)N2] |

TABLE 1-continued
| No. | Structure |
|---|---|
| EX25 | 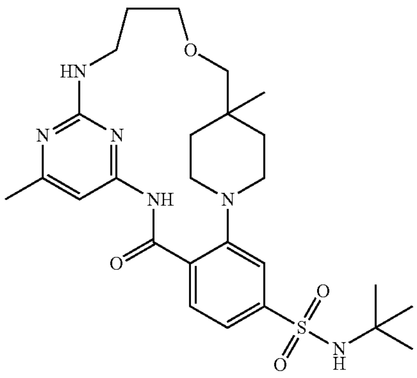 [SMILES: Cc1cc2nc(n1)NCCCOCC1(C)CCN(CC1)c1cc(S(=O)(=O)NC(C)(C)C)ccc1C(=O)N2] |
| EX25-A | 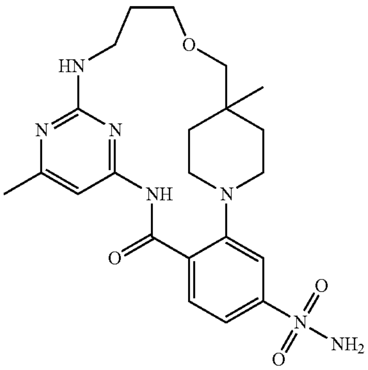 |
| EX26 | 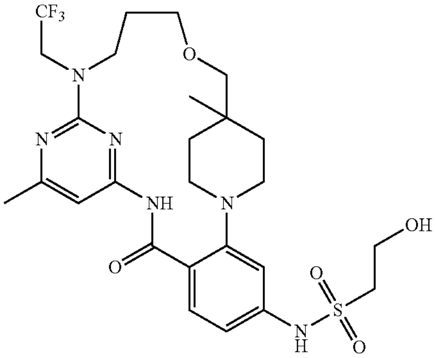 [SMILES: Cc1cc2nc(n1)N(CC(F)(F)F)CCCOCC1(C)CCN(CC1)c1cc(NS(=O)(=O)CCO)ccc1C(=O)N2] |
| EX27 | 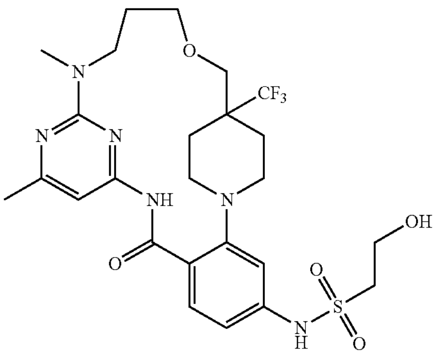 [SMILES: Cc1cc2nc(n1)N(C)CCCOCC1(C(F)(F)F)CCN(CC1)c1cc(NS(=O)(=O)CCO)ccc1C(=O)N2] |
TABLE 1-continued
| No. | Structure |
|---|---|
| EX28 | 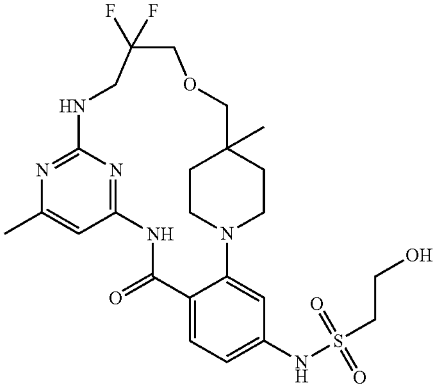 [SMILES: Cc1cc2nc(n1)NCC(F)(F)COCC1(C)CCN(CC1)c1cc(NS(=O)(=O)CCO)ccc1C(=O)N2] |
| EX29 | 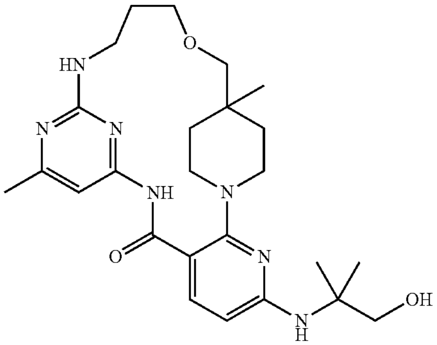 [SMILES: Cc1cc2nc(n1)NCCCOCC1(C)CCN(CC1)c1nc(NC(C)(C)CO)ccc1C(=O)N2] |
| EX30 | 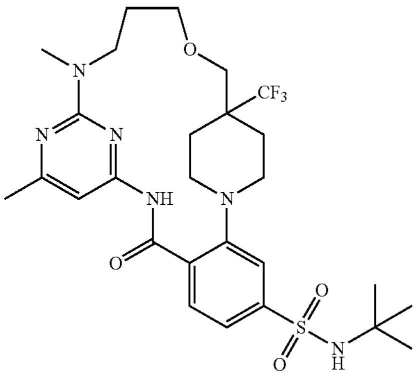 [SMILES: Cc1cc2nc(n1)N(C)CCCOCC1(C(F)(F)F)CCN(CC1)c1cc(S(=O)(=O)NC(C)(C)C)ccc1C(=O)N2] |
| EX31 | 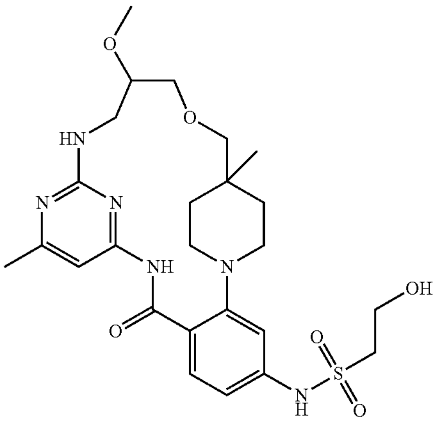 [SMILES: COC1CNc2nc(C)cc(n2)NC(=O)c2ccc(NS(=O)(=O)CCO)cc2N2CCC(C)(CC2)COC1] |

TABLE 1-continued
| No. | Structure |
|---|---|
| EX32-A and EX32-B | 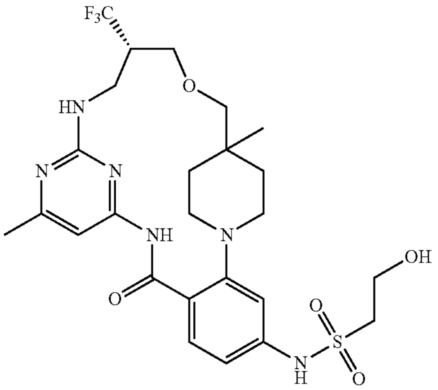 + 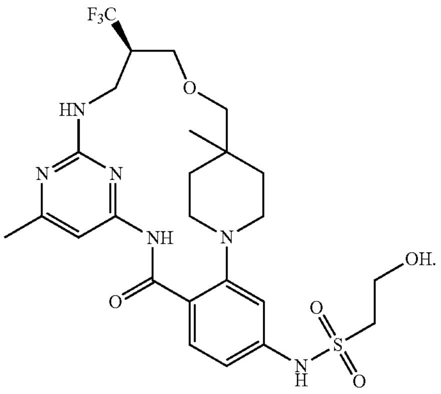 [SMILES: Cc1cc2nc(n1)NC[C@@H](C(F)(F)F)COCC1(C)CCN(CC1)c1cc(NS(=O)(=O)CCO)ccc1C(=O)N2] |
| EX33-A and EX33-B | 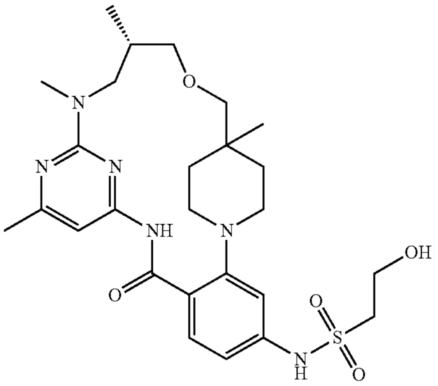 + |
TABLE 1-continued
| No. | Structure |
|---|---|
| | 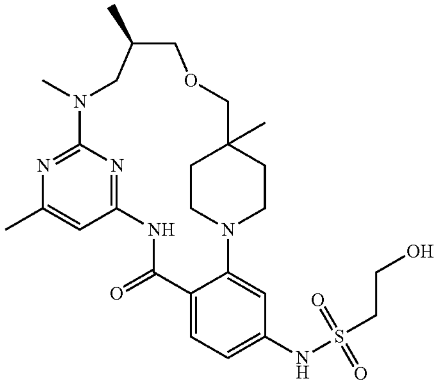 [SMILES: Cc1cc2nc(n1)N(C)C[C@@H](C)COCC1(C)CCN(CC1)c1cc(NS(=O)(=O)CCO)ccc1C(=O)N2] |
| EX34 | 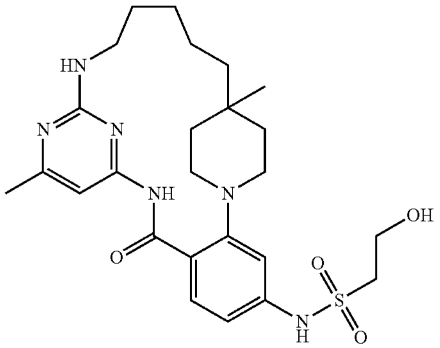 [SMILES: Cc1cc2nc(n1)NCCCCCC1(C)CCN(CC1)c1cc(NS(=O)(=O)CCO)ccc1C(=O)N2] |
| EX35 | 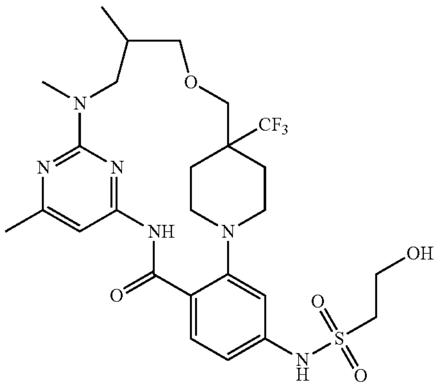 [SMILES: Cc1cc2nc(n1)N(C)CC(C)COCC1(C(F)(F)F)CCN(CC1)c1cc(NS(=O)(=O)CCO)ccc1C(=O)N2] |
| EX36-A and EX36-B | 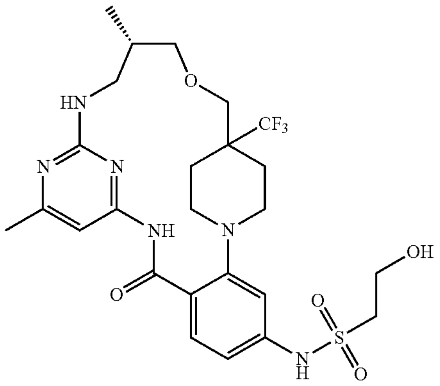 + |

TABLE 1-continued
| No. | Structure |
|---|---|
| | 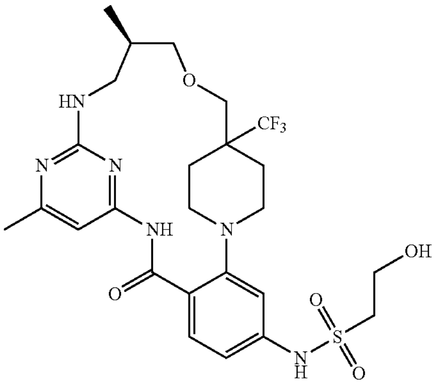 [SMILES: Cc1cc2nc(n1)NC[C@@H](C)COCC1(C(F)(F)F)CCN(CC1)c1cc(NS(=O)(=O)CCO)ccc1C(=O)N2] |
| EX37 | 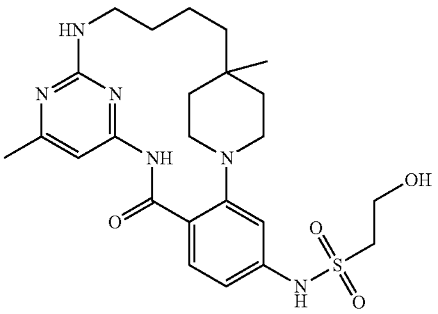 [SMILES: Cc1cc2nc(n1)NCCCCC1(C)CCN(CC1)c1cc(NS(=O)(=O)CCO)ccc1C(=O)N2] |
| EX38 | 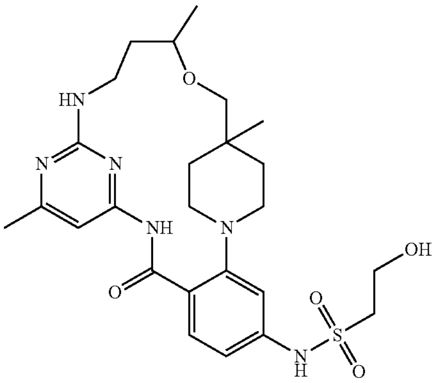 [SMILES: Cc1cc2nc(n1)NCCC(C)OCC1(C)CCN(CC1)c1cc(NS(=O)(=O)CCO)ccc1C(=O)N2] |
| EX39 | 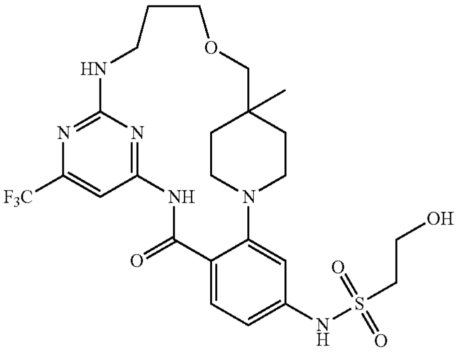 [SMILES: CC12CCN(CC1)c1cc(NS(=O)(=O)CCO)ccc1C(=O)Nc1cc(C(F)(F)F)nc(n1)NCCCOC2] |
TABLE 1-continued
| No. | Structure |
|---|---|
| EX40 | 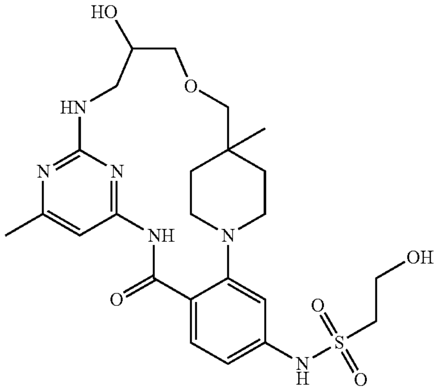 [SMILES: Cc1cc2nc(n1)NCC(O)COCC1(C)CCN(CC1)c1cc(NS(=O)(=O)CCO)ccc1C(=O)N2] |
| EX41 | 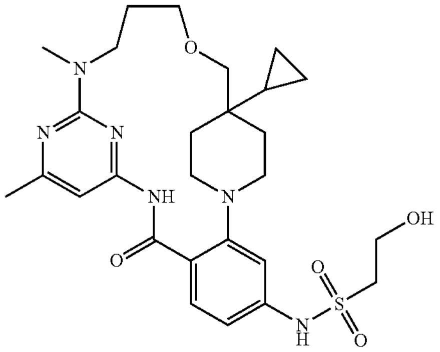 [SMILES: Cc1cc2nc(n1)N(C)CCCOCC1(C3CC3)CCN(CC1)c1cc(NS(=O)(=O)CCO)ccc1C(=O)N2] |
| EX42 | 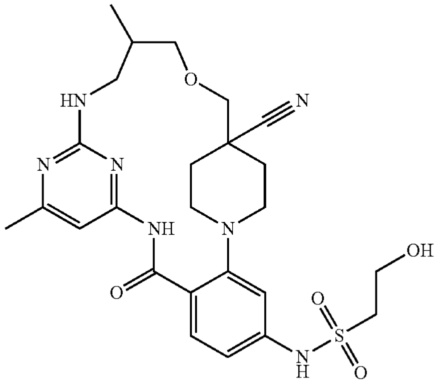 [SMILES: Cc1cc2nc(n1)NCC(C)COCC1(C#N)CCN(CC1)c1cc(NS(=O)(=O)CCO)ccc1C(=O)N2] |
| EX43 | 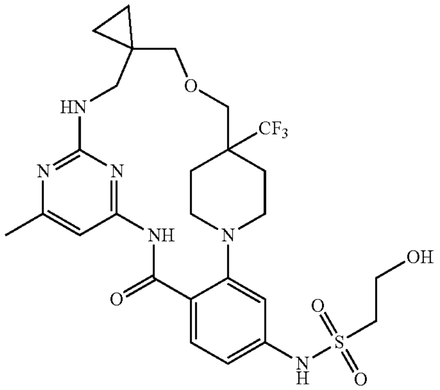 [SMILES: Cc1cc2nc(n1)NCC1(CC1)COCC1(C(F)(F)F)CCN(CC1)c1cc(NS(=O)(=O)CCO)ccc1C(=O)N2] |

TABLE 1-continued
| No. | Structure |
| --- | --- |
| EX44 | 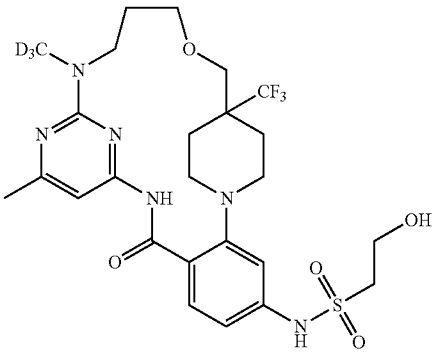 [SMILES: [2H]C([2H])([2H])N1CCCOCC2(C(F)(F)F)CCN(CC2)c2cc(NS(=O)(=O)CCO)ccc2C(=O)Nc2cc(C)nc1n2] |
| EX45 | 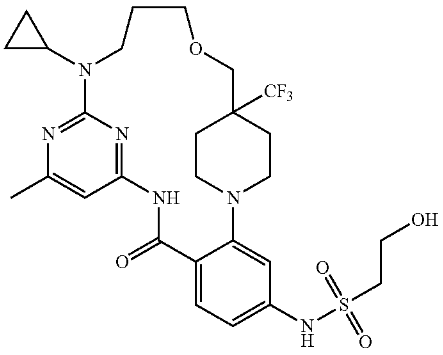 [SMILES: Cc1cc2nc(n1)N(C1CC1)CCCOCC1(C(F)(F)F)CCN(CC1)c1cc(NS(=O)(=O)CCO)ccc1C(=O)N2] |
| EX46-A and EX46-B | 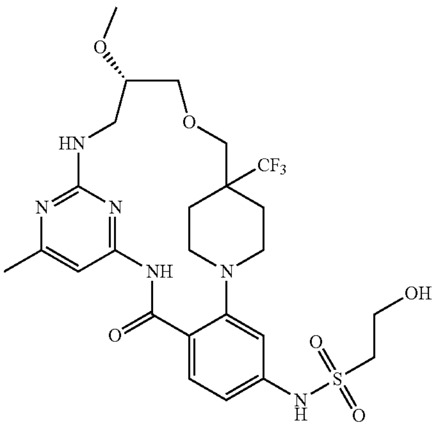 + 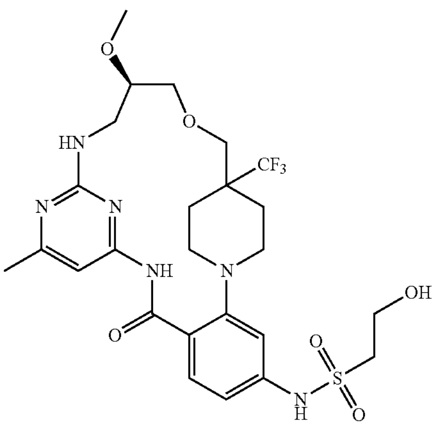 [SMILES: CO[C@@H]1CNc2nc(C)cc(n2)NC(=O)c2ccc(NS(=O)(=O)CCO)cc2N2CCC(C(F)(F)F)(CC2)COC1] |
| EX47 | 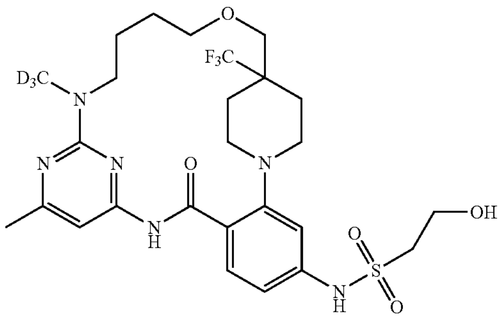 [SMILES: [2H]C([2H])([2H])N1CCCCOCC2(C(F)(F)F)CCN(CC2)c2cc(NS(=O)(=O)CCO)ccc2C(=O)Nc2cc(C)nc1n2] |
| EX48 | 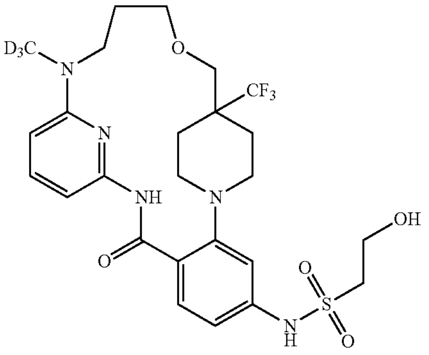 [SMILES: [2H]C([2H])([2H])N1CCCOCC2(C(F)(F)F)CCN(CC2)c2cc(NS(=O)(=O)CCO)ccc2C(=O)Nc2cccc1n2] |
| EX49 | 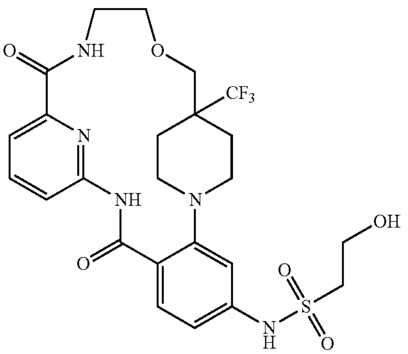 [SMILES: O=C1NCCOCC2(C(F)(F)F)CCN(CC2)c2cc(NS(=O)(=O)CCO)ccc2C(=O)Nc2cccc1n2] |
| EX50 | 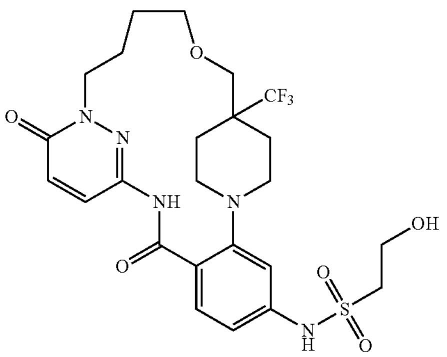 |

TABLE 1-continued
| No. | Structure |
|---|---|
| EX51 | 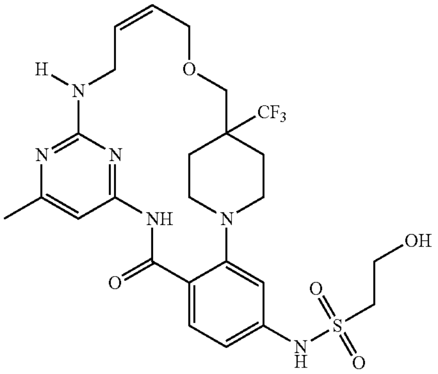 [SMILES: Cc1cc2nc(n1)NC/C=C\COCC1(C(F)(F)F)CCN(CC1)c1cc(NS(=O)(=O)CCO)ccc1C(=O)N2] |
| EX52 | 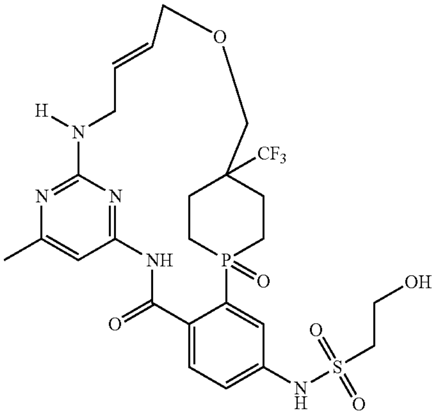 [SMILES: Cc1cc2nc(n1)NC/C=C/COCC1(C(F)(F)F)CCP(=O)(CC1)c1cc(NS(=O)(=O)CCO)ccc1C(=O)N2] |
| EX53 | 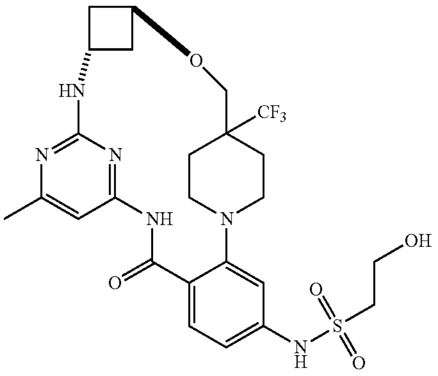 |
| EX54 | 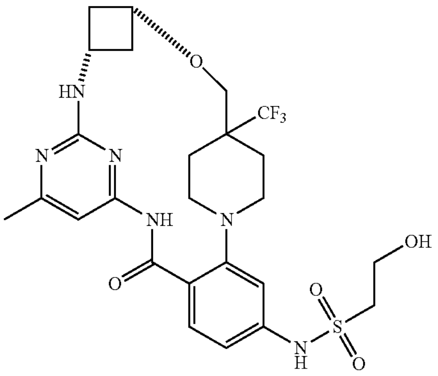 |
TABLE 1-continued
| No. | Structure |
|---|---|
| EX55 | 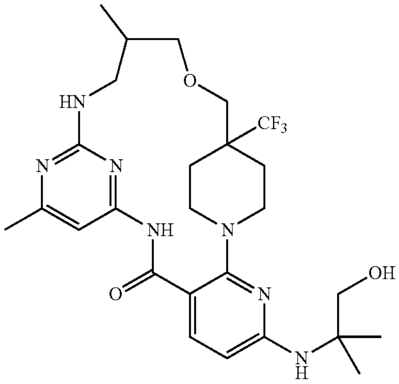 [SMILES: Cc1cc2nc(n1)NCC(C)COCC1(C(F)(F)F)CCN(CC1)c1nc(NC(C)(C)CO)ccc1C(=O)N2] |
| EX56 | 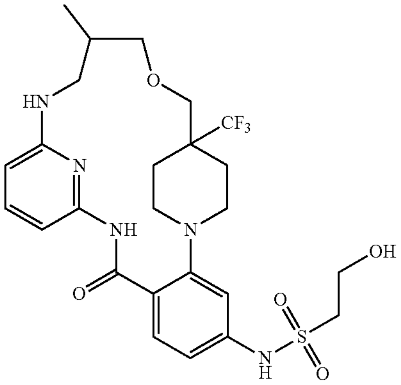 [SMILES: CC1CNc2cccc(n2)NC(=O)c2ccc(NS(=O)(=O)CCO)cc2N2CCC(C(F)(F)F)(CC2)COC1] |
| EX56-A and EX56-B | 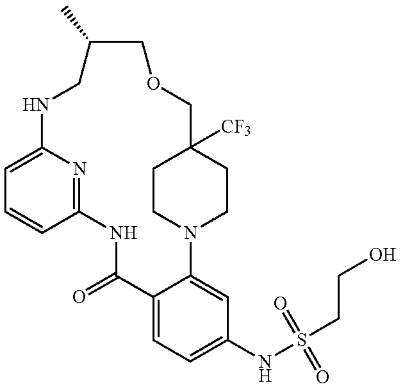 + 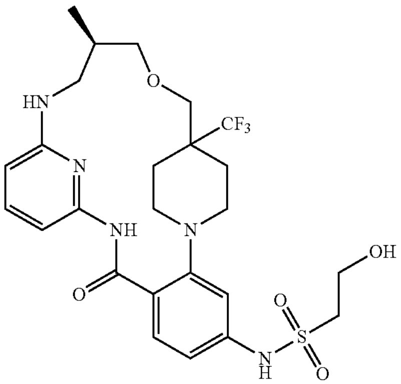 [SMILES: C[C@@H]1CNc2cccc(n2)NC(=O)c2ccc(NS(=O)(=O)CCO)cc2N2CCC(C(F)(F)F)(CC2)COC1] |

TABLE 1-continued
| No. | Structure |
|---|---|
| EX57 | 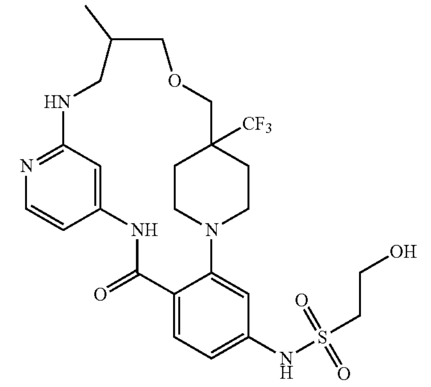 [SMILES: CC1CNc2cc(ccn2)NC(=O)c2ccc(NS(=O)(=O)CCO)cc2N2CCC(C(F)(F)F)(CC2)COC1] |
| EX58 | 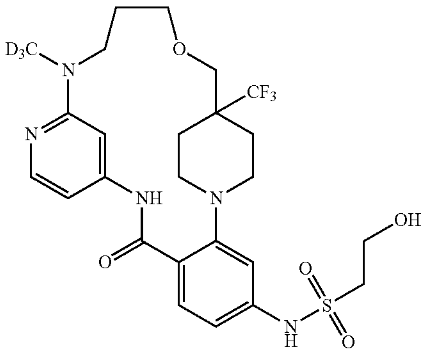 [SMILES: [2H]C([2H])([2H])N1CCCOCC2(C(F)(F)F)CCN(CC2)c2cc(NS(=O)(=O)CCO)ccc2C(=O)Nc2ccnc1c2] |
| EX59 | 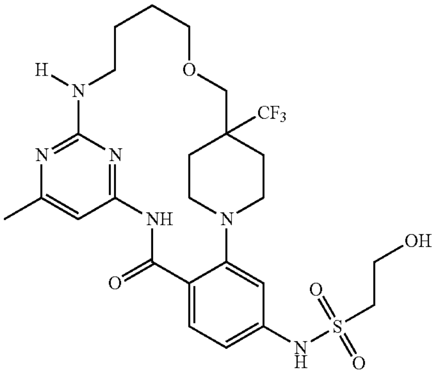 [SMILES: Cc1cc2nc(n1)NCCCCOCC1(C(F)(F)F)CCN(CC1)c1cc(NS(=O)(=O)CCO)ccc1C(=O)N2] |
| EX60 | 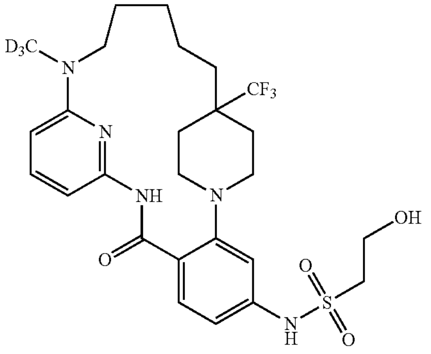 [SMILES: [2H]C([2H])([2H])N1CCCCCC2(C(F)(F)F)CCN(CC2)c2cc(NS(=O)(=O)CCO)ccc2C(=O)Nc2cccc1n2] |
TABLE 1-continued
| No. | Structure |
|---|---|
| EX61 | 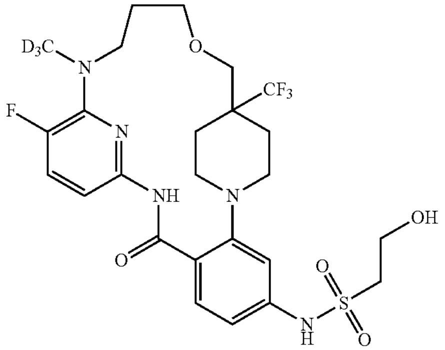 [SMILES: [2H]C([2H])([2H])N1CCCOCC2(C(F)(F)F)CCN(CC2)c2cc(NS(=O)(=O)CCO)ccc2C(=O)Nc2ccc(F)c1n2] |
| EX62 | 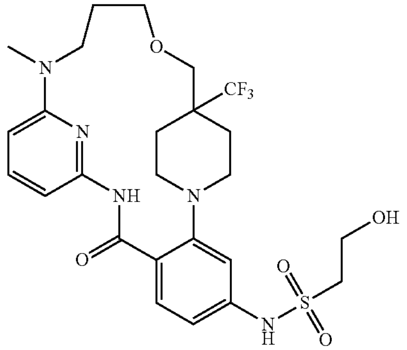 [SMILES: CN1CCCOCC2(C(F)(F)F)CCN(CC2)c2cc(NS(=O)(=O)CCO)ccc2C(=O)Nc2cccc1n2] |
| EX63 | 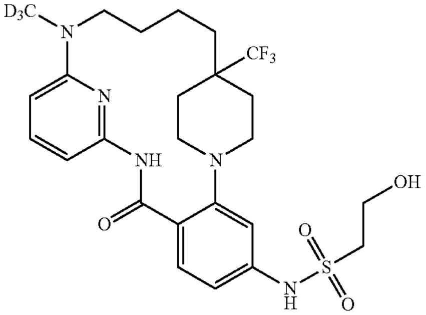 [SMILES: [2H]C([2H])([2H])N1CCCCC2(C(F)(F)F)CCN(CC2)c2cc(NS(=O)(=O)CCO)ccc2C(=O)Nc2cccc1n2] |
| EX64 | 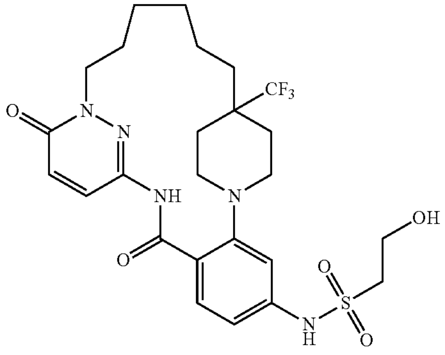 [SMILES: O=C1Nc2ccc(=O)n(n2)CCCCCCC2(C(F)(F)F)CCN(CC2)c2cc(NS(=O)(=O)CCO)ccc21] |

TABLE 1-continued
| No. | Structure |
|---|---|
| EX65 | 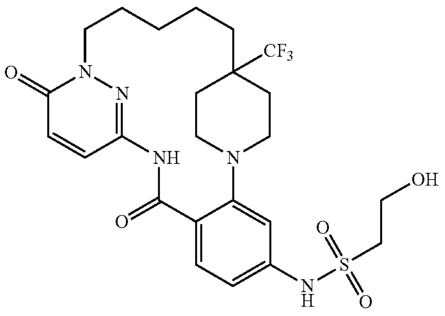 [SMILES: O=C1Nc2ccc(=O)n(n2)CCCCCC2(C(F)(F)F)CCN(CC2)c2cc(NS(=O)(=O)CCO)ccc21] |
| EX66 | 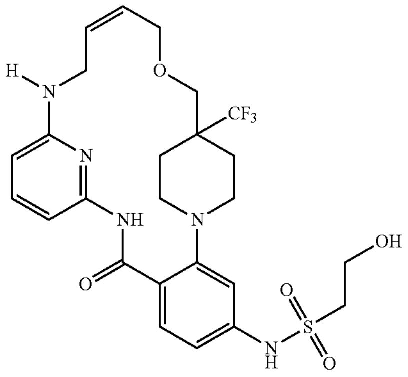 [SMILES: O=C1Nc2cccc(n2)NC/C=C\COCC2(C(F)(F)F)CCN(CC2)c2cc(NS(=O)(=O)CCO)ccc21] |
| EX67 | 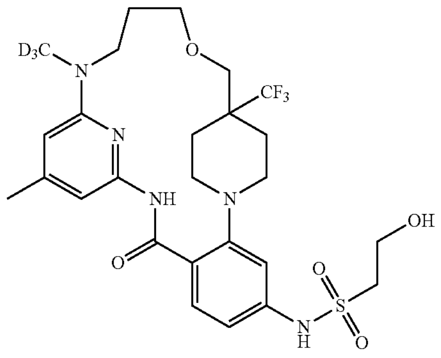 [SMILES: [2H]C([2H])([2H])N1CCCOCC2(C(F)(F)F)CCN(CC2)c2cc(NS(=O)(=O)CCO)ccc2C(=O)Nc2cc(C)cc1n2] |
| EX68 | 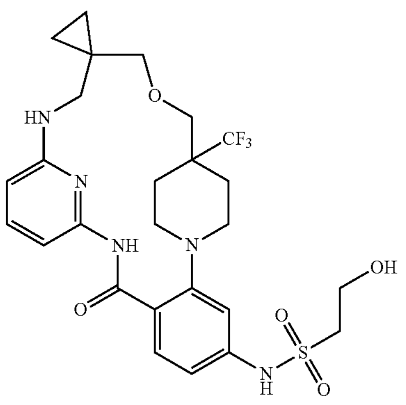 [SMILES: O=C1Nc2cccc(n2)NCC2(CC2)COCC2(C(F)(F)F)CCN(CC2)c2cc(NS(=O)(=O)CCO)ccc21] |
| EX69 | 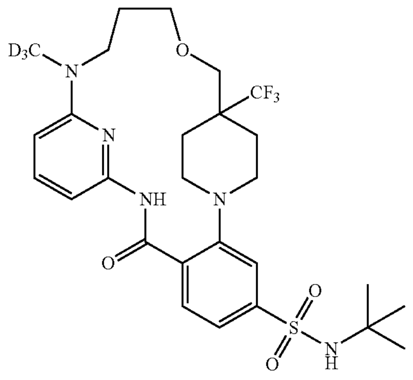 [SMILES: [2H]C([2H])([2H])N1CCCOCC2(C(F)(F)F)CCN(CC2)c2cc(S(=O)(=O)NC(C)(C)C)ccc2C(=O)Nc2cccc1n2] |
| EX70 | 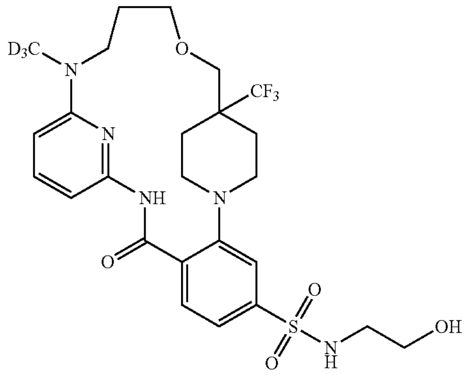 [SMILES: [2H]C([2H])([2H])N1CCCOCC2(C(F)(F)F)CCN(CC2)c2cc(S(=O)(=O)NCCO)ccc2C(=O)Nc2cccc1n2] |
| EX71 | 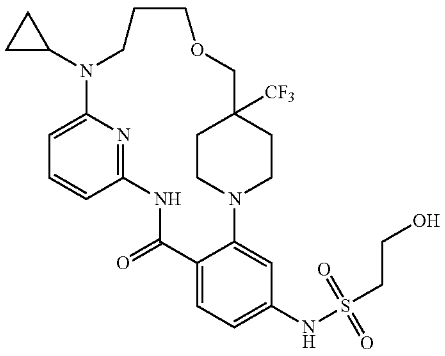 [SMILES: O=C1Nc2cccc(n2)N(C2CC2)CCCOCC2(C(F)(F)F)CCN(CC2)c2cc(NS(=O)(=O)CCO)ccc21] |
| EX72 | 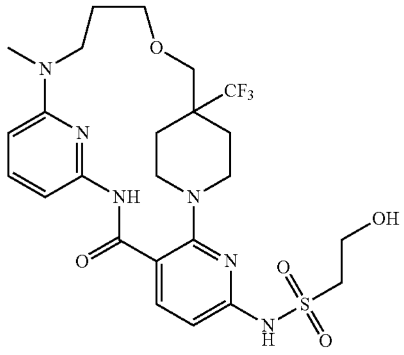 [SMILES: CN1CCCOCC2(C(F)(F)F)CCN(CC2)c2nc(NS(=O)(=O)CCO)ccc2C(=O)Nc2cccc1n2] |

TABLE 1-continued
| No. | Structure |
|---|---|
| EX73 | 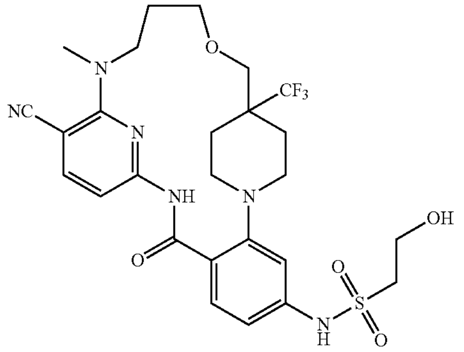 [SMILES: CN1CCCOCC2(C(F)(F)F)CCN(CC2)c2cc(NS(=O)(=O)CCO)ccc2C(=O)Nc2ccc(C#N)c1n2] |
| EX74 | 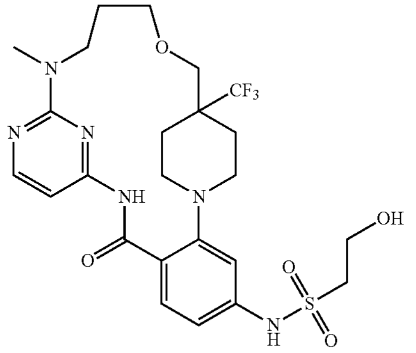 |
| EX75 | 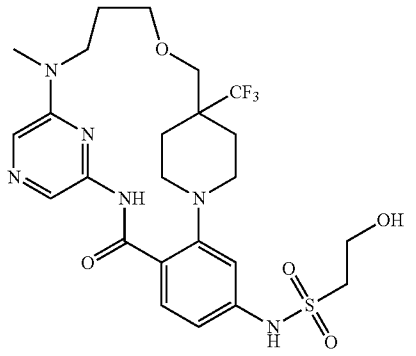 [SMILES: CN1CCCOCC2(C(F)(F)F)CCN(CC2)c2cc(NS(=O)(=O)CCO)ccc2C(=O)Nc2cncc1n2] |
| EX76-A and EX76-B | 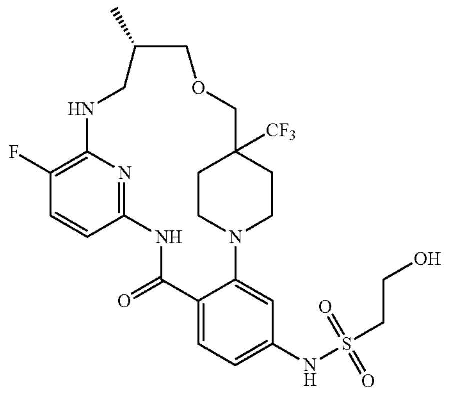 + |
TABLE 1-continued
| No. | Structure |
|---|---|
| | 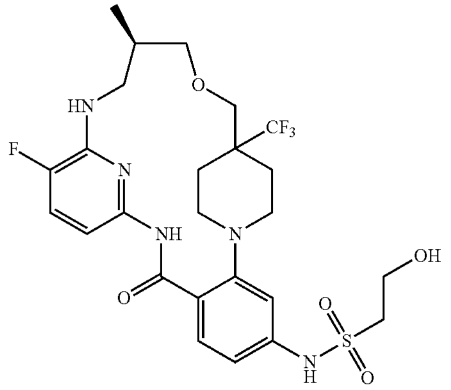 [SMILES: C[C@@H]1CNc2nc(ccc2F)NC(=O)c2ccc(NS(=O)(=O)CCO)cc2N2CCC(C(F)(F)F)(CC2)COC1] |
| EX77 | 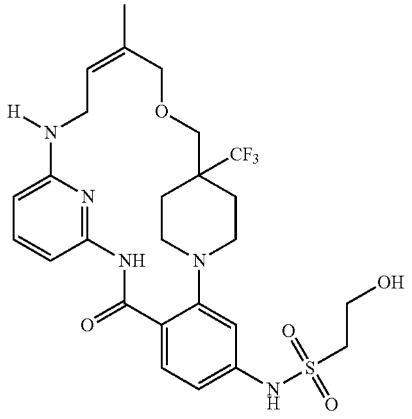 [SMILES: C/C1=C/CNc2cccc(n2)NC(=O)c2ccc(NS(=O)(=O)CCO)cc2N2CCC(C(F)(F)F)(CC2)COC1] |
| EX78-A And EX78-B | 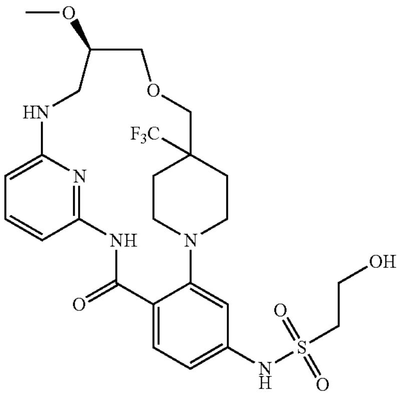 + |

TABLE 1-continued
| No. | Structure |
| --- | --- |
| | 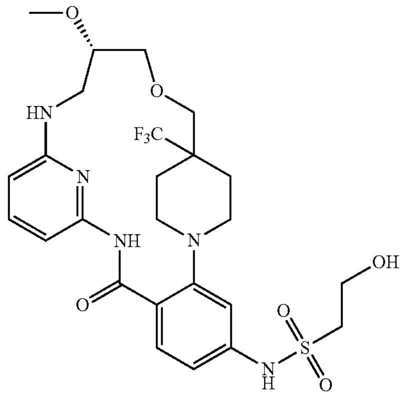 [SMILES: CO[C@H]1CNc2cccc(n2)NC(=O)c2ccc(NS(=O)(=O)CCO)cc2N2CCC(C(F)(F)F)(CC2)COC1] |
| EX79-A and EX79-B | 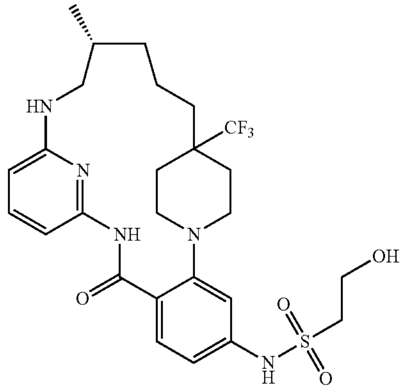 + 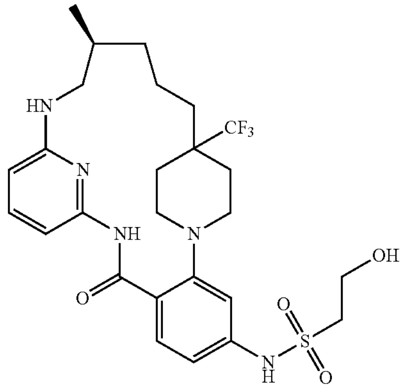 [SMILES: C[C@H]1CCCC2(C(F)(F)F)CCN(CC2)c2cc(NS(=O)(=O)CCO)ccc2C(=O)Nc2cccc(n2)NC1] |
| EX80 | 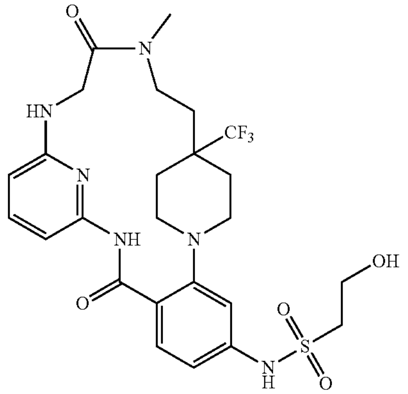 [SMILES: CN1CCC2(C(F)(F)F)CCN(CC2)c2cc(NS(=O)(=O)CCO)ccc2C(=O)Nc2cccc(n2)NCC1=O] |
TABLE 1-continued
| No. | Structure |
| --- | --- |
| EX81-A and EX81-B | 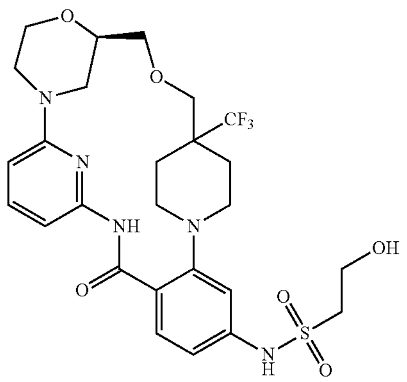 + 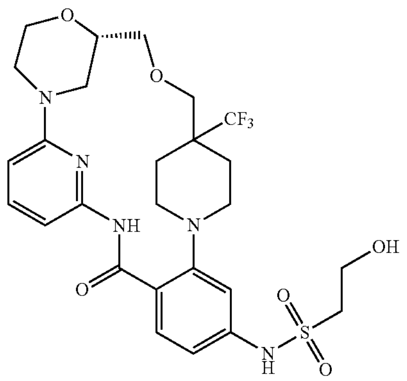 [SMILES: O=C1Nc2cccc(n2)N2CCO[C@H](COCC3(C(F)(F)F)CCN(CC3)c3cc(NS(=O)(=O)CCO)ccc31)C2] |
| EX82 | 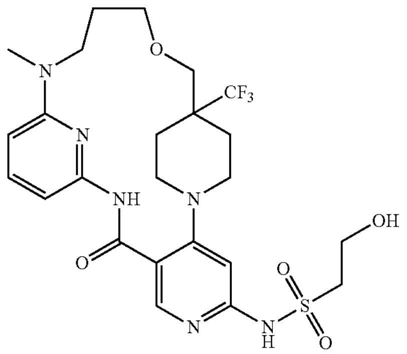 [SMILES: CN1CCCOCC2(C(F)(F)F)CCN(CC2)c2cc(NS(=O)(=O)CCO)ncc2C(=O)Nc2cccc1n2] |
| EX83 | 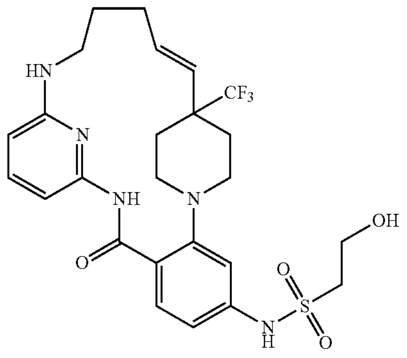 [SMILES: O=C1Nc2cccc(n2)NCCC/C=C/C2(C(F)(F)F)CCN(CC2)c2cc(NS(=O)(=O)CCO)ccc21] |

TABLE 1-continued
| No. | Structure |
|---|---|
| EX84-A And EX84-B | 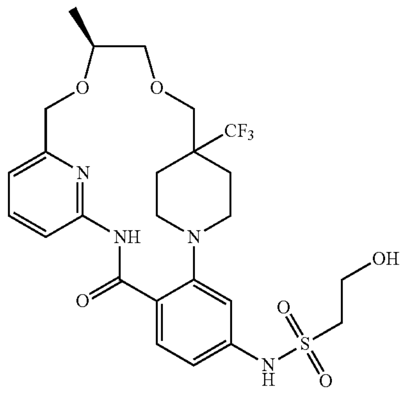 + 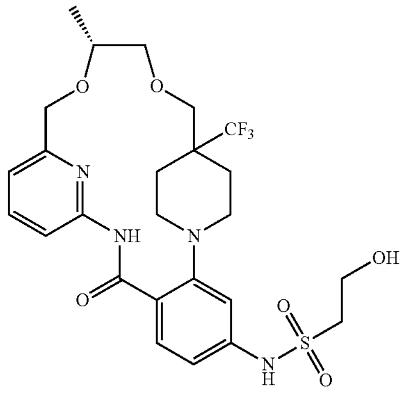 [SMILES: C[C@@H]1COCC2(C(F)(F)F)CCN(CC2)c2cc(NS(=O)(=O)CCO)ccc2C(=O)Nc2cccc(n2)CO1] |
| EX85-A And EX85-B | 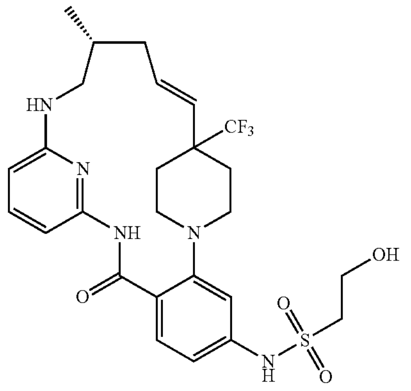 + |
TABLE 1-continued
| No. | Structure |
|---|---|
| | 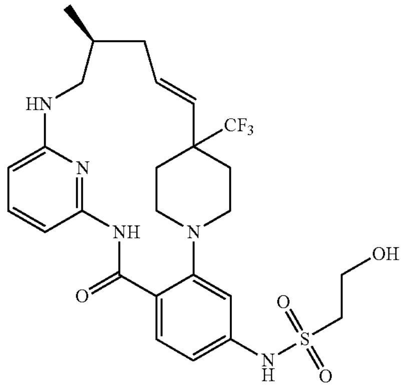 [SMILES: C[C@H]1C/C=C/C2(C(F)(F)F)CCN(CC2)c2cc(NS(=O)(=O)CCO)ccc2C(=O)Nc2cccc(n2)NC1] |
| EX86 | 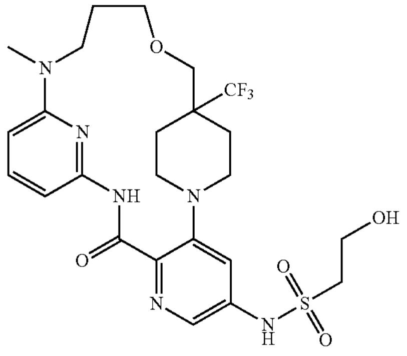 [SMILES: CN1CCCOCC2(C(F)(F)F)CCN(CC2)c2cc(NS(=O)(=O)CCO)cnc2C(=O)Nc2cccc1n2] |
| EX87 | 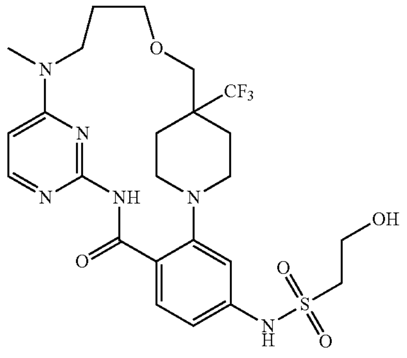 [SMILES: CN1CCCOCC2(C(F)(F)F)CCN(CC2)c2cc(NS(=O)(=O)CCO)ccc2C(=O)Nc2nccc1n2] |
| EX88-A And EX88-B | 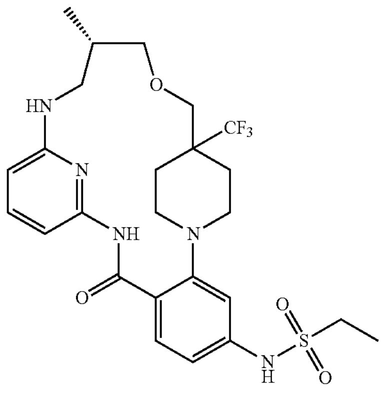 + |

TABLE 1-continued
| No. | Structure |
|---|---|
| | 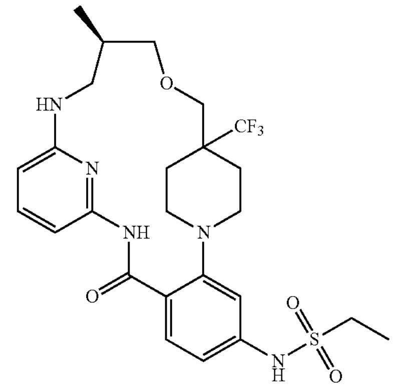 [SMILES: CCS(=O)(=O)Nc1ccc2c(c1)N1CCC(C(F)(F)F)(CC1)COC[C@H](C)CNc1cccc(n1)NC2=O] |
| EX89 | 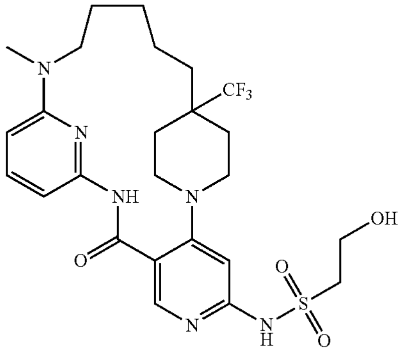 [SMILES: CN1CCCCCC2(C(F)(F)F)CCN(CC2)c2cc(NS(=O)(=O)CCO)ncc2C(=O)Nc2cccc1n2] |
| EX90 | 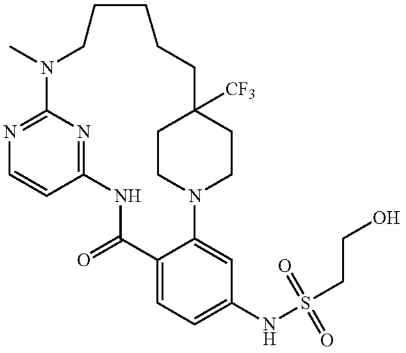 [SMILES: CN1CCCCCC2(C(F)(F)F)CCN(CC2)c2cc(NS(=O)(=O)CCO)ccc2C(=O)Nc2ccnc1n2] |
| EX91 | 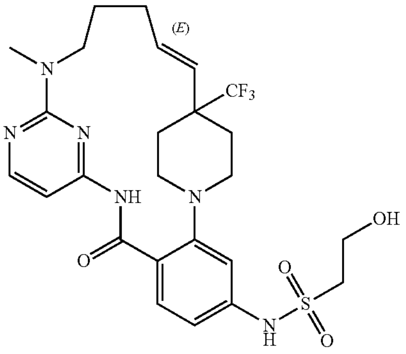 [SMILES: CN1CCC/C=C/C2(C(F)(F)F)CCN(CC2)c2cc(NS(=O)(=O)CCO)ccc2C(=O)Nc2ccnc1n2] |
TABLE 1-continued
| No. | Structure |
|---|---|
| EX92-A and EX92-B | 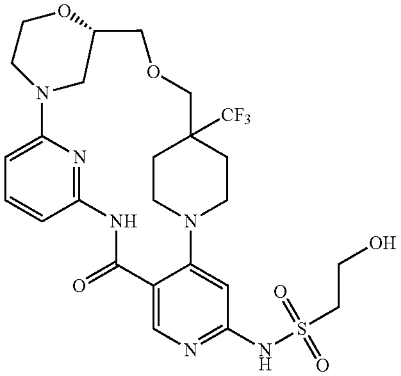 + 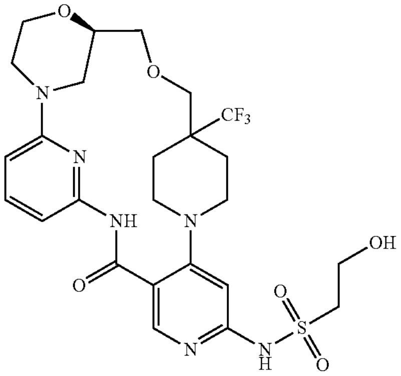 [SMILES: O=C1Nc2cccc(n2)N2CCO[C@@H](COCC3(C(F)(F)F)CCN(CC3)c3cc(NS(=O)(=O)CCO)ncc31)C2] |
| EX93-A and EX93-B | 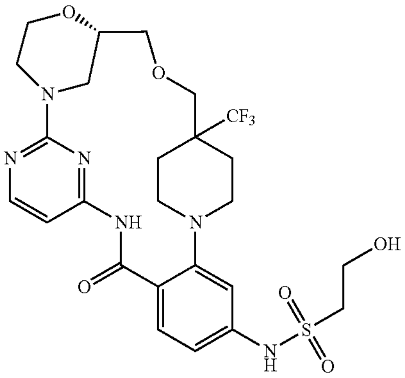 + 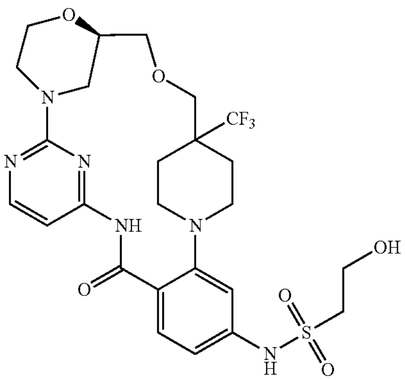 [SMILES: O=C1Nc2ccnc(n2)N2CCO[C@@H](COCC3(C(F)(F)F)CCN(CC3)c3cc(NS(=O)(=O)CCO)ccc31)C2] |

TABLE 1-continued
| No. | Structure |
|---|---|
| EX94 | 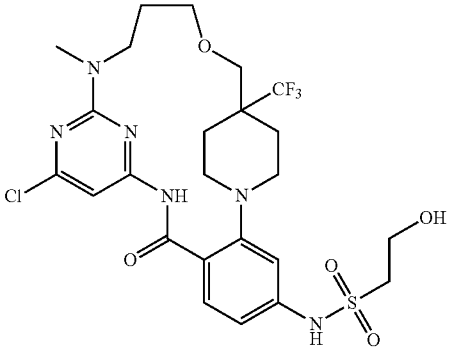 [SMILES: CN1CCCOCC2(C(F)(F)F)CCN(CC2)c2cc(NS(=O)(=O)CCO)ccc2C(=O)Nc2cc(Cl)nc1n2] |
| EX95 | 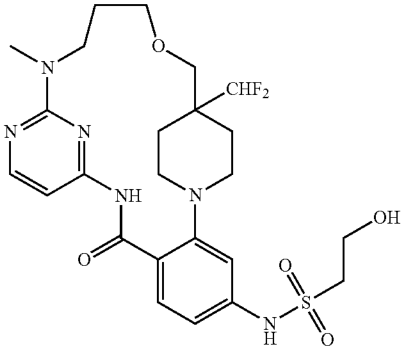 |
| EX96-A and EX96-B | 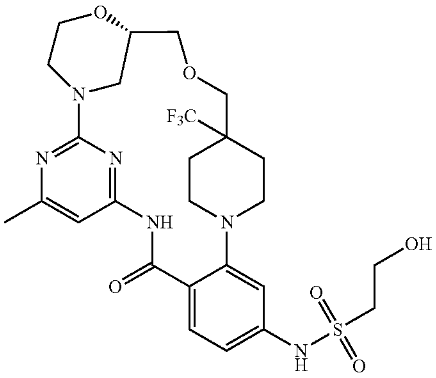 + 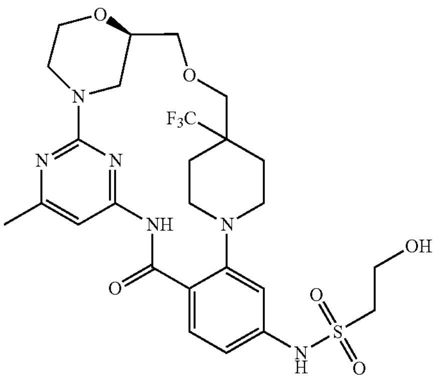 [SMILES: Cc1cc2nc(n1)N1CCO[C@@H](COCC3(C(F)(F)F)CCN(CC3)c3cc(NS(=O)(=O)CCO)ccc3C(=O)N2)C1] |
TABLE 1-continued
| No. | Structure |
|---|---|
| EX97 | 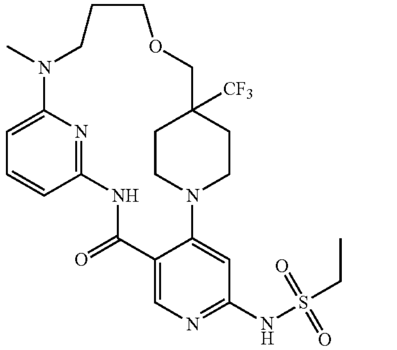 [SMILES: CCS(=O)(=O)Nc1cc2c(cn1)C(=O)Nc1cccc(n1)N(C)CCCOCC1(C(F)(F)F)CCN2CC1] |
| EX98 | 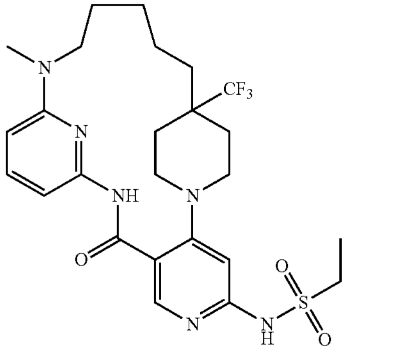 [SMILES: CCS(=O)(=O)Nc1cc2c(cn1)C(=O)Nc1cccc(n1)N(C)CCCCCC1(C(F)(F)F)CCN2CC1] |
| EX99 | 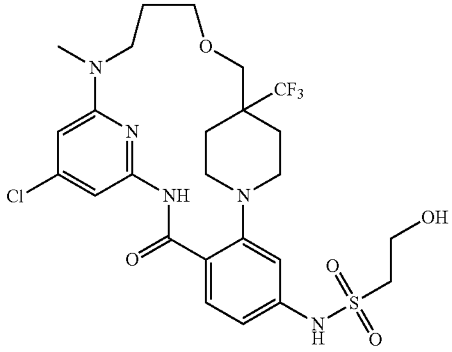 |
| EX100-A and EX100-B | 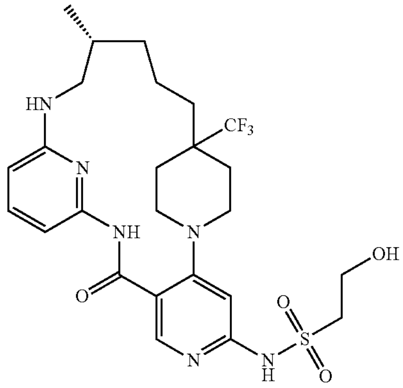 + |

TABLE 1-continued
| No. | Structure |
|---|---|
| | 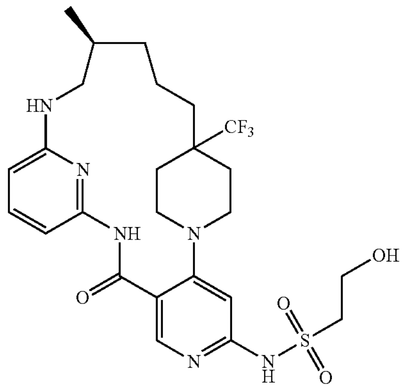 [SMILES: C[C@H]1CCCC2(C(F)(F)F)CCN(CC2)c2cc(NS(=O)(=O)CCO)ncc2C(=O)Nc2cccc(n2)NC1] |
| EX101-A and EX101-B | 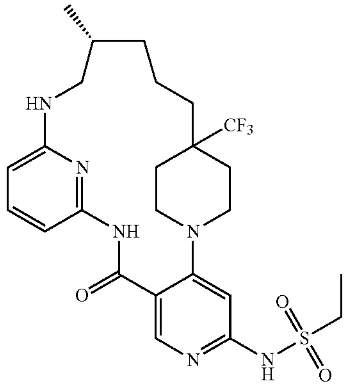 + 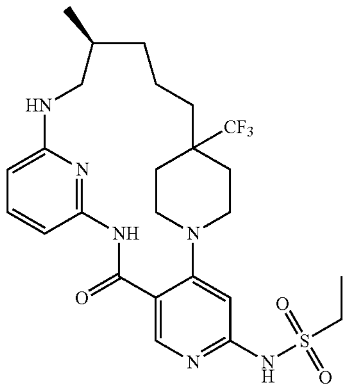 [SMILES: CCS(=O)(=O)Nc1cc2c(cn1)C(=O)Nc1cccc(n1)NC[C@@H](C)CCCC1(C(F)(F)F)CCN2CC1] |
| EX102-A and EX102-B | 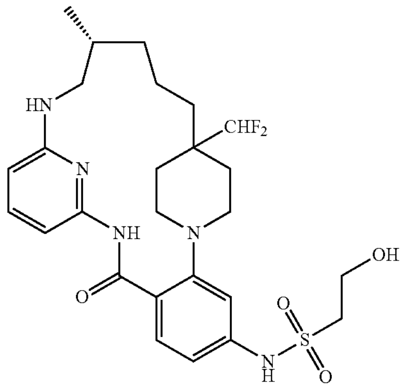 + 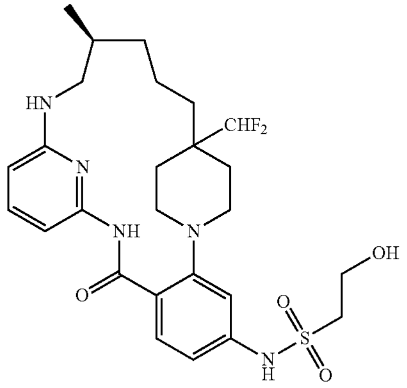 [SMILES: C[C@H]1CCCC2(C(F)F)CCN(CC2)c2cc(NS(=O)(=O)CCO)ccc2C(=O)Nc2cccc(n2)NC1] |
| EX103 | 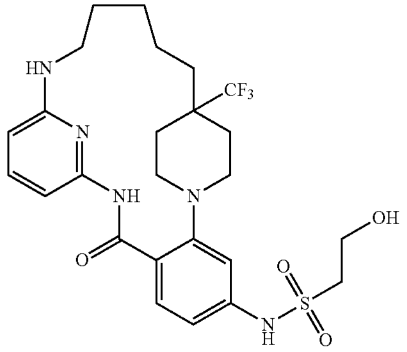 [SMILES: O=C1Nc2cccc(n2)NCCCCCC2(C(F)(F)F)CCN(CC2)c2cc(NS(=O)(=O)CCO)ccc21] |
| EX104 | 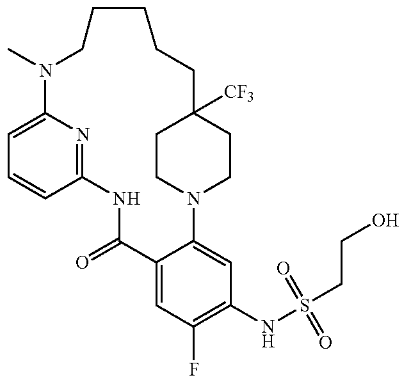 [SMILES: CN1CCCCCC2(C(F)(F)F)CCN(CC2)c2cc(NS(=O)(=O)CCO)c(F)cc2C(=O)Nc2cccc1n2] |

TABLE 1-continued
| No. | Structure |
|---|---|
| EX105-A And EX105-B | 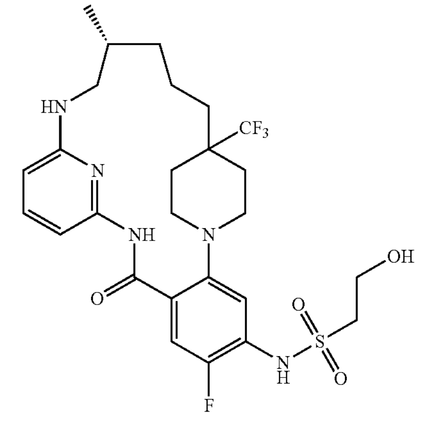<br>+<br>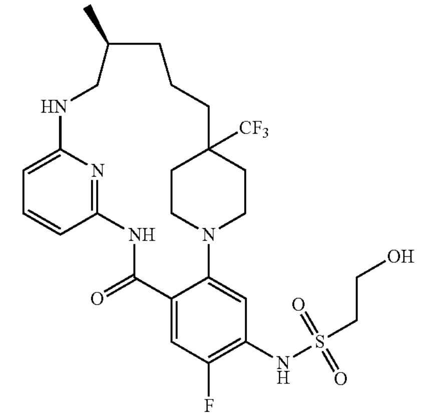 [SMILES: C[C@H]1CCCC2(C(F)(F)F)CCN(CC2)c2cc(NS(=O)(=O)CCO)c(F)cc2C(=O)Nc2cccc(n2)NC1] |
| EX106 | 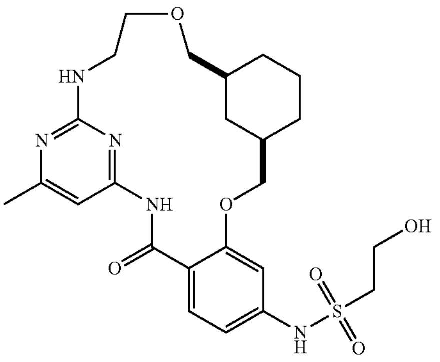 |
| EX107-A and EX107-B | 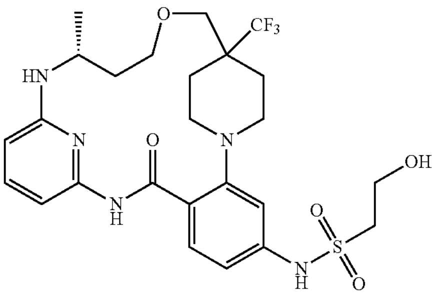<br>+ |
TABLE 1-continued
| No. | Structure |
|---|---|
| | 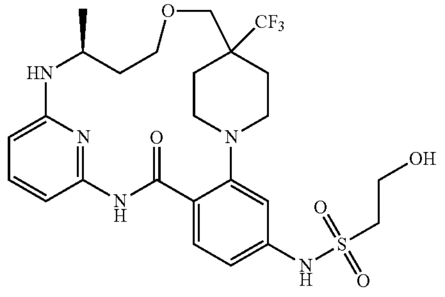 [SMILES: C[C@H]1CCOCC2(C(F)(F)F)CCN(CC2)c2cc(NS(=O)(=O)CCO)ccc2C(=O)Nc2cccc(n2)N1] |
| EX108 | 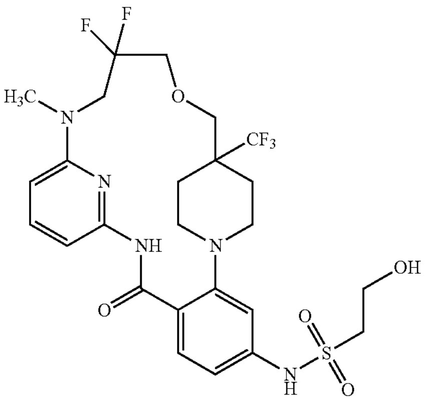 [SMILES: CN1CC(F)(F)COCC2(C(F)(F)F)CCN(CC2)c2cc(NS(=O)(=O)CCO)ccc2C(=O)Nc2cccc1n2] |
| EX109 | 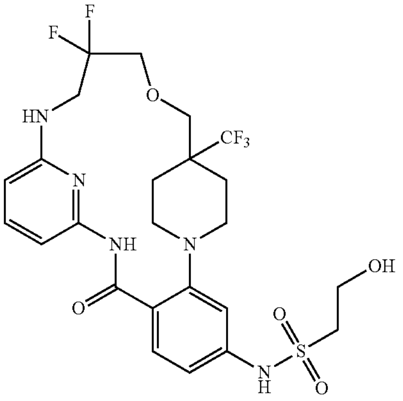 [SMILES: O=C1Nc2cccc(n2)NCC(F)(F)COCC2(C(F)(F)F)CCN(CC2)c2cc(NS(=O)(=O)CCO)ccc21] |
| EX110 | 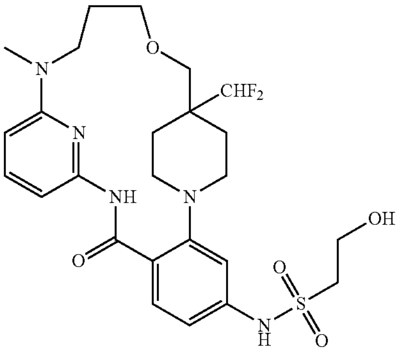 [SMILES: CN1CCCOCC2(C(F)F)CCN(CC2)c2cc(NS(=O)(=O)CCO)ccc2C(=O)Nc2cccc1n2] |

TABLE 1-continued
| No. | Structure |
|---|---|
| EX111-A And EX111-B | 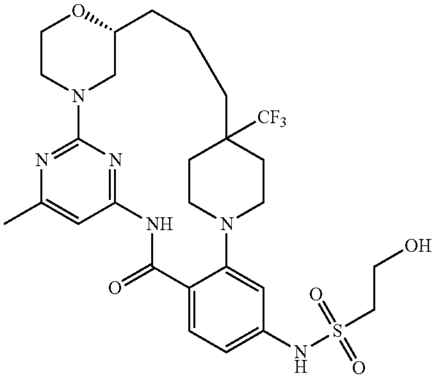 + 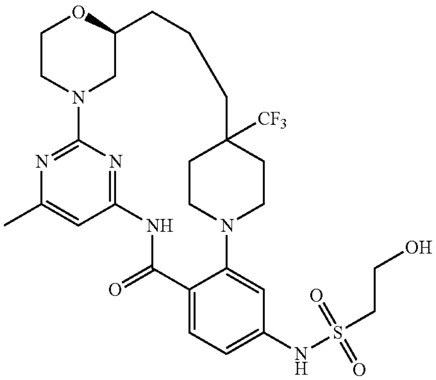 [SMILES: Cc1cc2nc(n1)N1CCO[C@@H](CCCC3(C(F)(F)F)CCN(CC3)c3cc(NS(=O)(=O)CCO)ccc3C(=O)N2)C1] |
| EX112 | 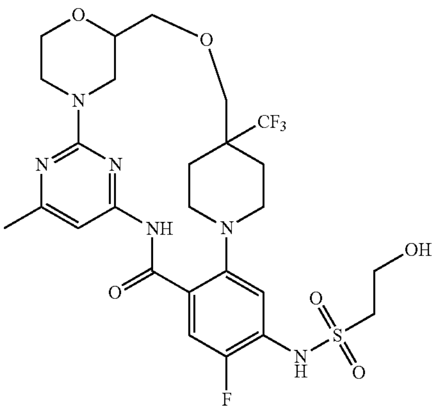 [SMILES: Cc1cc2nc(n1)N1CCOC(COCC3(C(F)(F)F)CCN(CC3)c3cc(NS(=O)(=O)CCO)c(F)cc3C(=O)N2)C1] |
| EX113-A And EX113-B | 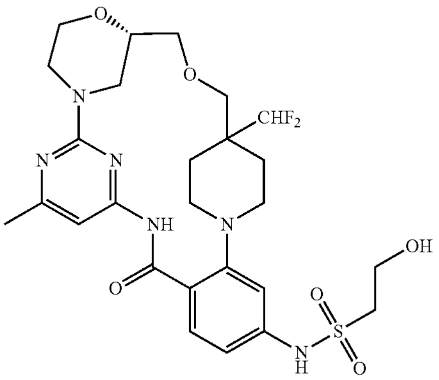 + 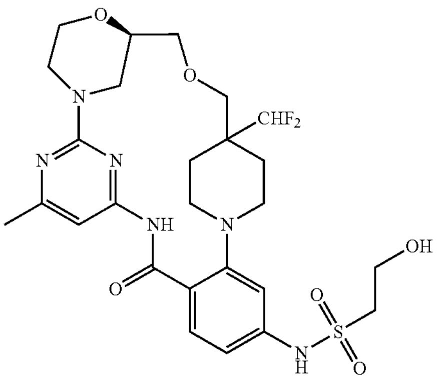 [SMILES: Cc1cc2nc(n1)N1CCO[C@@H](COCC3(C(F)F)CCN(CC3)c3cc(NS(=O)(=O)CCO)ccc3C(=O)N2)C1] |
| EX114-A And EX114-B | 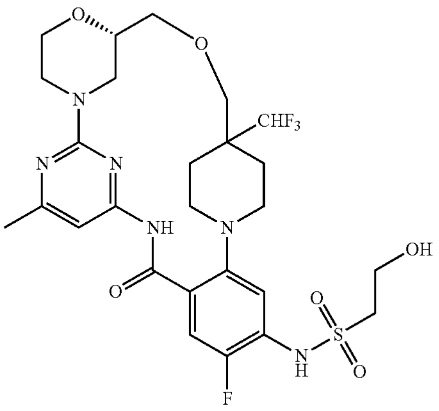 + |

TABLE 1-continued
| No. | Structure |
| --- | --- |
| | 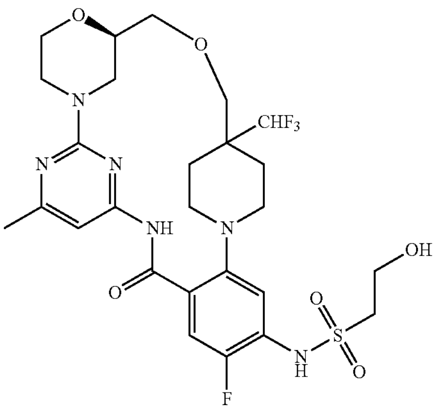 |
| EX115-A And EX115-B | 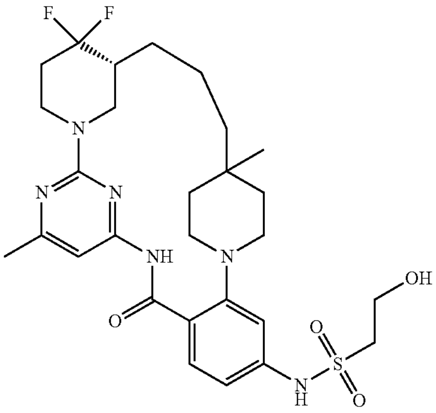 + 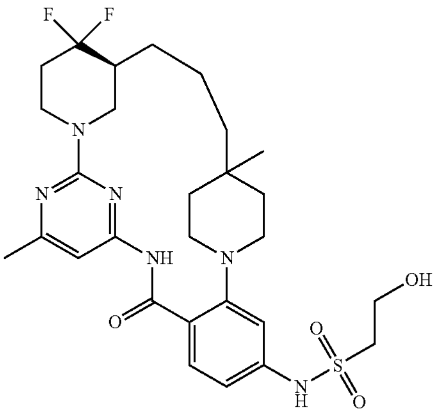 [SMILES: Cc1cc2nc(n1)N1CCC(F)(F)[C@@H](CCCC3(C)CCN(CC3)c3cc(NS(=O)(=O)CCO)ccc3C(=O)N2)C1] |
In some embodiments, disclosed herein is a compound, or a pharmaceutically acceptable salt thereof, selected from the compound provided in Table 2. In some embodiments of table 2, ---- represents a double bond. In some embodiments of table 2, ---- represents a single bond.
TABLE 2
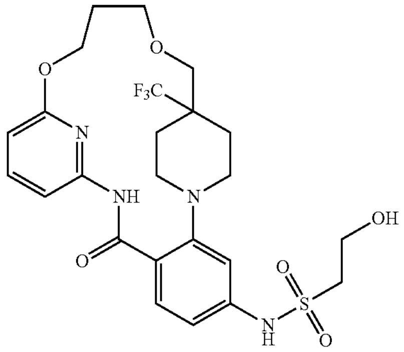 [SMILES: O=C1Nc2cccc(n2)OCCCOCC2(C(F)(F)F)CCN(CC2)c2cc(NS(=O)(=O)CCO)ccc21]
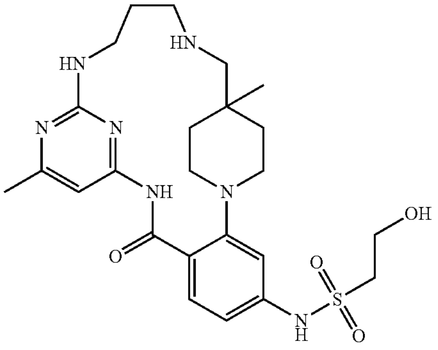 [SMILES: Cc1cc2nc(n1)NCCCNCC1(C)CCN(CC1)c1cc(NS(=O)(=O)CCO)ccc1C(=O)N2]
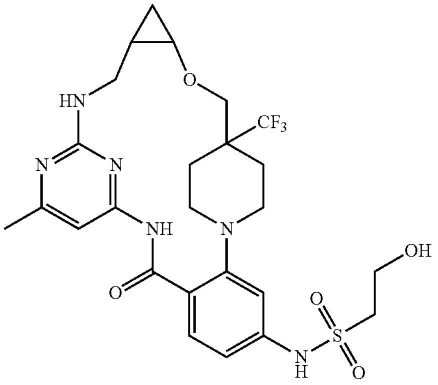 [SMILES: Cc1cc2nc(n1)NCC1CC1OCC1(C(F)(F)F)CCN(CC1)c1cc(NS(=O)(=O)CCO)ccc1C(=O)N2]
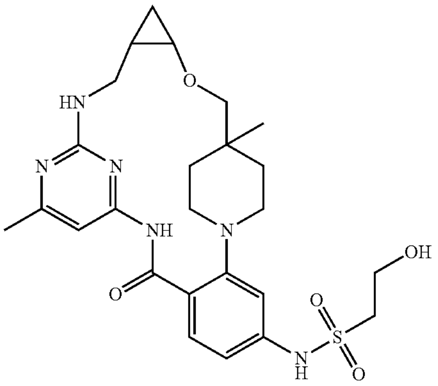 [SMILES: Cc1cc2nc(n1)NCC1CC1OCC1(C)CCN(CC1)c1cc(NS(=O)(=O)CCO)ccc1C(=O)N2]

TABLE 2-continued
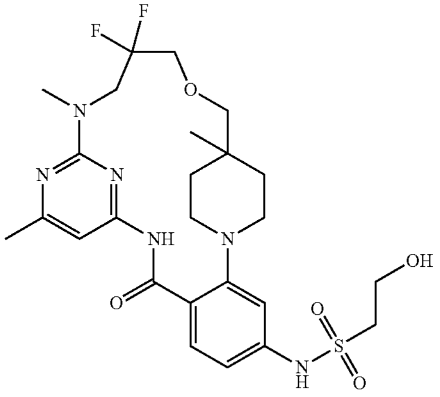 [SMILES: Cc1cc2nc(n1)N(C)CC(F)(F)COCC1(C)CCN(CC1)c1cc(NS(=O)(=O)CCO)ccc1C(=O)N2]
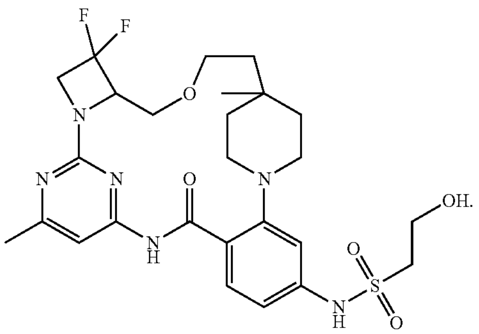 [SMILES: Cc1cc2nc(n1)N1CC(F)(F)C1COCCC1(C)CCN(CC1)c1cc(NS(=O)(=O)CCO)ccc1C(=O)N2]
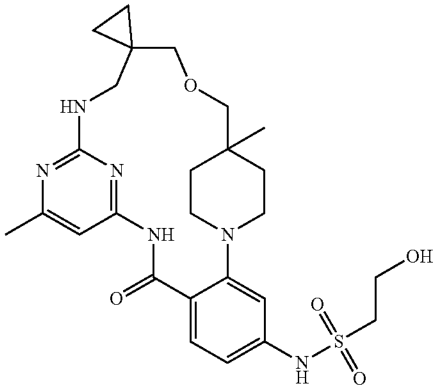 [SMILES: Cc1cc2nc(n1)NCC1(CC1)COCC1(C)CCN(CC1)c1cc(NS(=O)(=O)CCO)ccc1C(=O)N2]
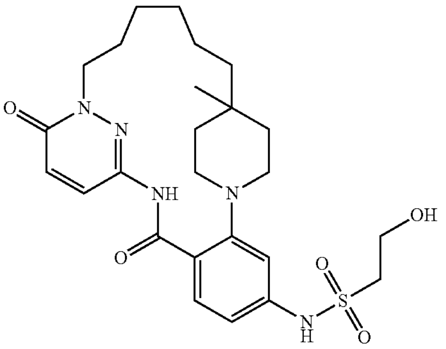 [SMILES: CC12CCCCCCn3nc(ccc3=O)NC(=O)c3ccc(NS(=O)(=O)CCO)cc3N(CC1)CC2]
TABLE 2-continued
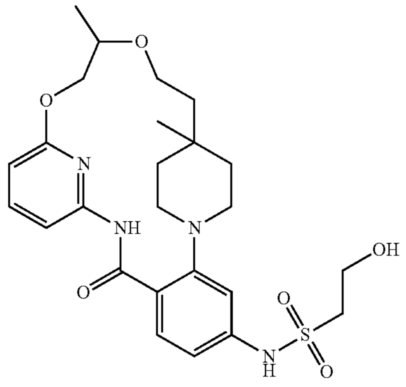 [SMILES: CC1COc2cccc(n2)NC(=O)c2ccc(NS(=O)(=O)CCO)cc2N2CCC(C)(CCO1)CC2]
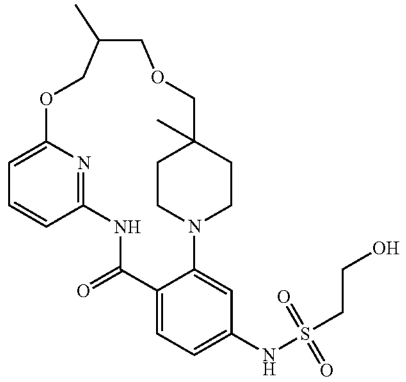 [SMILES: CC1COCC2(C)CCN(CC2)c2cc(NS(=O)(=O)CCO)ccc2C(=O)Nc2cccc(n2)OC1]
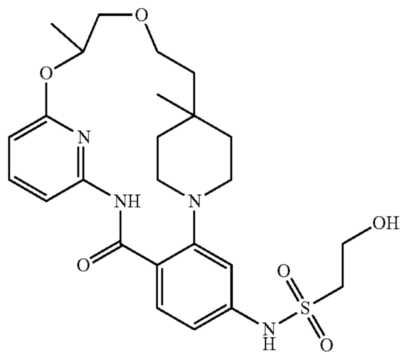 [SMILES: CC1COCCC2(C)CCN(CC2)c2cc(NS(=O)(=O)CCO)ccc2C(=O)Nc2cccc(n2)O1]
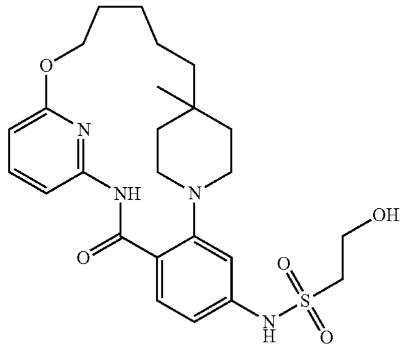 [SMILES: CC12CCCCCOc3cccc(n3)NC(=O)c3ccc(NS(=O)(=O)CCO)cc3N(CC1)CC2]

TABLE 2-continued
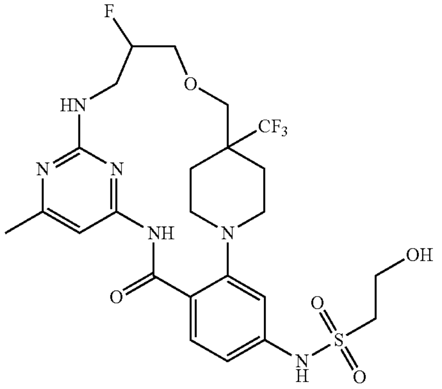 [SMILES: Cc1cc2nc(n1)NCC(F)COCC1(C(F)(F)F)CCN(CC1)c1cc(NS(=O)(=O)CCO)ccc1C(=O)N2]
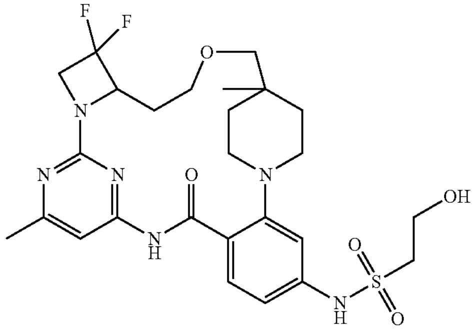 [SMILES: Cc1cc2nc(n1)N1CC(F)(F)C1CCOCC1(C)CCN(CC1)c1cc(NS(=O)(=O)CCO)ccc1C(=O)N2]
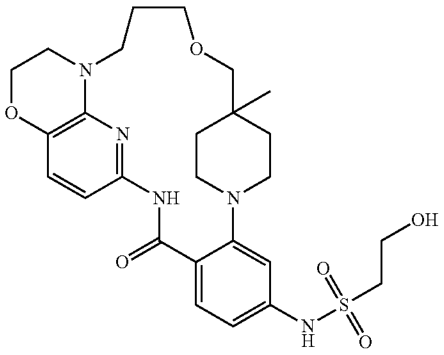 [SMILES: CC12CCN(CC1)c1cc(NS(=O)(=O)CCO)ccc1C(=O)Nc1ccc3c(n1)N(CCCOC2)CCO3]
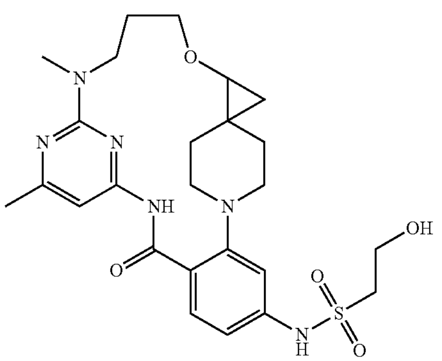 [SMILES: Cc1cc2nc(n1)N(C)CCCOC1CC13CCN(CC3)c1cc(NS(=O)(=O)CCO)ccc1C(=O)N2]
TABLE 2-continued
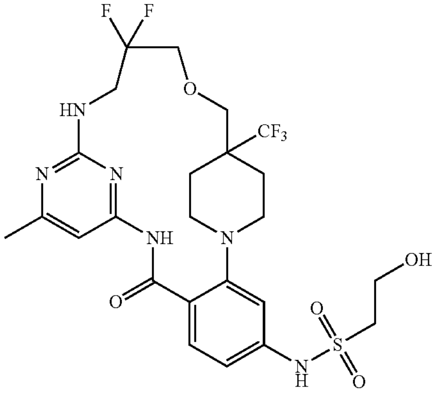 [SMILES: Cc1cc2nc(n1)NCC(F)(F)COCC1(C(F)(F)F)CCN(CC1)c1cc(NS(=O)(=O)CCO)ccc1C(=O)N2]
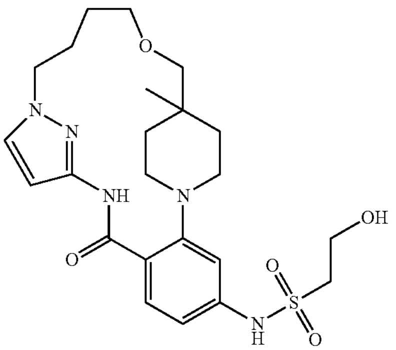 [SMILES: CC12CCN(CC1)c1cc(NS(=O)(=O)CCO)ccc1C(=O)Nc1ccn(n1)CCCCOC2]
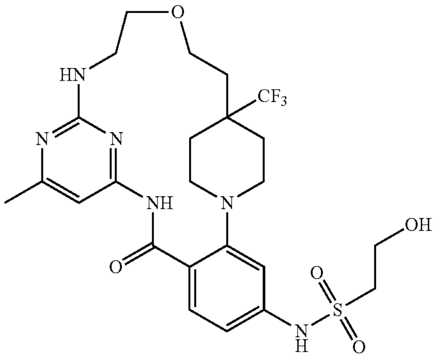 [SMILES: Cc1cc2nc(n1)NCCOCCC1(C(F)(F)F)CCN(CC1)c1cc(NS(=O)(=O)CCO)ccc1C(=O)N2]
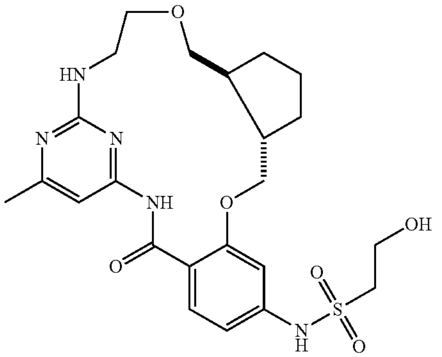

TABLE 2-continued
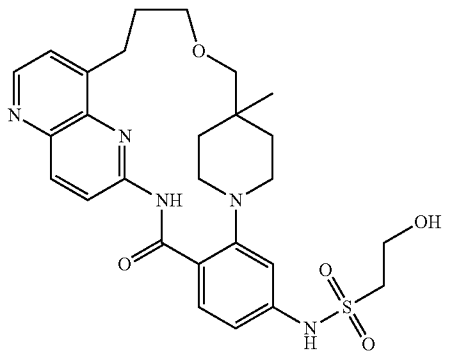 [SMILES: CC12CCN(CC1)c1cc(NS(=O)(=O)CCO)ccc1C(=O)Nc1ccc3nccc(c3n1)CCCOC2]
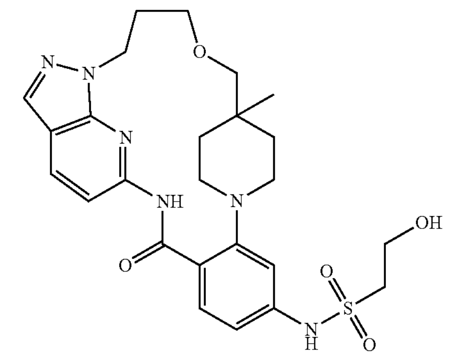
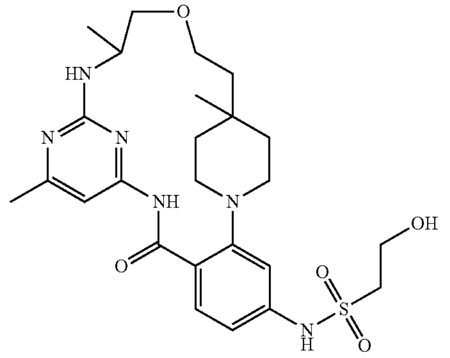 [SMILES: Cc1cc2nc(n1)NC(C)COCCC1(C)CCN(CC1)c1cc(NS(=O)(=O)CCO)ccc1C(=O)N2]
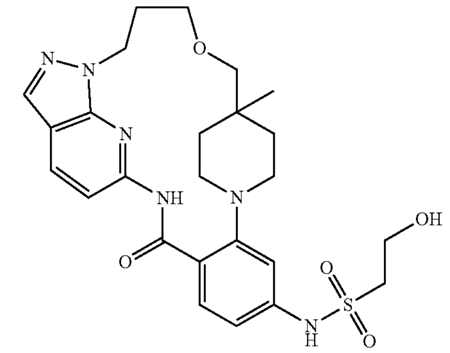
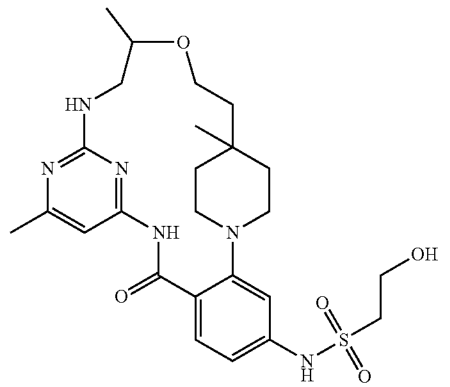 [SMILES: Cc1cc2nc(n1)NCC(C)OCCC1(C)CCN(CC1)c1cc(NS(=O)(=O)CCO)ccc1C(=O)N2]
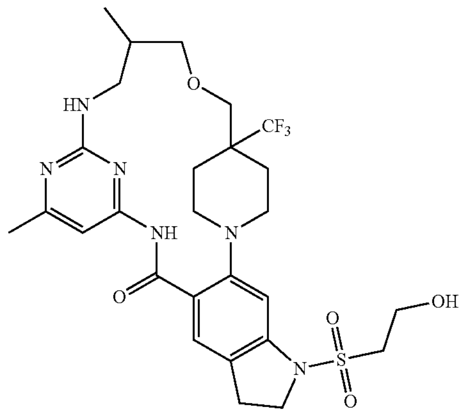
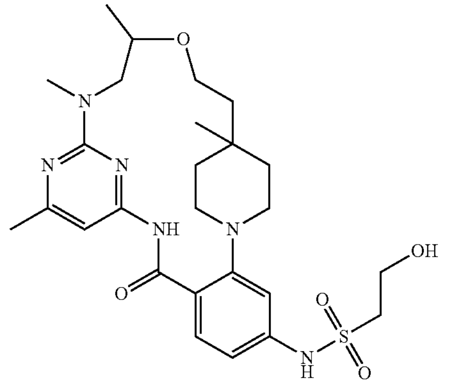 [SMILES: Cc1cc2nc(n1)N(C)CC(C)OCCC1(C)CCN(CC1)c1cc(NS(=O)(=O)CCO)ccc1C(=O)N2]
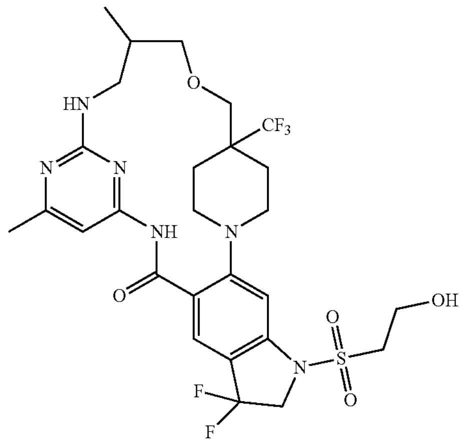 [SMILES: Cc1cc2nc(n1)NCC(C)COCC1(C(F)(F)F)CCN(CC1)c1cc3c(cc1C(=O)N2)C(F)(F)CN3S(=O)(=O)CCO]

TABLE 2-continued
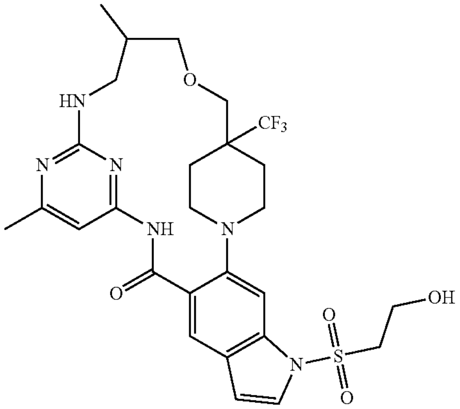 [SMILES: Cc1cc2nc(n1)NCC(C)COCC1(C(F)(F)F)CCN(CC1)c1cc3c(ccn3S(=O)(=O)CCO)cc1C(=O)N2]
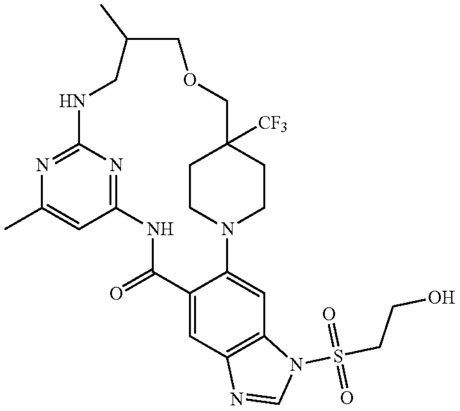 [SMILES: Cc1cc2nc(n1)NCC(C)COCC1(C(F)(F)F)CCN(CC1)c1cc3c(cc1C(=O)N2)ncn3S(=O)(=O)CCO]
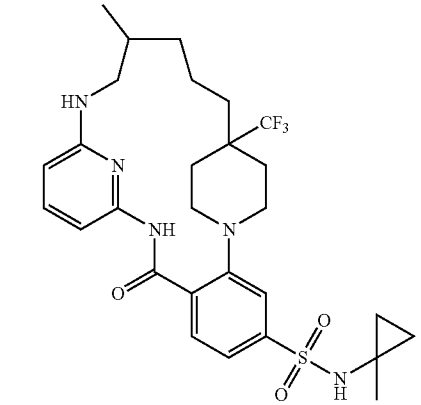 [SMILES: CC1CCCC2(C(F)(F)F)CCN(CC2)c2cc(S(=O)(=O)NC3(C)CC3)ccc2C(=O)Nc2cccc(n2)NC1]
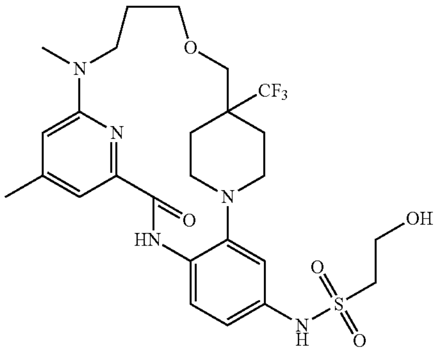 [SMILES: Cc1cc2nc(c1)N(C)CCCOCC1(C(F)(F)F)CCN(CC1)c1cc(NS(=O)(=O)CCO)ccc1NC2=O]
TABLE 2-continued
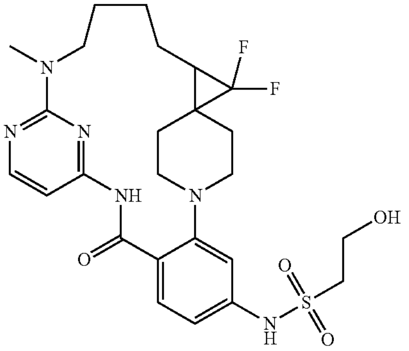 [SMILES: CN1CCCCC2C(F)(F)C23CCN(CC3)c2cc(NS(=O)(=O)CCO)ccc2C(=O)Nc2ccnc1n2]
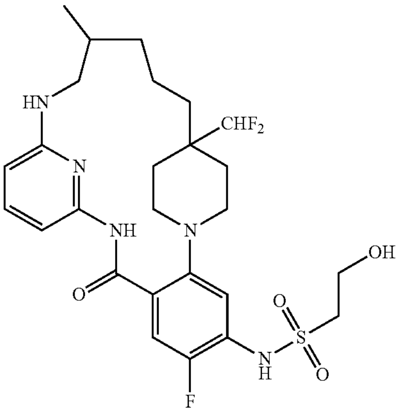 [SMILES: CC1CCCC2(C(F)F)CCN(CC2)c2cc(NS(=O)(=O)CCO)c(F)cc2C(=O)Nc2cccc(n2)NC1]
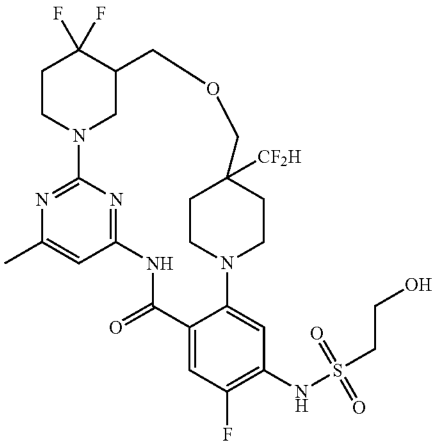 [SMILES: Cc1cc2nc(n1)N1CCC(F)(F)C(COCC3(C(F)F)CCN(CC3)c3cc(NS(=O)(=O)CCO)c(F)cc3C(=O)N2)C1]
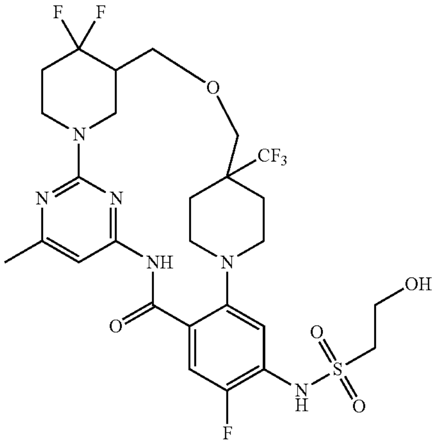 [SMILES: Cc1cc2nc(n1)N1CCC(F)(F)C(COCC3(C(F)(F)F)CCN(CC3)c3cc(NS(=O)(=O)CCO)c(F)cc3C(=O)N2)C1]

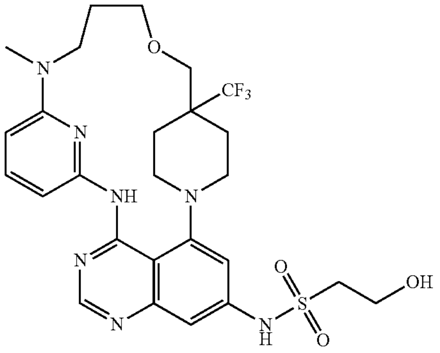 [SMILES: CN1CCCOCC2(C(F)(F)F)CCN(CC2)c2cc(NS(=O)(=O)CCO)cc3ncnc(c23)Nc2cccc1n2]
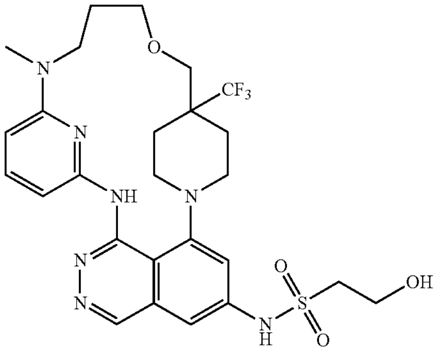 [SMILES: CN1CCCOCC2(C(F)(F)F)CCN(CC2)c2cc(NS(=O)(=O)CCO)cc3cnnc(c23)Nc2cccc1n2]
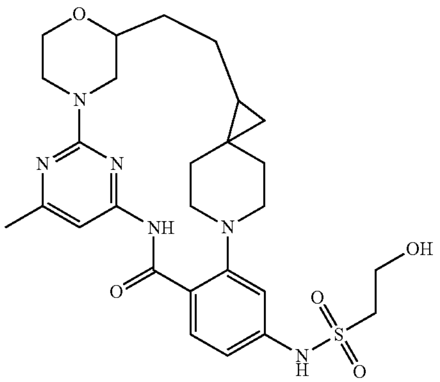 [SMILES: Cc1cc2nc(n1)N1CCOC(CCC3CC34CCN(CC4)c3cc(NS(=O)(=O)CCO)ccc3C(=O)N2)C1]
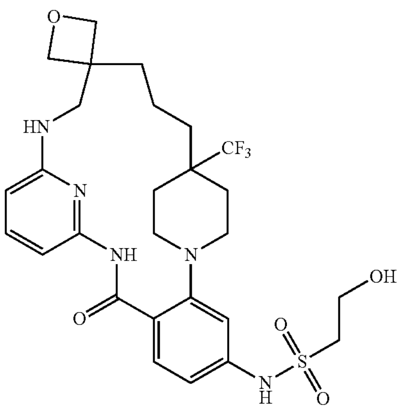 [SMILES: O=C1Nc2cccc(n2)NCC2(CCCC3(C(F)(F)F)CCN(CC3)c3cc(NS(=O)(=O)CCO)ccc31)COC2]
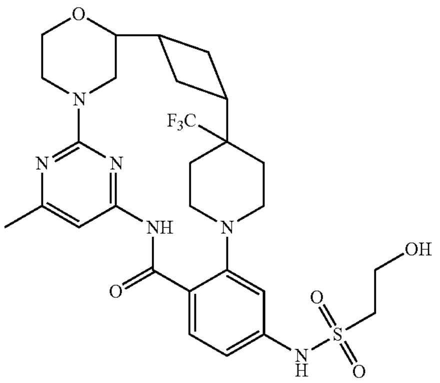 [SMILES: Cc1cc2nc(n1)N1CCOC(C1)C1CC(C1)C1(C(F)(F)F)CCN(CC1)c1cc(NS(=O)(=O)CCO)ccc1C(=O)N2]
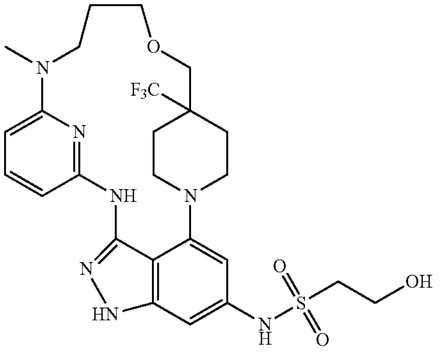 [SMILES: CN1CCCOCC2(C(F)(F)F)CCN(CC2)c2cc(NS(=O)(=O)CCO)cc3[nH]nc(c23)Nc2cccc1n2]
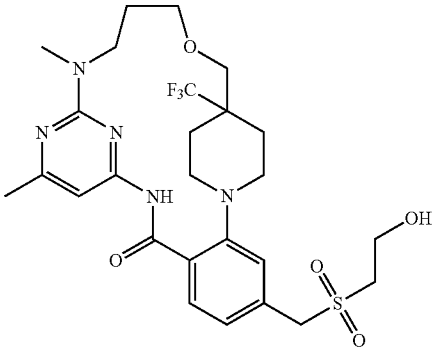 [SMILES: Cc1cc2nc(n1)N(C)CCCOCC1(C(F)(F)F)CCN(CC1)c1cc(CS(=O)(=O)CCO)ccc1C(=O)N2]
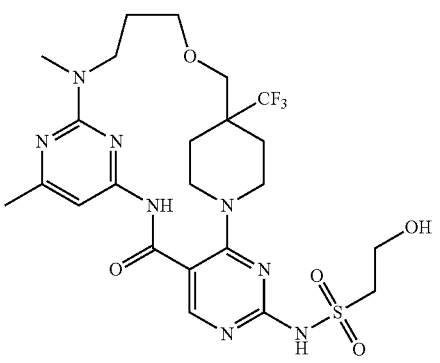 [SMILES: Cc1cc2nc(n1)N(C)CCCOCC1(C(F)(F)F)CCN(CC1)c1nc(NS(=O)(=O)CCO)ncc1C(=O)N2]

TABLE 2-continued
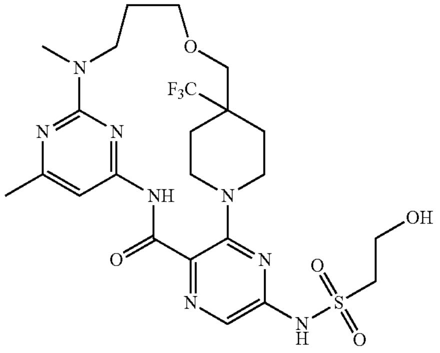 [SMILES: Cc1cc2nc(n1)N(C)CCCOCC1(C(F)(F)F)CCN(CC1)c1nc(NS(=O)(=O)CCO)cnc1C(=O)N2]
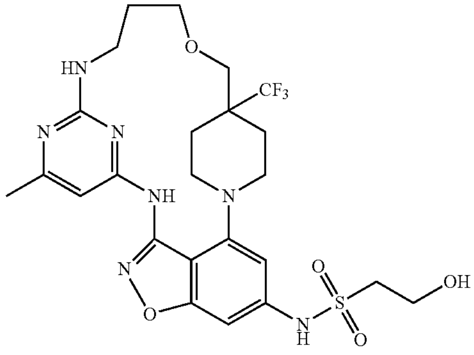 [SMILES: Cc1cc2nc(n1)NCCCOCC1(C(F)(F)F)CCN(CC1)c1cc(NS(=O)(=O)CCO)cc3onc(c13)N2]
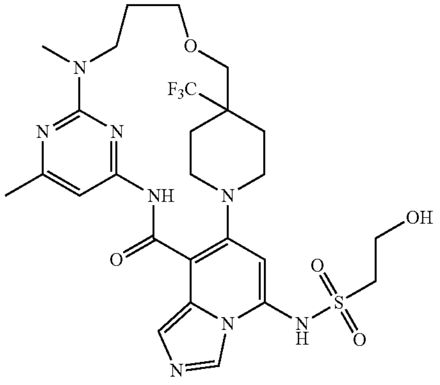 [SMILES: Cc1cc2nc(n1)N(C)CCCOCC1(C(F)(F)F)CCN(CC1)c1cc(NS(=O)(=O)CCO)n3cncc3c1C(=O)N2]
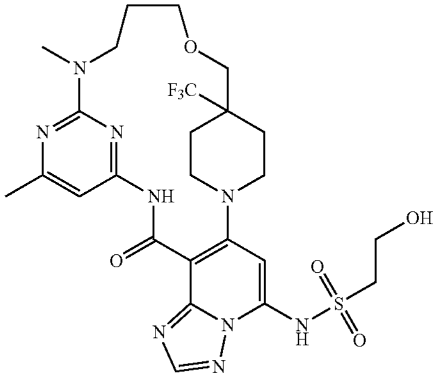 [SMILES: Cc1cc2nc(n1)N(C)CCCOCC1(C(F)(F)F)CCN(CC1)c1cc(NS(=O)(=O)CCO)n3ncnc3c1C(=O)N2]
TABLE 2-continued
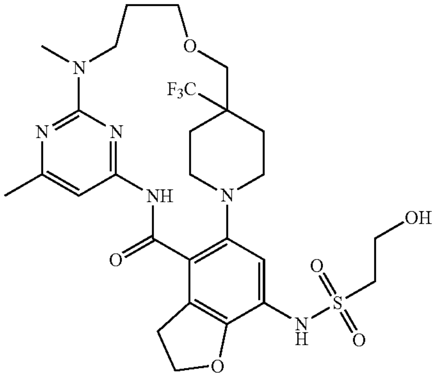 [SMILES: Cc1cc2nc(n1)N(C)CCCOCC1(C(F)(F)F)CCN(CC1)c1cc(NS(=O)(=O)CCO)c3c(c1C(=O)N2)CCO3]
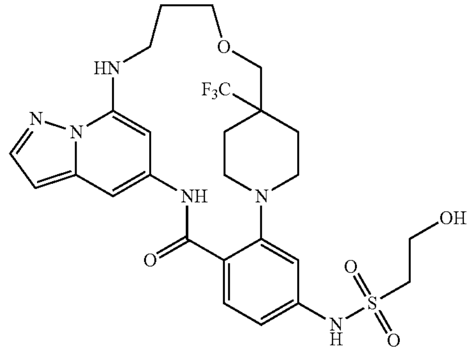 [SMILES: O=C1Nc2cc(n3nccc3c2)NCCCOCC2(C(F)(F)F)CCN(CC2)c2cc(NS(=O)(=O)CCO)ccc21]
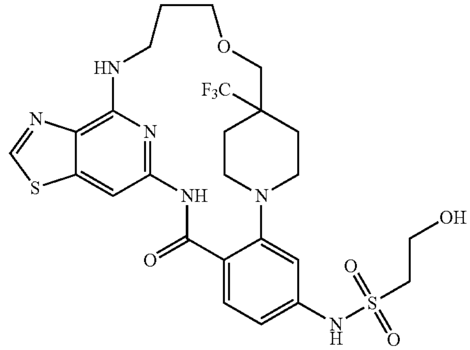 [SMILES: O=C1Nc2cc3scnc3c(n2)NCCCOCC2(C(F)(F)F)CCN(CC2)c2cc(NS(=O)(=O)CCO)ccc21]
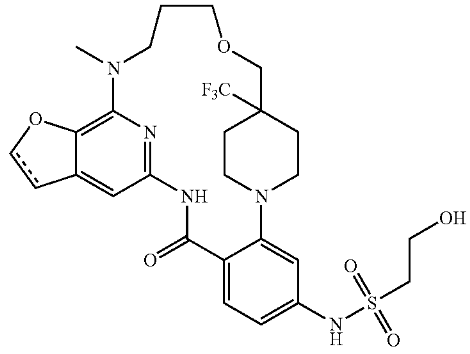

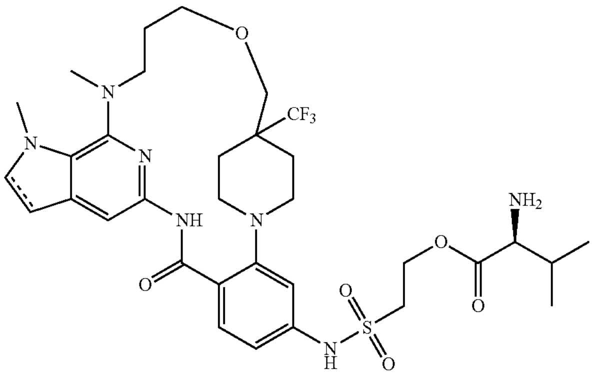
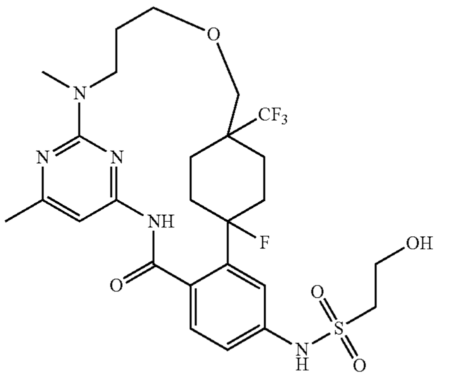 [SMILES: Cc1cc2nc(n1)N(C)CCCOCC1(C(F)(F)F)CCC(F)(CC1)c1cc(NS(=O)(=O)CCO)ccc1C(=O)N2]
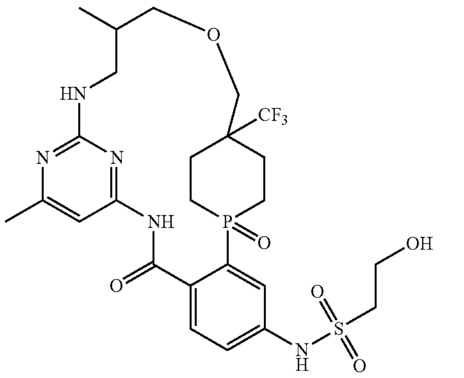 [SMILES: Cc1cc2nc(n1)NCC(C)COCC1(C(F)(F)F)CCP(=O)(CC1)c1cc(NS(=O)(=O)CCO)ccc1C(=O)N2]
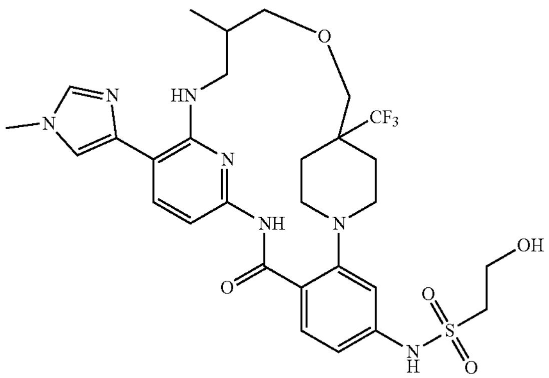 [SMILES: CC1CNc2nc(ccc2-c2cn(C)cn2)NC(=O)c2ccc(NS(=O)(=O)CCO)cc2N2CCC(C(F)(F)F)(CC2)COC1]
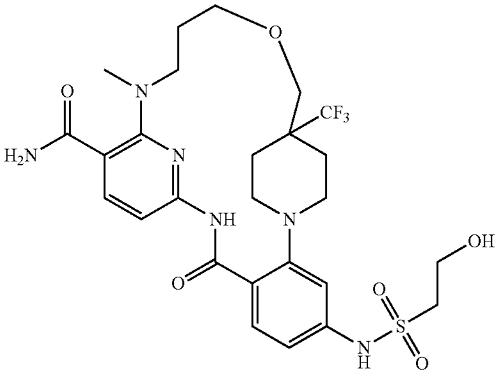 [SMILES: CN1CCCOCC2(C(F)(F)F)CCN(CC2)c2cc(NS(=O)(=O)CCO)ccc2C(=O)Nc2ccc(C(N)=O)c1n2]
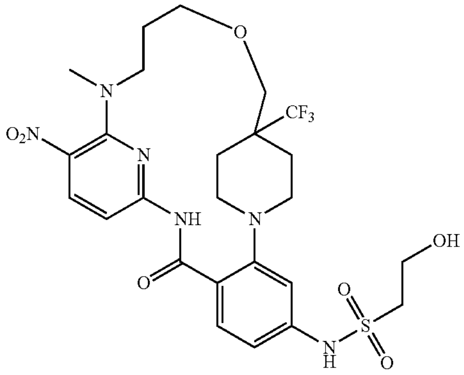 [SMILES: CN1CCCOCC2(C(F)(F)F)CCN(CC2)c2cc(NS(=O)(=O)CCO)ccc2C(=O)Nc2ccc([N+](=O)[O-])c1n2]
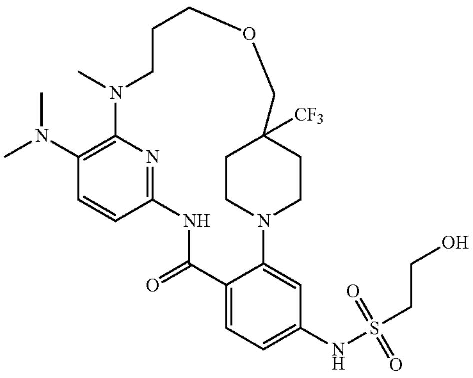 [SMILES: CN(C)c1ccc2nc1N(C)CCCOCC1(C(F)(F)F)CCN(CC1)c1cc(NS(=O)(=O)CCO)ccc1C(=O)N2]
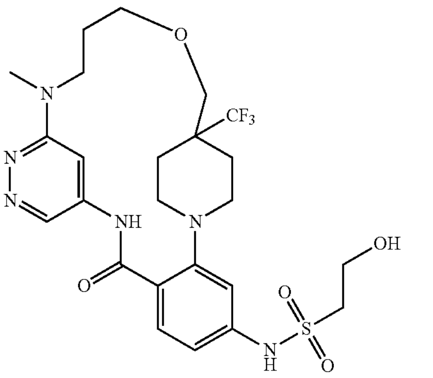 [SMILES: CN1CCCOCC2(C(F)(F)F)CCN(CC2)c2cc(NS(=O)(=O)CCO)ccc2C(=O)Nc2cnnc1c2]

TABLE 2-continued
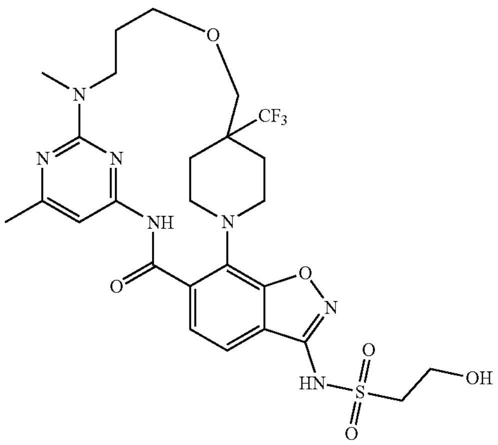 [SMILES: Cc1cc2nc(n1)N(C)CCCOCC1(C(F)(F)F)CCN(CC1)c1c(ccc3c(NS(=O)(=O)CCO)noc13)C(=O)N2]
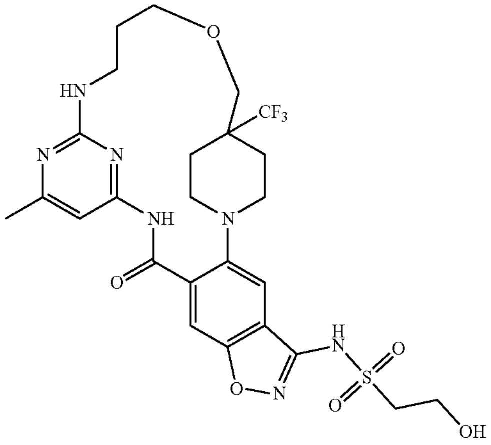 [SMILES: Cc1cc2nc(n1)NCCCOCC1(C(F)(F)F)CCN(CC1)c1cc3c(NS(=O)(=O)CCO)noc3cc1C(=O)N2]
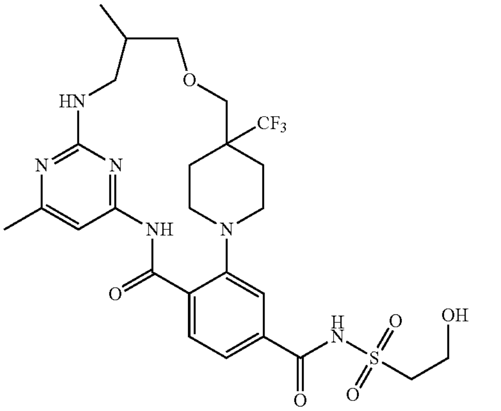 [SMILES: Cc1cc2nc(n1)NCC(C)COCC1(C(F)(F)F)CCN(CC1)c1cc(C(=O)NS(=O)(=O)CCO)ccc1C(=O)N2]
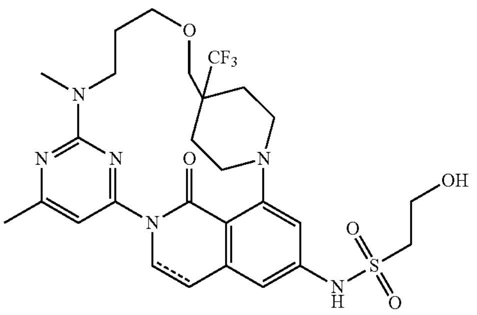
TABLE 2-continued
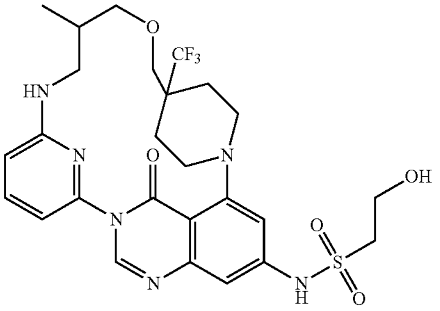 [SMILES: CC1CNc2cccc(n2)-n2cnc3cc(NS(=O)(=O)CCO)cc(c3c2=O)N2CCC(C(F)(F)F)(CC2)COC1]
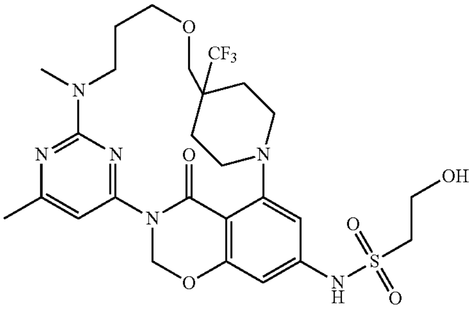 [SMILES: Cc1cc2nc(n1)N(C)CCCOCC1(C(F)(F)F)CCN(CC1)c1cc(NS(=O)(=O)CCO)cc3c1C(=O)N2CO3]
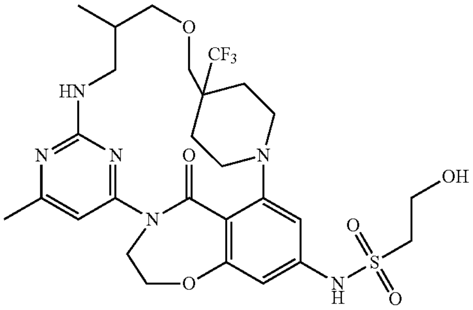 [SMILES: Cc1cc2nc(n1)NCC(C)COCC1(C(F)(F)F)CCN(CC1)c1cc(NS(=O)(=O)CCO)cc3c1C(=O)N2CCO3]
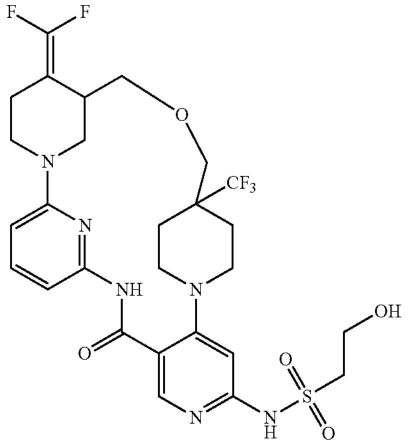 [SMILES: O=C1Nc2cccc(n2)N2CCC(=C(F)F)C(COCC3(C(F)(F)F)CCN(CC3)c3cc(NS(=O)(=O)CCO)ncc31)C2]

TABLE 2-continued

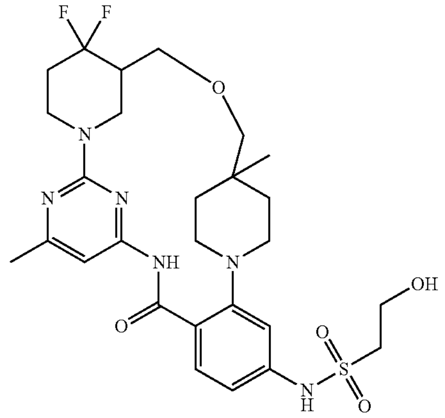 [SMILES: Cc1cc2nc(n1)N1CCC(F)(F)C(COCC3(C)CCN(CC3)c3cc(NS(=O)(=O)CCO)ccc3C(=O)N2)C1]

Further Forms of Compounds Disclosed Herein

Isomers Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine and chloride, such as $^{2}H$ (D), $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability.

In some embodiments, the abundance of deuterium in each of the substituents disclosed herein is independently at least 1%, at least 10%, at least 20%, at least 30%, at least 40%, at least 50%, at least 60%, at least 70%, at least 80%, at least 90%, or 100% by molar. In some embodiments, one or more of the substituents disclosed herein comprise deuterium at a percentage higher than the natural abundance of deuterium. In some embodiments, one or more $^{1}H$ are replaced with one or more deuteriums in one or more of the substituents disclosed herein.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\ alkyl)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. In some embodiments, the disclosure provides for methods of treating diseases by administering the compounds in the form of such solvates. In some embodiments, the disclosure provides for methods of treating diseases by administering a composition comprising the compounds in the form of such solvates. Solvates contain either stoichiometric or non-stoichiometric amounts of a solvent, and, in some embodiments, are formed during the process of crystallization with pharmaceutically acceptable solvents.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Disclosed herein is a method of treating a disease in which inhibition of KIF18A is beneficial, the method comprising administering a compound of Formula (IV), (IVa), (III), (IIIa), (I), (Ia), (Ia-1), (Ib), (Id), (Ie), or (Ic), disclosed herein, or a pharmaceutically acceptable salt thereof.

Disclosed herein is a method of treating a disease or disorder associated with KIF18A, the method comprising administering to the subject a compound of Formula (IV), (IVa), (III), (IIIa), (I), (Ia), (Ia-1), (Ib), (Id), (Ie), or (Ic), disclosed herein, or a pharmaceutically acceptable salt thereof.

Disclosed herein is a method of treating cancer in a subject, the method comprising administering to the subject a compound of Formula (IV), (IVa), (III), (IIIa), (I), (Ia), (Ia-1), (Ib), (Id), (Ie), or (Ic), disclosed herein, or a pharmaceutically acceptable salt thereof. In some embodiments of a method of treating cancer in a subject, the method comprising administering to the subject a compound of Formula (IV), (IVa), (III), (IIIa), (I), (Ia), (Ia-1), (Ib), (Id), (Ie), or (Ic), disclosed herein, or a pharmaceutically acceptable salt thereof, wherein the cancer is selected from the group consisting of (a) a solid or hematologically derived tumor selected from cancer of the bladder, endometrial, lung squamous cell, breast, colon, kidney, liver, lung, small cell lung cancer, esophagus, gallbladder, brain, head and neck, ovary, pancreas, stomach, cervix, thyroid, prostate, and skin; (b) a hematopoietic tumor of lymphoid lineage selected from leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, and Burkett's lymphoma; (c) a hematopoietic tumor of myeloid lineage selected from acute and chronic myelogenous leukemias, myelodysplastic syndrome and promyelocytic leukemia; (d) a tumor of mesenchymal origin selected from fibrosarcoma and rhabdomyosarcoma; (e) a tumor of the central and peripheral nervous system selected from astrocytoma, neuroblastoma, glioma, and schwannoma; and (f) a melanoma, seminoma, teratocarcinoma, osteosarcoma, xenoderoma pigmentosum, keratoctanthoma, thyroid follicular cancer or Karposi's sarcoma. In some embodiments of a method of treating a solid or hematologically derived tumor selected from cancer of the bladder, endometrial, lung squamous cell, breast, colon, kidney, liver, lung, small cell lung cancer, esophagus, gallbladder, brain, head and neck, ovary, pancreas, stomach, cervix, thyroid, prostate, and skin in a subject, the method comprising administering to the subject a compound of Formula (IV), (IVa), (III), (IIIa), (I), (Ia), (Ia-1), (Ib), (Id), (Ie), or (Ic), disclosed herein, or a pharmaceutically acceptable salt thereof. In some embodiments of a method of treating a hematopoietic tumor of lymphoid lineage selected from leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, and Burkett's lymphoma in a subject, the method comprising administering to the subject a compound of Formula (IV), (IVa), (III), (IIIa), (I), (Ia), (Ia-1), (Ib), (Id), (Ie), or (Ic), disclosed herein, or a pharmaceutically acceptable salt thereof. In some embodiments of a method of treating a hematopoietic tumor of myeloid lineage selected from acute and chronic myelogenous leukemias, myelodysplastic syndrome and promyelocytic leukemia in a subject, the method comprising administering to the subject a compound of Formula (IV), (IVa), (III), (IIIa), (I), (Ia), (Ia-1), (Ib), (Id), (Ie), or (Ic), disclosed herein, or a pharmaceutically acceptable salt thereof. In some embodiments of a method of treating a tumor of mesenchymal origin selected from fibrosarcoma and rhabdomyosarcoma in a subject, the method comprising administering to the subject a compound of Formula (IV), (IVa), (III), (IIIa), (I), (Ia), (Ia-1), (Ib), (Id), (Ie), or (Ic), disclosed herein, or a pharmaceutically acceptable salt thereof. In some embodiments of a method of treating a tumor of the central and peripheral nervous system selected from astrocytoma, neuroblastoma, glioma, and schwannoma in a subject, the method comprising administering to the subject a compound of Formula (IV), (IVa), (III), (IIIa), (I), (Ia), (Ia-1), (Ib), (Id), (Ie), or (Ic), disclosed herein, or a pharmaceutically acceptable salt thereof. In some embodiments of a method of treating a melanoma, seminoma, teratocarcinoma, osteosarcoma, xenoderoma pigmentosum, keratoctanthoma, thyroid follicular cancer or Karposi's sarcoma in a subject, the method comprising administering to the subject a compound of Formula (IV), (IVa), (III), (IIIa), (I), (Ia), (Ia-1), (Ib), (Id), (Ie), or (Ic), disclosed herein, or a pharmaceutically acceptable salt thereof.

Dosing

In certain embodiments, the compositions containing the compound(s) described herein are administered for therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician.

Pharmaceutical Compositions/Formulations

The compounds described herein are administered to a subject in need thereof, either alone or in combination with pharmaceutically acceptable carriers, excipients, or diluents, in a pharmaceutical composition.

Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

EXAMPLES

The following examples are provided for illustrative purposes only and not to limit the scope of the claims provided herein.

I. Chemical Synthesis

As used above, and throughout the description of the invention, the following abbreviations, unless otherwise indicated, shall be understood to have the following meanings:

ACN or MeCN acetonitrile
AcOH acetic acid
Ac acetyl
Bn benzyl
BOC or Boc tert-butyl carbamate
i-Bu iso-butyl
t-Bu tert-butyl
CDI 1,1-carbonyldiimidazole
DBU 1,8-diazabicyclo[5.4.0]undec-7-ene
DCE dichloroethane ($ClCH_2CH_2Cl$)
DCM dichloromethane ($CH_2Cl_2$)
DIBAL-H diisobutylaluminum hydride
DIPEA or DIEA diisopropylethylamine
DMAP 4-(N,N-dimethylamino)pyridine
DME 1,2-dimethoxyethane
DMF N,N-dimethylformamide
DMA N,N-dimethylacetamide
DMPU N,N'-dimethylpropyleneurea
DMSO dimethylsulfoxide
DPPA diphenyl phosphoryl azide
Dppf or dppf 1,1'-bis(diphenylphosphino)ferrocene
EDC or EDCI N-(3-dimethylaminopropyl)-N'-ethylcarbodiimide hydrochloride
eq equivalent(s)
Et ethyl
$Et_2O$ diethyl ether
EtOH ethanol
EA or EtOAc ethyl acetate
HATU 1-[bis(dimethylamino)methylene]-1H-1,2,3-triazolo[4,5-b]pyridinium 3-oxid hexafluorophosphate
HOBt 1-hydroxybenzotriazole
HPLC high performance liquid chromatography
KOAc potassium acetate
KOtBu potassium tert-butoxide
KHMDS potassium bis(trimethylsilyl)amide
NaHMDS sodium bis(trimethylsilyl)amide
LiHMDS lithium bis(trimethylsilyl)amide
LAH/$LiAlH_4$ lithium aluminum anhydride
LCMS liquid chromatography mass spectrometry
Me methyl
MeOH methanol
MS mass spectroscopy
MTBE methyl tert-butyl ether
NBS N-bromosuccinimide
NMP N-methyl-pyrrolidin-2-one
NMR nuclear magnetic resonance
PE petroleum ether
Ph phenyl
iPr/i-Pr iso-propyl
PyAOP 7-azabenzotriazol-1-yloxy)tripyrrolidinophosphonium hexafluorophosphate
RP-HPLC reverse-phase high-pressure liquid chromatography
rt room temperature
SEM 2-(trimethylsilyl)ethoxymethyl
TBS tert-butyldimethylsilyl
TEA triethylamine
TFA trifluoroacetic acid
THF tetrahydrofuran
TLC thin layer chromatography
TMS trimethylsilyl Example 1 (EX01)

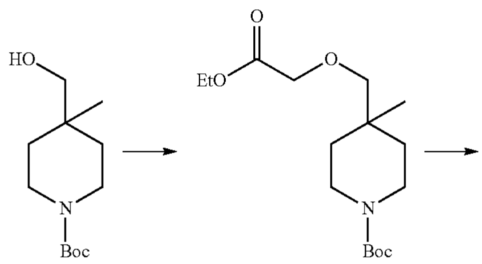

EX01-1

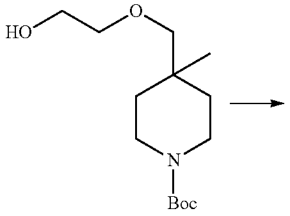

EX01-2

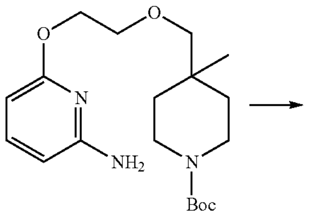

EX01-3

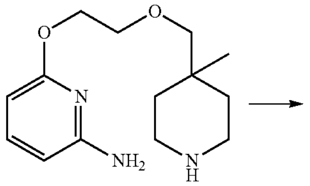

EX01-4

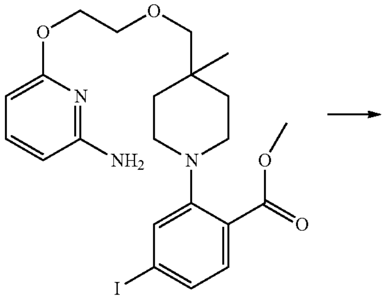

EX01-5

-continued

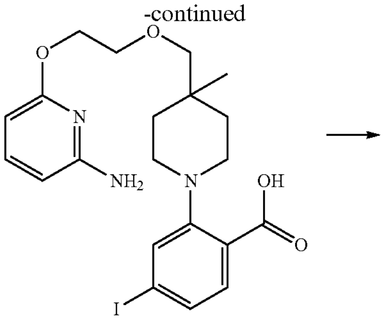

EX01-6

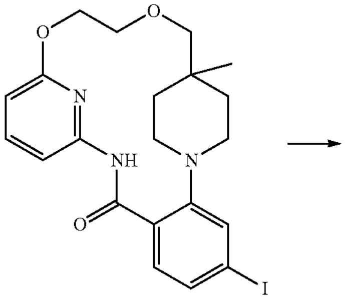

EX01-7

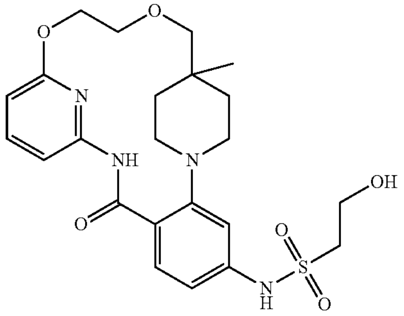

EX01

Step 1:

To a solution of tert-butyl 4-(hydroxymethyl)-4-methylpiperidine-1-carboxylate (5.0 g, 21.8 mmol) in THF (100 mL) were added NaH (1.04 g, 26.16 mmol) and ethyl bromoacetate (3.64 g, 21.8 mmol). The reaction was stirred at 25° C. for 2 hrs. The reaction was diluted with EtOAc (200 mL) and water (100 mL). The organic layer was separated, washed with brine (50 mL), and concentrated under reduced pressure. The residue was purified by silica gel chromatography to afford EX01-1 (2.43 g).

Step 2:

To a solution of EX01-1 (1.02 g, 3.23 mmol) in MeOH (50 mL) was added $NaBH_4$ (367 mg, 9.70 mmol) at 0° C. The reaction was stirred at 25° C. for 24 hrs. The reaction was diluted with water (10 mL) and DCM (50 mL). The organic layer was separated, washed with brine (50 mL), and concentrated under reduced pressure to afford EX01-2 (800 mg).

Step 3:

To a solution of compound EX01-2 (200 mg, 0.732 mmol) in THF (2.00 mL) were added 6-fluoropyridin-2-amine (73.8 mg, 0.658 mmol) and $^t$BuOK (180 mg, 1.61 mmol). The reaction was stirred at 80° C. for 2 hrs. The reaction was diluted with EtOAc (10 mL) and water (3 mL). The organic layer was separated, washed with brine, and concentrated under reduced pressure. The residue was purified by silica gel chromatography to afford EX01-3 (150 mg). LCMS $[M+H]^+$: 366.4.

Step 4:

To a solution of compound EX01-3 (150 mg, 0.41 mmol) in EtOAc (2 mL) was added HCl (12 M, 0.21 mL) and the reaction was stirred at rt for 1 hr. The reaction was concentrated under reduced pressure to afford EX01-4 (105 mg). LCMS $[M+H]^+$: 266.4.

Step 5:

To a solution of EX01-4 (140 mg, 0.528 mmol) in DMSO (1.0 mL) were added methyl 2-fluoro-4-iodobenzoate (221 mg, 0.792 mmol) and $K_2CO_3$ (182 mg, 1.32 mmol). The reaction was stirred at 100° C. for 2 hrs. The reaction was diluted with EtOAc (10 mL) and water (4 mL). The organic layer was separated, washed with brine, and concentrated under reduced pressure. The residue was purified by silica gel chromatography to afford EX01-5 (100 mg). LCMS $[M+H]^+$: 526.6.

Step 6:

To a solution of compound EX01-5 (100 mg, 0.19 mmol) in MeOH (5.0 mL) was added aq. NaOH (1 M, 0.57 mL, 0.57 mmol). The reaction was stirred at rt for 2 hrs. The reaction was diluted with DCM (10 mL) and water (2 mL). The organic layer was separated, washed with brine, and concentrated under reduced pressure. The residue was purified by silica gel chromatography to afford EX01-6 (95 mg). LCMS $[M+H]^+$: 512.3.

Step 7:

To a solution of EX01-6 (80.0 mg, 0.156 mmol) in DCM (2 mL) were added $POCl_3$ (0.044 mL, 0.469 mmol) and pyridine (0.126 mL, 1.56 mmol) at 0° C. The reaction was stirred at 25° C. for 2 hrs. The reaction mixture was quenched with water (20 mL) at 25° C., and then extracted with EtOAc (30 mL×3). The combined organic layer was concentrated and purified by prep-TLC to afford EX01-7 (40 mg). LCMS $[M+H]^+$: 494.2.

Step 8:

A mixture of EX01-7 (35 mg, 0.06 mmol), 2-hydroxyethane-1-sulfonamide (26.63 mg, 0.213 mmol), CuI (2.32 mg, 0.012 mmol), $Cs_2CO_3$ (13.87 mg, 0.043 mmol) and 2,5-diazahexane (2.14 mg, 0.024 mmol) in DMF (1 mL) was degassed and purged with $N_2$ for 3 times. The mixture was stirred at 100° C. for 3 hrs under $N_2$ atmosphere. The reaction mixture was filtered, concentrated under reduced pressure, and purified by prep-HPLC to afford EX01 (5 mg). $^1H$ NMR (400 MHz, $CD_3OD$) δ 8.02 (d, J=8.5 Hz, 1H), 7.88 (d, J=7.8 Hz, 1H), 7.64 (t, J=8.0 Hz, 1H), 7.21 (d, J=2.1 Hz, 1H), 7.10 (dd, J=8.6, 2.1 Hz, 1H), 6.49 (d, J=8.0 Hz, 1H), 4.63 (t, J=4.7 Hz, 2H), 3.95 (t, J=6.2 Hz, 2H), 3.77 (t, J=4.8 Hz, 2H), 3.37 (t, J=6.2 Hz, 2H), 3.19 (s, 2H), 3.10-3.03 (m, 2H), 2.99 (t, J=12.2 Hz, 2H), 2.65 (td, J=13.1, 4.9 Hz, 2H), 1.19 (d, J=13.1 Hz, 2H), 0.94 (s, 3H). LCMS $[M+H]^+$: 491.3.

Example 2 (EX02)

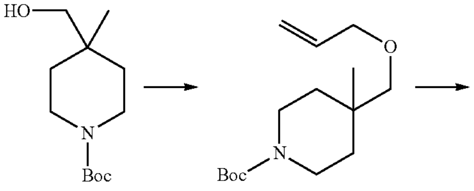

EX02-1

-continued

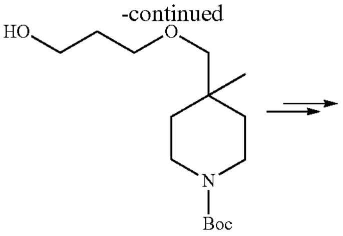

EX02-2

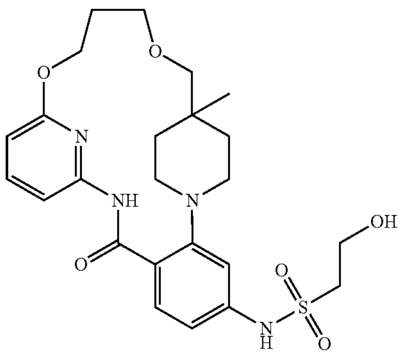

EX02

Step 1:

To a solution of tert-butyl 4-(hydroxymethyl)-4-methylpiperidine-1-carboxylate (5.0 g, 21.0 mmol) in THF (15 mL) were added NaH (1.31 g, 32.7 mmol) and 3-bromoprop-1-ene (1.32 mg, 109 mmol). The reaction was stirred at 25° C. for 2 hrs. The reaction was diluted with EtOAc (20 mL) and water (10 mL). The organic layer was separated, washed with brine (5 mL), and concentrated under reduced pressure. The residue was purified by silica gel chromatography to afford EX02-1 (4.0 g).

Step 2:

To a solution of EX02-1 (2.0 g, 7.42 mmol) in THF (50 mL) was added 9-borabicyclo [3.3.1]nonan-9-yl (0.5 M in THF, 32.7 mL, 16.334 mmol) at 0° C. under Ar atmosphere. The reaction was stirred at 0° C. for 1 hr and then stirred at rt for 10 hrs. The reaction was cooled to 0° C., followed by the sequential addition of water (20 ml), aq. NaOH (3 M, 13.6 mL, 40.8 mmol) and $H_2O_2$ (13 mL, 4.82 mmol). The reaction was stirred at 0° C. for 1 hr and then stirred at rt for 12 hrs. The reaction was extracted with EtOAc (100 ml×3). The combined organic layer was washed with brine (100 ml×2) and dried over anhydrous sodium sulfate. The organic solution was concentrated under reduced pressure and purified by silica gel chromatography to afford EX02-2 (1.5 g).

Step 3:

EX02 (5.53 mg) was prepared as described in Example 1 (EX01) Steps 3-8, except EX02-2 was used instead of EX01-2 in Step 3. $^1H$ NMR (400 MHz, $CD_3OD$) δ 8.08 (d, J=8.7 Hz, 1H), 7.90 (d, J=7.8 Hz, 1H), 7.63 (t, J=8.0 Hz, 1H), 7.29 (d, J=2.2 Hz, 1H), 7.11 (dd, J=8.6, 2.1 Hz, 1H), 6.46 (d, J=8.0 Hz, 1H), 4.79 (t, J=6.8 Hz, 2H), 3.95 (t, J=6.3 Hz, 2H), 3.46 (t, J=5.3 Hz, 2H), 3.37 (t, J=6.3 Hz, 2H), 3.18 (s, 2H), 3.09-2.98 (m, 4H), 2.60 (td, J=12.8, 5.4 Hz, 2H), 1.95-1.86 (m, 2H), 1.23 (d, J=13.4 Hz, 2H), 0.97 (s, 3H). LCMS $[M+H]^+$: 505.3.

Example 3 (EX03)

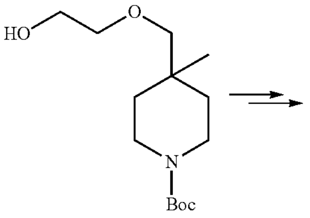

EX01-2

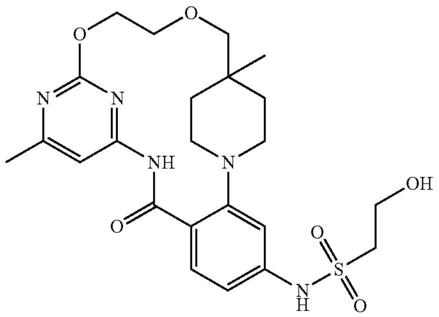

EX03

Step 1:

EX03 (1.0 mg) was prepared as described in Example 1 (EX01) Steps 3-8, except 2-chloro-6-methylpyrimidin-4-amine was used instead of 6-fluoropyridin-2-amine in Step 3. $^1$H NMR (400 MHz, $CD_3OD$) δ 8.03 (d, J=8.5 Hz, 1H), 7.85 (s, 1H), 7.22 (d, J=2.1 Hz, 1H), 7.15-7.10 (m, 1H), 4.74-4.67 (m, 2H), 3.97 (t, J=6.2 Hz, 2H), 3.84-3.77 (m, 2H), 3.40 (t, J=6.3 Hz, 2H), 3.19 (s, 2H), 3.09-2.96 (m, 4H), 2.60 (td, J=12.9, 5.2 Hz, 2H), 2.45 (s, 3H), 1.21 (d, J=13.4 Hz, 2H), 0.96 (s, 3H). LCMS $[M+H]^+$: 506.4.

Example 4 (EX04)

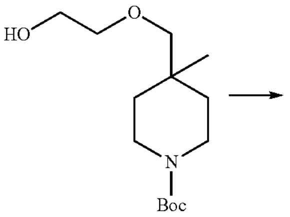

EX01-2

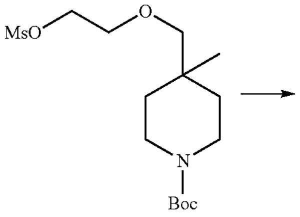

EX04-1

-continued

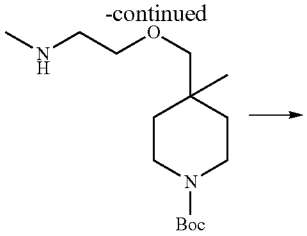

EX04-2

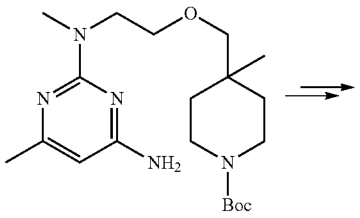

EX04-3

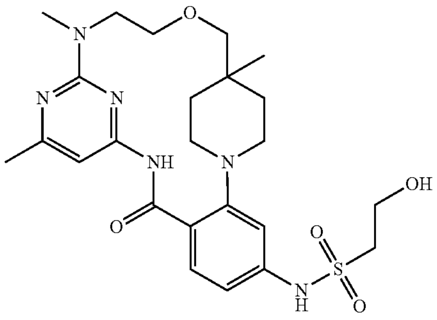

EX04

Step 1:

To a solution of EX01-2 (0.700 g, 2.56 mmol) in DCM (20 mL) were add $Ms_2O$ (1.34 g, 7.68 mmol) and TEA (1.06 mL, 7.68 mmol) at 0° C. The mixture was stirred at 25° C. for 3 hrs under $N_2$ atmosphere. The mixture was diluted with water (10.0 mL) and extracted with DCM (20 mL×3). The combined organic layer was dried over anhydrous sodium sulfate and concentrated under reduced pressure to afford EX04-1 (800 mg).

Step 2:

To a solution of EX04-1 (0.80 g, 2.27 mmol) in EtOH (8.00 mL) was added methanamine (10.0 g, 321 mmol) at 25° C. The mixture was stirred at 80° C. for 12 hrs under $N_2$ atmosphere. The mixture was diluted with water (10 mL) and extracted with EtOAc (20 mL×3). The combined organic layer was dried over anhydrous sodium sulfate and concentrated under reduced pressure to afford EX04-2 (600 mg). LCMS $[M+H]^+$: 287.2.

Step 3:

To a solution of EX04-2 (700 mg, 2.44 mmol) and 2-chloro-6-methylpyrimidin-4-amine (351 mg, 2.44 mmol) in DMF (10 mL) was added $K_2CO_3$ (1.01 g, 7.33 mmol) at 25° C. The mixture was stirred at 100° C. for 12 hrs under $N_2$ atmosphere. The mixture was diluted with water (10 mL) and extracted with EtOAc (10 mL×3). The combined organic layer was dried over $Na_2SO_4$ and concentrated under reduced pressure to afford EX04-3 (600 mg). LCMS $[M+H]^+$: 394.3.

Step 4:

EX04 (11.42 mg) was prepared as described in Example 1 (EX01) Steps 4-8, except EX04-3 was used instead of EX01-3 in Step 4. $^1$H NMR (400 MHz, $CD_3OD$) δ 8.02 (s, 1H), 7.39 (s, 1H), 7.21 (s, 1H), 7.11 (s, 1H), 4.08-3.91 (m, 2H), 3.91-3.81 (m, 2H), 3.73 (t, J=5.3 Hz, 2H), 3.40 (s, 2H), 3.22 (s, 2H), 3.19 (s, 3H), 3.11-2.95 (m, 4H), 2.68-2.52 (m, 2H), 2.37 (s, 3H), 1.20 (d, J=13.1 Hz, 2H), 0.94 (s, 3H). LCMS $[M+H]^+$: 519.4.

Example 5 (EX05)

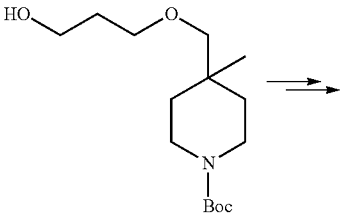

EX02-2

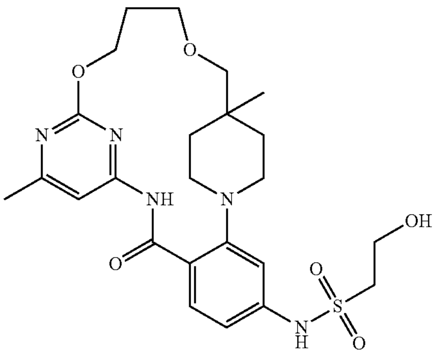

EX05

Step 1:

EX05 (70 mg) was prepared as described in Example 1 (EX01) Steps 3-8, except EX02-2 and 2-chloro-6-methylpyrimidin-4-amine were used instead of EX01-2 and 6-fluoropyridin-2-amine in Step 3. $^1H$ NMR (400 MHz, DMSO-$d_6$) δ 12.50 (s, 1H), 8.35 (s, 1H), 7.95 (d, J=8.7 Hz, 1H), 7.79 (s, 1H), 7.15 (s, 1H), 7.00 (d, J=8.7 Hz, 1H), 4.70 (t, J=7.0 Hz, 2H), 4.36 (brs, 1H), 3.74 (t, J=6.5 Hz, 2H), 3.16 (s, 2H), 2.99-2.88 (m, 4H), 2.41-2.31 (m, 4H), 2.08 (s, 3H), 1.89-1.81 (m, 2H), 1.23 (d, J=11.0 Hz, 2H), 1.06 (t, J=7.0 Hz, 2H), 0.92 (s, 3H). LCMS $[M+H]^+$: 520.3.

Example 6 (EX06)

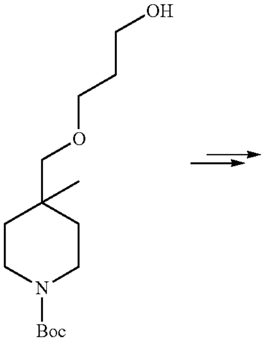

EX02-2

-continued

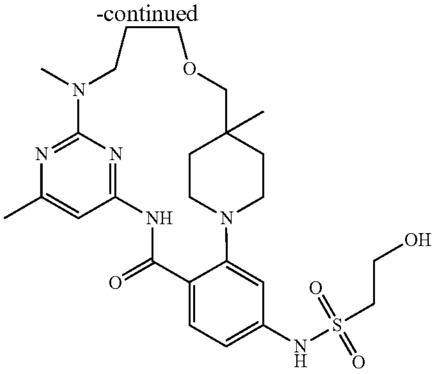

EX06

Step 1:

EX06 (15.89 mg) was prepared as described in Example 4 (EX04), except EX02-2 was used instead of EX01-2 in Step 1. $^1H$ NMR (400 MHz, $CD_3OD$) δ 8.09 (d, J=8.7 Hz, 1H), 7.44 (s, 1H), 7.30 (d, J=2.2 Hz, 1H), 7.12 (dd, J=8.7, 2.2 Hz, 1H), 3.94 (td, J=7.2, 6.7, 3.0 Hz, 4H), 3.46-3.41 (m, 2H), 3.37 (t, J=6.2 Hz, 2H), 3.18 (s, 2H), 3.10 (s, 3H), 3.02 (dd, J=7.9, 2.3 Hz, 4H), 2.61 (dt, J=13.6, 9.4 Hz, 2H), 2.34 (s, 3H), 1.86-1.77 (m, 2H), 1.28-1.19 (m, 2H), 0.98 (s, 3H). LCMS $[M+H]^+$: 533.4.

Example 7 (EX07)

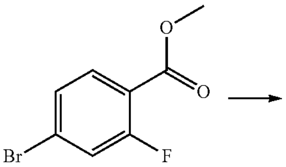

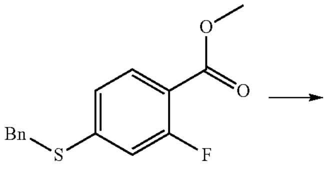

EX07-1

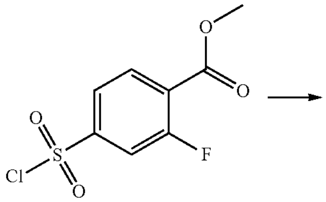

EX07-2

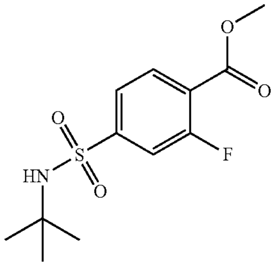

EX07-3

-continued

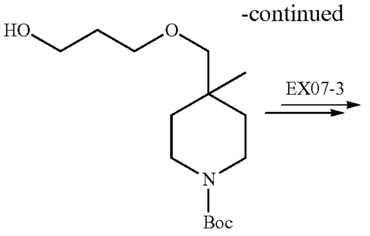

EX02-2

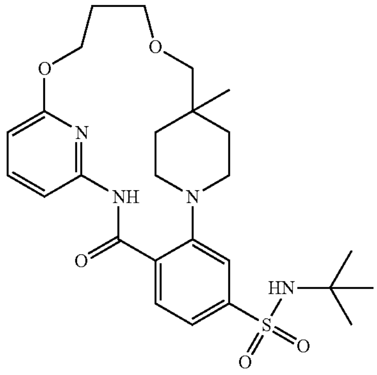

EX07

Step 1:

A mixture of methyl 4-bromo-2-fluorobenzoate (5.0 g, 21.5 mmol), phenylmethanethiol (7.99 g, 64.4 mmol), DIEA (10.6 mL, 64.4 mmol), Xantphos (1.24 g, 2.15 mmol) and $Pd_2(dba)_3$ (0.98 g, 1.07 mmol) in dioxane (10 mL) was degassed and purged with $N_2$ for 3 times. The mixture was stirred at 100° C. for 18 hrs under $N_2$ atmosphere. The reaction mixture was quenched with aq. NaClO (10 mL) and extracted with EtOAc (20 mL×3). The combined organic layer was washed with brine (50 mL), dried over anhydrous sodium sulfate, and concentrated under reduced pressure to afford EX07-1 (7.0 g). LCMS $[M+H]^+$: 277.2.

Step 2:

To a solution of EX07-1 (10.0 g, 36.2 mmol) in AcOH (100 mL) and $H_2O$ (10 mL) was added NCS (14.5 g, 108 mmol). Then the mixture was stirred at 25° C. for 3 hrs. The reaction mixture was diluted with saturated aq. $NaHCO_3$ (200 mL) and extracted with EtOAc (200 mL×3). The combined organic layer was washed with brine (500 mL), dried over anhydrous sodium sulfate, and concentrated under reduced pressure to afford EX07-2 (8.60 g).

Step 3:

To a solution of EX07-2 (8.00 g, 31.7 mmol) in DCM (80 mL) were added DIEA (26.2 mL, 158 mmol) and 2-methylpropan-2-amine (11.6 g, 158 mmol) at 0° C. Then the mixture was stirred at 25° C. for 3 hrs. The reaction mixture was diluted with water (50 mL) and extracted with DCM (50 mL×3). The combined organic layer was washed with brine (100 mL) and dried over anhydrous sodium sulfate. The organic solution was concentrated under reduced pressure and purified by silica gel chromatography to afford EX07-3 (1.10 g).

Step 4:

EX07 (5.0 mg) was prepared as described in Example 1 (EX01) Steps 3-7, except EX02-2 was used instead of EX01-2 in Step 3 and EX07-3 was used instead of methyl 2-fluoro-4-iodobenzoate in Step 5.

$^1H$ NMR (400 MHz, DMSO-$d_6$) δ 11.96 (s, 1H), 8.21 (d, J=8.1 Hz, 1H), 7.95-7.87 (m, 2H), 7.77-7.65 (m, 3H), 6.53 (d, J=8.0 Hz, 1H), 4.74 (t, J=6.9 Hz, 2H), 3.41 (t, J=5.2 Hz, 2H), 3.15 (s, 2H), 3.07-2.97 (m, 4H), 2.46-2.34 (m, 2H), 1.89-1.78 (m, 2H), 1.21 (d, J=13.1 Hz, 2H), 1.11 (s, 9H), 0.93 (s, 3H). LCMS $[M+H]^+$: 517.3.

Example 8 (EX08)

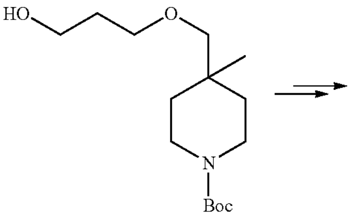

EX02-2

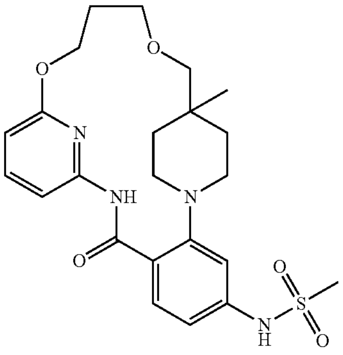

EX08

Step 1:

EX08 (2.75 mg) was prepared as described in Example 1 (EX01) Steps 3-8, except EX02-2 was used instead of EX01-2 in Step 3 and methanesulfonamide was used instead of 2-hydroxyethane-1-sulfonamide in Step 8. $^1H$ NMR (400 MHz, $CD_3OD$) δ 8.09 (d, J=8.6 Hz, 1H), 7.90 (d, J=7.8 Hz, 1H), 7.63 (t, J=7.9 Hz, 1H), 7.27 (d, J=2.2 Hz, 1H), 7.11 (dd, J=8.6, 2.1 Hz, 1H), 6.46 (d, J=8.0 Hz, 1H), 4.79 (t, J=6.8 Hz, 2H), 3.46 (t, J=5.3 Hz, 2H), 3.19 (s, 2H), 3.10-2.97 (m, 7H), 2.61 (td, J=12.8, 5.3 Hz, 2H), 1.91 (p, J=6.4 Hz, 2H), 1.24 (d, J=13.5 Hz, 2H), 0.97 (s, 3H). LCMS $[M+H]^+$: 475.4.

Example 9 (EX09)

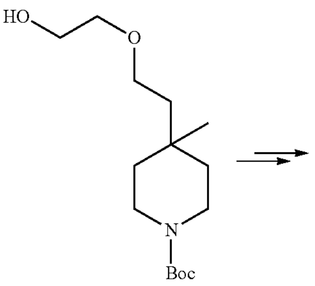

EX09-1

-continued

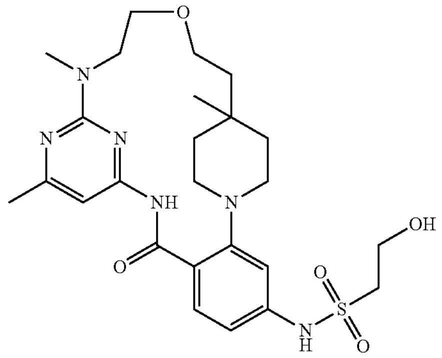

EX09

Step 1:

EX09 (2.64 mg) was prepared as described in Example 4 (EX04), except EX09-1 was used instead of EX01-2 in Step 1. $^1$H NMR (400 MHz, DMSO-$d_6$) δ 11.85 (s, 1H), 7.89 (d, J=8.6 Hz, 1H), 7.36 (s, 1H), 7.20 (d, J=2.1 Hz, 1H), 7.04 (dd, J=8.5, 2.1 Hz, 1H), 3.78-3.71 (m, 4H), 3.59-3.53 (m, 4H), 3.06 (s, 3H), 2.92 (d, J=8.5 Hz, 4H), 2.28 (s, 3H), 2.25-2.14 (m, 2H), 2.04-1.95 (m, 1H), 1.49 (t, J=5.4 Hz, 2H), 1.23-1.18 (m, 4H), 0.99 (s, 3H), 0.88-0.81 (m, 1H). LCMS [M+H]$^+$: 533.5.

Example 10 (EX10)

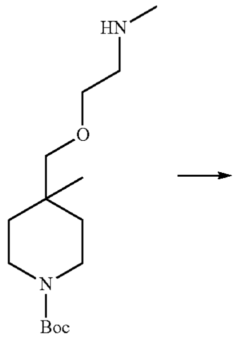

EX04-2

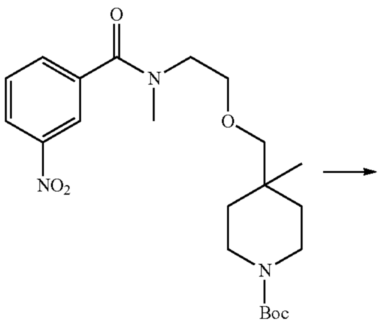

EX10-1

-continued

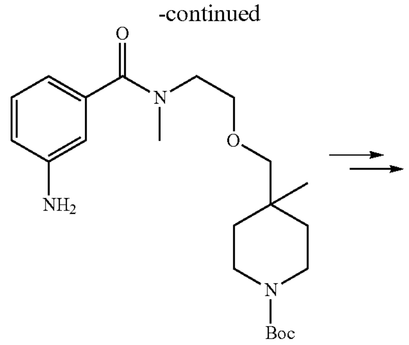

EX10-2

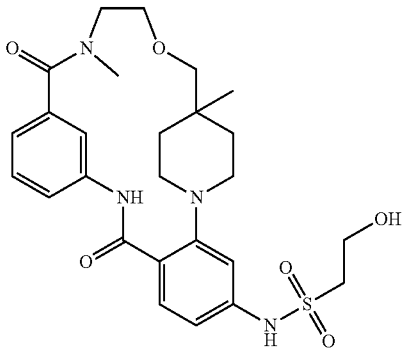

EX10

Step 1:

To a solution of EX04-2 (2.10 g, 7.33 mmol) in DCM (20 mL) were added DIEA (3.64 mL, 22.0 mmol) and 3-nitrobenzoyl chloride (1.60 g, 8.80 mmol). The mixture was stirred at 25° C. for 12 hrs. The reaction mixture was diluted with water (25 mL) and extracted with DCM (15 mL×3). The combined organic layer was washed with brine (20 mL×2) and dried over anhydrous sodium sulfate. The organic solution was concentrated under reduced pressure and purified by silica gel chromatography to afford EX10-1 (1.60 g). LCMS [M-Boc+H]$^+$: 336.4.

Step 2:

To a solution of EX10-1 (1.60 g, 3.67 mmol) in MeOH (20 mL) were added $NH_4Cl$ (1.0 g, 18.4 mmol) in $H_2O$ (6.5 mL) and iron powder (1.0 g, 18.4 mmol). The mixture was stirred at 70° C. for 2 hrs. The reaction mixture was filtered and concentrated under reduced pressure to EX10-2 (1.40 g). LCMS [M-Boc+H]$^+$: 306.4.

Step 3:

EX10 (10 mg) was prepared as described in Example 1 (EX01) Steps 4-8, except EX10-2 was used instead of EX01-3 in Step 4. $^1$H NMR (400 MHz, DMSO-$d_6$) δ12.88 (s, 1H), 8.45 (d, J=8.0 Hz, 1H), 7.97 (d, J=8.4 Hz, 1H), 7.41 (t, J=8.0 Hz, 1H), 7.20 (brs, 2H), 6.97-7.11 (m, 2H), 3.75 (t, J=6.4 Hz, 2H), 3.50-3.61 (m, 2H), 3.41-3.49 (m, 2H), 3.13-3.22 (m, 3H), 2.87-3.01 (m, 8H), 2.24 (td, J=12.8, 5.2 Hz, 2H), 1.25 (d, J=13.2 Hz, 2H), 0.94 (s, 3H). LCMS [M+H]$^+$: 531.4.

Example 11 (EX11)

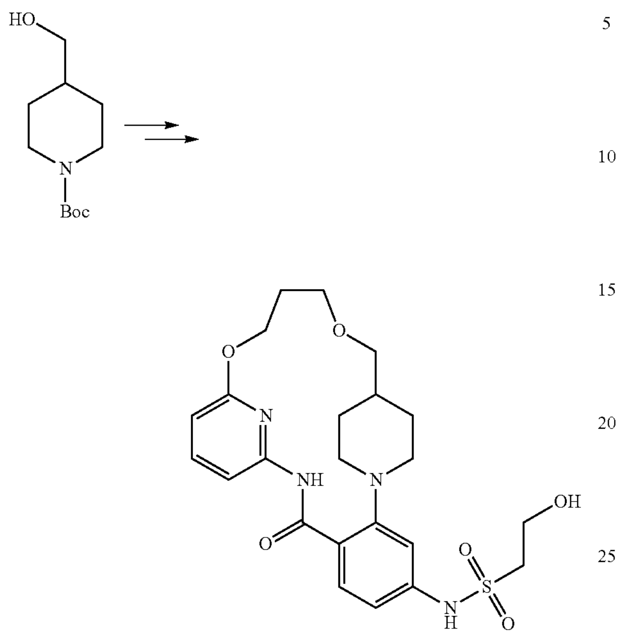

EX11

Step 1:

EX11 (14.02 mg) was prepared as described in Example 2 (EX02), except tert-butyl 4-(hydroxymethyl)piperidine-1-carboxylate was used instead of tert-butyl 4-(hydroxymethyl)-4-methylpiperidine-1-carboxylate in Step 1. $^1$H NMR (400 MHz, $CD_3OD$) δ 8.09 (dd, J=8.6, 1.7 Hz, 1H), 7.91 (d, J=7.8 Hz, 1H), 7.64 (t, J=8.0 Hz, 1H), 7.24 (t, J=2.1 Hz, 1H), 7.11 (dt, J=8.8, 1.6 Hz, 1H), 6.46 (d, J=8.0 Hz, 1H), 4.76 (t, J=6.8 Hz, 2H), 3.94 (t, J=6.3 Hz, 2H), 3.54 (d, J=1.8 Hz, 2H), 3.52-3.47 (m, 2H), 3.36 (t, J=6.3 Hz, 2H), 3.28-3.21 (m, 2H), 2.83 (t, J=12.0 Hz, 2H), 2.47-2.33 (m, 2H), 1.96-1.86 (m, 2H), 1.70-1.55 (m, 3H). LCMS $[M+H]^+$: 491.2.

Example 12 (EX12)

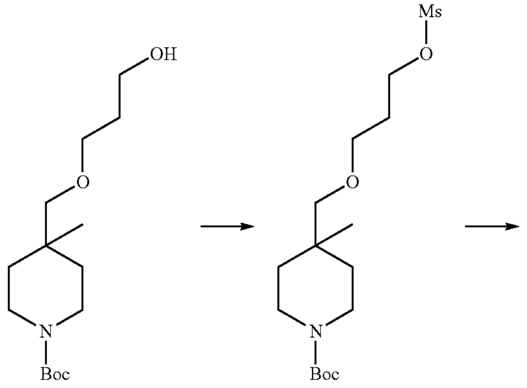

EX02-2 EX12-1

-continued

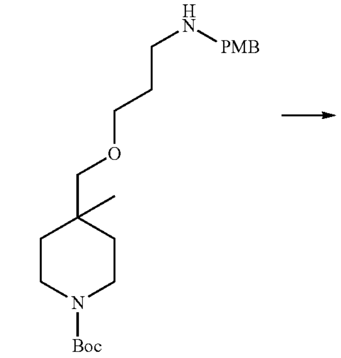

EX12-2

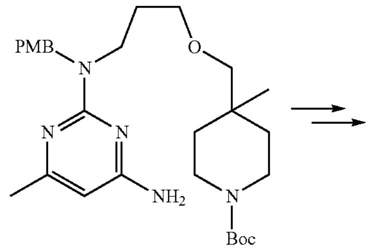

EX12-3

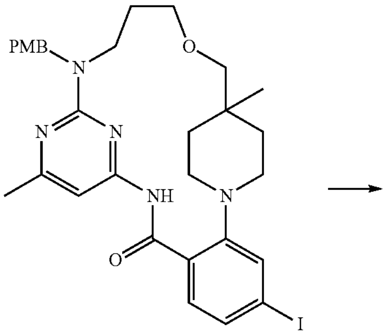

EX12-4

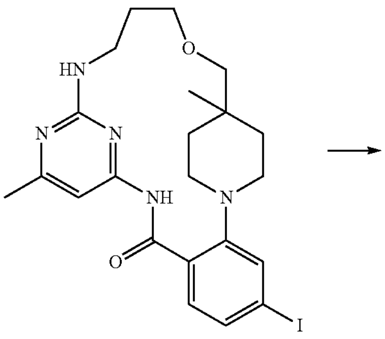

EX12-5

-continued

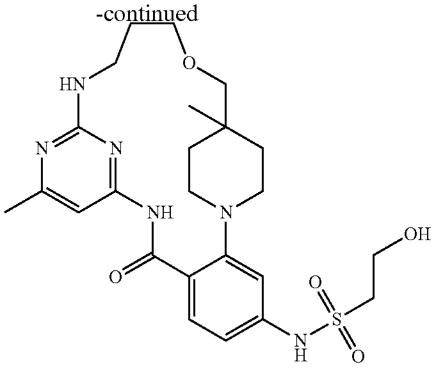

EX12

Step 1:

EX12-1 (5.4 g) was prepared as described in Example 4 (EX04) Step 1, except EX02-2 was used instead of EX01-2. LCMS [M-$^{t}$Bu+H]$^{+}$: 310.0.

Step 2:

To a solution of EX12-1 (2.6 g, 7.11 mmol) and 4-methoxybenzylamine (2.00 g, 14.22 mmol) in DMSO (25 mL) were added CsF (2.2 g, 14.22 mmol) and DIEA (3.53 mL, 21.34 mmol) under $N_2$ protection. The mixture was stirred at 120° C. for 2 hrs. The reaction mixture was quenched with water (200 mL). The mixture was extracted with EtOAc (200 mL×3). The combined organic layer was dried over $MgSO_4$ and concentrated under reduced pressure to give a residue. The residue was purified by silica gel chromatography to afford EX12-2 (1.8 g). LCMS [M+H]$^{+}$: 407.2.

Step 3:

EX12-3 (950 mg) was prepared as described in Example 4 (EX04) Step 3, except EX12-2 was used instead of EX04-2. LCMS [M+H]$^{+}$: 514.4.

Step 4:

EX12-4 (220 mg) was prepared as described in Example 1 (EX01) Steps 4-7, except EX12-3 was used instead of EX01-3 in Step 4. LCMS [M+H]$^{+}$: 642.3.

Step 5:

A solution of EX12-4 (200 mg, 0.312 mmol) in TFA (2 mL, 0.312 mmol) was stirred at 50° C. for 1 hr. The mixture was concentrated under reduced pressure, neutralized with aq. $Na_2CO_3$ (pH=8), and extracted with EtOAc (20 mL×3). The combined organic layer was dried over $MgSO_4$ and concentrated under reduced pressure to give EX12-5 (160 mg). LCMS [M+H]$^{+}$: 522.2.

Step 6:

EX12 (43.98 mg) was prepared as described in Example 1 (EX01) Step 8, except EX12-5 was used instead of EX01-7. $^{1}$H NMR (400 MHz, $CD_3OD$) δ 8.08 (d, J=8.6 Hz, 1H), 7.48 (s, 1H), 7.30 (d, J=2.2 Hz, 1H), 7.13 (dd, J=8.7, 2.2 Hz, 1H), 3.95 (t, J=6.2 Hz, 2H), 3.73 (t, J=6.9 Hz, 2H), 3.45 (t, J=5.2 Hz, 2H), 3.38 (t, J=6.2 Hz, 2H), 3.19 (s, 2H), 3.07-2.98 (m, 4H), 2.65-2.54 (m, 2H), 2.32 (s, 3H), 1.76 (p, J=6.2 Hz, 2H), 1.24 (d, J=13.1 Hz, 2H), 0.97 (s, 3H). LCMS [M+H]$^{+}$: 519.1.

Example 13 (EX13)

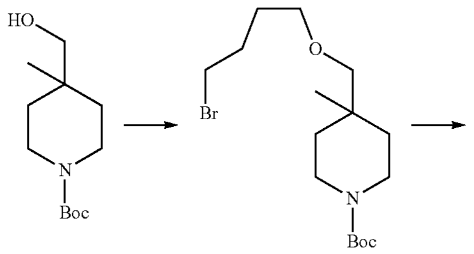

EX13-1

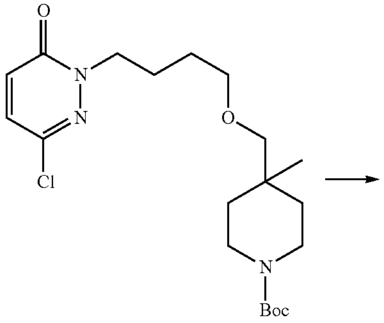

EX13-2

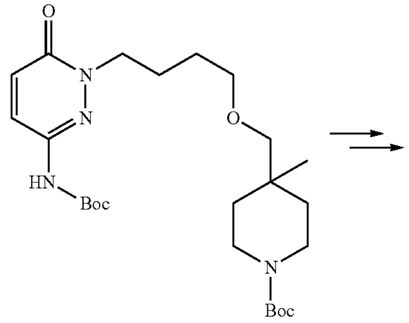

EX13-3

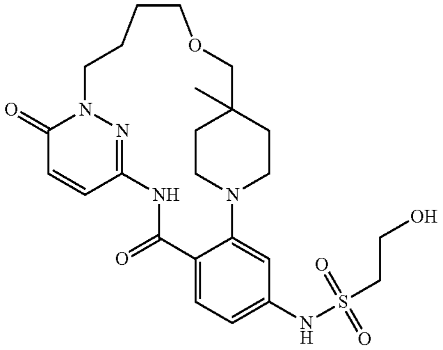

EX13

Step 1:

To a solution of NaOH (2.2 g, 54.51 mmol) in $H_2O$ (50 mL) were added tert-butyl 4-(hydroxymethyl)-4-methylpiperidine-1-carboxylate (5.0 g, 21.81 mmol), 1,4-dibromobutane (6.5 mL, 54.51 mmol) and tetrabutylammonium bisulfate (0.2 g, 0.55 mmol). The reaction mixture was stirred at 70° C. for 3 hrs and then extracted with EtOAc (100 mL×3). The combined organic layer was dried over $MgSO_4$, concentrated under reduced pressure, and purified by silica gel chromatography to afford EX13-1 (2 g). LCMS [M-$^t$Bu+H]$^+$: 308.0.

Step 2:

To a solution of EX13-1 (2 g, 5.49 mmol) and 6-chloro-pyridazin-3(2H)-one (1.4 g, 10.98 mmol) in DMF (20 mL) was added $K_2CO_3$ (2.3 g, 16.47 mmol) under $N_2$ atmosphere. The mixture was stirred at 80° C. for 1 hr. The reaction mixture was filtrated and concentrated under reduced pressure to give a residue. The residue was purified by silica gel chromatography to afford EX13-2 (2.2 g). LCMS [M-Boc+H]$^+$: 314.3.

Step 3:

To a solution of EX13-2 (2 g, 4.83 mmol) and tert-butyl carbamate (1.1 g, 9.66 mmol) in toluene (20 mL) were added $Cs_2CO_3$ (4.7 g, 14.5 mmol), XantPhos (0.6 g, 0.97 mmol) and $Pd_2(dba)_3$ (0.4 g, 0.48 mmol) under $N_2$ atmosphere. The reaction mixture was stirred at 100° C. for 16 hrs. The reaction was quenched with water (50 mL) and extracted with EtOAc (50 mL×3). The combined organic layer was dried over $MgSO_4$, concentrated under reduced pressure, and purified by silica gel chromatography to give EX13-3. LCMS [M-Boc+H]$^+$: 395.3.

Step 4:

EX13 was prepared as described in Example 1 (EX01) Steps 4-8, except EX13-3 was used instead of EX01-3 in Step 4. $^1$H NMR (400 MHz, $CD_3OD$) δ 8.35 (d, J=9.8 Hz, 1H), 8.10 (d, J=8.7 Hz, 1H), 7.34 (d, J=2.2 Hz, 1H), 7.17 (dd, J=8.6, 2.2 Hz, 1H), 7.04 (d, J=9.9 Hz, 1H), 4.21 (t, J=6.7 Hz, 2H), 3.95 (t, J=6.2 Hz, 2H), 3.48 (t, J=5.4 Hz, 2H), 3.37 (t, J=6.2 Hz, 2H), 3.17 (s, 2H), 3.09 (t, J=11.7 Hz, 2H), 3.01 (d, J=11.3 Hz, 2H), 2.55 (td, J=13.3, 4.6 Hz, 2H), 2.12 (p, J=7.0 Hz, 2H), 1.55 (p, J=6.5 Hz, 2H), 1.33-1.22 (m, 2H), 1.00 (s, 3H). LCMS [M+H]$^+$: 520.1.

Example 14 (EX14)

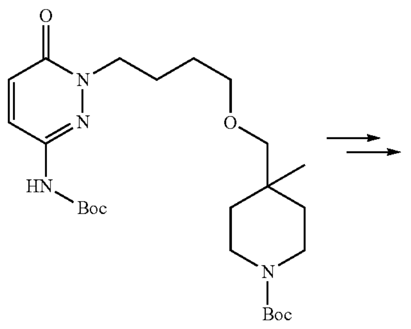

EX13-3

-continued

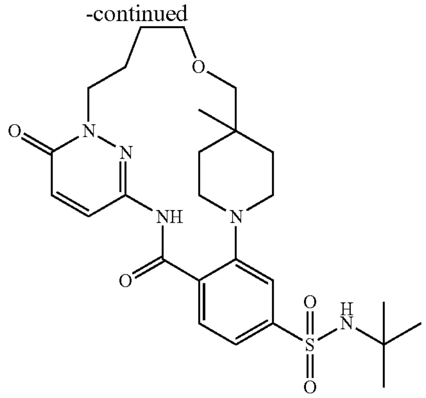

EX14

Step 1:

EX14 (10.59 mg) was prepared as described in Example 1 (EX01) Steps 4-7, except EX13-3 was used instead of EX01-3 in Step 4 and EX07-3 was used instead of methyl 2-fluoro-4-iodobenzoate in Step 5. $^1$H NMR (400 MHz, $CD_3OD$) δ 8.41 (d, J=9.8 Hz, 1H), 8.27 (d, J=8.2 Hz, 1H), 7.98 (d, J=1.8 Hz, 1H), 7.80 (dd, J=8.2, 1.8 Hz, 1H), 7.08 (d, J=9.8 Hz, 1H), 4.23 (t, J=6.6 Hz, 2H), 3.49 (t, J=5.4 Hz, 2H), 3.19 (s, 2H), 3.15 (d, J=11.7 Hz, 2H), 3.08 (d, J=8.8 Hz, 2H), 2.57 (td, J=13.1, 4.7 Hz, 2H), 2.15 (p, J=6.8 Hz, 2H), 1.56 (p, J=6.6 Hz, 2H), 1.31 (d, J=12.4 Hz, 2H), 1.23 (s, 9H), 1.03 (s, 3H). LCMS[M+H]$^+$: 532.1.

Example 15 (EX15)

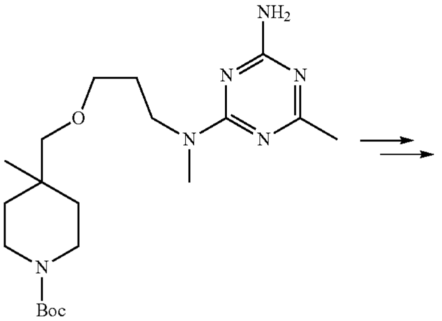

EX15-1

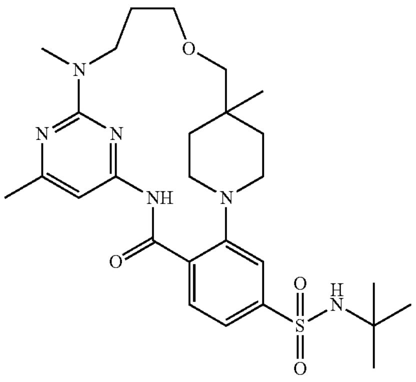

EX15

Step 1:

EX15 (4.27 mg) was prepared as described in Example 1 (EX01) Steps 4-7, except EX15-1 was used instead of EX01-3 in Step 4 and EX07-3 was used instead of methyl 2-fluoro-4-iodobenzoate in Step 5. ${}^1$H NMR (400 MHz, $CD_3OD$) δ 8.26 (d, J=8.3 Hz, 1H), 7.93 (s, 1H), 7.74 (d, J=8.1 Hz, 1H), 7.45 (s, 1H), 3.94 (t, J=7.1 Hz, 2H), 3.44 (t, J=5.2 Hz, 2H), 3.19 (s, 2H), 3.13-3.05 (m, 7H), 2.68-2.56 (m, 2H), 2.35 (s, 3H), 1.82 (p, J=5.6 Hz, 2H), 1.31-1.23 (m, 2H), 1.21 (s, 9H), 0.99 (s, 3H). LCMS [M+H]$^+$: 545.3.

Example 16 (EX16)

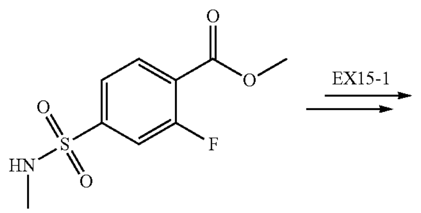

EX16-1

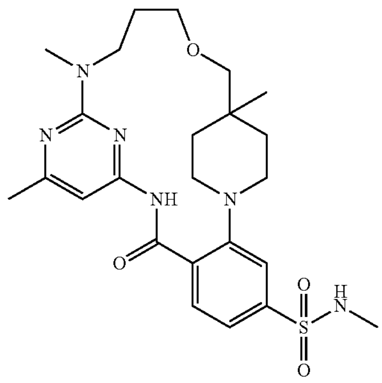

EX16

Step 1:

EX16 (1.87 mg) was prepared as described in Example 1 (EX01) Steps 4-7, except EX15-1 was used instead of EX01-3 in Step 4 and EX16-1 was used instead of methyl 2-fluoro-4-iodobenzoate in Step 5. ${}^1$H NMR (400 MHz, $CD_3OD$) δ 8.30 (d, J=8.2 Hz, 1H), 7.85 (d, J=1.8 Hz, 1H), 7.70 (dd, J=8.2, 1.7 Hz, 1H), 7.47 (s, 1H), 3.97 (t, J=7.1 Hz, 2H), 3.47-3.42 (m, 2H), 3.20 (s, 2H), 3.11 (d, J=10.0 Hz, 7H), 2.68-2.60 (m, 2H), 2.59 (s, 3H), 2.37 (s, 3H), 1.84 (p, J=6.1 Hz, 2H), 1.28 (d, J=13.8 Hz, 2H), 1.01 (s, 3H). LCMS [M+H]$^+$: 503.2.

Example 17 (EX17)

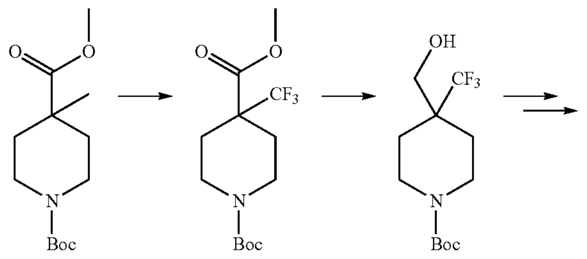

EX17-1 EX17-2

-continued

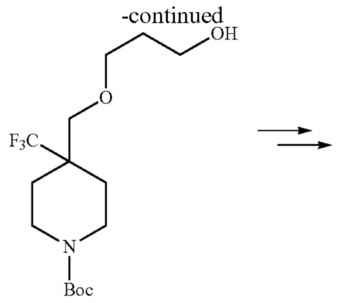

EX17-3

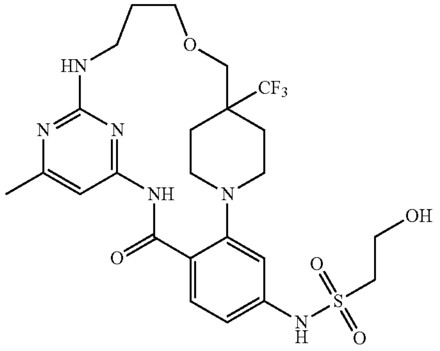

EX17

Step 1:

To a solution of 2-methylpropan-2-yl 4-(methoxycarbonyl) hexahydropyridine-1-carboxylate (10 g, 41.1 mmol) in THF (350 mL) was added LDA (2 M, 41.1 mL, 82.20 mmol) under $N_2$ atmosphere at −78° C. The mixture was stirred at −78° C. for 1 hr, followed by the addition of 5-(trifluoromethyl)dibenzothiophenium trifluoromethanesulfonate (CAS: 129946-88-9, 33.1 g, 82.20 mmol) at −78° C. The mixture was stirred at 25° C. for 16 hrs. The reaction was quenched with saturated aq. $NH_4Cl$ (600 mL) and extracted with EtOAc (600 mL×3). The combined organic layer was washed with brine (500 mL), dried over $MgSO_4$ and concentrated under reduced pressure. The obtained residue was purified by silica gel chromatography to afford EX17-1 (3.8 g). LCMS [M-${}^t$Bu+H]$^+$: 256.0.

Step 2

To a solution of EX17-1 (3.8 g, 12.21 mmol) in THF (50 mL) was added $LiBHEt_3$ (36.6 mL, 36.62 mmol) under $N_2$ atmosphere at 0° C. The mixture was stirred at 25° C. for 2 hrs. The mixture was quenched with MeOH (50 mL) and concentrated under reduced pressure. The residue was diluted with saturated aq. $NH_4Cl$ (50 mL) and extracted with EtOAc (50 mL×3). The combined organic layer was dried over $MgSO_4$, concentrated under reduced pressure and purified by silica gel chromatography to afford EX17-2 (2.6 g). LCMS [M-${}^t$Bu+H]$^+$: 228.0.

Step 3:

EX17-3 (1.6 g) was prepared as described in Example 2 (EX02) Steps 1-2, except EX17-2 was used instead of tert-butyl 4-(hydroxymethyl)-4-methylpiperidine-1-carboxylate in Step 1. LCMS [M-${}^t$Bu+H]$^+$: 286.0.

Step 4:

EX17 (37 mg) was prepared as described in Example 12 (EX12), except EX17-3 was used instead of EX02-2 in Step 1. H NMR (400 MHz, $CD_3OD$) δ 8.15 (s, 1H), 8.10 (d, J=8.6 Hz, 1H), 7.49 (s, 1H), 7.29 (d, J=2.2 Hz, 1H), 7.17 (dd, J=8.8, 2.1 Hz, 1H), 3.94 (t, J=6.2 Hz, 2H), 3.70 (t, J=7.1 Hz, 2H), 3.49 (t, J=5.3 Hz, 2H), 3.43 (s, 2H), 3.37 (t, J=6.2 Hz, 2H), 3.16-3.07 (m, 4H), 2.73-2.61 (m, 2H), 2.33 (s, 3H), 1.94 (d, J=14.4 Hz, 2H), 1.78 (p, J=6.5 Hz, 2H). LCMS $[M+H]^+$: 573.3.

Example 18 (EX18)

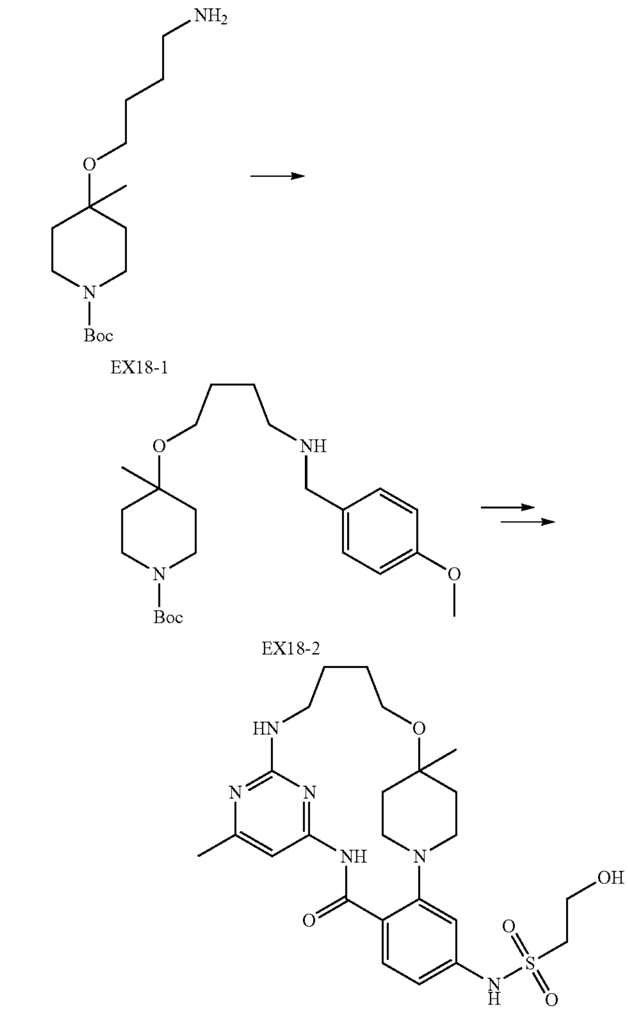

EX18-1

EX18-2

EX18

Step 1:

To a solution of EX18-1 (5 g, 8.73 mmol) and 4-methoxybenzene-1-carbaldehyde (2.4 g, 17.46 mmol) in MeOH (25 mL) was added $Na_2CO_3$ (4.6 g, 43.65 mmol). The reaction was stirred at 25° C. for 16 hrs, followed by the addition of $NaBH_4$ (1.24 g, 32.8 mmol) at 0° C. The reaction was stirred at 25° C. for 2 hrs. The reaction mixture was filtrated and concentrated under reduced pressure. The residue was diluted with water (200 mL) and extracted with EtOAc (200 mL×3). The combined organic layer was dried over $MgSO_4$, concentrated under reduced pressure, and purified by silica gel chromatography to afford EX18-2 (2 g). LCMS $[M+H]^+$: 407.3.

Step 2:

EX18 (20.12 mg) was prepared as described in Example 12 (EX12) Steps 3-6, except EX18-2 was used instead of EX12-2 in Step 3. $^1H$ NMR (400 MHz, DMSO-$d_6$) δ 13.23 (s, 1H), 10.25 (brs, 1H), 8.08 (d, J=8.6 Hz, 1H), 7.27-7.22 (m, 2H), 7.14 (dd, J=8.7, 2.1 Hz, 1H), 6.94 (t, J=6.7 Hz, 1H), 4.95 (s, 1H), 3.75 (t, J=6.5 Hz, 2H), 3.54-3.43 (m, 4H), 3.38-3.36 (m, 2H), 3.07 (d, J=11.4 Hz, 2H), 2.84 (d, J=12.6 Hz, 2H), 2.44-2.30 (m, 2H), 2.20 (s, 3H), 1.86 (d, J=12.4 Hz, 2H), 1.55-1.40 (m, 4H), 1.27 (s, 3H). LCMS $[M+H]^+$: 519.4.

Example 19 (EX19)

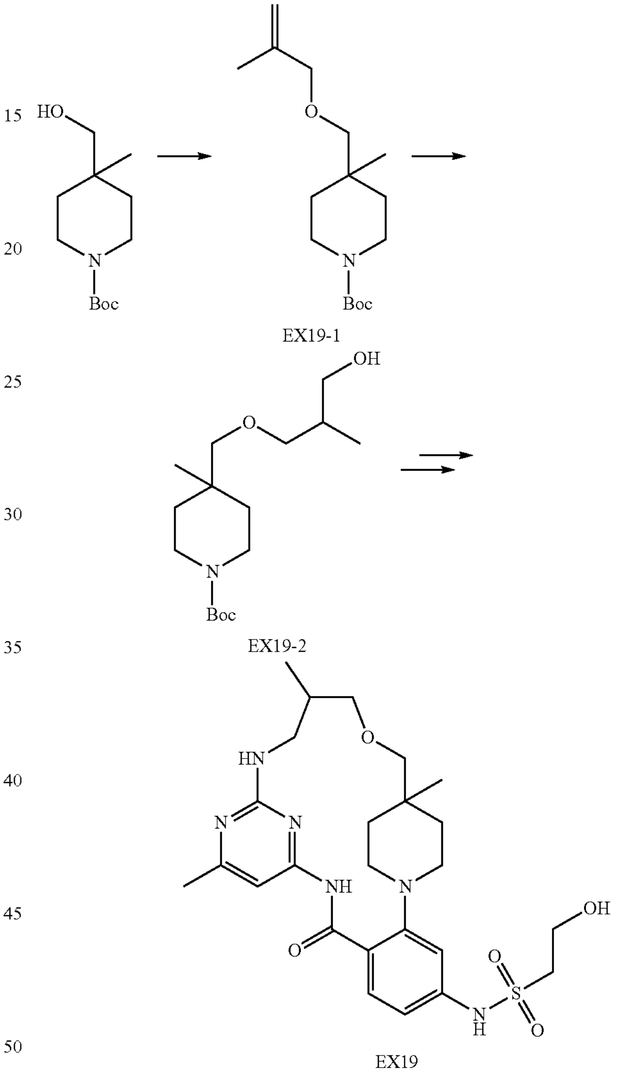

EX19-1

EX19-2

EX19

Step 1:

EX19-1 (10 g) was prepared as described in Example 2 (EX02) Step 1, except 3-bromo-2-methylprop-1-ene was used instead of 3-bromoprop-1-ene.

Step 2:

To a solution of EX19-1 (10 g, 35.29 mmol) in THF (200 mL) was added $BH_3$·THF (1 M, 38.8 mL) under $N_2$ atmosphere. The mixture was stirred at 25° C. for 2 hrs, followed by the addition of aq. NaOH (3 M, 30 mL, 90 mmol) and $H_2O_2$ (83.9 mL, 821.82 mmol) at 0° C. The mixture was stirred at 25° C. for 2 hrs. The mixture was diluted with water (500 mL) and extracted with EtOAc (500 mL×3). The combined organic layer was washed with saturated aq. $Na_2SO_3$, dried over $MgSO_4$, and concentrated under reduced pressure. The obtained residue was purified by silica gel chromatography to afford EX19-2 (10.5 g). LCMS [M-$^{t}$Bu+H]$^{+}$: 246.1.

Step 3:

EX19 (122.81 mg) was prepared as described in Example 12 (EX12), except EX19-2 was used instead of EX02-2. $^{1}$H NMR (400 MHz, $D_2O$+DMSO-$d_6$) δ 8.02 (d, J=8.6 Hz, 1H), 7.31 (s, 1H), 7.27 (d, J=2.2 Hz, 1H), 7.10 (dd, J=8.6, 2.0 Hz, 1H), 4.13 (dd, J=13.2, 3.7 Hz, 1H), 3.75 (t, J=6.4 Hz, 2H), 3.35 (t, J=6.4 Hz, 2H), 3.26 (dd, J=9.1, 3.6 Hz, 1H), 3.18 (d, J=8.9 Hz, 1H), 3.13-3.04 (m, 2H), 3.03-2.94 (m, 2H), 2.93-2.78 (m, 2H), 2.70 (dd, J=13.3, 8.0 Hz, 1H), 2.49-2.37 (m, 2H), 2.21 (s, 3H), 1.70 (brs, 1H), 1.24 (d, J=13.0 Hz, 1H), 1.12 (d, J=12.9 Hz, 1H), 0.90 (s, 3H), 0.86 (d, J=6.9 Hz, 3H). LCMS [M+H]$^{+}$: 533.2.

Example 20 (EX20)

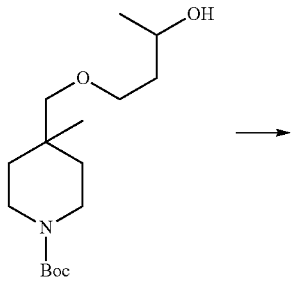

EX20-1

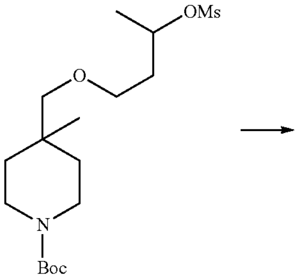

EX20-2

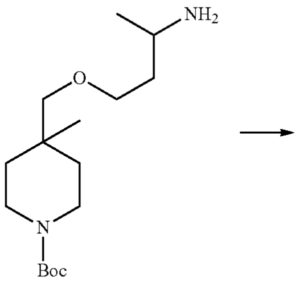

EX20-3

-continued

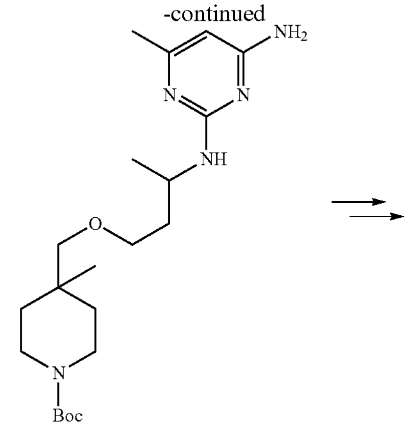

EX20-4

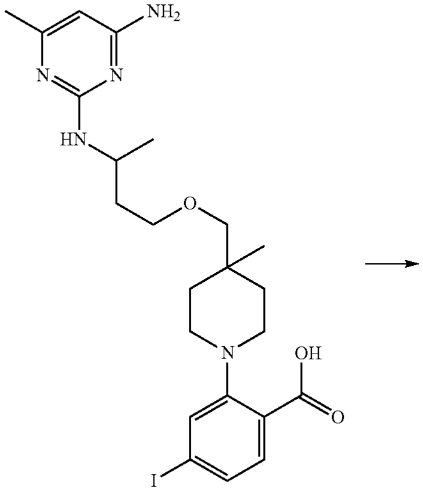

EX20-5

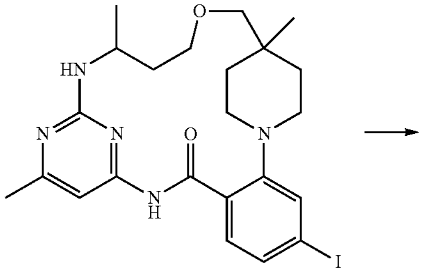

EX20-6

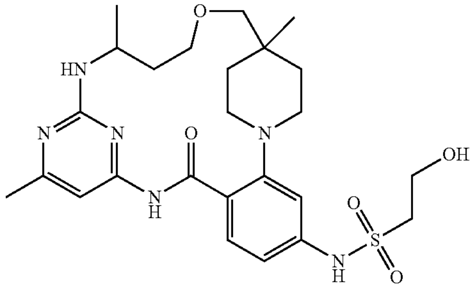

EX20

Step 1:

EX20-2 (700 mg, crude) was prepared as described in Example 4 (EX04) Step 1, except EX20-1 was used instead of EX01-2. LCMS [M+Na]$^{+}$: 402.1.

Step 2:

A solution of EX20-2 (700 mg, 1.16 mmol) in ammonium hydroxide (4 mL, 104 mmol) was stirred at 80° C. for 2 hrs. The mixture was concentrated under reduced pressure to afford EX20-3 (300 mg, crude). LCMS [M+H]$^+$: 301.2.

Step 3:

EX20-4 (1.2 g) was prepared as described in Example 4 (EX04) Step 3, except EX20-3 was used instead of EX04-2. LCMS [M+H]$^+$: 408.3.

Step 4:

EX20-5 (50 mg) was prepared as described in Example 1 (EX01) Steps 4-6, except EX20-4 was used instead of EX01-3 in Step 4. LCMS [M+H]$^+$: 554.1.

Step 5:

To a solution of EX20-5 (30 mg, 0.043 mmol) in DCM (0.5 mL) were added $POCl_3$ (14.7 mg, 0.087 mmol) and DIEA (22 uL, 0.13 mmol). The mixture was stirred at 25° C. for 2 hrs. The mixture was diluted with $H_2O$ (3 mL) and extracted with DCM (3 mL×3). The combined organic layer was dried over $MgSO_4$, concentrated under reduced pressure, and purified by silica gel chromatography to afford EX20-6 (12 mg). LCMS [M+H]$^+$: 536.2.

Step 6:

EX20 (1.17 mg) was prepared as described in Example 1 (EX01) Step 8, except EX20-6 was used instead of EX01-7. $^1$H NMR (400 MHz, $CD_3OD$) δ 8.05 (d, J=8.63 Hz, 1H), 7.44 (s, 1H), 7.28 (d, J=2.13 Hz, 1H), 7.12 (dd, J=8.63, 2.13 Hz, 1H), 3.95 (t, J=6.19 Hz, 2H), 3.42-3.51 (m, 2H), 3.37 (t, J=6.25 Hz, 2H), 3.11 (br s, 2H), 2.93-3.05 (m, 3H), 2.80-2.89 (m, 2H), 2.48-2.65 (m, 2H), 2.30 (s, 3H), 1.69 (dt, J=8.35, 3.46 Hz, 2H) 1.34-1.41 (m, 2H), 1.19 (d, J=6.75 Hz, 3H), 0.96 (s, 3H). LCMS [M+H]$^+$: 533.3.

Example 21 (EX21)

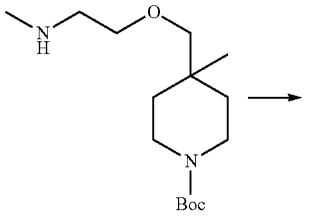

EX04-2

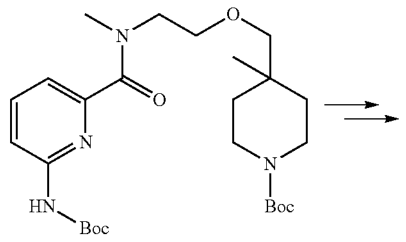

EX21-1

-continued

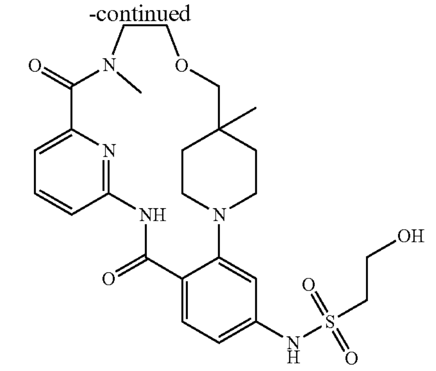

EX21

Step 1:

To a solution of EX04-2 (1.1 g, 3.84 mmol) and 6-((tert-butoxycarbonyl)amino) picolinic acid (1.1 g, 4.61 mmol) in DMF (24 mL) were added HATU (2.2 g, 5.76 mmol) and DIEA (1.27 mL, 7.68 mmol). The mixture was stirred at 30° C. for 2 hrs. The reaction mixture was diluted with water (50 mL) and extracted with EtOAc (30 mL×3). The combined organic layer was dried over $MgSO_4$, concentrated under reduced pressure and purified by silica gel chromatography to afford EX21-1 (920 mg). LCMS [M+H]$^+$:507.1.

Step 2:

EX21 was prepared as described in Example 10 (EX10) Step 3, except EX21-1 was used instead of EX10-2. $^1$H NMR (400 MHz, Methanol-$d_4$) δ 8.35-8.26 (m, 1H), 8.26-8.03 (m, 1H), 7.92 (dd, J=7.6, 15.5 Hz, 1H), 7.48-7.00 (m, 3H), 4.61-4.51 (m, 1H), 3.97 (t, J=6.2 Hz, 2H), 3.85-3.65 (m, 1H), 3.60-3.48 (m, 2H), 3.39 (t, J=6.2 Hz, 2H), 3.29-3.23 (m, 1H), 3.21-3.07 (m, 5H), 3.05 (br s, 3H), 2.87-2.47 (m, 2H), 1.48-1.15 (m, 2H), 1.07-0.96 (m, 3H). LCMS [M+H]$^+$: 532.2.

Example 22 (EX22)

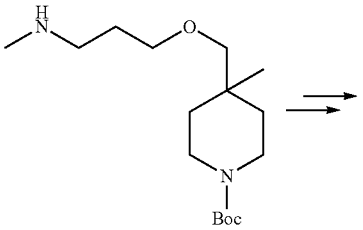

EX22-1

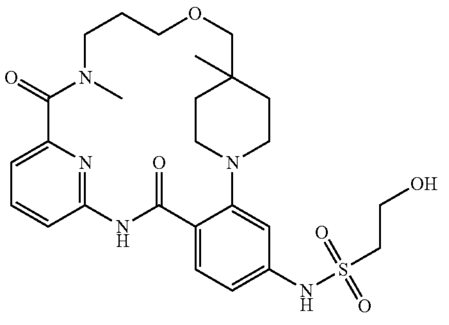

EX22

Step 1:

EX22 (15.84 mg) was prepared as described in Example 21 (EX21), except EX22-1 was used instead of EX04-2 in Step 1. $^1$H NMR (400 MHz, DMSO-$d_6$) δ 13.19-10.76 (m, 1H), 8.33-8.18 (m, 1H), 8.14-7.71 (m, 2H), 7.38-7.28 (m, 1H), 7.21-6.97 (m, 2H), 4.45-3.83 (m, 1H), 3.80 (t, J=6.5 Hz, 2H), 3.60 (m, 1H), 3.37-3.31 (m, 3H), 3.22-3.09 (m, 2H), 3.08-2.82 (m, 8H), 2.81-2.52 (m, 2H), 2.35 (d, J=18.8 Hz, 1H), 2.09-1.62 (m, 3H), 1.33-1.09 (m, 2H), 1.02-0.82 (m, 3H). LCMS $[M+H]^+$: 546.2.

Example 23 (EX23)

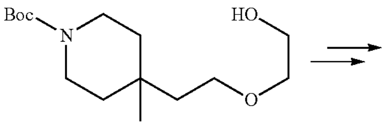

EX09-2

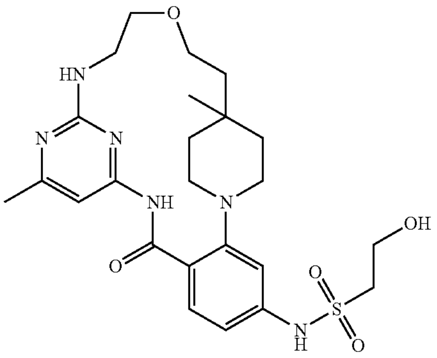

EX23

Step 1:

EX23 (14.37 mg) was prepared as described in Example 12 (EX12), except EX09-1 was used instead of EX02-2 in Step 1. $^1$H NMR (400 MHz, $CD_3OD$) δ 8.03 (d, J=8.6 Hz, 1H), 7.48 (s, 1H), 7.31 (d, J=2.2 Hz, 1H), 7.12 (dd, J=8.6, 2.2 Hz, 1H), 3.95 (t, J=6.2 Hz, 2H), 3.68 (t, J=5.5 Hz, 2H), 3.64 (t, J=5.4 Hz, 2H), 3.57 (t, J=5.3 Hz, 2H), 3.37 (t, J=6.2 Hz, 2H), 3.15-2.97 (m, 4H), 2.40-2.33 (m, 2H), 2.33 (s, 3H), 1.60 (t, J=5.5 Hz, 2H), 1.31 (d, J=13.1 Hz, 2H), 1.08 (s, 3H). LCMS $[M+H]^+$: 519.2.

Example 24 (EX24)

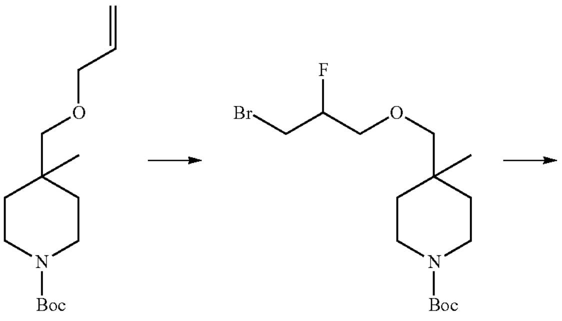

EX02-1 EX24-1

-continued

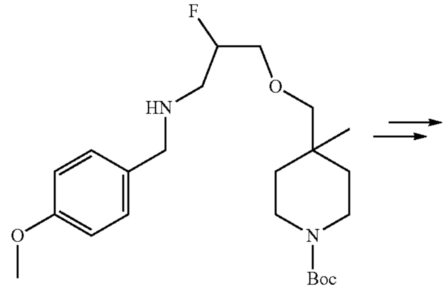

EX24-2

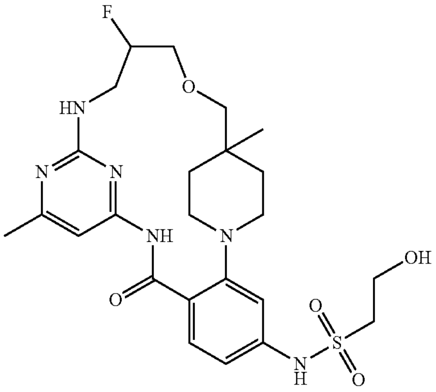

EX24

Step 1:

To a solution of EX02-1 (6 g, 22.27 mmol) in DCM (350 mL) were added NBS (7.93 g, 44.54 mmol) and triethylamine trihydrofluoride (4.31 g, 26.73 mmol) at 0° C. The reaction was stirred at 25° C. for 16 hrs. The reaction mixture was concentrated under reduced pressure and purified by silica gel chromatography to afford EX24-1 (3.4 g). LCMS $[M-{}^tBu+H]^+$: 312.0.

Step 2:

EX24-2 was prepared as described in Example 12 (EX12) Step 2, except EX24-1 was used instead of EX12-1. LCMS $[M+H]^+$: 425.3.

Step 3:

EX24 (13.58 mg) was prepared as described in Example 12 (EX12) Steps 3-6, except EX24-2 was used instead of EX12-2 in Step 3. $^1$H NMR (400 MHz, $D_2O$+DMSO-$d_6$) δ 7.97 (d, J=8.6 Hz, 1H), 7.34 (s, 1H), 7.21 (s, 1H), 7.07 (d, J=8.7 Hz, 1H), 4.53 (d, J=46.7 Hz, 1H), 4.18-4.03 (m, 2H), 3.75 (t, J=6.3 Hz, 2H), 3.64-3.40 (m, 2H), 3.34 (t, J=6.3 Hz, 2H), 3.23 (d, J=9.1 Hz, 1H), 3.14 (d, J=9.1 Hz, 1H), 2.90 (d, J=26.9 Hz, 4H), 2.41-2.24 (m, 2H), 2.22 (s, 3H), 1.22 (d, J=11.6 Hz, 1H), 1.13 (d, J=13.2 Hz, 1H), 0.87 (s, 3H). LCMS $[M+H]^+$: 537.3.

Example 25 (EX25-A)

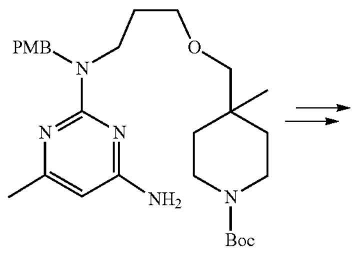

EX12-3

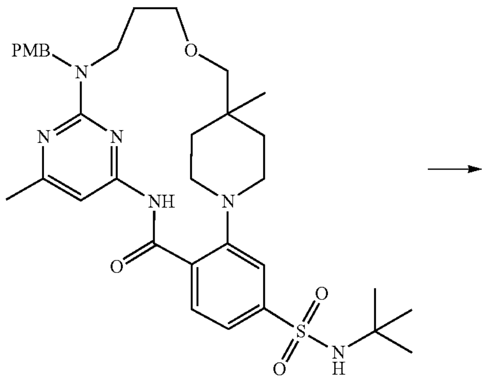

EX25-1

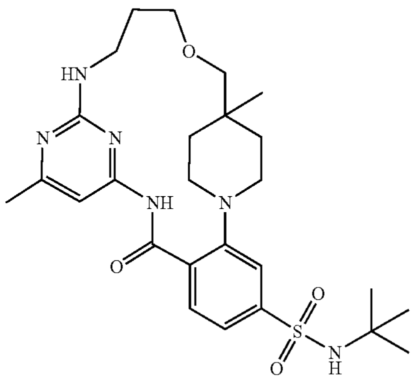

EX25

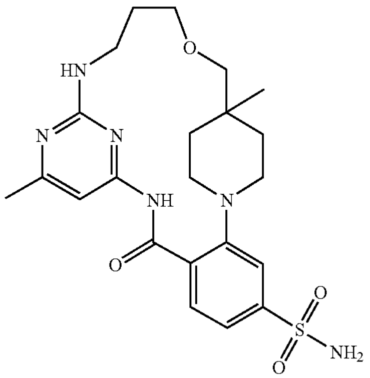

EX25-A

Step 1:

EX25-1 (80 mg) was prepared as described in Example 1 (EX01) Steps 4-7, except EX12-3 was used instead of EX01-3 in Step 4 and EX07-3 was used instead of methyl 2-fluoro-4-iodobenzoate in Step 5. LCMS $[M+H]^+$: 651.5.

Step 2:

To a solution of EX25-1 (60 mg, 0.09 mmol) in DCM (2 mL) was added TFA (0.21 mL, 2.77 mmol). The resulting mixture was stirred at 25° C. for 1 hr. The mixture was concentrated under reduced pressure, neutralized with saturated aq. $Na_2CO_3$ (pH=8) and extracted with EtOAc (20 mL×3). The combined organic layer was dried over $MgSO_4$ and concentrated under reduced pressure. The residue was purified by prep-HPLC to afford EX25 (16.03 mg) and EX25-A (7.31 mg).

EX25: $^1$H NMR (400 MHz, $CD_3OD$) δ 8.26 (d, J=8.2 Hz, 1H), 7.94 (d, J=1.7 Hz, 1H), 7.76 (dd, J=8.2, 1.8 Hz, 1H), 7.49 (s, 1H), 3.75 (t, J=6.8 Hz, 2H), 3.47 (t, J=4.2 Hz, 2H), 3.22 (s, 2H), 3.14-3.06 (m, 4H), 2.63 (tt, J=12.4, 5.5 Hz, 2H), 2.34 (s, 3H), 1.78 (p, J=6.7, 6.1 Hz, 2H), 1.28 (d, J=13.8 Hz, 2H), 1.23 (s, 9H), 1.00 (s, 3H). LCMS $[M+H]^+$: 531.3.

EX25-A: $^1$H NMR (400 MHz, $CD_3OD$) δ 8.26 (d, J=8.3 Hz, 1H), 7.95 (d, J=1.8 Hz, 1H), 7.77 (dd, J=8.3, 1.8 Hz, 1H), 7.49 (s, 1H), 3.75 (t, J=6.7 Hz, 2H), 3.47 (t, J=5.6 Hz, 2H), 3.22 (s, 2H), 3.15-3.08 (m, 4H), 2.62 (td, J=12.7, 5.9 Hz, 2H), 2.34 (s, 3H), 1.78 (p, J=6.1 Hz, 2H), 1.28 (d, J=13.4 Hz, 2H), 1.00 (s, 3H). LCMS $[M+H]^+$: 475.2.

Example 26 (EX26)

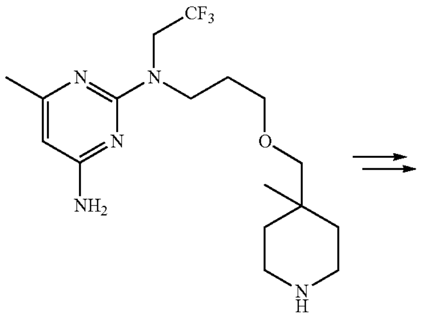

EX26-1

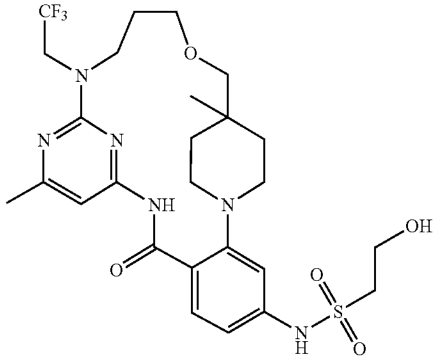

EX26

Step 1:

EX26 (52.11 mg) was prepared as described in Example 1 (EX01) Steps 5-8, except EX26-1 was used instead of EX01-4 in Step 5. $^1$H NMR (400 MHz, $CD_3OD$) δ 8.12 (dd, J=8.7, 1.4 Hz, 1H), 7.58 (s, 1H), 7.33 (t, J=2.1 Hz, 1H), 7.14 (ddd, J=8.6, 2.2, 1.3 Hz, 1H), 4.46 (q, J=9.3 Hz, 2H), 4.03 (dd, J=9.1, 6.3 Hz, 2H), 3.95 (t, J=6.2 Hz, 2H), 3.46-3.43 (m, 2H), 3.37 (t, J=6.2 Hz, 2H), 3.18 (s, 2H), 3.02 (dd, J=9.1, 4.6 Hz, 4H), 2.61 (td, J=12.6, 5.9 Hz, 2H), 2.35 (s, 3H), 1.81 (td, J=10.4, 5.0 Hz, 2H), 1.25 (d, J=13.2 Hz, 2H), 0.99 (s, 3H). LCMS $[M+H]^+$: 601.3.

Example 27 (EX27)

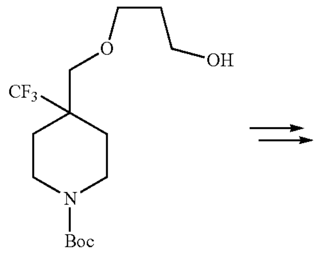

EX17-3

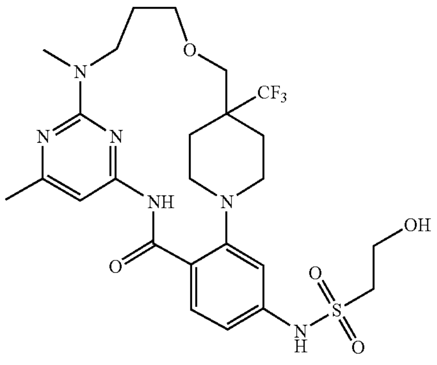

EX27

Step 1:

EX27 (43.76 mg) was prepared as described in Example 4 (EX04), except EX17-3 was used instead of EX01-2 in Step 1. $^1H$ NMR (400 MHz, $CD_3OD$) δ 8.09 (d, J=8.7 Hz, 1H), 7.44 (s, 1H), 7.27 (d, J=2.2 Hz, 1H), 7.16 (dd, J=8.7, 2.1 Hz, 1H), 3.98-3.86 (m, 4H), 3.46 (t, J=5.2 Hz, 2H), 3.41 (s, 2H), 3.36 (t, J=6.2 Hz, 2H), 3.12-3.06 (m, 7H), 2.71-2.59 (m, 2H), 2.35 (s, 3H), 1.91 (d, J=14.6 Hz, 2H), 1.83 (p, J=6.0 Hz, 2H). LCMS $[M+H]^+$: 587.2.

Example 28 (EX28)

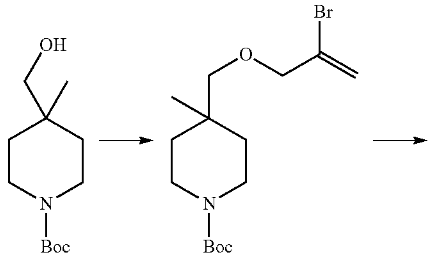

EX28-1

-continued

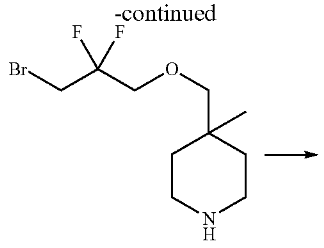

EX28-2

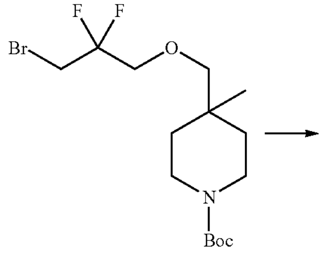

EX28-3

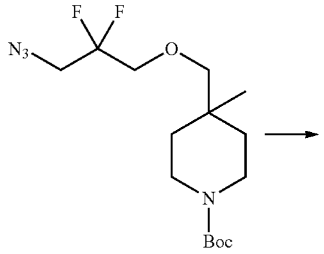

EX28-4

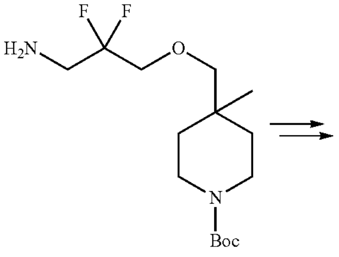

EX28-5

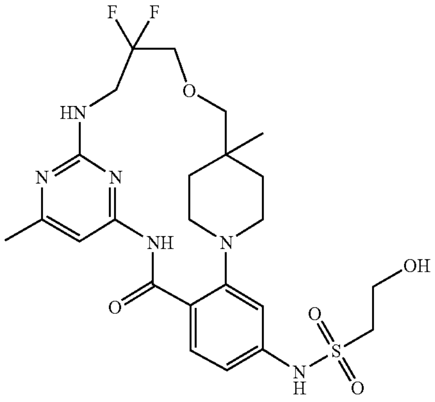

EX28

Step 1:

To a solution of 2-methylpropan-2-yl 4-(hydroxymethyl)-4-methylhexahydropyridine-1-carboxylate (15 g, 65.42 mmol) in THF (300 mL) was portion wise added NaH (7.8 g, 196.25 mmol, 60% in oil) at 0° C. under $N_2$ protection. The mixture was stirred at 0° C. for 30 min. Then 2,3-dibromoprop-1-ene (65.4 g, 327.08 mmol) was added at 0° C. The resulting mixture was stirred at 25° C. for 3 hrs. The mixture was poured into water (1 L) and extracted with EtOAc (1 L×3). The combined organic layer was washed with brine, dried over $MgSO_4$, concentrated under reduced pressure and purified by silica gel chromatography to afford EX28-1 (5 g). LCMS [M-$^t$Bu+H]$^+$: 292.0, 294.0.

Step 2:

To a solution of EX28-1 (4.5 g, 12.92 mmol) in DCM (15 mL) were added 1-[(acetoxyphenyl-V-iodanyl) oxy]ethan-1-one (6.28 g, 19.38 mmol) and PyHF (64.02 g, 645.99 mmol), and the reaction was stirred at 25° C. for 2 hrs. The reaction was filtrated and concentrated under reduced pressure to afford crude product EX28-2 (3.7 g, crude). LCMS [M+H]$^+$: 286.0, 288.0.

Step 3:

To a solution of EX28-2 (3.7 g, 12.93 mmol) in THF (60 mL) were added aq. $Na_2CO_3$ (2 M, 65 mL) and $Boc_2O$ (6 mL, 25.86 mmol) at 0° C. The resulting mixture was stirred at 25° C. for 1 hr. The mixture was extracted with EtOAc (50 mL×3). The combined organic layer was dried over $MgSO_4$, concentrated, and purified by silica gel chromatography to afford EX28-3 (1.5 g). LCMS [M-$^t$Bu+H]$^+$: 330.0, 332.0. $^1$H NMR (400 MHz, DMSO-$d_6$) δ 3.98-3.74 (m, 4H), 3.49 (td, J=4.9, 13.5 Hz, 2H), 3.29 (s, 2H), 3.18-3.01 (m, 2H), 1.40-1.34 (m, 11H), 1.25-1.17 (m, 2H), 0.93 (s, 3H).

Step 4:

To a solution of EX28-3 (1.5 g, 3.88 mmol) in DMF (4 mL) were added $TMSN_3$ (1.342 g, 11.65 mmol) and $K_2CO_3$ (1.61 g, 11.65 mmol) under $N_2$ protection. The resulting mixture was stirred at 120° C. for 1 hr. The mixture was filtrated, concentrated, and purified by silica gel chromatography to afford EX28-4 (1.2 g). LCMS [M-$^t$Bu+H]$^+$: 293.0.

Step 5:

To a solution of EX28-4 (1.2 g, 3.44 mmol) in EtOAc (20 mL) was added Pd/C (1.83 g, 17.22 mmol, 10% purity). The mixture was purged and degassed with $H_2$ for 3 times. The mixture was stirred at 25° C. for 1 hr. The mixture was filtrated through Celite and concentrated to afford EX28-5 (1.05 g). LCMS [M-Boc+H]$^+$: 223.1.

Step 6:

EX28 (12.90 mg) was prepared as described in Example 20 (EX20) Steps 5-8, except EX28-5 was used instead of EX20-4 in Step 5. $^1$H NMR (400 MHz, $CD_3OD$) δ 8.03 (d, J=8.6 Hz, 1H), 7.54 (s, 1H), 7.25 (d, J=2.1 Hz, 1H), 7.11 (dd, J=8.7, 2.1 Hz, 1H), 4.12 (t, J=14.4 Hz, 2H), 3.95 (t, J=6.2 Hz, 2H), 3.65 (t, J=11.8 Hz, 2H), 3.37 (t, J=6.2 Hz, 2H), 3.27 (s, 2H), 3.07-2.98 (m, 4H), 2.61-2.48 (m, 2H), 2.33 (s, 3H), 1.27-1.20 (m, 2H), 0.97 (s, 3H). LCMS [M+H]$^+$: 555.3.

Example 29 (EX29)

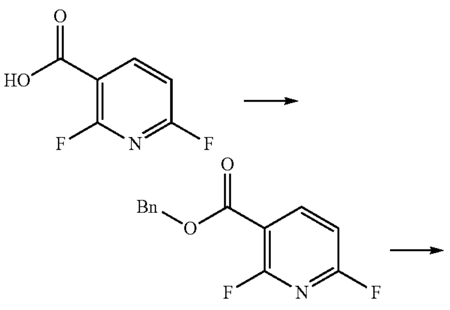

EX29-1

-continued

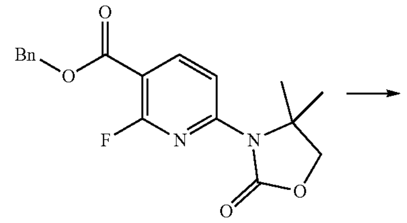

EX29-2

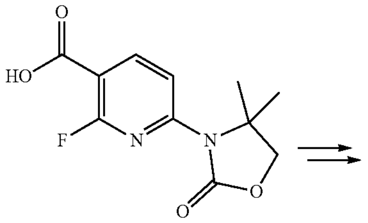

EX29-3

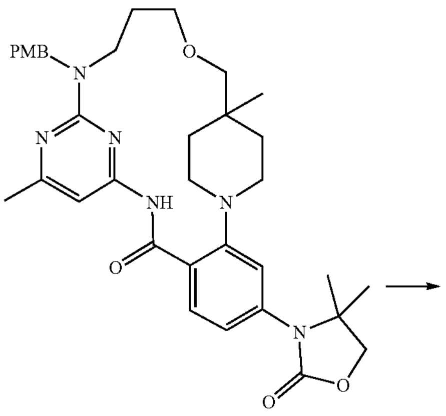

EX29-4

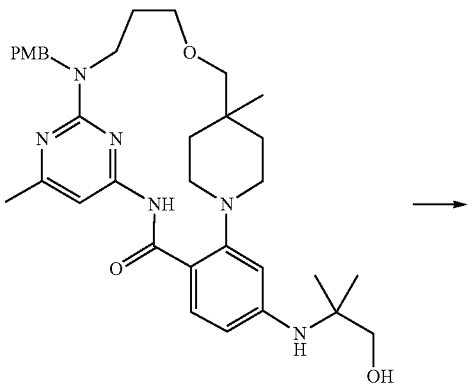

EX29-5

-continued

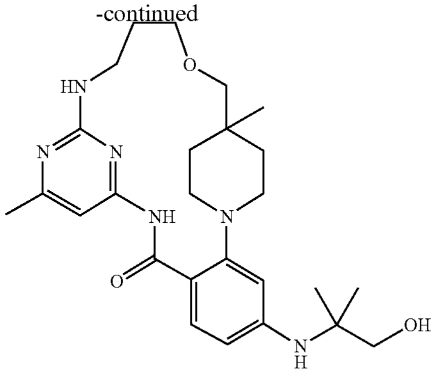

EX29

Step 1:

2,6-difluoropyridine-3-carboxylic acid (10.6 g, 66.63 mmol) was dissolved in $SOCl_2$ (35 mL, 482.35 mmol) at 0° C. and the resulting mixture was stirred at 50° C. for 2 hrs. The solvent was removed under reduced pressure and toluene (100 mL) was added. The solvent was removed again and the crude acid chloride was dissolved in DCM (50 mL) and cooled to 0° C. Subsequently, a solution of TEA (25 mL, 180.34 mmol) and phenyl methanol (7.25 mL, 69.75 mmol) in DCM (50 mL) was added dropwise over 10 min. The resulting mixture was stirred at 25° C. for 30 min. Then the mixture was concentrated under reduced pressure, diluted with water (200 mL) and extracted with DCM (3×200 mL). The combined organic layer was dried over $MgSO_4$, concentrated under reduced pressure and purified by silica gel chromatography to afford EX29-1 (5.2 g). LCMS $[M+H]^+$: 250.0.

Step 2:

To a solution of 4,4-dimethyl-1,3-oxazolidin-2-one (0.8 g, 6.95 mmol) in THF (15 mL) was added $^t$BuOK (0.75 g, 6.42 mmol) and the reaction was stirred at 25° C. for 5 min. A solution of EX29-1 (1.6 g, 6.42 mmol) in DMA (40 mL) was added and the resulting mixture was stirred at 25° C. for 25 min. The mixture was diluted with water (70 mL) and extracted with EtOAc (3×50 mL). The combined organic layer was dried over $MgSO_4$, concentrated under reduced pressure and purified by silica gel chromatography to afford EX29-2 (1.4 g). LCMS $[M+H]^+$: 345.0.

Step 3:

To a solution of EX29-2 (400 mg, 1.16 mmol) in EtOAc (9 mL) and EtOH (18 mL) was added Pd/C (400 mg, 3.76 mmol). The mixture was purged and degassed with $H_2$ for 3 times. The mixture was stirred at 25° C. under $H_2$ (40 psi) for 3 hrs. The mixture was filtered through a pad of celite and the solid was washed with EtOAc (15 mL). The filtrate was concentrated under reduced pressure to afford EX29-3 (270 mg). LCMS $[M+H]^+$: 255.0.

Step 4:

EX29-4 (30.0 mg) was prepared as described in Example 1 (EX01) Steps 5-7, except EX29-3 was used instead of EX01-4 in Step 5. LCMS $[M+H]^+$: 630.5.

Step 5:

To a solution of EX29-4 (15 mg, 0.024 mmol) in MeOH (0.5 mL) was added NaOH (480 μL, 0.24 mmol). The resulting mixture was stirred at 70° C. for 1 hr. The mixture was concentrated under reduced pressure, neutralized by aq. HCl and extracted with DCM (3×5 mL). The combined organic layer was dried over $MgSO_4$ and concentrated under reduced pressure to afford compound EX29-5 (13 mg). LCMS $[M+H]^+$: 604.5.

Step 6:

A solution of EX29-5 (13 mg, 0.019 mmol) in TFA (0.44 mL, 0.19 mmol) was stirred at 50° C. for 1 hr. The reaction mixture was concentrated under reduced pressure and the residue was purified by prep-HPLC to give EX29 (4.72 mg). $^1H$ NMR (400 MHz, DMSO-$d_6$) δ 7.86 (d, J=8.7 Hz, 1H), 7.24 (s, 1H), 6.36 (d, J=8.7 Hz, 1H), 3.58 (s, 2H), 3.52 (t, J=6.9 Hz, 2H), 3.36 (t, J=5.1 Hz, 2H), 3.12 (s, 2H), 2.98 (d, J=9.0 Hz, 4H), 2.44-2.30 (m, 2H), 2.17 (s, 3H), 1.65-1.56 (m, 2H), 1.33 (s, 6H), 1.14 (d, J=12.8 Hz, 2H), 0.83 (s, 3H). LCMS $[M+H]^+$: 484.4.

Example 30 (EX30)

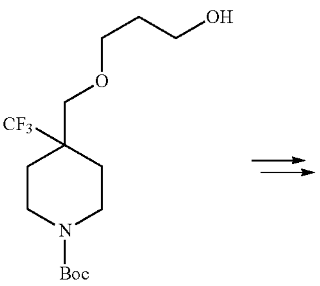

EX17-3

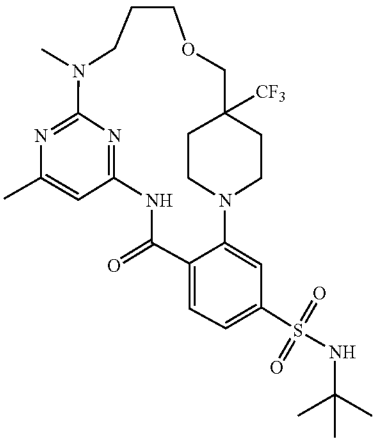

EX30

Step 1:

EX30 (19.37 mg) was prepared as described in Example 15 (EX15), except EX17-3 was used instead of EX02-2 in Step 1. $^1H$ NMR (400 MHz, $CD_3OD$) δ 8.26 (d, J=8.3 Hz, 1H), 7.89 (d, J=1.8 Hz, 1H), 7.77 (dd, J=8.2, 1.7 Hz, 1H), 7.45 (s, 1H), 3.93 (t, J=7.1 Hz, 2H), 3.48 (t, J=5.2 Hz, 2H), 3.43 (s, 2H), 3.17 (d, J=9.2 Hz, 4H), 3.12 (s, 3H), 2.68 (dt, J=18.8, 9.5 Hz, 2H), 2.37 (s, 3H), 1.96 (d, J=14.6 Hz, 2H), 1.90-1.79 (m, 2H), 1.22 (s, 9H). LCMS $[M+H]^+$: 599.3

Example 31 (EX31)

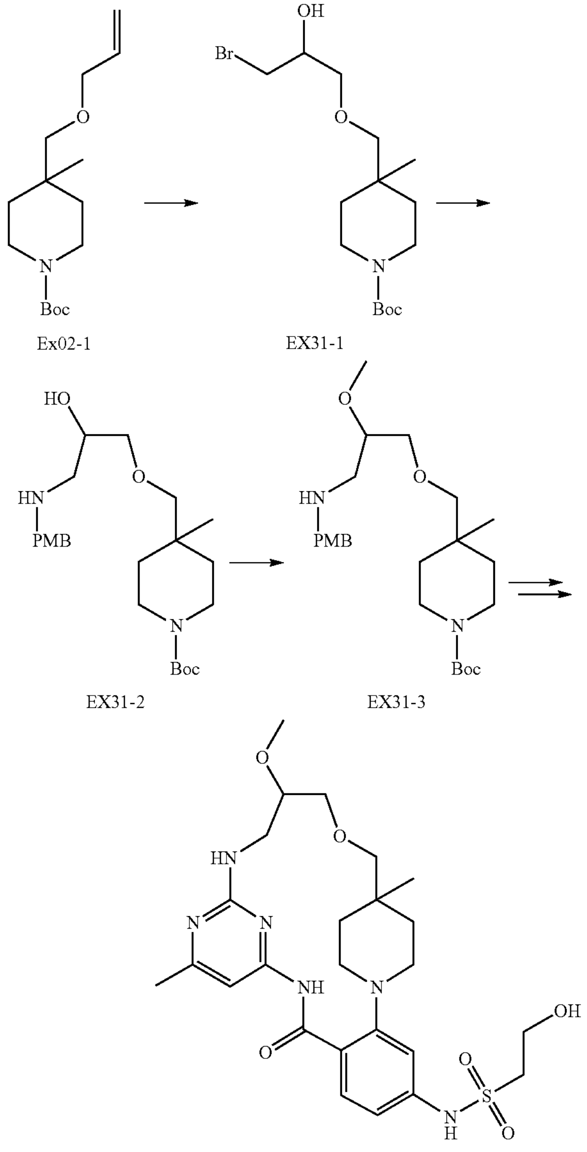

Ex02-1

EX31-1

EX31-2

EX31-3

EX31

Step 1:

To a solution of EX02-1 (5 g, 18.6 mmol) in DMSO (40 mL) and $H_2O$ (10 mL) was added NBS (3.63 g, 20.4 mmol). The mixture was stirred at 25° C. for 0.5 hr. The reaction mixture was quenched with water (50 mL) and extracted with EtOAc (50 mL×3). The combined organic layer was dried over $MgSO_4$, concentrated and purified by silica gel chromatography to afford EX31-1 (5 g). LCMS [M-$^t$Bu+H]$^+$: 312.0.

Step 2:

EX31-2 was prepared as described in Example 12 (EX12) Step 2, except EX31-1 was used instead of EX12-1. LCMS [M+H]$^+$: 423.3.

Step 3:

To a solution of EX31-2 (4.47 g, 10.6 mmol) in THF (80 mL) was added KHMDS (12 mL, 11.6 mmol) at −20° C. under $N_2$ atmosphere and the resulting mixture was stirred for 30 min. The mixture was added dimethyl sulfate (2.05 g, 16.3 mmol) at −20° C. and stirred for another 1 hr. Then the reaction was allowed to warm to 25° C. and stirred for another 2 hrs. The reaction was quenched with aq. NaOH (1 M, 200 mL) and extracted with EtOAc (200 mL×3). The combined organic layer was dried over $MgSO_4$, concentrated and purified by silica gel chromatography to afford EX31-3 (2.3 g). LCMS [M+H]$^+$: 437.3.

Step 4:

EX31 (19.19 mg) was prepared as described in Example 12 (EX12) Steps 3-6, except EX31-3 was used instead of EX12-2 in Step 3. $^1$H NMR (400 MHz, DMSO-$d_6$) δ 8.00 (dd, J=8.6, 1.6 Hz, 1H), 7.34 (s, 1H), 7.24 (d, J=2.2 Hz, 1H), 7.08 (dt, J=8.7, 1.9 Hz, 1H), 4.16 (dd, J=13.9, 2.6 Hz, 1H), 3.74 (t, J=6.4 Hz, 2H), 3.34 (t, J=6.4 Hz, 2H), 3.31 (s, 3H), 3.26-3.18 (m, 4H), 3.11 (d, J=9.0 Hz, 1H), 3.00-2.87 (m, 4H), 2.81 (t, J=12.2 Hz, 1H), 2.47-2.30 (m, 2H), 2.21 (s, 3H), 1.17 (dd, J=43.6, 12.9 Hz, 2H), 0.89 (s, 3H). LCMS [M+H]$^+$: 549.5.

Example 32 (EX32, EX32-A, EX32-1B)

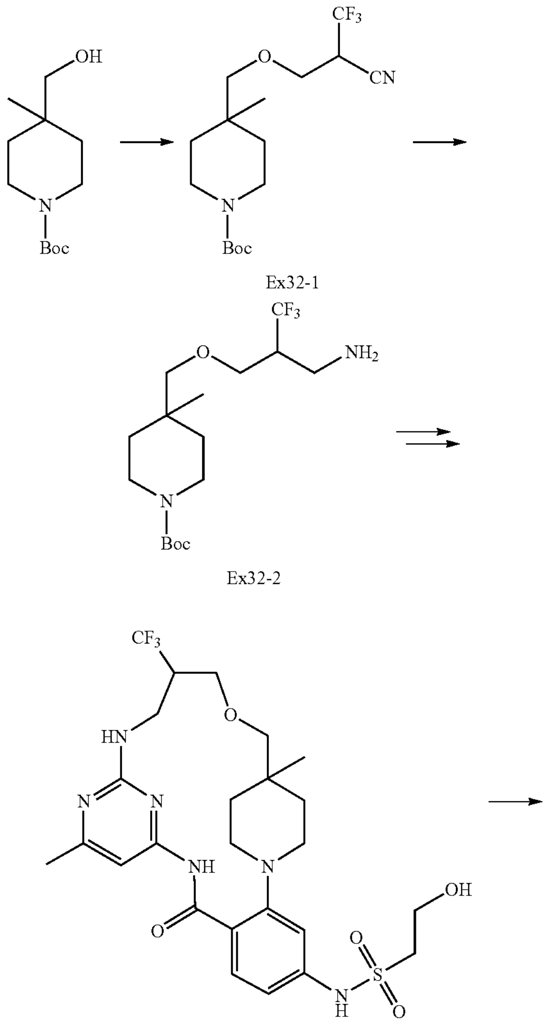

Ex32-1

Ex32-2

EX32

-continued

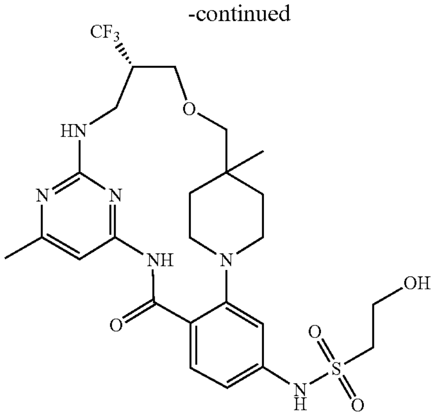

+

EX32-A&B

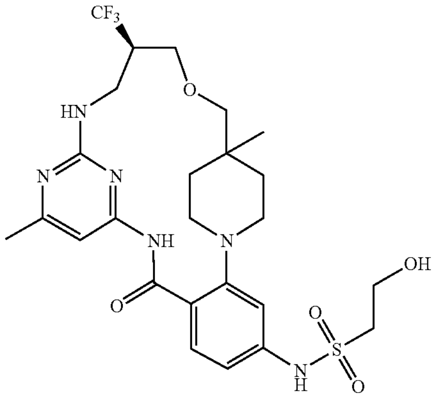

Step 1:

To a solution of tert-butyl 4-(hydroxymethyl)-4-methylpiperidine-1-carboxylate (5 g, 21.81 mmol) in THF (5 mL) were added DBU (33.2 mg, 0.22 mmol) and 2-(trifluoromethyl)acrylonitrile (6.6 g, 54.51 mmol). The reaction mixture was stirred at 75° C. for 12 hrs. The mixture was diluted with water (50 mL) and extracted with EtOAc (50 mL×3). The combined organic layer was dried over $MgSO_4$, concentrated under reduced pressure and purified by silica gel chromatography to afford EX32-1 (2.3 g). LCMS $[M\text{-}^tBu+H]^+$: 295.0.

Step 2:

To a solution of EX32-1 (2.8 g, 7.991 mmol) in MeOH (50 mL) were added $CoCl_2$ (5.2 g, 39.95 mmol) and $NaBH_4$ (0.95 g, 25.13 mmol) at 0° C., and the reaction was stirred at 25° C. for 1 hr. The reaction was quenched with saturated aq. $NH_4Cl$ (500 mL) and extracted with EtOAc (500 mL×3). The combined organic layer was dried over $MgSO_4$ and concentrated under reduced pressure to afford EX32-2. LCMS $[M+H]^+$: 355.1.

Step 3:

EX32 (45.56 mg) was prepared as described in Example 20 (EX20), except EX32-2 was used instead of EX20-4 in Step 5. $^1$H NMR (400 MHz, $CD_3OD$) δ 8.12 (d, J=8.8 Hz, 1H), 7.54 (s, 1H), 7.33 (d, J=2.0 Hz, 1H), 7.15 (dd, J=2.1, 8.7 Hz, 1H), 4.69-4.63 (m, 1H), 3.95 (t, J=6.2 Hz, 2H), 3.67 (dd, J=3.5, 9.0 Hz, 1H), 3.46 (t, J=9.0 Hz, 1H), 3.37 (t, J=6.3 Hz, 2H), 3.27 (br d, J=5.7 Hz, 1H), 3.24 (d, J=6.4 Hz, 2H), 3.18-3.12 (m, 1H), 3.08-3.02 (m, 1H), 2.99-2.93 (m, 2H), 2.71-2.52 (m, 3H), 2.32 (s, 3H), 1.39-1.33 (m, 1H), 1.23-1.16 (m, 1H), 1.01 (s, 3H). LCMS $[M+H]^+$: 587.3.

Step 4:

EX32-A (15.56 mg) and EX32-B (12.95 mg) were separated from EX32 by SFC. SFC analytic condition: column: Chiralpak IE-3, 100*4.6 mm, 3.0 μm; mobile phase A: supercritical $CO_2$, mobile phase B: isopropanol (0.05% DEA), 40% mobile phase B, 5 min; flow rate: 2.8 mL/min; column temp: 35° C.

EX32-A: $^1$H NMR (400 MHz, $CD_3OD$) δ 8.10 (d, J=8.8 Hz, 1H), 7.53 (s, 1H), 7.31 (s, 1H), 7.13 (d, J=8.1 Hz, 1H), 4.66 (d, J=14.3 Hz, 1H), 3.99-3.89 (m, 2H), 3.69-3.62 (m, 1H), 3.45 (t, J=8.8 Hz, 1H), 3.36 (d, J=6.1 Hz, 2H), 3.27 (s, 1H), 3.23 (d, J=3.5 Hz, 2H), 3.15 (d, J=12.5 Hz, 1H), 3.07-3.01 (m, 1H), 2.96 (d, J=6.8 Hz, 2H), 2.70-2.51 (m, 3H), 2.31 (s, 3H), 1.31 (d, J=14.5 Hz, 1H), 1.19 (d, J=13.1 Hz, 1H), 1.01 (s, 3H). LCMS $[M+H]^+$: 587.4. Retention time @SFC: 1.496 min.

EX32-B: $^1$H NMR (400 MHz, $CD_3OD$) δ 8.09 (d, J=8.1 Hz, 1H), 7.53 (s, 1H), 7.30 (s, 1H), 7.12 (d, J=9.1 Hz, 1H), 4.66 (d, J=13.6 Hz, 1H), 3.95 (s, 2H), 3.66 (d, J=8.0 Hz, 1H), 3.44 (t, J=8.6 Hz, 1H), 3.38-3.34 (m, 2H), 3.26 (d, J=3.8 Hz, 1H), 3.23 (s, 2H), 3.14 (d, J=12.5 Hz, 1H), 3.04 (d, J=9.6 Hz, 1H), 2.95 (d, J=7.4 Hz, 2H), 2.70-2.51 (m, 3H), 2.31 (s, 3H), 1.31 (d, J=14.9 Hz, 1H), 1.19 (d, J=12.9 Hz, 1H), 1.01 (s, 3H). LCMS $[M+H]^+$: 587.1. Retention time @SFC: 1.870 min.

Example 33 (EX33-A&B)

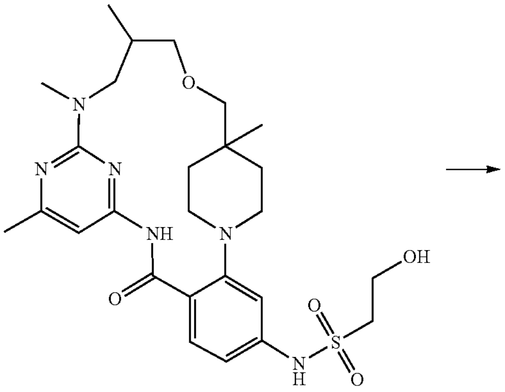

EX33

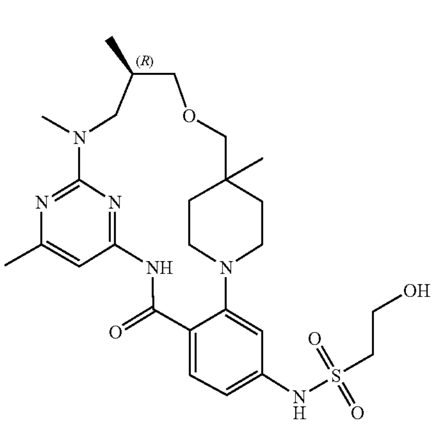

+

EX33-A&B

-continued

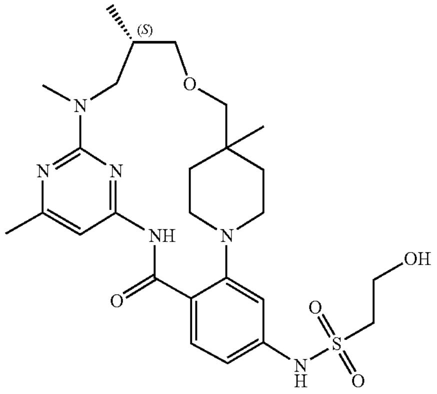

Step 1:

EX33-A (12.66 mg) and EX33-B (12.43 mg) were prepared as described in Example 32 (EX32) Step 4, except EX33 was used instead of EX32. SFC analytic condition: column: Chiralpak AD-3, 50*4.6 mm, 3.0 μm; mobile phase A: supercritical $CO_2$, mobile phase B: ethanol (0.05% DEA), 5-40% mobile phase B, 5 min; flow rate: 4 mL/min; column temp: 35° C.

EX33-A: $^1H$ NMR (400 MHz, $CD_3OD$) δ 8.08 (d, J=8.6 Hz, 1H), 7.43 (s, 1H), 7.29 (d, J=2.2 Hz, 1H), 7.12 (dd, J=8.7, 2.2 Hz, 1H), 4.29 (dd, J=13.5, 7.1 Hz, 1H), 3.94 (t, J=6.2 Hz, 2H), 3.46-3.34 (m, 4H), 3.26-3.20 (m, 2H), 3.12 (s, 3H), 3.09-3.02 (m, 3H), 2.99-2.92 (m, 2H), 2.71-2.52 (m, 2H), 2.34 (s, 3H), 2.12-2.01 (m, 1H), 1.31-1.26 (m, 1H), 1.13 (d, J=13.1 Hz, 1H), 0.98-0.94 (m, 6H). LCMS $[M+H]^+$: 547.3. Retention time @SFC: 1.948 min.

EX33-B: $^1H$ NMR (400 MHz, $CD_3OD$) δ 8.08 (d, J=8.7 Hz, 1H), 7.43 (s, 1H), 7.29 (d, J=2.2 Hz, 1H), 7.12 (dd, J=8.7, 2.2 Hz, 1H), 4.30 (dd, J=13.6, 7.2 Hz, 1H), 3.94 (t, J=6.2 Hz, 2H), 3.46-3.34 (m, 4H), 3.26-3.21 (m, 2H), 3.13 (s, 3H), 3.09-3.02 (m, 3H), 3.00-2.91 (m, 2H), 2.72-2.53 (m, 2H), 2.34 (s, 3H), 2.12-2.05 (m, 1H), 1.35-1.29 (m, 1H), 1.17-1.09 (m, 1H), 0.99-0.95 (m, 6H). LCMS $[M+H]^+$: 547.3. Retention time @SFC: 2.953 min.

Example 34 (EX34)

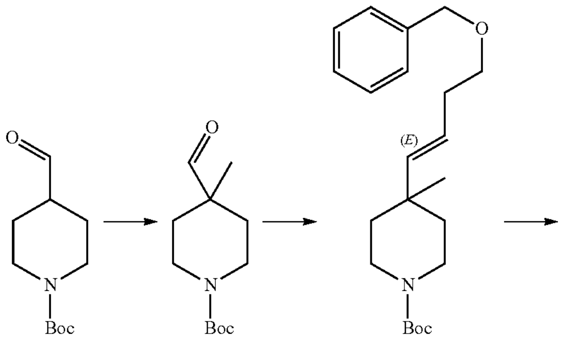

EX34-1 EX34-2

-continued

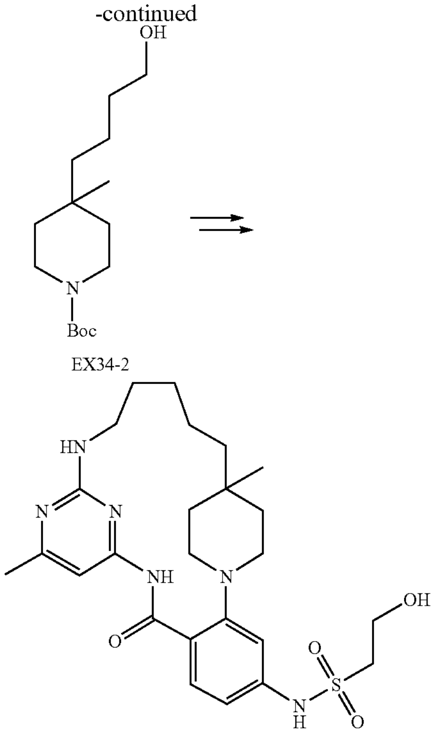

EX34-2

EX34

Step 1:

To a solution of 2-methylpropan-2-yl 4-formylhexahydropyridine-1-carboxylate (35 g, 164.09 mmol) in DCM (200 mL) were added t-BuOK (23.9 g, 213.01 mmol) and $CH_3I$ (69.9 g, 492.6 mmol) at 0° C. The mixture was stirred at 0° C. for 30 min and then stirred at 25° C. for another 2 hrs. The mixture was extracted with brine (400 mL) and DCM (3×200 mL). The combined organic layer was dried over $MgSO_4$, concentrated and purified by flash silica gel chromatography to afford EX34-1 (5 g). LCMS $[M-^tBu+H]^+$: 172.1.

Step 2:

To a solution of [3-(benzyloxy) propyl]triphenylphosphanium bromide (9.08 g, 18.48 mmol) in THF (90 mL) was added NaHMDS in THF (19.8 mL, 1 M, 19.8 mmol) at −78° C. under $N_2$ atmosphere. The mixture was stirred at −78° C. for 1 hr. Then the mixture was added EX34-1 (3 g, 13.2 mmol) in THF (90 mL) dropwise at −78° C. The mixture was stirred at 25° C. for another 4 hrs under $N_2$ atmosphere. The mixture was quenched with aq. $NH_4Cl$ (200 mL) and extracted with EtOAc (3×200 mL). The combined organic layer was dried over $MgSO_4$, concentrated and purified by flash silica gel chromatography to afford EX34-2 (3 g). LCMS $[M-Boc+H]^+$: 260.2.

Step 3:

To a solution of EX34-2 (3 g, 8.35 mmol) in EtOH (500 mL) was added Pd/C (1.3 g, 12.5 mmol, 10% purity). The mixture was purged and degassed with $H_2$ for 3 times. The mixture was stirred at 25° C. for 6 hrs under $H_2$ (15 psi). The mixture was filtrated through Celite and concentrated under reduced pressure to afford EX34-3 (2.1 g). LCMS $[M-^tBu+H]^+$: 216.1.

Step 4:

EX34 (29.07 mg) was prepared as described in Example 18 (EX18) Steps 2-6, except EX34-3 was used instead of EX18-1 in Step 2. $^1H$ NMR (400 MHz, DMSO-$d_6$) δ 13.23

(s, 1H), 10.25 (brs, 1H), 8.08 (d, J=8.6 Hz, 1H), 7.27-7.22 (m, 2H), 7.14 (dd, J=8.7, 2.1 Hz, 1H), 6.94 (t, J=6.7 Hz, 1H), 4.95 (s, 1H), 3.75 (t, J=6.5 Hz, 2H), 3.54-3.43 (m, 4H), 3.38-3.36 (m, 2H), 3.07 (d, J=11.4 Hz, 2H), 2.84 (d, J=12.6 Hz, 2H), 2.44-2.30 (m, 3H), 2.20 (s, 3H), 1.86 (d, J=12.4 Hz, 2H), 1.55-1.40 (m, 4H), 1.27 (s, 3H). LCMS $[M+H]^+$: 517.3.

Example 35 (EX35)

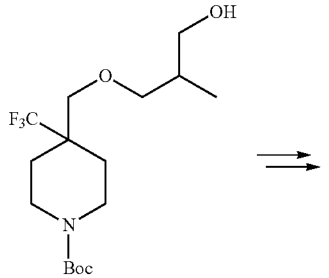

EX35-1

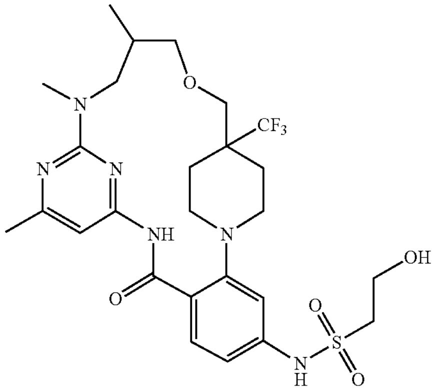

EX35

Step 1:

EX35 (36 mg) was prepared as described in Example 4 (EX04), except EX35-1 was used instead of EX01-2 in Step 1. $^1$H NMR (400 MHz, $CD_3OD$) δ 8.09 (d, J=8.6 Hz, 1H), 7.45 (s, 1H), 7.27 (d, J=2.1 Hz, 1H), 7.17 (dd, J=8.7, 2.1 Hz, 1H), 4.40 (dd, J=13.6, 7.9 Hz, 1H), 3.96 (t, J=6.2 Hz, 2H), 3.56-3.45 (m, 2H), 3.38 (t, J=6.2 Hz, 2H), 3.31-3.21 (m, 3H), 3.21-3.16 (m, 2H), 3.15 (s, 3H), 3.07-2.98 (m, 2H), 2.81-2.69 (m, 1H), 2.63-2.51 (m, 1H), 2.36 (s, 3H), 2.16-2.07 (m, 1H), 2.00 (d, J=14.6 Hz, 1H), 1.84 (d, J=14.6 Hz, 1H), 1.02 (d, J=6.9 Hz, 3H). LCMS $[M+H]^+$: 601.3.

Example 36 (EX36-A&B)

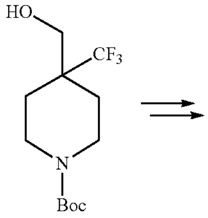

EX17-2

-continued

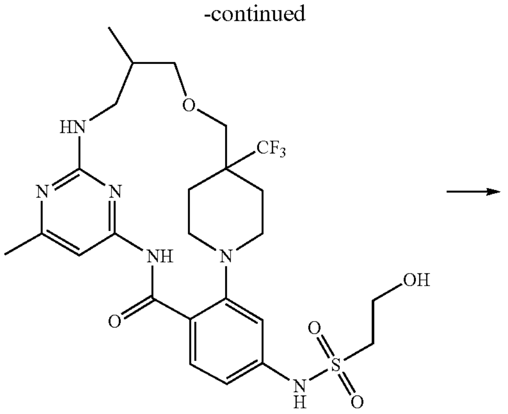

EX36

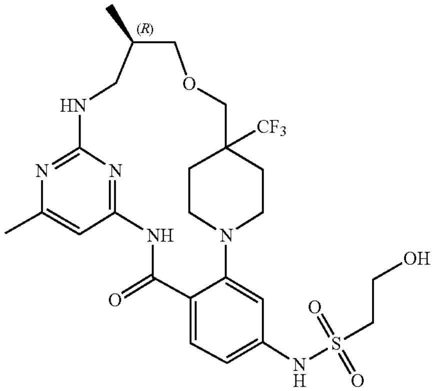

EX36-A&B

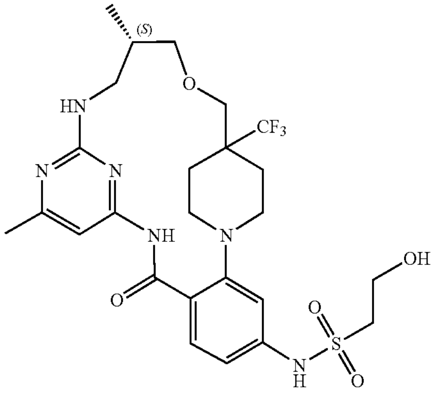

Step 1:

EX36-1 (15 mg) was prepared as described in Example 19 (EX19), except EX17-2 was used instead of tert-butyl 4-(hydroxymethyl)-4-methylpiperidine-1-carboxylate in Step 1. LCMS $[M+H]^+$: 587.2.

Step 2:

EX36-A (2.85 mg) and EX36-B (4.85 mg) were prepared as described in Example 32 (EX32-A&B) in step 4, except EX36-1 was used instead of EX32. SFC analytic condition: column: Chiralpak AD-3, 50*4.6 mm, 3.0 μm; mobile phase A: supercritical $CO_2$, mobile phase B: ethanol (0.05% DEA), 5-40% mobile phase B, 5 min; flow rate: 4 mL/min; column temp: 35° C.

EX36-A: $^1$H NMR (400 MHz, DMSO-$d_6$) δ 8.00 (d, J=8.6 Hz, 1H), 7.28 (s, 1H), 7.21 (s, 1H), 7.09 (d, J=8.4 Hz, 1H), 3.74 (t, J=6.3 Hz, 2H), 3.39-3.29 (m, 5H), 3.13 (t, J=9.1 Hz, 1H), 3.02 (s, 3H), 2.90-2.71 (m, 3H), 2.40-2.31 (m, 2H), 2.20 (s, 3H), 1.95-1.88 (m, 1H), 1.85-1.77 (m, 1H), 1.75-1.66 (m, 1H), 0.85 (d, J=6.8 Hz, 3H). LCMS $[M+H]^+$: 587.3. Retention time @SFC: 1.539 min.

EX36-B: $^1H$ NMR (400 MHz, DMSO-$d_6$) δ 7.98 (d, J=8.7 Hz, 1H), 7.29 (s, 1H), 7.16 (s, 1H), 7.05 (d, J=8.2 Hz, 1H), 4.03-3.96 (m, 1H), 3.73 (t, J=6.4 Hz, 2H), 3.40-3.36 (m, 1H), 3.36-3.31 (m, 2H), 3.27 (t, J=6.3 Hz, 2H), 3.13 (t, J=9.0 Hz, 1H), 3.04-2.94 (m, 3H), 2.90-2.81 (m, 1H), 2.77-2.67 (m, 2H), 2.44-2.37 (m, 1H), 2.20 (s, 3H), 1.94-1.88 (m, 1H), 1.85-1.78 (m, 1H), 1.74-1.65 (m, 1H), 0.85 (d, J=6.9 Hz, 3H). LCMS $[M+H]^+$: 587.2. Retention time @SFC: 2.291 min.

Example 37 (EX37)

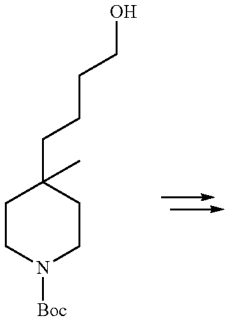

EX34-3

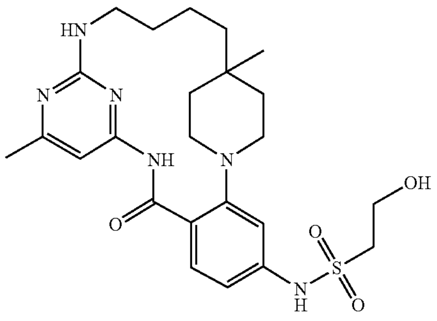

EX37

Step 1:

EX37 (11.74 mg) was prepared as described in Example 12 (EX12), except EX34-3 was used instead of EX02-2 in Step 1. H NMR (400 MHz, $CD_3OD$) δ 8.11 (d, J=8.6 Hz, 1H), 7.51 (s, 1H), 7.30 (d, J=2.2 Hz, 1H), 7.14 (dd, J=8.7, 2.2 Hz, 1H), 3.97 (t, J=6.2 Hz, 2H), 3.40 (t, J=6.2 Hz, 2H), 3.30-3.24 (m, 2H), 3.10-3.04 (m, 4H), 2.64-2.52 (m, 2H), 2.34 (s, 3H), 1.92-1.80 (m, 2H), 1.61 (q, J=8.4, 6.9 Hz, 2H), 1.52-1.46 (m, 2H), 1.32 (d, J=12.9 Hz, 2H), 1.09 (s, 3H). LCMS $[M+H]^+$: 587.2.

Example 38 (EX38)

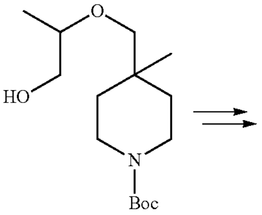

EX38-1

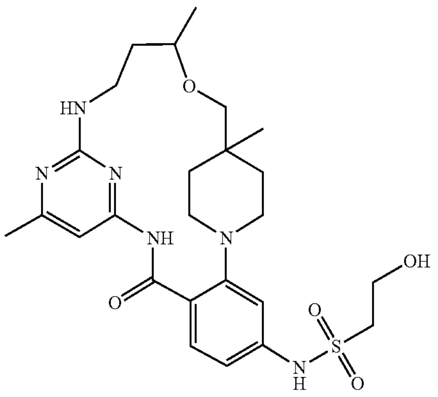

EX38

Step 1:

EX38 (19.91 mg) was prepared as described in Example 12 (EX12), except EX38-1 was used instead of EX02-2 in Step 1. $^1H$ NMR (400 MHz, $CD_3OD$) δ 8.15 (d, J=8.7 Hz, 1H), 7.47 (s, 1H), 7.38 (d, J=2.2 Hz, 1H), 7.17 (dd, J=8.7, 2.2 Hz, 1H), 3.95 (t, J=6.2 Hz, 2H), 3.84 (ddd, J=14.1, 10.4, 4.2 Hz, 1H), 3.61 (ddd, J=13.4, 9.8, 6.4 Hz, 1H), 3.52-3.43 (m, 2H), 3.38 (t, J=6.2 Hz, 2H), 3.17-3.09 (m, 1H), 3.08-2.91 (m, 4H), 2.76 (td, J=12.4, 5.9 Hz, 1H), 2.56 (td, J=13.4, 4.6 Hz, 1H), 2.31 (s, 3H), 1.92-1.81 (m, 1H), 1.58-1.48 (m, 1H), 1.32-1.20 (m, 2H), 1.15 (d, J=6.2 Hz, 3H), 1.02 (s, 3H). LCMS $[M+H]^+$: 533.3.

Example 39 (EX39)

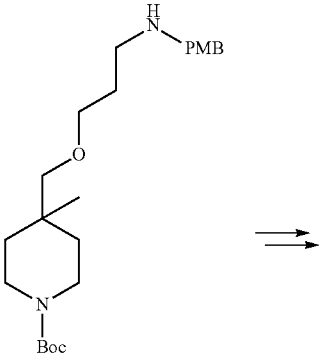

EX12-2

-continued

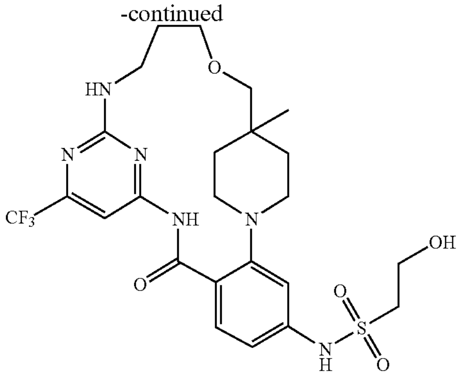

EX39

Step 1:

EX39 (30.72 mg) was prepared as described in Example 12 (EX12) Steps 3-6, except 2-chloro-6-(trifluoromethyl) pyrimidin-4-amine was used instead of 2-chloro-6-methylpyrimidin-4-amine in Step 3. $^1$H NMR (400 MHz, DMSO-$d_6$) δ 12.57 (s, 1H), 8.02 (d, J=8.7 Hz, 1H), 7.76 (s, 1H), 7.28 (s, 1H), 7.11 (d, J=8.7 Hz, 1H), 3.75 (t, J=6.3 Hz, 2H), 3.63-3.55 (m, 2H), 3.40-3.33 (m, 4H), 3.15 (s, 2H), 3.01-2.86 (m, 4H), 2.45-2.34 (m, 2H), 1.70-1.60 (m, 2H), 1.24-1.17 (m, 2H), 0.91 (s, 3H). LCMS $[M+H]^+$: 573.1.

Example 40 (EX40)

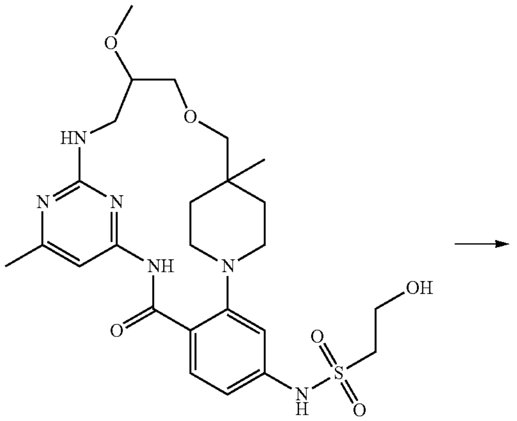

EX31

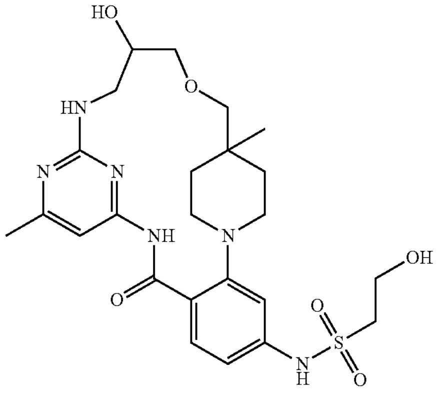

EX40

Step 1:

To a solution of EX31 (35 mg, 0.064 mmol) in ACN (1 mL) were added NaI (95.6 mg, 0.64 mmol) and TMSCl (81 μL, 0.64 mmol) at 0° C. under $N_2$ atmosphere. The reaction was stirred at 50° C. for 18 hrs. The reaction was quenched with water (5 mL) and extracted with EtOAc (5 mL×3). The combined organic layer was dried over $MgSO_4$, concentrated, and purified by prep-HPLC to afford EX40 (4.23 mg). $^1$H NMR (400 MHz, $CD_3OD$) δ 8.11 (d, J=8.7 Hz, 1H), 7.51 (s, 1H), 7.33 (d, J=2.0 Hz, 1H), 7.15 (dd, J=8.6, 2.1 Hz, 1H), 4.31 (dd, J=14.1, 2.8 Hz, 1H), 3.97 (t, J=6.2 Hz, 2H), 3.78-3.68 (m, 1H), 3.44 (dd, J=8.7, 4.1 Hz, 1H), 3.42-3.34 (m, 3H), 3.31-3.27 (m, 1H), 3.21-3.15 (m, 2H), 3.15-3.09 (m, 1H), 3.07-2.91 (m, 3H), 2.65-2.52 (m, 2H), 2.33 (s, 3H), 1.34-1.26 (m, 1H), 1.26-1.17 (m, 1H), 1.00 (s, 3H). LCMS $[M+H]^+$: 535.2.

Example 41 (EX41)

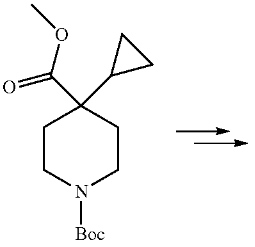

EX41-1

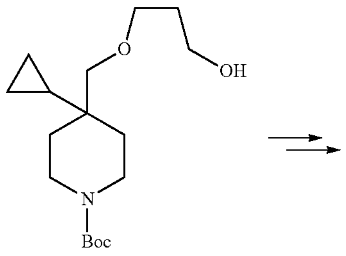

EX41-2

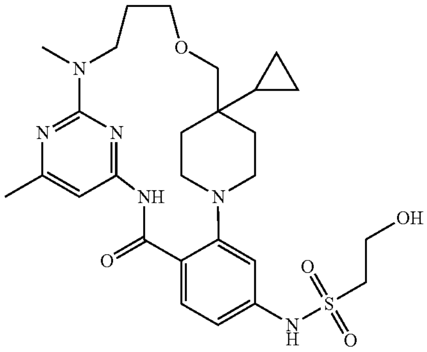

EX41

Step 1:

EX41-2 (1.2 g) was prepared as described in Example 17 (EX17) Steps 2-3, except EX41-1 was used instead of EX17-1 in Step 2. LCMS $[M-Boc+H]^+$: 214.2.

Step 2:

EX41 (37.18 mg) was prepared as described in Example 4 (EX04), except EX41-2 was used instead of EX01-2 in Step 1. $^1$H NMR (400 MHz, $CD_3OD$) δ 8.08 (d, J=8.6 Hz, 1H), 7.42 (s, 1H), 7.28 (d, J=2.0 Hz, 1H), 7.13 (dd, J=8.6, 2.1 Hz, 1H), 3.98-3.87 (m, 4H), 3.44-3.35 (m, 4H), 3.27-3.21 (m, 4H), 3.09 (s, 3H), 2.75 (t, J=11.0 Hz, 2H), 2.37 (s, 3H), 2.29-2.15 (m, 2H), 1.93-1.79 (m, 4H), 0.71-0.60 (m, 1H), 0.49-0.36 (m, 4H). LCMS $[M+H]^+$: 559.3.

Example 42 (EX42)

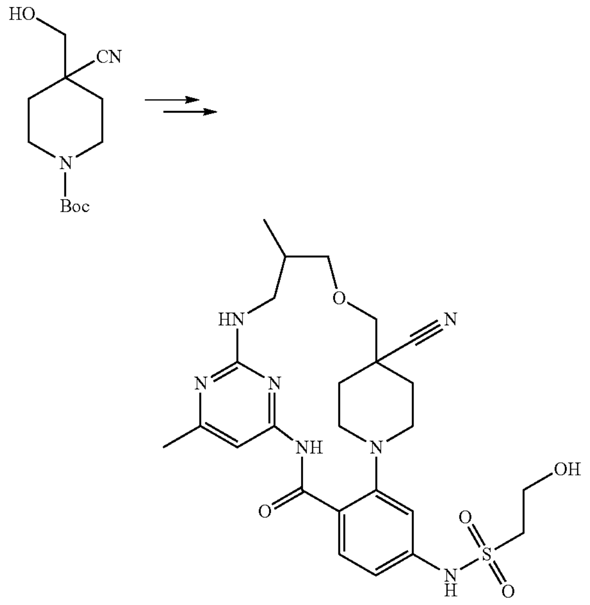

EX42

Step 1:

EX42 (2.63 mg) was prepared as described in Example 19 (EX19), except tert-butyl 4-cyano-4-(hydroxymethyl)piperidine-1-carboxylate instead of tert-butyl 4-(hydroxymethyl)-4-methylpiperidine-1-carboxylate in Step 1. $^1$H NMR (400 MHz, DMSO-$d_6$) δ 8.03 (d, J=8.5 Hz, 1H), 7.31 (s, 1H), 7.22 (s, 1H), 7.13 (d, J=8.7 Hz, 1H), 4.02-3.97 (m, 1H), 3.85-3.78 (m, 3H), 3.72-3.69 (m, 2H), 3.63-3.57 (m, 1H), 3.38-3.31 (m, 3H), 3.25-3.11 (m, 3H), 2.98 (t, J=11.8 Hz, 1H), 2.81 (t, J=12.2 Hz, 1H), 2.73-2.64 (m, 1H), 2.21 (s, 3H), 1.92 (d, J=12.8 Hz, 1H), 1.82 (d, J=12.3 Hz, 1H), 1.76-1.68 (m, 1H), 0.84 (d, J=6.9 Hz, 3H). LCMS $[M+H]^+$: 544.3.

Example 43 (EX43)

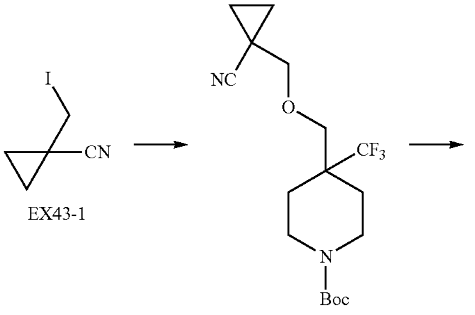

EX43-1

EX43-2

-continued

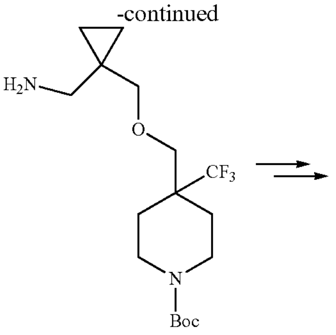

EX43-3

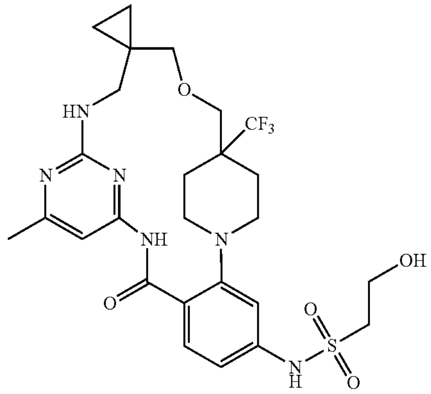

EX43

Step 1:

NaOH (0.6 g, 15.88 mmol) was slowly dissolved in water (18 mL) and toluene (18 mL). The mixture was cooled to 20° C. Tert-butyl 4-(hydroxymethyl)-4-(trifluoromethyl)piperidine-1-carboxylate (1.8 g, 6.35 mmol), EX43-1 (201.1 mg, 0.882 mmol) and TBAB (2.0 g, 6.354 mmol) were added to the mixture under $N_2$ atmosphere. The reaction was stirred at 70° C. for 3 hrs under $N_2$ atmosphere. The mixture was diluted with water (20 mL) and extracted with EA (20 mL×3). The combined organic layer was dried over $MgSO_4$, concentrated, and purified by silica gel chromatography to afford EX43-2 (1.8 g). LCMS $[M-{}^tBu+H]^+$: 307.0.

Step 2:

EX43-3 (1.7 g, crude) was prepared as described in Example 32 (EX32) Step 2, except EX43-2 was used instead of EX32-1. LCMS $[M+H]^+$: 367.1.

Step 3:

EX43 (37.13 mg) was prepared as described in Example 20 (EX20) Steps 5-8, except EX43-3 was used instead of EX20-4 in Step 5. $^1$H NMR (400 MHz, DMSO-$d_6$) δ 11.83 (s, 1H), 7.95 (d, J=8.6 Hz, 1H), 7.28 (s, 1H), 7.15 (s, 1H), 7.09 (d, J=8.4 Hz, 1H), 3.74 (t, J=6.2 Hz, 2H), 3.51-3.41 (m, 2H), 3.38-3.31 (m, 4H), 3.22-3.15 (m, 2H), 3.11-3.00 (m, 2H), 2.90 (t, J=12.3 Hz, 2H), 2.50-2.41 (m, 2H), 2.21 (s, 3H), 1.87 (d, J=13.8 Hz, 2H), 0.50-0.40 (m, 2H), 0.34-0.24 (m, 2H). LCMS $[M+H]^+$: 599.3.

Example 44 (EX44)

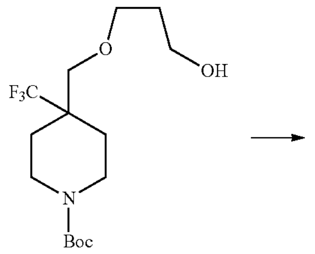

EX17-3

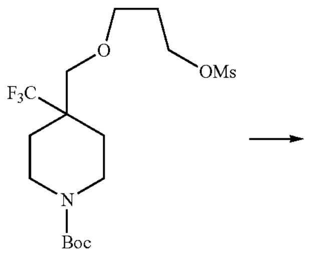

EX44-1

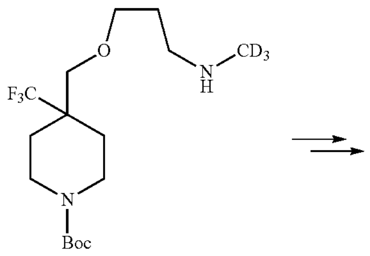

EX44-2

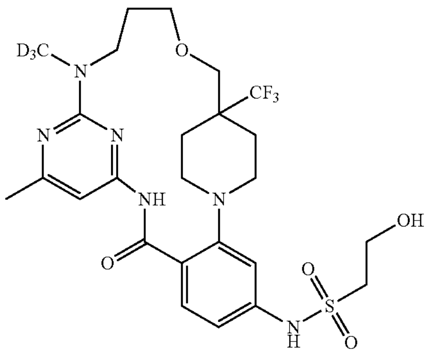

EX44

Step 1:

EX44-1 (4.0 g) was prepared as described in Example 4 (EX04) Step 1, except EX17-3 was used instead of EX01-2.

Step 2:

To a solution of EX44-1 (4 g, 9.54 mmol) and $CD_3NH_2$ (HCl salt, 3.4 g, 47.68 mmol) in DMSO (40 mL) were added CsF (2.9 g, 19.07 mmol) and DIEA (12.64 mL, 76.28 mmol) under $N_2$ atmosphere. The mixture was stirred at 80° C. for 12 hrs. The mixture was diluted with water (80 mL) and extracted with EtOAc (80 mL×3). The combined organic layer was dried over $MgSO_4$, concentrated under reduced pressure, and purified by flash silica gel chromatography to afford EX44-2 (2.4 g). LCMS $[M+H]^+$: 358.2.

Step 3:

EX44 (65.35 mg) was prepared as described in in Example 4 (EX04) Steps 3-4, except EX44-2 was used instead of EX04-2 in Step 3. $^1H$ NMR (400 MHz, $CD_3OD$) δ 8.11 (d, J=8.7 Hz, 1H), 7.46 (s, 1H), 7.29 (d, J=2.1 Hz, 1H), 7.18 (dd, J=8.7, 2.1 Hz, 1H), 3.99-3.89 (m, 4H), 3.52-3.46 (m, 2H), 3.43 (s, 2H), 3.38 (t, J=6.2 Hz, 2H), 3.11 (d, J=8.8 Hz, 4H), 2.74-2.61 (m, 2H), 2.37 (s, 3H), 1.94 (d, J=15.1 Hz, 2H), 1.89-1.80 (m, 2H). LCMS $[M+H]^+$: 590.3.

Example 45 (EX45)

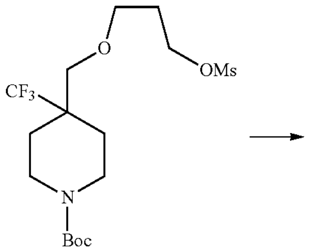

EX44-1

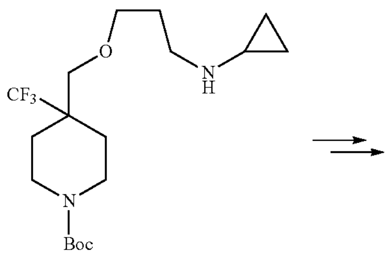

EX45-1

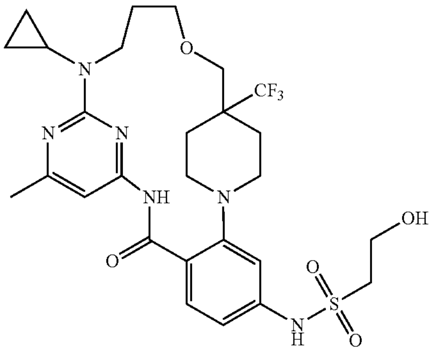

EX45

Step 1:

To a solution of EX44-1 (1.9 g, 4.53 mmol) and cyclopropanamine (388 mg, 6.80 mmol) in DMSO (25 mL) was added DIEA (2.2 mL, 13.35 mmol) and the resulting reaction was stirred at 100° C. for 1 hr. The mixture was diluted with water (200 mL) and extracted with EtOAc (100 mL×3). The combined organic layer was dried over $MgSO_4$, concentrated, and purified by silica gel chromatography to afford EX45-1 (2.2 g). LCMS $[M+H]^+$: 381.3.

Step 2:

EX45 (23.04 mg) was prepared as described in Example 4 (EX04) Steps 3-4, except EX45-1 was used instead of EX04-2 in Step 3. $^1H$ NMR (400 MHz, $CD_3OD$) δ 8.11 (d, J=8.7 Hz, 1H), 7.55 (s, 1H), 7.29 (d, J=2.0 Hz, 1H), 7.18 (dd, J=8.7, 2.1 Hz, 1H), 3.99-3.88 (m, 4H), 3.52-3.46 (m, 2H), 3.43 (s, 2H), 3.38 (t, J=6.2 Hz, 2H), 3.11 (d, J=8.6 Hz, 4H), 2.74-2.58 (m, 3H), 2.42 (s, 3H), 1.99-1.91 (m, 2H), 1.90-1.83 (m, 2H), 0.96-0.88 (m, 2H), 0.68-0.61 (m, 2H). LCMS $[M+H]^+$: 613.3.

Example 46 (EX46-A & EX46-B)

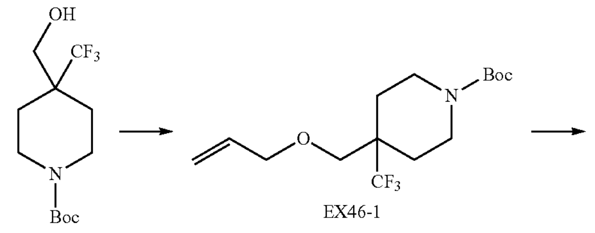

EX17-2

EX46-1

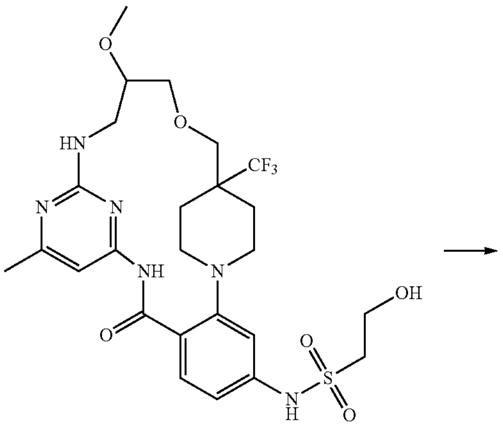

EX46

-continued

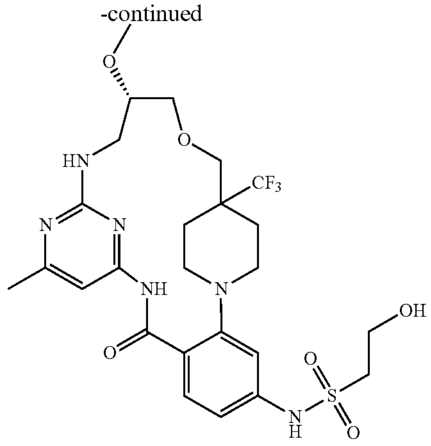

EX46-A & EX46-B

Step 1:

EX46-1 was prepared as described in Example 2 (EX02) Step 1, except EX17-2 was used instead of tert-butyl 4-(hydroxymethyl)-4-methylpiperidine-1-carboxylate.

Step 2:

EX46 was prepared as described in Example 31 (EX31), except EX46-1 was used instead of EX02-1 in Step 1.

Step 3:

EX46-A (8.87 mg) and EX46-B (10.65 mg) were separated from EX46 by SFC. SFC analytic condition: column: Chiralpak AD-3, 150*4.6 mm, 3.0 m; mobile phase A: supercritical $CO_2$, mobile phase B: ethanol (0.05% DEA), 40% mobile phase B, 5 min; flow rate: 2.5 mL/min; column temp: 35° C.

EX46-A: $^1H$ NMR (400 MHz, $CD_3OD$) δ 8.09 (d, J=8.6 Hz, 1H), 7.48 (s, 1H), 7.28 (d, J=2.0 Hz, 1H), 7.17 (dd, J=2.0, 8.6 Hz, 1H), 4.16 (dd, J=2.8, 14.0 Hz, 1H), 3.94 (t, J=6.2 Hz, 2H), 3.63 (dd, J=2.2, 7.8 Hz, 1H), 3.48 (s, 2H), 3.44 (s, 3H), 3.39-3.34 (m, 4H), 3.30-3.25 (m, 1H), 3.21-3.01 (m, 4H), 2.71-2.56 (m, 2H), 2.31 (s, 3H), 1.99-1.87. LCMS $[M+H]^+$: 603.3. Retention time @SFC: 1.202 min.

EX46-B: $^1H$ NMR (400 MHz, $CD_3OD$) δ 8.11 (d, J=8.7 Hz, 1H), 7.50 (s, 1H), 7.30 (d, J=2.1 Hz, 1H), 7.19 (dd, J=8.6, 2.1 Hz, 1H), 4.18 (dd, J=14.0, 2.8 Hz, 1H), 3.96 (t, J=6.2 Hz, 2H), 3.64 (dd, J=7.8, 2.2 Hz, 1H), 3.50 (s, 2H), 3.46 (s, 3H), 3.42-3.35 (m, 4H), 3.32-3.28 (m, 1H), 3.25-3.01 (m, 4H), 2.73-2.57 (m, 2H), 2.33 (s, 3H), 2.01-1.88 (m, 2H). LCMS $[M+H]^+$: 603.3. Retention time @SFC: 1.722 min.

Example 47 (EX-47)

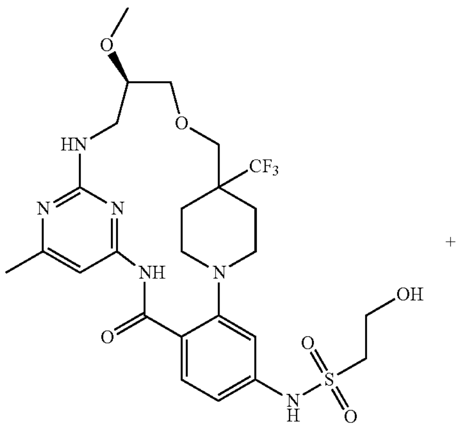

+

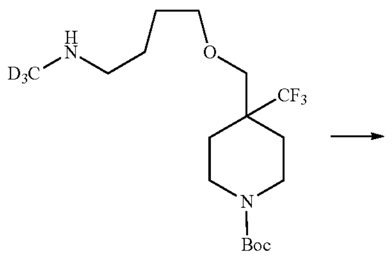

EX47-1

-continued

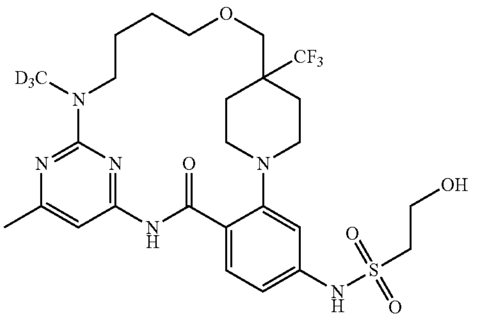

EX47

Step 1:

EX47 (2.49 mg) was prepared as described in Example 4 (EX04) Steps 3-4, except EX47-1 was used instead of EX04-2 in Step 3. $^{1}$H NMR (400 MHz, $CD_3OD$) δ 8.04 (d, J=8.2 Hz, 1H), 7.44 (s, 1H), 7.30 (s, 1H), 7.13 (d, J=7.8 Hz, 1H), 4.04-3.88 (m, 2H), 3.73-3.62 (m, 2H), 3.59-3.52 (m, 2H), 3.50 (s, 2H), 3.41-3.36 (m, 3H), 3.28-3.25 (m, 1H), 3.23-3.10 (m, 2H), 2.52-2.39 (m, 2H), 2.36 (s, 3H), 2.00 (d, J=14.0 Hz, 2H), 1.93-1.83 (m, 2H), 1.68-1.59 (m, 2H). LCMS $[M+H]^+$: 604.3.

Example 48 (EX48)

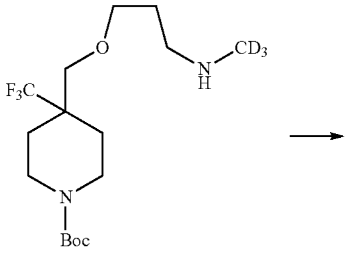

EX44-2

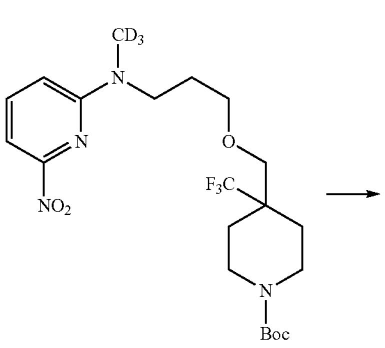

EX48-1

-continued

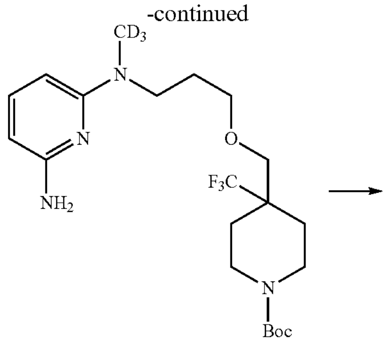

EX48-2

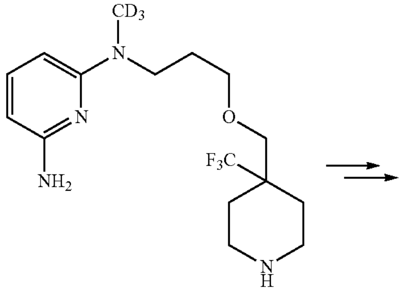

EX48-3

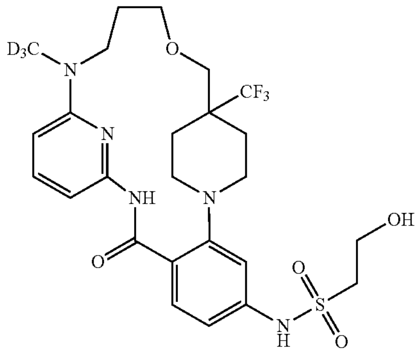

EX48

Step 1:

To a solution of EX44-2 (950 mg, 2.39 mmol) and 2-chloro-6-nitropyridine (758 mg, 4.79 mmol) in NMP (8 mL) was added DIEA (1.19 mL, 7.178 mmol). The resulting mixture was stirred at 140° C. for 2 hrs. The mixture was cooled to room temperature, diluted with water (15 mL) and extracted with EtOAc (15 mL×3). The combined organic layer was dried over $MgSO_4$, concentrated under reduced pressure and purified by flash silica gel chromatography to afford EX48-1 (710 mg). LCMS $[M-Boc+H]^+$: 380.2.

Step 2:

To a solution of EX48-1 (560 mg, 1.17 mmol) in MeOH (5 mL) were added Pd/C (621.3 mg, 0.58 mmol, 10% purity) and TES (1.36 g, 11.68 mmol) under $N_2$ atmosphere. The mixture was stirred at 40° C. for 0.5 hr. The reaction mixture was filtered through a pad of celite, washed with MeOH (20 mL) and concentrated under reduced pressure to give EX48-2 (800 mg, crude). LCMS $[M+H]^+$: 450.3.

Step 3:

EX48-3 was prepared as described in Example 1 (EX01) Step 4, except EX48-2 was used instead of EX01-3.

Step 4:

EX48 (16.88 mg) was prepared as described in Example 1 (EX01) Steps 5-8, except EX48-3 was used instead of EX01-4 in Step 5. $^1$H NMR (400 MHz, $CD_3OD$) δ 8.09 (d, J=8.6 Hz, 1H), 7.59 (d, J=7.5 Hz, 1H), 7.53 (t, J=8.0 Hz, 1H), 7.26 (d, J=2.1 Hz, 1H), 7.16 (dd, J=8.6, 2.1 Hz, 1H), 6.35 (d, J=8.1 Hz, 1H), 4.01-3.91 (m, 4H), 3.49-3.45 (m, 2H), 3.41 (s, 2H), 3.38 (t, J=6.3 Hz, 2H), 3.19-3.05 (m, 4H), 2.75-2.63 (m, 2H), 1.93 (d, J=14.8 Hz, 2H), 1.85-1.77 (m, 2H). LCMS $[M+H]^+$: 575.3.

Example 49 (EX49)

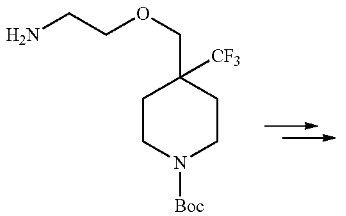

EX49-1

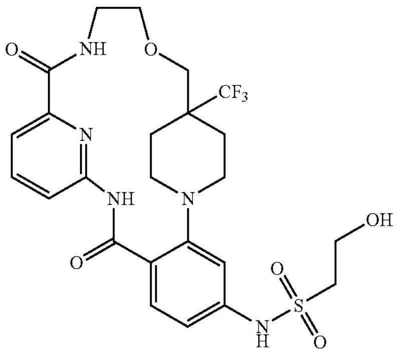

EX49

Step 1:

EX49 (0.51 mg) was prepared as described in Example 21 (EX21), except EX49-1 was used instead of EX04-2 in Step 1. $^1$H NMR (400 MHz, $CD_3OD$) δ 8.60 (d, J=8.6 Hz, 1H), 8.25 (d, J=8.7 Hz, 1H), 8.02 (d, J=7.9 Hz, 1H), 7.83 (d, J=7.6 Hz, 1H), 7.44 (s, 1H), 7.26-7.21 (m, 1H), 3.97 (t, J=6.2 Hz, 2H), 3.72-3.66 (m, 4H), 3.63 (s, 2H), 3.41-3.39 (m, 2H), 3.25-3.12 (m, 4H), 2.70-2.61 (m, 2H), 2.09-2.04 (m, 2H). LCMS $[M+H]^+$: 572.3.

Example 50 (EX50)

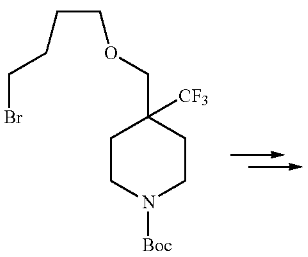

EX47-1

-continued

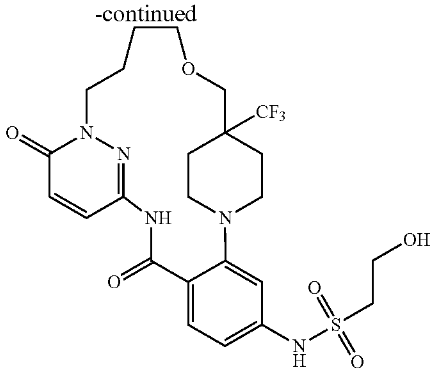

EX50

Step 1:

EX50 (4.36 mg) was prepared as described in Example 13 (EX13) Steps 2-4, except EX47-1 was used instead of EX13-1 in Step 2. $^1$H NMR (400 MHz, $CD_3OD$) δ 8.36 (d, J=9.8 Hz, 1H), 8.12 (d, J=8.5 Hz, 1H), 7.32 (s, 1H), 7.22 (d, J=8.2 Hz, 1H), 7.07 (d, J=9.6 Hz, 1H), 4.29-4.17 (m, 2H), 3.96 (t, J=6.1 Hz, 2H), 3.57-3.51 (m, 2H), 3.44 (s, 2H), 3.38 (t, J=6.3 Hz, 2H), 3.19-3.05 (m, 4H), 2.71-2.57 (m, 2H), 2.20-2.09 (m, 2H), 1.98 (d, J=14.4 Hz, 2H), 1.59-1.47 (m, 2H). LCMS $[M+H]^+$: 574.3.

Example 51 (EX51)

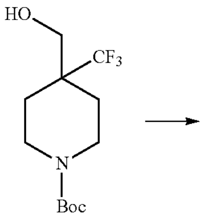

EX17-2

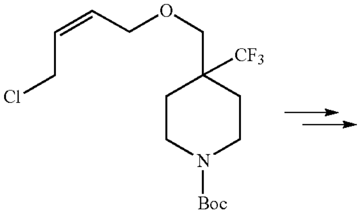

EX51-1

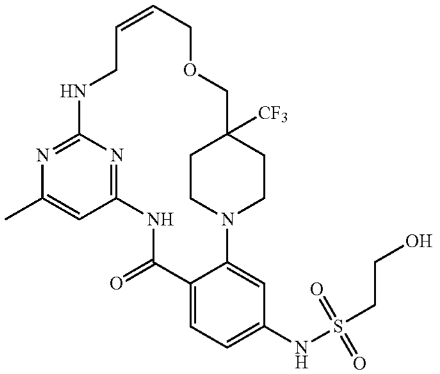

EX51

Step 1:

To a solution of NaOH (1.1 g, 26.47 mmol) in $H_2O$ (30 mL) were added EX17-2 (3.0 g, 10.59 mmol), (2Z)-1,4-dichlorobut-2-ene (3.3 g, 26.47 mmol) and tetrabutylammonium bisulfate (0.2 g, 0.53 mmol) at 0° C. The mixture was stirred at 70° C. for 6 hrs. The mixture was extracted with EtOAc (30 mL×3). The combined organic layer was dried over $MgSO_4$, concentrated under reduced pressure and purified by silica gel chromatography to afford EX51-1 (1.5 g). LCMS $[M-{}^{t}Bu+H]^+$: 316.1.

Step 2:

EX51 (18.83 mg) was prepared as described in Example 12 (EX12) Steps 2-5, except EX51-2 was used instead of EX12-2 in Step 2. $^1$H NMR (400 MHz, DMSO-$d_6$) δ 8.12 (s, 1H), 8.02 (d, J=8.7 Hz, 1H), 7.30 (s, 1H), 7.25 (s, 1H), 7.13 (d, J=8.7 Hz, 1H), 5.70-5.63 (m, 1H), 5.48-5.40 (m, 1H), 4.26-4.17 (m, 2H), 4.10-4.02 (m, 2H), 3.74 (t, J=6.3 Hz, 2H), 3.45 (s, 2H), 3.33 (t, J=6.3 Hz, 2H), 3.09-3.01 (m, 2H), 3.01-2.91 (m, 2H), 2.22 (s, 3H), 2.19-2.09 (m, 2H), 2.07-2.01 (m, 2H). LCMS $[M+H]^+$: 585.3.

Example 52 (EX52)

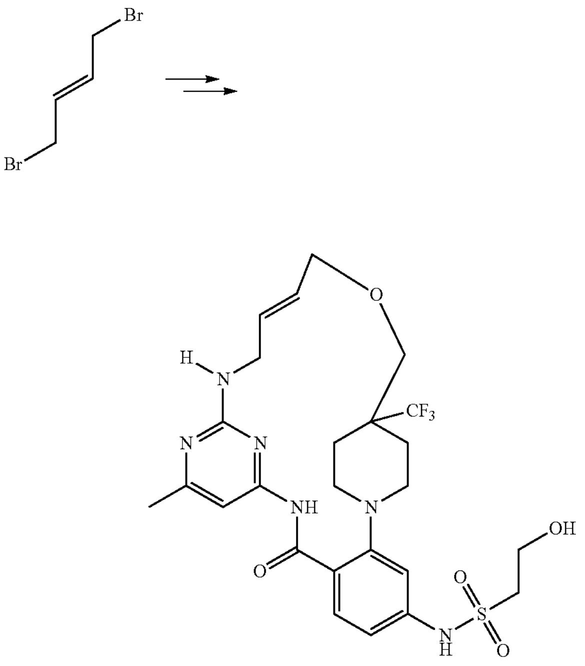

EX52

Step 1:

EX52 (12.88 mg) was prepared as described in Example 51 (EX51), except (E)-1,4-dibromobut-2-ene was used instead of (Z)-1,4-dichlorobut-2-ene in Step 1. $^1$H NMR (400 MHz, DMSO-$d_6$) δ 11.84 (s, 1H), 7.95 (d, J=8.6 Hz, 1H), 7.34 (s, 1H), 7.23 (d, J=1.7 Hz, 1H), 7.13 (dd, J=8.6, 1.9 Hz, 1H), 6.43 (s, 1H), 5.77-5.66 (m, 1H), 5.64-5.54 (m, 1H), 4.13 (d, J=6.1 Hz, 2H), 4.01 (t, J=5.9 Hz, 2H), 3.80 (t, J=6.4 Hz, 2H), 3.61 (s, 2H), 3.35 (t, J=6.4 Hz, 2H), 3.04-2.96 (m, 4H), 2.28 (s, 3H), 2.17-2.09 (m, 2H), 2.00-1.88 (m, 2H). LCMS $[M+H]^+$: 585.4.

Example 53 (EX53)

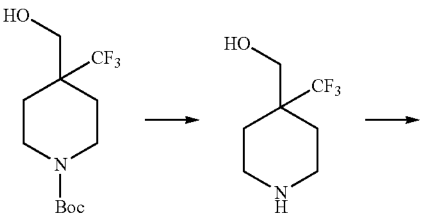

EX17-2 EX53-1

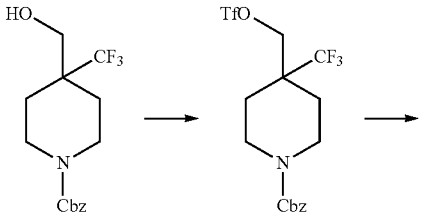

EX53-2 EX53-3

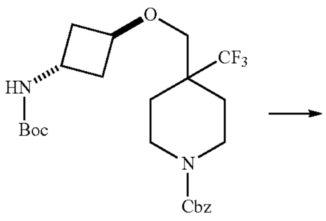

EX53-4

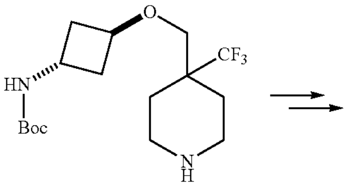

EX53-5

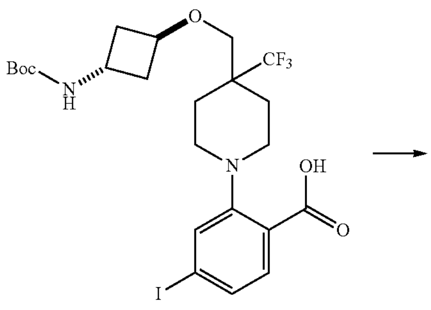

EX53-6

-continued

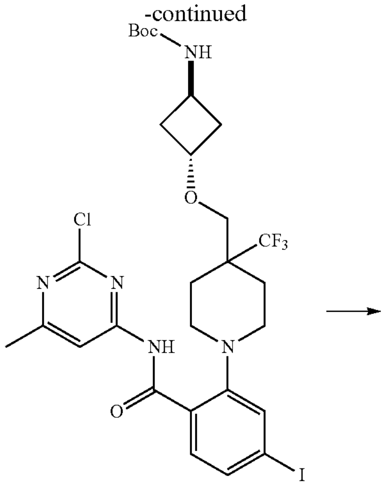

EX53-7

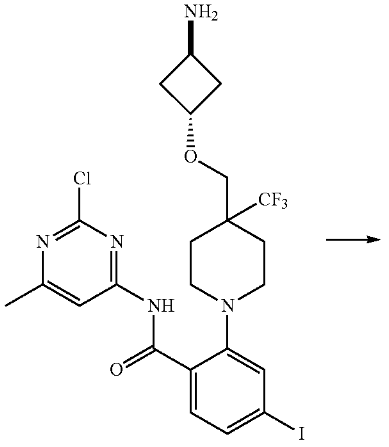

EX53-8

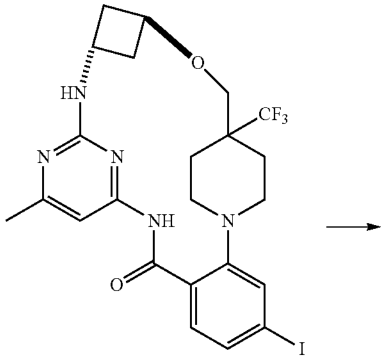

EX53-9

-continued

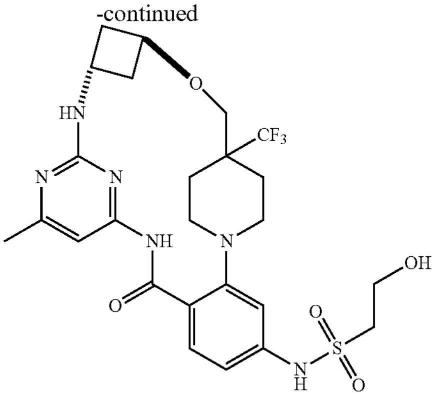

EX53

Step 1:

EX53-1 (8 g, crude) was prepared as described in Example 1 (EX01) Step 4, except EX17-2 was used instead of EX01-3. LCMS $[M+H]^+$:184.1.

Step 2:

To a solution of EX53-1 (7.37 g, 40.2 mmol) and CbzCl (6.24 mL, 44.25 mmol) in THF (85 mL) was added NaOH (5 M, 32 mL, 160.9 mmol) at 0° C. The reaction mixture was stirred at 25° C. for 2 hrs. The mixture was extracted with EtOAc (100 mL×3). The combined organic layer was dried over $MgSO_4$, concentrated under reduced pressure and purified by silica gel chromatography to afford EX53-2 (9.6 g). LCMS $[M+H]^+$: 318.1.

Step 3:

To a solution of EX53-2 (2.3 g, 7.25 mmol) and 2,6-lutidine (0.9 g, 8.7 mmol) in DCM (250 mL) was added $Tf_2O$ (2.5 g, 8.7 mmol) dropwise at −78° C. The resulting mixture was stirred at −78° C. for 1 hr. The reaction was quenched with saturated aq. $NH_4Cl$ (150 mL) and extracted with DCM (200 mL×3). The combined organic layer was dried over $MgSO_4$ and concentrated under vacuum to afford EX53-3 (3.1 g). LCMS $[M+Na]^+$: 472.0.

Step 4:

To a solution of EX53-3 (3.1 g, 6.9 mmol) and tert-butyl trans-(3-hydroxycyclobutyl)carbamate (1.5 g, 8.28 mmol) in $H_2O$ (70 mL) were added NaOH (2.2 g, 55.19 mmol) and TBAS (2.3 g, 6.9 mmol). The mixture was stirred at 70° C. for 3 hrs. The reaction mixture was extracted with EtOAc (100 mL×3). The combined organic layer was dried over $MgSO_4$, concentrated under vacuum and purified by silica gel chromatography to afford EX53-4 (480 mg). LCMS $[M-{}^tBu+H]^+$: 431.1.

Step 5:

EX53-5 (280 mg, crude) was prepared as described in Example 49 (EX49) Step 3, except EX53-4 was used instead of EX49-3. LCMS $[M+H]^+$: 353.1.

Step 6:

EX53-6 (330 mg) was prepared as described in Example 1 (EX01) Steps 5-6, except EX53-5 was used instead of EX01-4 in Step 5. LCMS $[M+H]^+$: 599.3.

Step 7:

To a solution of EX53-6 (330 mg, 0.55 mmol) and 2-chloro-6-methylpyrimidin-4-amine (237.4 mg, 1.65 mmol) in dioxane (6 mL) were added $T_4P$ (3 mL, 11.02 mmol, 50% in EtOAc) and TEA (1.99 mL, 14.3 mmol). The mixture was stirred at 100° C. for 1 hr. The reaction was quenched with water (10 mL) and extracted with EtOAc (10 mL×3). The combined organic layer was dried over $MgSO_4$, concentrated under vacuum, and purified by silica gel chromatography to afford EX53-7 (300 mg). LCMS $[M+H]^+$: 724.2.

Step 8:

EX53-8 (210 mg) was prepared as described in Example 1 (EX01) Step 4, except EX53-7 was used instead of EX01-3. LCMS $[M+H]^+$: 624.3.

Step 9:

To a solution of EX53-8 (210 mg, 0.34 mmol) in i-PrOH (18 mL) were added DIEA (669 μL, 4.04 mmol) and CsF (511.4 mg, 3.37 mmol). The mixture was stirred at 120° C. for 24 hrs. The reaction was concentrated under reduced pressure and the residue was diluted with water (20 mL) and extracted with EtOAc (30 mL×3). The combined organic layer was dried over $MgSO_4$, concentrated under vacuum, and purified by silica gel chromatography to afford EX53-9 (60 mg). LCMS $[M+H]^+$: 588.2.

Step 10:

EX53 (13.4 mg) was prepared as described in Example 1 (EX01) Step 8, except EX53-9 was used instead of EX01-7. $^1H$ NMR (400 MHz, DMSO-$d_6$) δ 8.08 (d, J=8.1 Hz, 1H), 7.33 (s, 1H), 7.26 (s, 1H), 7.15 (d, J=8.9 Hz, 1H), 3.78 (t, J=6.4 Hz, 2H), 3.50 (s, 2H), 3.33 (t, J=6.4 Hz, 2H), 3.17-3.09 (m, 2H), 3.08-2.97 (m, 2H), 2.46-2.37 (m, 4H), 2.24 (s, 3H), 2.21-2.11 (m, 4H), 2.04-1.98 (m, 2H). LCMS $[M+H]^+$: 585.3.

Example 54 (EX54)

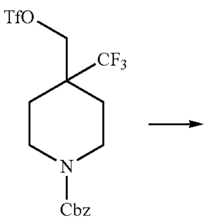

EX53-3

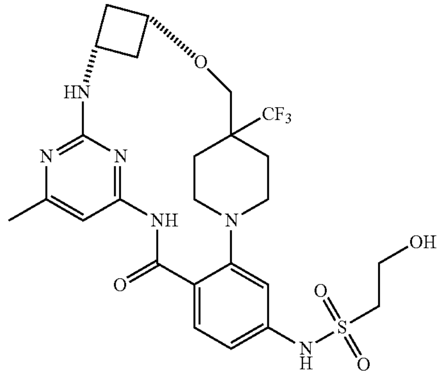

EX54

Step 1:

EX54 (37.69 mg) was prepared as described in Example 53 (EX53) Steps 4-10, except tert-butyl cis-(3-hydroxycyclobutyl)carbamate was used instead of tert-butyl trans-(3-hydroxycyclobutyl)carbamate in Step 4. $^1H$ NMR (400 MHz, DMSO-$d_6$) δ 10.48 (s, 1H), 8.00 (d, J=8.7 Hz, 1H), 7.48 (s, 1H), 7.12 (s, 1H), 7.08-7.03 (m, 1H), 3.89-3.82 (m, 1H), 3.74 (t, J=6.4 Hz, 2H), 3.51-3.45 (m, 1H), 3.34 (t, J=6.4 Hz, 2H), 3.27-3.18 (m, 4H), 3.07-2.98 (m, 2H), 2.84 (t, J=13.0 Hz, 2H), 2.69-2.58 (m, 2H), 2.38-2.32 (m, 2H), 2.21 (s, 3H), 1.89 (d, J=14.8 Hz, 2H). LCMS $[M+H]^+$: 585.3.

Example 55 (EX55)

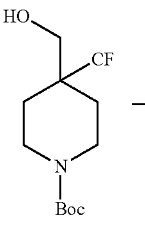

EX17-2

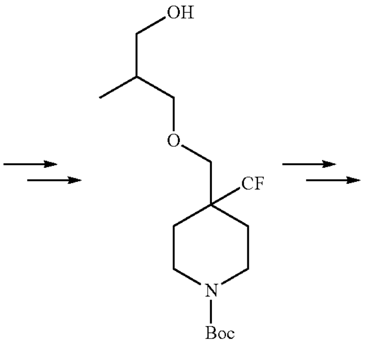

EX55-1

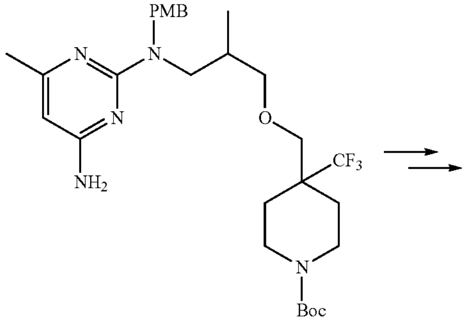

EX55-2

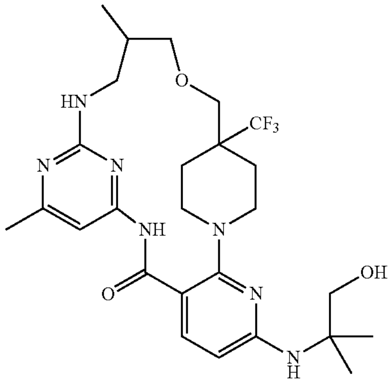

EX55

Step 1:

EX55-1 was prepared as described in Example 19 (EX19) Steps 1-2, except EX17-2 was used instead of tert-butyl 4-(hydroxymethyl)-4-methylpiperidine-1-carboxylate in Step 1.

Step 2:

EX55-2 was prepared as described in Example 12 (EX12) Steps 1-3, except EX55-1 was used instead of EX02-2 in Step 1.

Step 3:

EX55 (9.13 mg) was prepared as described in Example 29 (EX29) Steps 4-6, except EX55-2 was used instead of EX12-3 in Step 4. $^1H$ NMR (400 MHz, DMSO-$d_6$) δ 12.06 (s, 1H), 7.93 (d, J=8.8 Hz, 1H), 7.27 (s, 1H), 6.43 (d, J=8.7

Hz, 1H), 4.06 (d, J=10.9 Hz, 1H), 3.56 (s, 2H), 3.43-3.37 (m, 1H), 3.36-3.29 (m, 2H), 3.23-3.10 (m, 2H), 3.08-2.93 (m, 3H), 2.70-2.55 (m, 2H), 2.48-2.40 (m, 1H), 2.19 (s, 3H), 1.94-1.67 (m, 3H), 1.32 (s, 6H), 0.85 (d, J=6.8 Hz, 3H). LCMS $[M+H]^+$: 552.3.

Example 56 (EX56)

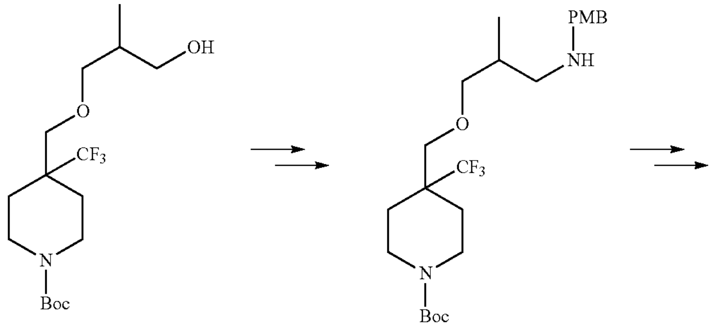

EX55-1

EX56-1

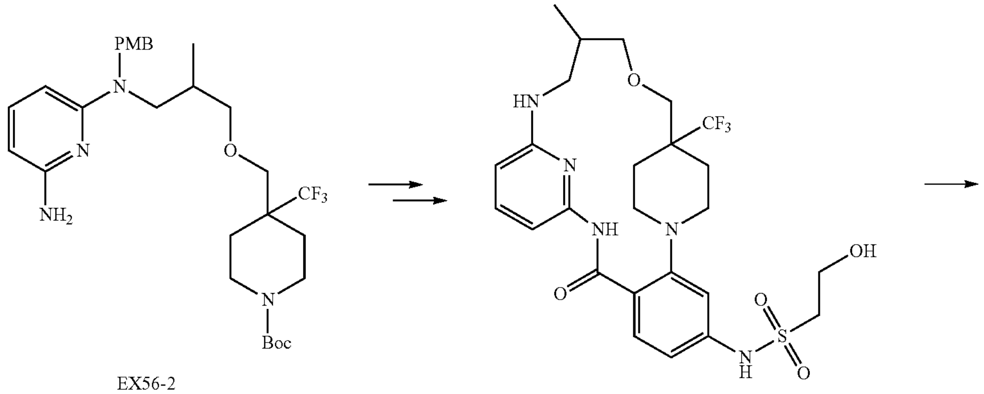

EX56-2

EX56

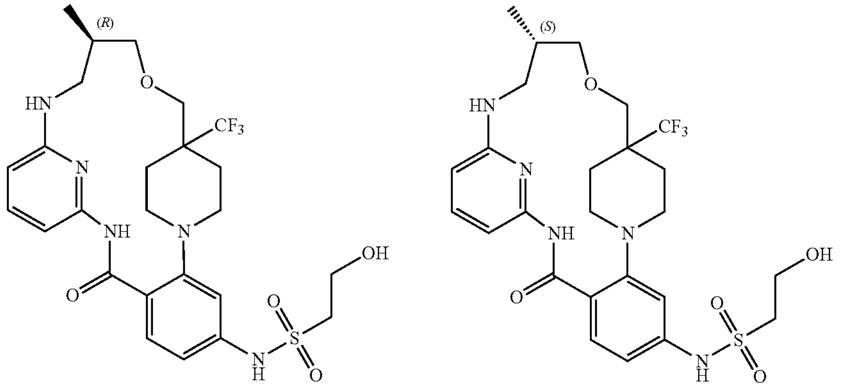

EX56-A&B

Step 1:

EX56-1 was prepared as described in Example 12 (EX12) Steps 1-2, except EX55-1 was used instead of EX02-2 in Step 1.

Step 2:

EX56-3 (350 mg) was prepared as described in Example 48 (EX48) Steps 3-4, except EX56-1 was used instead of EX48-2 in Step 3. LCMS $[M+H]^+$: 567.3.

Step 3:

EX56 (3.96 mg) was prepared as described in Example 12 (EX12) Steps 4-6, except EX56-2 was used instead of EX12-3 in Step 4. $^1H$ NMR (400 MHz, $CD_3OD$) δ 8.09 (d, J=8.6 Hz, 1H), 7.47 (d, J=7.7 Hz, 1H), 7.36 (t, J=7.9 Hz, 1H), 7.27 (s, 1H), 7.16 (d, J=8.7 Hz, 1H), 6.25 (d, J=8.0 Hz, 1H), 4.19 (dd, J=13.3, 4.7 Hz, 1H), 3.96 (t, J=6.2 Hz, 2H), 3.47-3.41 (m, 3H), 3.38 (t, J=6.2 Hz, 2H), 3.23-3.12 (m, 4H), 3.08-2.97 (m, 2H), 2.85-2.61 (m, 2H), 2.01-1.81 (m, 3H), 0.99 (d, J=6.9 Hz, 3H). LCMS $[M+H]^+$: 572.3.

Step 4

EX56-A (8.87 mg) and EX56-B (10.65 mg) were separated from EX56 by SFC. SFC analytic condition: column: Phenomenex Lux Cellulose-4, 100*4.6 mm, 3.0 m; mobile phase A: supercritical $CO_2$, mobile phase B: MeOH (0.05% DEA), 40% mobile phase B, 5 min; flow rate: 2.8 mL/min; column temp: 40° C.

EX56-A: $^1H$ NMR (400 MHz, $CD_3OD$) δ 8.09 (d, J=8.6 Hz, 1H), 7.47 (d, J=7.8 Hz, 1H), 7.36 (t, J=7.7 Hz, 1H), 7.28 (d, J=1.7 Hz, 1H), 7.16 (d, J=8.6 Hz, 1H), 6.25 (d, J=8.1 Hz, 1H), 4.19 (dd, J=13.4, 4.4 Hz, 1H), 3.96 (t, J=6.2 Hz, 2H), 3.43 (t, J=6.6 Hz, 3H), 3.38 (t, J=6.3 Hz, 2H), 3.17 (dd, J=23.5, 14.7 Hz, 4H), 3.02 (dd, J=13.3, 7.2 Hz, 2H), 2.77 (s, 1H), 2.68 (s, 1H), 1.98 (d, J=14.2 Hz, 1H), 1.89 (d, J=14.7 Hz, 2H), 0.99 (d, J=6.9 Hz, 3H). LCMS $[M+H]^+$: 572.3. Retention time @SFC: 2.399 min.

EX56-B: $^1H$ NMR (400 MHz, $CD_3OD$) δ 8.07 (d, J=8.6 Hz, 1H), 7.45 (d, J=7.8 Hz, 1H), 7.38-7.31 (m, 1H), 7.25 (d, J=1.4 Hz, 1H), 7.14 (dd, J=1.2, 8.6 Hz, 1H), 6.23 (d, J=8.1 Hz, 1H), 4.17 (dd, J=4.6, 13.4 Hz, 1H), 3.94 (t, J=6.2 Hz, 2H), 3.45-3.39 (m, 3H), 3.36 (t, J=6.3 Hz, 2H), 3.23-3.09 (m, 5H), 3.04-2.95 (m, 2H), 2.83-2.60 (m, 2H), 1.85 (s, 3H), 0.97 (d, J=7.0 Hz, 3H). LCMS $[M+H]^+$: 572.3. Retention time @SFC: 3.210 min.

Example 57 (EX57)

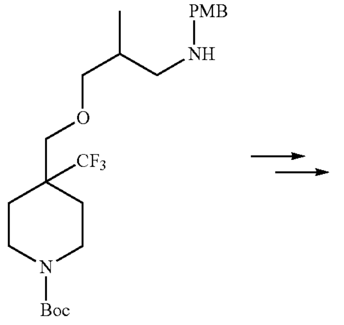

EX56-1

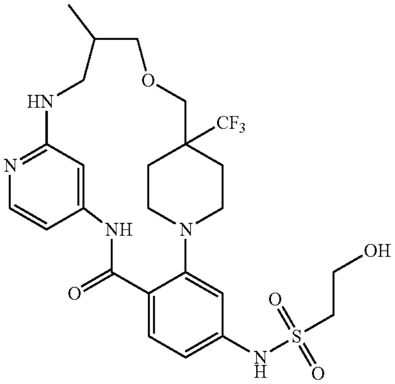

EX57

Step 1:

EX57 was prepared as described in Example 56 (EX56) Steps 2-3, except 2-fluoro-4-nitropyridine was used instead of 2-fluoro-6-nitropyridine in Step 2. $^1H$ NMR (400 MHz, $CD_3OD$) δ 8.20 (d, J=8.7 Hz, 1H), 7.88 (d, J=6.0 Hz, 1H), 7.79 (d, J=4.5 Hz, 1H), 7.39 (d, J=2.0 Hz, 1H), 7.23 (dd, J=8.7, 2.0 Hz, 1H), 6.41 (s, 1H), 3.96 (t, J=6.2 Hz, 2H), 3.64-3.59 (m, 1H), 3.59-3.53 (m, 1H), 3.48-3.43 (m, 2H), 3.38 (t, J=6.2 Hz, 2H), 3.32-3.06 (m, 5H), 2.94-2.85 (m, 1H), 2.71-2.57 (m, 2H), 2.16-2.08 (m, 1H), 2.05-1.98 (m, 1H), 1.97-1.87 (m, 1H), 1.03 (d, J=6.9 Hz, 3H). LCMS $[M+H]^+$: 572.3.

Example 58 (EX58)

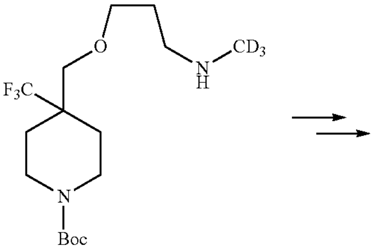

EX44-2

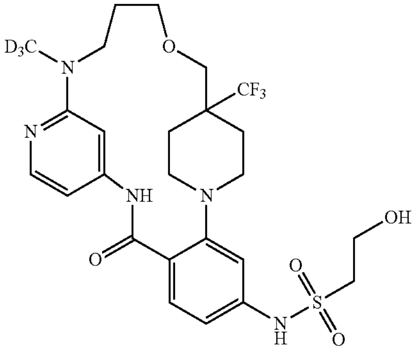

EX58

Step 1:

EX58 was prepared as described in Example 48 (EX48), except 2-fluoro-4-nitropyridine was used instead of 2-fluoro-6-nitropyridine in Step 1. $^1H$ NMR (400 MHz, $CD_3OD$) δ 8.18 (d, J=8.5 Hz, 1H), 7.98 (d, J=5.9 Hz, 1H), 7.78 (d, J=5.3 Hz, 1H), 7.37 (s, 1H), 7.22 (d, J=8.8 Hz, 1H), 6.53 (s, 1H), 4.02-3.90 (m, 2H), 3.60-3.48 (m, 6H), 3.41-3.36 (m, 2H), 3.22-3.08 (m, 4H), 2.69-2.55 (m, 2H), 2.10-2.01 (m, 2H), 1.98-1.86 (m, 2H). LCMS $[M+H]^+$: 575.3.

Example 59 (EX59)

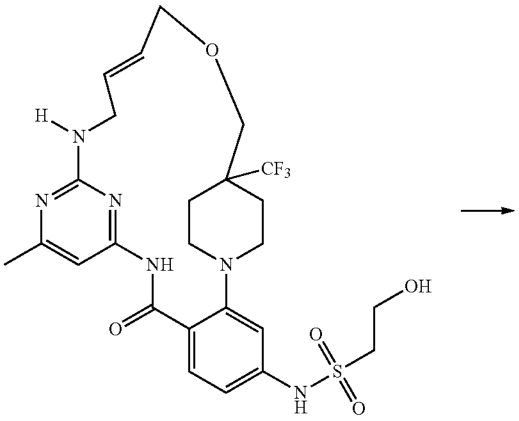

EX52

-continued

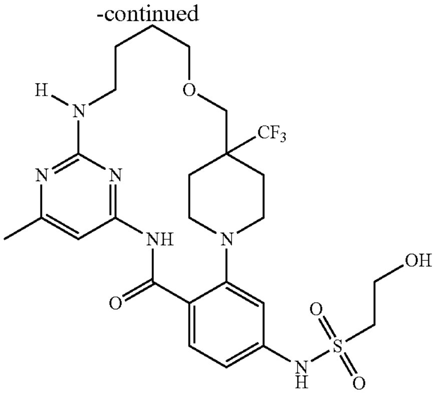

EX59

Step 1:

To a solution of EX52 (50 mg, 0.071 mmol) in EtOAc (5 mL) was added Pd/C (200 mg, 1.88 mmol, 10% purity). The mixture was purged and degassed with $H_2$ for 3 times. The mixture was stirred at 25° C. for 2 hrs under $H_2$ (15 psi). The mixture was filtrated through a pad of celite and concentrated under reduced pressure. The residue was purified by prep-HPLC to afford EX59 (15 mg). $^1$H NMR (400 MHz, DMSO-$d_6$) δ 8.12 (s, 1H), 7.95 (d, J=8.6 Hz, 1H), 7.26 (s, 1H), 7.23 (d, J=1.8 Hz, 1H), 7.08 (dd, J=8.7, 1.9 Hz, 1H), 3.74 (t, J=6.3 Hz, 2H), 3.47 (t, J=5.0 Hz, 2H), 3.39 (s, 2H), 3.35-3.29 (m, 4H), 3.15-3.08 (m, 2H), 3.02-2.93 (m, 2H), 2.30-2.23 (m, 2H), 2.20 (s, 3H), 1.95-1.87 (m, 2H), 1.74-1.64 (m, 2H), 1.57-1.49 (m, 2H). LCMS [M+H]$^+$: 572.3.

Example 60 (EX60)

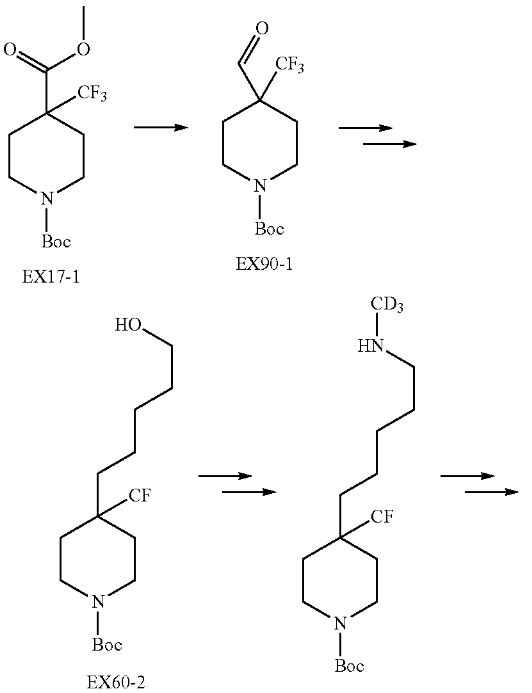

EX17-1 EX90-1 EX60-2 EX60-3

-continued

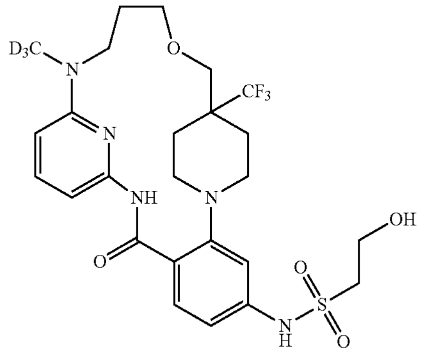

EX60

Step 1:

To a mixture of EX17-1 (10.0 g, 33 mmol) in DCM (200 mL) was dropwise added DIBAL-H (66 mL, 66 mL) at −78° C. under $N_2$ atmosphere. The resulting mixture was stirred at −78° C. for 2 h. The reaction was quenched by MeOH (80 mL) and neutralized by saturated potassium sodium tartrate. The mixture was extracted with DCM (300 mL) three times and the combined organic layer was concentrated under vacuum and purified with silica gel chromatography to afford EX60-1 (5.9 g). LCMS [M+H]$^+$: 282.3.

Step 2:

EX60-2 (2 g, crude) was prepared as described in Example 34 (EX34) Steps 2-3, except EX60-1 was used instead of EX34-1 in Step 2. LCMS [M-$^t$Bu+H]$^+$: 284.1.

Step 3:

EX60-3 was prepared as described in Example 44 (EX44) Steps 1-2, except EX60-2 was used instead of EX17-3 in Step 1.

Step 4:

EX60 was prepared as described in Example 48 (EX48), except EX60-3 was used instead of EX44-2 in step 1. $^1$H NMR (400 MHz, DMSO-$d_6$) δ 7.88 (d, J=8.4 Hz, 1H), 7.53-7.43 (m, 2H), 7.05-7.00 (m, 2H), 6.31 (d, J=8.0 Hz, 1H), 3.74 (t, J=6.3 Hz, 2H), 3.62 (t, J=6.5 Hz, 2H), 3.31 (t, J=6.3 Hz, 2H), 3.05 (d, J=8.9 Hz, 2H), 2.82 (t, J=11.6 Hz, 2H), 2.09 (s, 2H), 1.87 (d, J=14.7 Hz, 2H), 1.57 (d, J=26.1 Hz, 4H), 1.40 (s, 2H), 1.23 (s, 2H). LCMS [M+H]$^+$: 573.3.

Example 61 (EX61)

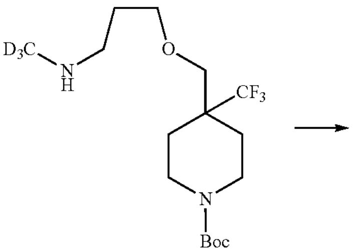

EX44-2

-continued

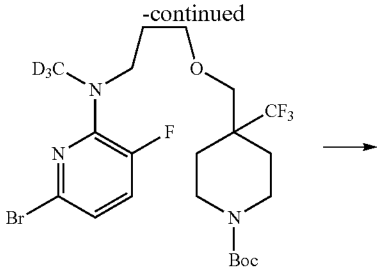

EX61-1

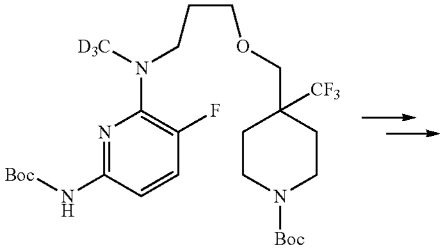

EX61-2

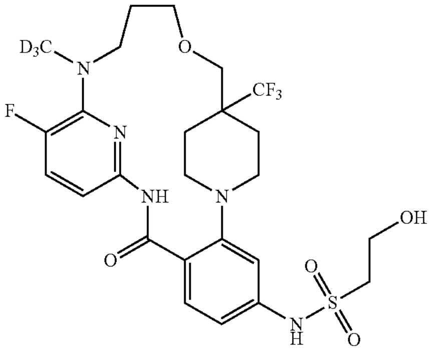

EX61

Step 1:

To a solution of EX44-2 (354 mg, 0.99 mmol) and 6-bromo-2,3-difluoropyridine (250 mg, 1.29 mmol) in NMP (5 mL) was added DIEA (493 μL, 2.97 mmol). The mixture was stirred at 120° C. for 1 hr. The reaction was quenched with water (50 mL) and extracted with EtOAc (50 mL×3). The combined organic layer was dried over $MgSO_4$, concentrated under reduced pressure and purified by silica gel chromatography to afford EX61-1 (200 mg). LCMS $[M\text{-}Boc+H]^+$: 431.2, 433.1.

Step 2:

To a solution of EX61-1 (200 mg, 0.38 mmol) and 2-methylpropan-2-yl aminomethanoate (44 mg, 0.38 mmol) in toluene (2 mL) was added $Cs_2CO_3$ (368 mg, 1.13 mmol), XantPhos (43.6 mg, 0.075 mmol) and $Pd_2(dba)_3$ (35 mg, 0.038 mmol) under $N_2$ atmosphere. The reaction was stirred at 100° C. for 2 hrs. The reaction was quenched with water (10 mL) and extracted with EtOAc (10 mL×3). The combined organic layer was dried over $MgSO_4$, concentrated and purified by silica gel chromatography to afford EX61-2 (170 mg). LCMS $[M+H]^+$: 568.5.

Step 3:

EX61 was prepared as described in Example 1 (EX01) Steps 4-8, except EX61-2 was used instead of EX01-3 in Step 4. $^1H$ NMR (400 MHz, $CD_3OD$) δ 8.07 (d, J=8.6 Hz, 1H), 7.56 (dd, J=8.4, 2.1 Hz, 1H), 7.34-7.27 (m, 1H), 7.26 (d, J=2.1 Hz, 1H), 7.15 (dd, J=8.6, 2.1 Hz, 1H), 3.99-3.89 (m, 4H), 3.54-3.47 (m, 2H), 3.42 (s, 2H), 3.38 (t, J=6.3 Hz, 2H), 3.18-3.05 (m, 4H), 2.64 (dd, J=18.5, 9.3 Hz, 2H), 1.93 (d, J=14.7 Hz, 2H), 1.89-1.80 (m, 2H). LCMS $[M+H]^+$: 593.3.

Example 62 (EX62)

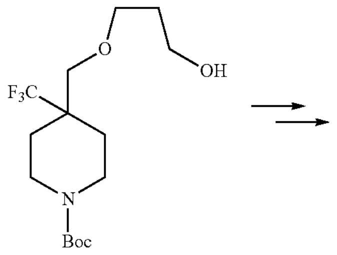

EX17-3

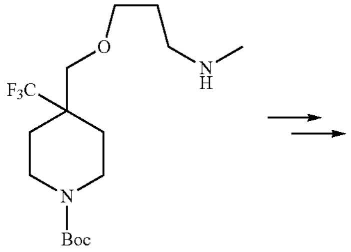

EX62-1

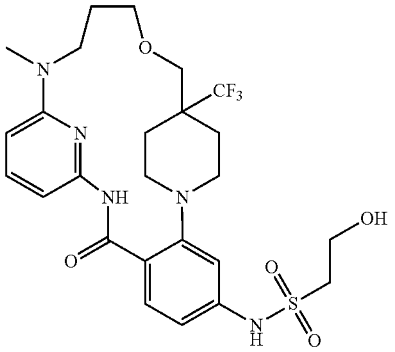

EX62

Step 1:

EX62-1 was prepared as described in Example 2 (EX02) Steps 1-2, except EX17-3 was used instead of EX01-2 in Step 1.

Step 2:

EX62 was prepared as described in Example 48 (EX48), except EX62-1 was used instead of EX44-2 in Step 1. $^1H$ NMR (400 MHz, $CD_3OD$) δ 8.09 (d, J=8.6 Hz, 1H), 7.61-7.50 (m, 2H), 7.26 (d, J=2.1 Hz, 1H), 7.16 (dd, J=8.6, 2.1 Hz, 1H), 6.36 (d, J=8.1 Hz, 1H), 3.96 (td, J=6.6, 3.6 Hz, 4H), 3.50-3.44 (m, 2H), 3.41 (s, 2H), 3.38 (t, J=6.2 Hz, 2H), 3.20-3.05 (m, 4H), 2.94 (s, 3H), 2.70 (t, J=10.9 Hz, 2H), 1.93 (d, J=15.2 Hz, 2H), 1.81 (dd, J=11.9, 6.3 Hz, 2H). LCMS $[M+H]^+$: 572.3.

Example 63 (EX63)

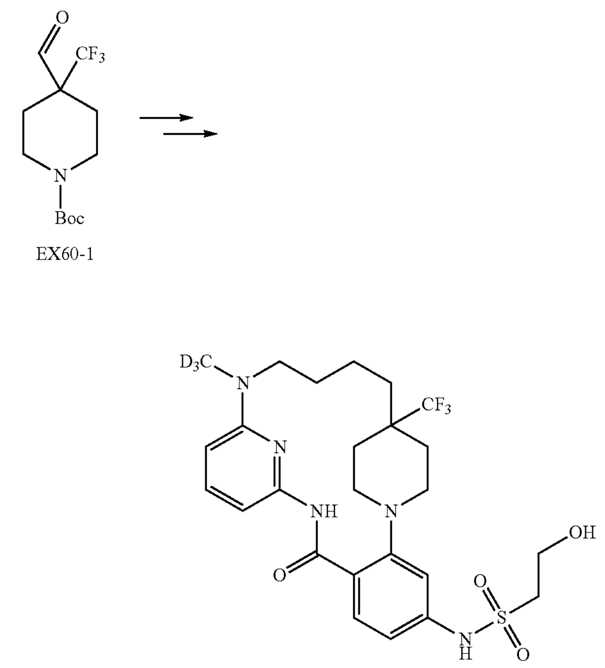

EX60-1

EX63

Step 1:

EX63 was prepared as described in Example 60 (EX60) Steps 2-4, except (3-(benzyloxy)propyl)triphenylphosphonium bromide was used instead of (4-(benzyloxy)butyl) triphenylphosphonium bromide in Step 2. H NMR (400 MHz, $CD_3OD$) δ 8.07 (d, J=8.6 Hz, 1H), 7.57-7.50 (m, 2H), 7.20 (s, 1H), 7.13 (d, J=8.6 Hz, 1H), 6.34 (d, J=7.3 Hz, 1H), 3.96 (t, J=6.2 Hz, 2H), 3.57 (t, J=6.7 Hz, 2H), 3.38 (t, J=6.2 Hz, 2H), 3.17 (s, 2H), 3.08 (t, J=11.7 Hz, 2H), 2.54 (d, J=10.4 Hz, 2H), 2.02 (d, J=14.9 Hz, 2H), 1.75 (dt, J=20.5, 10.6 Hz, 6H). LCMS $[M+H]^+$: 559.3.

Example 64 (EX64)

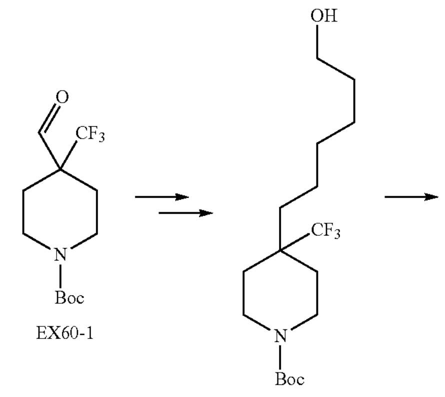

EX60-1

EX64-1

-continued

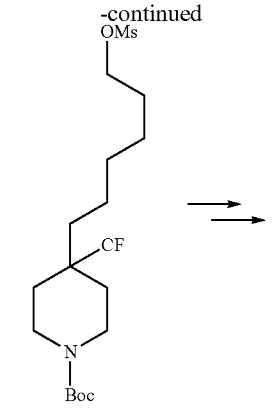

EX64-2

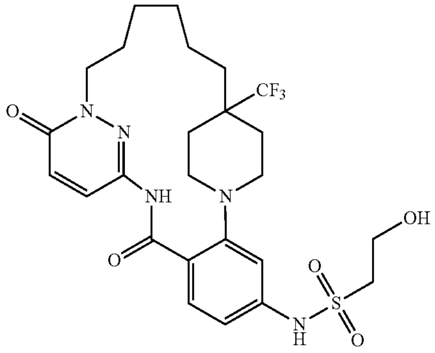

EX64

Step 1:

EX64-1 was prepared as described in Example 60 (EX60) Step 2, except (5-(benzyloxy)pentyl)triphenylphosphonium bromide was used instead of (4-(benzyloxy)butyl)triphenylphosphonium bromide. LCMS $[M-^tBu+H]^+$: 298.1.

Step 2:

EX64-2 was prepared as described in Example 4 (EX04) Step 1, except EX64-1 was used instead of EX01-2. LCMS $[M-^tBu+H]^+$: 376.1.

Step 3:

EX64 was prepared as described in Example 13 (EX13) Steps 2-4, except EX64-2 was used instead of EX13-1 in Step 2. $^1H$ NMR (400 MHz, DMSO-$d_6$) δ 8.24 (d, J=9.9 Hz, 1H), 7.94 (d, J=8.6 Hz, 1H), 7.15 (s, 1H), 7.09 (d, J=8.6 Hz, 1H), 7.03 (d, J=9.9 Hz, 1H), 3.99 (t, J=7.1 Hz, 2H), 3.74 (t, J=6.3 Hz, 2H), 3.32 (t, J=6.4 Hz, 2H), 3.03 (s, 2H), 2.92 (d, J=11.7 Hz, 2H), 2.12 (s, 2H), 1.95 (d, J=14.4 Hz, 2H), 1.72 (s, 2H), 1.44 (d, J=30.1 Hz, 8H). LCMS $[M+H]^+$: 572.3.

Example 65 (EX65)

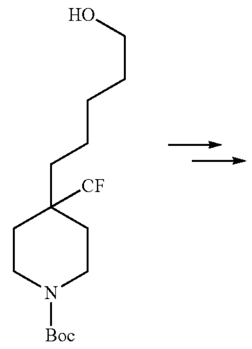

EX60-3

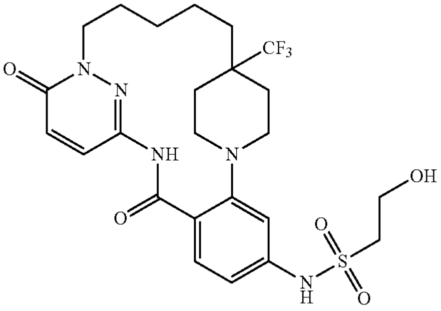

EX65

Step 1:

EX65 was prepared as described in Example 64 (EX64) Steps 2-3, except EX60-3 was used instead of EX64-1 in step 2. $^1$H NMR (400 MHz, $CD_3OD$) δ 8.70 (d, J=9.9 Hz, 1H), 8.02 (d, J=8.5 Hz, 1H), 7.20 (s, 1H), 7.16 (d, J=8.6 Hz, 1H), 7.11 (d, J=9.9 Hz, 1H), 4.27-4.22 (m, 2H), 3.96 (t, J=6.2 Hz, 2H), 3.39 (t, J=6.2 Hz, 2H), 3.11 (d, J=15.1 Hz, 4H), 2.25 (s, 2H), 1.95-1.79 (m, 6H), 1.71 (s, 2H), 1.44 (s, 2H). LCMS $[M+H]^+$: 572.3.

Example 66 (EX66)

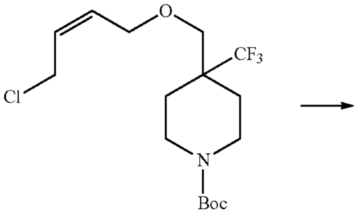

EX51-1

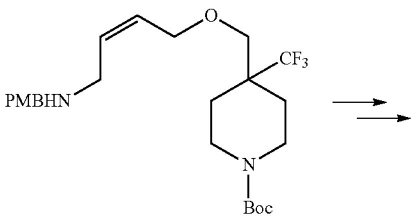

EX66-1

-continued

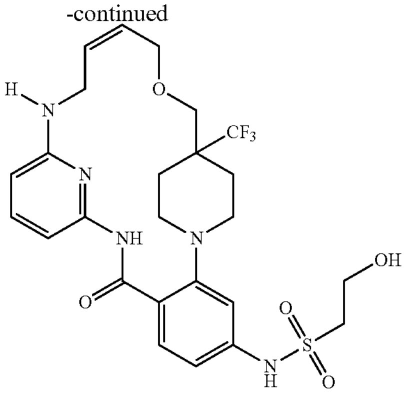

EX66

Step 1:

EX66-1 was prepared as described in Example 12 (EX12) Step 2, except EX51-1 was used instead of EX12-1.

Step 2:

EX66 was prepared as described in Example 56 (EX56) Steps 2-3, except EX51-2 was used instead of EX56-1 in Step 2. $^1$H NMR (400 MHz, $CD_3OD$) δ 8.16 (d, J=8.7 Hz, 1H), 7.47 (d, J=7.6 Hz, 1H), 7.40 (dd, J=11.1, 4.9 Hz, 2H), 7.19 (dd, J=8.7, 2.1 Hz, 1H), 6.29 (d, J=7.8 Hz, 1H), 5.75 (dd, J=11.5, 5.8 Hz, 1H), 5.53 (d, J=11.4 Hz, 1H), 4.38 (d, J=5.6 Hz, 2H), 4.19 (d, J=5.3 Hz, 2H), 3.96 (t, J=6.3 Hz, 2H), 3.58 (s, 2H), 3.38 (t, J=6.2 Hz, 2H), 3.21 (d, J=12.4 Hz, 4H), 2.49 (s, 2H), 2.12 (d, J=14.1 Hz, 2H). LCMS $[M+H]^+$: 570.3.

Example 67 (EX67)

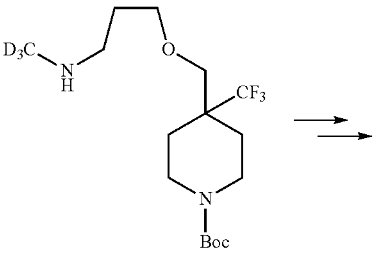

EX44-2

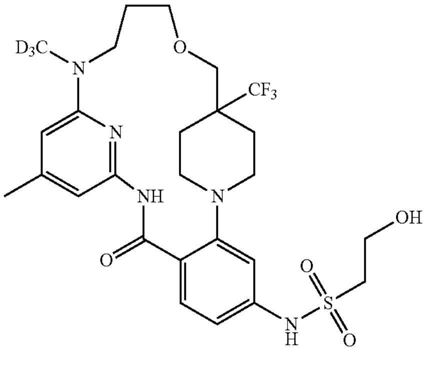

EX67

Step 1:

EX67 was prepared as described in Example 61 (EX61), except 2-bromo-6-fluoro-4-methylpyridine was used instead of 6-bromo-2,3-difluoropyridine in Step 1. H NMR (400 MHz, $CD_3OD$) δ 8.09 (d, J=8.6 Hz, 1H), 7.49 (s, 1H), 7.26 (s, 1H), 7.15 (dd, J=8.7, 1.3 Hz, 1H), 6.20 (s, 1H), 3.99-3.91 (m, 4H), 3.46 (t, J=5.1 Hz, 2H), 3.38 (dd, J=11.8, 5.5 Hz, 4H), 3.17-3.04 (m, 4H), 2.75-2.63 (m, 2H), 2.31 (s, 3H), 1.92 (d, J=14.6 Hz, 2H), 1.83-1.76 (m, 2H). LCMS $[M+H]^+$: 589.4.

Example 68 (EX68)

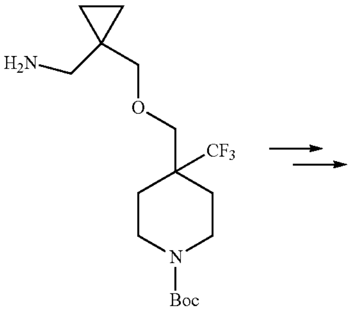

EX43-3

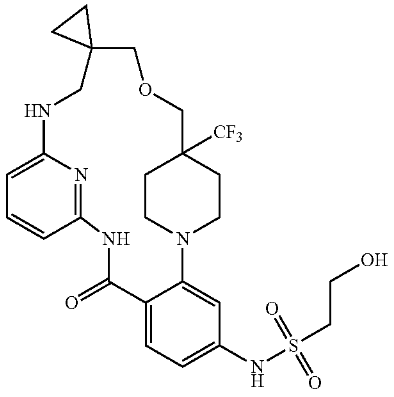

EX68

Step 1:

EX68 was prepared as described in Example 58 (EX58), except EX43-3 was used instead of EX44-2 and 2-chloro-6-nitropyridine was used instead of 2-fluoro-4-nitropyridine in Step 1. $^1H$ NMR (400 MHz, $CD_3OD$) δ 8.02 (d, J=8.6 Hz, 1H), 7.44 (d, J=7.5 Hz, 1H), 7.37 (t, J=7.9 Hz, 1H), 7.21 (d, J=2.0 Hz, 1H), 7.14 (dd, J=8.6, 2.0 Hz, 1H), 6.24 (d, J=7.9 Hz, 1H), 3.96 (t, J=6.2 Hz, 2H), 3.64 (s, 2H), 3.42 (s, 2H), 3.38 (t, J=6.2 Hz, 2H), 3.28 (s, 2H), 3.18 (s, 2H), 3.08 (t, J=12.1 Hz, 2H), 2.73 (s, 2H), 1.93 (d, J=14.5 Hz, 2H), 0.51 (d, J=4.6 Hz, 2H), 0.42 (d, J=4.3 Hz, 2H). LCMS $[M+H]^+$: 584.2.

Example 69 (EX69)

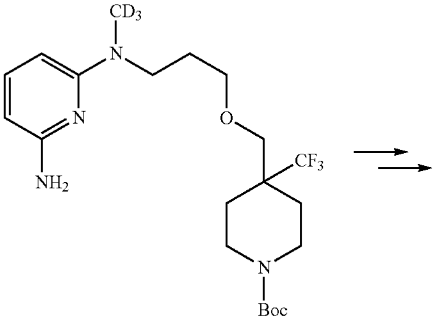

EX48-3

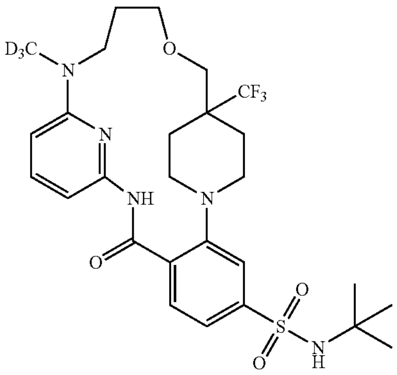

EX69

Step 1:

EX69 was prepared as described in Example 15 (EX15) Step 2, except EX48-3 was used instead of EX15-1. $^1H$ NMR (400 MHz, DMSO-$d_6$) δ 11.42 (s, 1H), 8.17 (d, J=8.2 Hz, 1H), 7.78 (s, 1H), 7.69 (d, J=8.3 Hz, 1H), 7.52 (q, J=7.8 Hz, 2H), 6.34 (d, J=7.4 Hz, 1H), 3.84 (t, J=6.8 Hz, 2H), 3.38 (d, J=5.0 Hz, 2H), 3.35 (s, 2H), 3.11 (s, 2H), 2.97 (t, J=12.4 Hz, 2H), 2.47 (s, 2H), 1.88 (d, J=14.4 Hz, 2H), 1.70 (s, 2H), 1.08 (s, 9H). LCMS $[M+H]^+$: 587.4.

Example 70 (EX70)

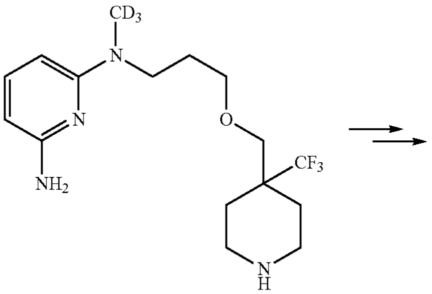

EX48-3

-continued

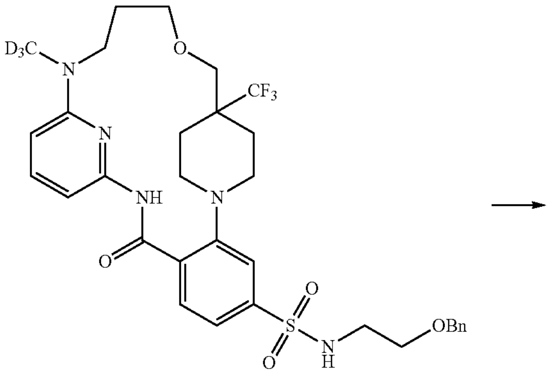

EX70-1

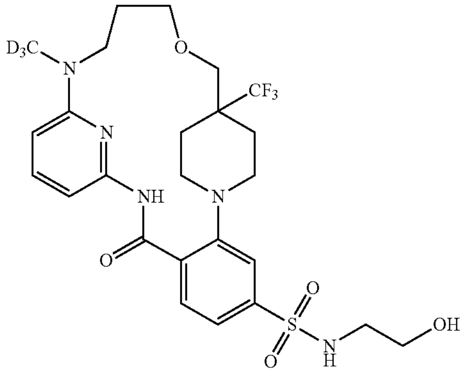

EX70

Step 1:

EX70-1 was described as in Example 69, except methyl 4-(N-(2-(benzyloxy)ethyl)sulfamoyl)-2-fluorobenzoate was used instead of methyl 4-(N-(tert-butyl)sulfamoyl)-2-fluorobenzoate. LCMS $[M+H]^+$: 665.4.

Step 2:

To a solution of EX70-1 (17 mg, 0.026 mmol) in MeOH (3 mL) was added Pd/C (10%, 20 mg). The mixture was purged and degasses with $H_2$ for 3 times. The mixture was stirred at 25° C. for 5 hrs. The mixture was filtered through a pad of celite and the solid was washed with MeOH (20 mL). The combined filtrate was evaporated to dryness under reduced pressure. The residue was purified by prep-HPLC to afford EX70. $^1$H NMR (400 MHz, $CD_3OD$) δ 8.25 (d, J=8.2 Hz, 1H), 7.81 (s, 1H), 7.73 (d, J=8.3 Hz, 1H), 7.62-7.53 (m, 2H), 6.39 (d, J=8.2 Hz, 1H), 3.98 (t, J=6.9 Hz, 2H), 3.57 (t, J=5.8 Hz, 2H), 3.49-3.45 (m, 2H), 3.42 (s, 2H), 3.24 (s, 2H), 3.17 (d, J=13.0 Hz, 2H), 3.02 (t, J=5.9 Hz, 2H), 2.70 (s, 2H), 1.95 (d, J=14.7 Hz, 2H), 1.83 (s, 2H). LCMS $[M+H]^+$: 575.1.

Example 71 (EX71)

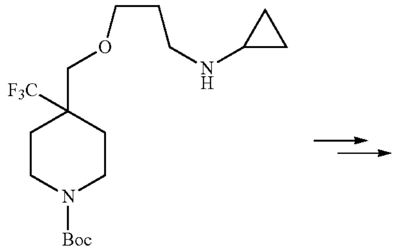

EX45-1

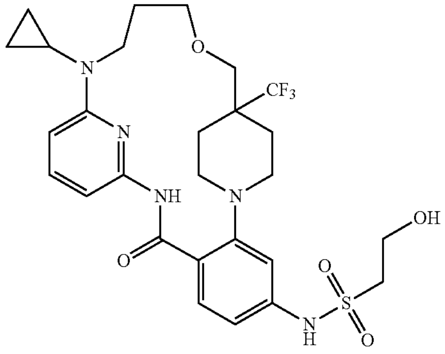

EX71

Step 1:

EX71 was prepared as described in Example 48 (EX48), except EX45-1 was used instead of EX44-2 in Step 1. $^1$H NMR (400 MHz, $CD_3OD$) δ 8.07 (d, J=8.6 Hz, 1H), 7.64-7.61 (m, 1H), 7.58-7.52 (m, 1H), 7.26 (d, J=2.0 Hz, 1H), 7.14 (dd, J=2.0, 8.6 Hz, 1H), 6.82 (d, J=8.1 Hz, 1H), 3.94 (q, J=5.9 Hz, 4H), 3.45 (t, J=5.0 Hz, 2H), 3.39 (s, 2H), 3.36 (t, J=6.3 Hz, 2H), 3.15-3.04 (m, 4H), 2.71-2.59 (m, 2H), 2.49-2.43 (m, 1H), 1.92 (br d, J=15.0 Hz, 2H), 1.85-1.78 (m, 2H), 0.94-0.89 (m, 2H), 0.64-0.59 (m, 2H). LCMS $[M+H]^+$: 598.3.

Example 72 (EX72)

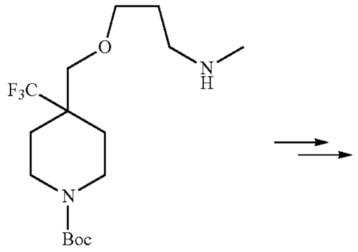

EX62-1

-continued

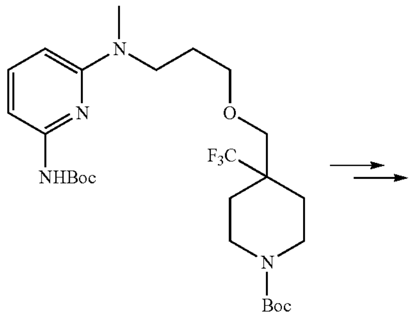

EX72-1

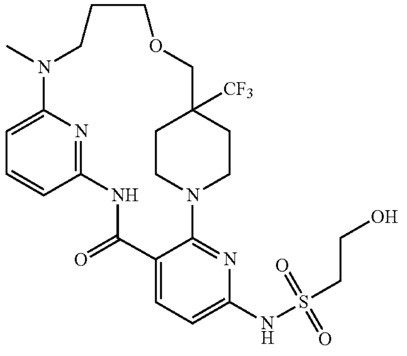

EX72

Step 1:

EX72-1 was prepared as described in Example 61 (EX61) Steps 1-2, except EX62-1 was used instead of EX44-2 and 2-bromo-6-fluoropyridine was used instead of 6-bromo-2,3-difluoropyridine in Step 1. LCMS $[M+H]^+$: 347.2.

Step 2:

EX72 was prepared as described in Example 1 (EX01) Steps 4-8, except EX72-1 was used instead of EX01-3 in Step 4 and methyl 6-bromo-2-fluoronicotinate was used instead of methyl 2-fluoro-4-iodobenzoate in Step 5. $^1H$ NMR (400 MHz, $CD_3OD$) δ 8.27 (d, J=8.4 Hz, 1H), 7.57-7.49 (m, 2H), 6.74 (d, J=8.4 Hz, 1H), 6.39-6.32 (m, 1H), 4.03-3.93 (m, 4H), 3.80 (t, J=6.3 Hz, 2H), 3.49-3.40 (m, 6H), 3.24 (t, J=12.9 Hz, 2H), 2.93 (s, 3H), 2.64 (t, J=11.9 Hz, 2H), 1.91 (d, J=14.9 Hz, 2H), 1.87-1.79 (m, 2H). LCMS $[M+H]^+$: 573.2.

Example 73 (EX73)

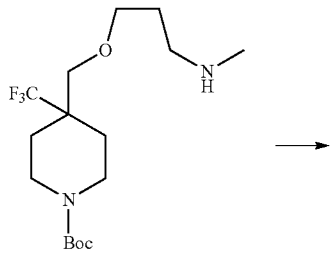

EX62-1

-continued

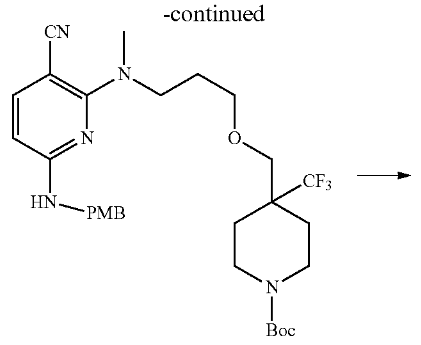

EX73-1

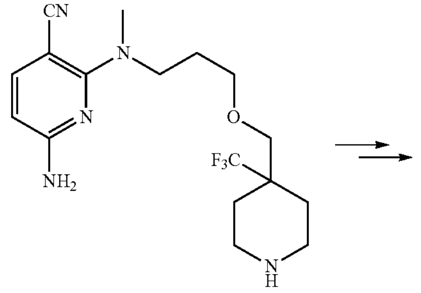

EX73-2

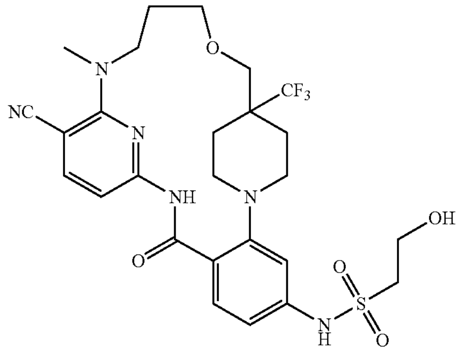

EX73

Step 1:

To a solution of EX62-1 (800 mg, 2.26 mmol) and 2-chloro-6-((4-methoxybenzyl)amino)nicotinonitrile in NMP (10 mL) was added DIEA (1.12 mL, 6.77 mmol). The reaction was stirred at 140° C. for 12 hrs. The reaction was quenched with water (50 mL), and extracted with EtOAc (50 mL×3). The combined organic layer was dried over $MgSO_4$, concentrated under reduced pressure, and purified by silica gel chromatography to give EX73-1. LCMS $[M+H]^+$: 592.4.

Step 2:

A solution of EX73-1 (1.1 g, 1.86 mmol) in TFA (10 mL) was stirred at 50° C. for 2 hrs. The reaction mixture was concentrated under reduced pressure and the obtained residue was neutralized by DIEA (pH=7) to afford EX73-2. LCMS $[M+H]^+$: 372.3.

Step 3:

EX73 was prepared as described in Example 1 (EX01) Steps 5-8, except EX73-2 was used instead of EX01-4 in Step 5. $^1H$ NMR (400 MHz, DMSO-$d_6$) δ 11.77 (s, 1H), 7.99-7.94 (m, 1H), 7.89-7.85 (m, 1H), 7.61 (d, J=8.6 Hz, 1H), 7.19-7.15 (m, 1H), 7.11-7.06 (m, 1H), 3.91 (br t, J=7.2 Hz, 2H), 3.73 (t, J=6.3 Hz, 2H), 3.43-3.37 (m, 2H), 3.35-3.30 (m, 4H), 3.29-3.26 (m, 3H), 3.03 (br d, J=9.7 Hz, 2H), 2.94-2.83 (m, 2H), 2.43-2.29 (m, 2H), 1.85 (br d, J=14.7 Hz, 2H), 1.78-1.70 (m, 2H). LCMS $[M+H]^+$: 597.2.

Example 74 (EX74)

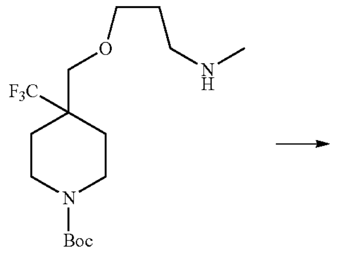

EX62-1

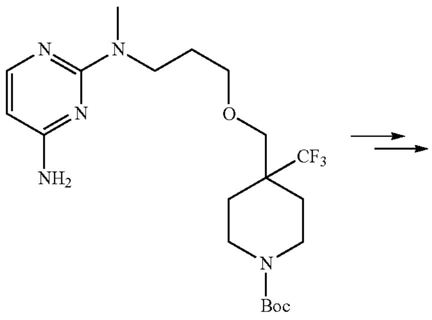

EX74-1

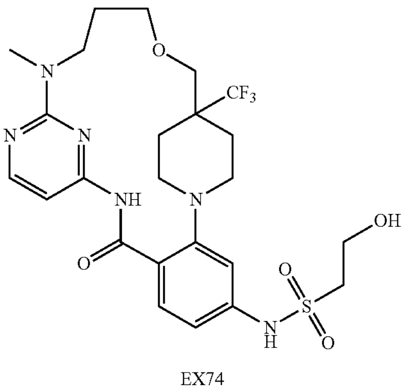

EX74

Step 1:

To a solution of EX62-1 (401.9 mg, 3.1 mmol) and 2-chloropyrimidin-4-amine in NMP (10 mL) was added DIEA (771 μL, 4.66 mmol) under $N_2$ atmosphere. The mixture was stirred at 140° C. for 2 hrs. The mixture was diluted with water (50 mL) and extracted with EtOAc (50 mL×3). The combined organic layer was dried over $MgSO_4$, concentrated under reduced pressure and purified by silica gel chromatography to afford EX74-1. LCMS $[M+H]^+$: 448.3.

Step 2:

EX74 was prepared as described in Example 1 (EX01) Steps 4-8, except EX74-1 was used instead of EX01-3 in Step 4. H NMR (400 MHz, $CD_3OD$) δ 8.23 (d, J=5.7 Hz, 1H), 8.13 (dd, J=8.7, 1.7 Hz, 1H), 7.56 (d, J=5.7 Hz, 1H), 7.31 (t, J=2.0 Hz, 1H), 7.22-7.14 (m, 1H), 3.99-3.89 (m, 4H), 3.52-3.47 (m, 2H), 3.44 (s, 2H), 3.38 (t, J=6.2 Hz, 2H), 3.17-3.05 (m, 7H), 2.67 (s, 2H), 1.96 (d, J=14.7 Hz, 2H), 1.86 (s, 2H). LCMS $[M+H]^+$: 573.2.

Example 75 (EX75)

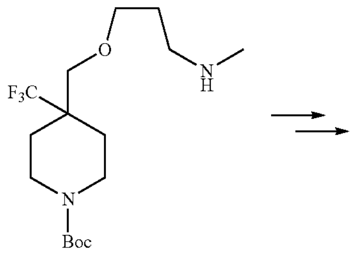

EX62-1

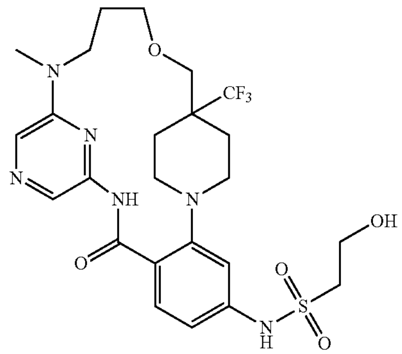

EX75

Step 1:

EX75 was prepared as described in Example 74, except 6-chloropyrazin-2-amine was used instead of 2-chloropyrimidin-4-amine in Step 1. $^1H$ NMR (400 MHz, $CD_3OD$) δ 12.21 (s, 1H), 8.80 (s, 1H), 8.16 (d, J=8.7 Hz, 1H), 7.74 (s, 1H), 7.32 (d, J=2.0 Hz, 1H), 7.20 (dd, J=8.7, 2.0 Hz, 1H), 3.99-3.89 (m, 4H), 3.52-3.46 (m, 2H), 3.44 (s, 2H), 3.39 (t, J=6.2 Hz, 2H), 3.13 (d, J=8.0 Hz, 4H), 3.07 (s, 3H), 2.66 (s, 2H), 1.96 (d, J=14.8 Hz, 2H), 1.85 (s, 2H). LCMS $[M+H]^+$: 573.3.

Example 76 (EX76-A&B)

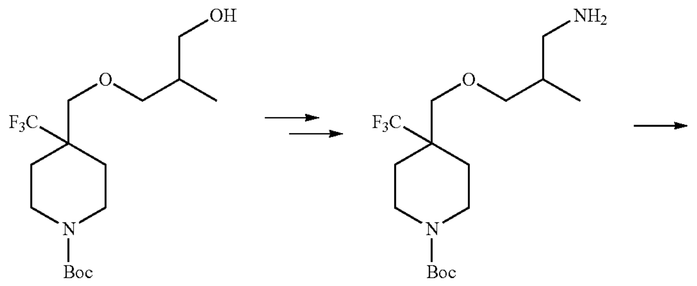

EX35-1

EX76-1

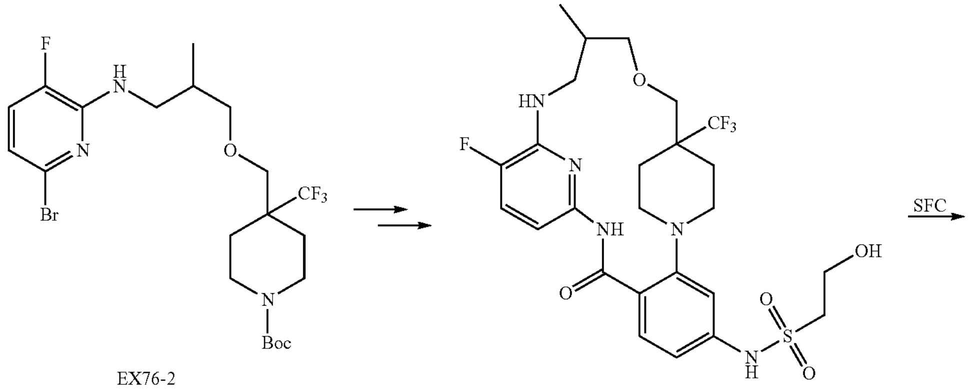

EX76-2

EX76

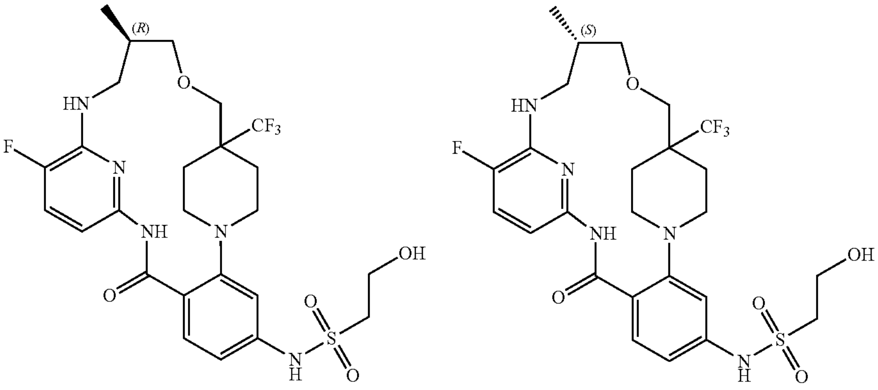

EX76-A&B

Step 1:

EX76-1 was prepared as described Example 20 (EX20) Steps 3-4, except EX35-1 was used instead of EX20-2 in Step 3. LCMS $[M+H]^+$: 355.3.

Step 2:

To a solution of EX76-1 (3 g, 8.47 mmol) and 6-bromo-2,3-difluoropyridine (1.0 g, 5.08 mmol) in NMP (60 mL) was added DIEA (7.0 mL, 42.3 mmol). The mixture was stirred at 140° C. under $N_2$ atmosphere for 2 hrs. The mixture was diluted with water (300 mL) and extracted with EtOAc (200 mL×3). The combined organic layer was dried over $MgSO_4$, filtrated and concentrated under reduced pressure and purified by silica gel chromatography to afford EX76-2. LCMS $[M+H]^+$: 428.2, 430.2.

Step 3:

EX76 was prepared as described in Example 61 (EX61) Steps 2-3, except EX76-2 was used instead of EX61-1 in Step 2.

Step 4:

EX76-A (51.12 mg) and EX76-B (52.57 mg) were separated from EX76 by SFC. SFC analytic condition: column: (S,S)Whelk-01, 100*4.6 mm, 5.0 m; mobile phase A: supercritical $CO_2$, mobile phase B: ethanol (0.05% DEA), 40% mobile phase B, 5 min; flow rate: 2.5 mL/min; column temp: 40° C.

EX76-A: $^1H$ NMR (400 MHz, $CD_3OD$) δ 8.10 (d, J=8.6 Hz, 1H), 7.48 (dd, J=2.7, 8.4 Hz, 1H), 7.28 (d, J=2.0 Hz, 1H), 7.25-7.15 (m, 2H), 4.27 (dd, J=5.0, 13.5 Hz, 1H), 3.96 (t, J=6.3 Hz, 2H), 3.50-3.45 (m, 2H), 3.42-3.36 (m, 3H), 3.26-3.15 (m, 3H), 3.12-2.98 (m, 3H), 2.85-2.60 (m, 2H), 2.00 (br dd, J=1.7, 14.8 Hz, 1H), 1.92-1.84 (m, 2H), 1.01 (d, J=7.0 Hz, 3H). LCMS $[M+H]^+$: 590.2. Retention time @SFC: 2.637 min.

EX76-B: $^1H$ NMR (400 MHz, $CD_3OD$) δ 8.10 (d, J=8.6 Hz, 1H), 7.48 (dd, J=2.5, 8.3 Hz, 1H), 7.29 (s, 1H), 7.25-7.14 (m, 2H), 4.27 (br dd, J=5.0, 13.4 Hz, 1H), 3.96 (t, J=6.1

Hz, 2H), 3.50-3.44 (m, 2H), 3.41-3.36 (m, 3H), 3.26-3.15 (m, 3H), 3.11-2.99 (m, 3H), 2.83-2.60 (m, 2H), 2.00 (br d, J=14.0 Hz, 1H), 1.88 (br d, J=13.0 Hz, 2H), 1.01 (br d, J=6.9 Hz, 3H). LCMS $[M+H]^+$: 590.3. Retention time @SFC: 3.151 min.

Example 77 (EX77)

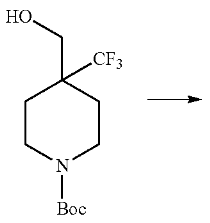

EX17-2

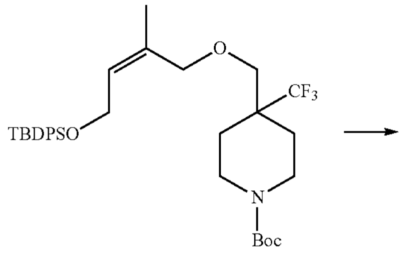

EX77-1

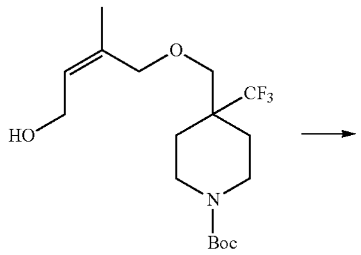

EX77-2

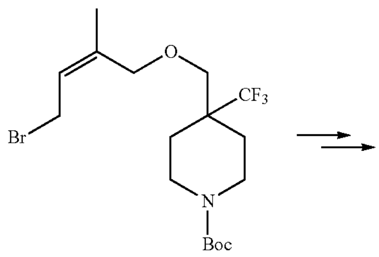

EX77-3

-continued

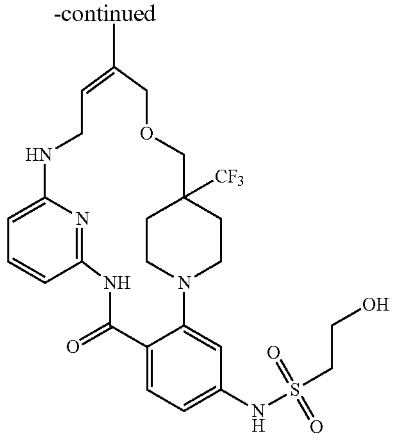

EX77

Step 1:

The mixture of EX17-2 (2 g, 7.06 mmol) in $H_2O$ (60 mL) was added (E)-((4-bromo-3-methylbut-2-en-1-yl)oxy)(tert-butyl)diphenylsilane (4.3 g, 10.59 mmol) and NaOH (2.8 g, 70.6 mmol). The mixture was stirred 25° C. for 10 min, then TBAS (0.5 g, 1.41 mmol) was added. The mixture was stirred at 70° C. for 3 hrs. The mixture was extracted with EtOAc (50 mL×3). The combined organic layer was dried over $MgSO_4$, concentrated and purified by silica gel chromatography to afford EX77-1. LCMS $[M+Na]^+$: 628.3.

Step 2:

The solution of EX77-1 (2.7 g, 4.46 mmol) in THF (10 mL) was added TBAF (22.28 mL, 22.28 mmol). The mixture was stirred at 25° C. for 16 hrs. The mixture was diluted with brine (40 mL) and extracted with EtOAc (30 mL×3). The combined organic layer was dried over $MgSO_4$ and concentrated under reduced pressure. The residue was purified by silica gel chromatography to afford EX77-2.

Step 3:

The solution of EX77-2 (1.5 g, 4.08 mmol) in THF (20 mL) was added $PBr_3$ (460 μL, 4.9 mmol) at −10° C. The solution was stirred at −10° C. for 1 hr. The reaction was quenched with water (5 mL) and extracted with EtOAc (20 mL×3). The combined organic layer was dried over $MgSO_4$ and concentrated. The residue was purified by silica gel chromatography to afford EX77-3. LCMS $[M-^tBu+H]^+$: 374.1, 376.1.

Step 4:

EX77 was prepared as described in Example 66 (EX66), except EX77-3 was used instead of EX51-1 in step 1. $^1H$ NMR (400 MHz, $CD_3OD$) δ 7.91 (d, J=8.6 Hz, 1H), 7.48 (d, J=7.7 Hz, 1H), 7.39 (t, J=7.9 Hz, 1H), 7.19 (d, J=2.0 Hz, 1H), 7.09 (dd, J=8.5, 2.0 Hz, 1H), 6.28 (d, J=8.0 Hz, 1H), 5.80 (s, 1H), 3.96 (t, J=6.2 Hz, 4H), 3.80 (s, 2H), 3.49 (s, 2H), 3.37 (t, J=6.3 Hz, 2H), 3.28 (d, J=12.1 Hz, 2H), 3.08 (t, J=11.7 Hz, 2H), 2.10 (d, J=14.6 Hz, 2H), 1.93 (t, J=10.6 Hz, 2H), 1.74 (s, 3H). LCMS $[M+H]^+$: 584.3.

Example 78 (EX78-A&B)

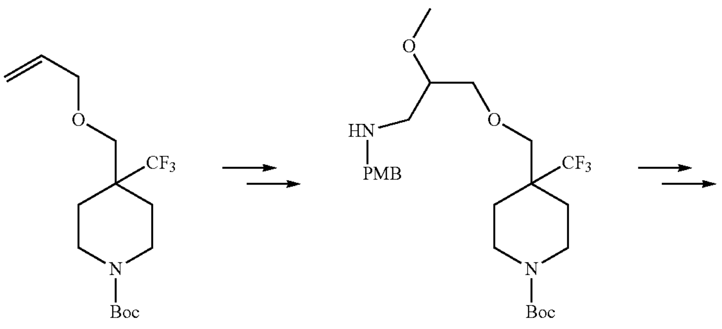

EX48-1 EX78-1

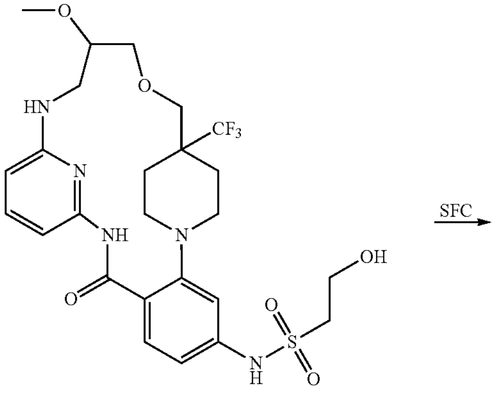

EX78

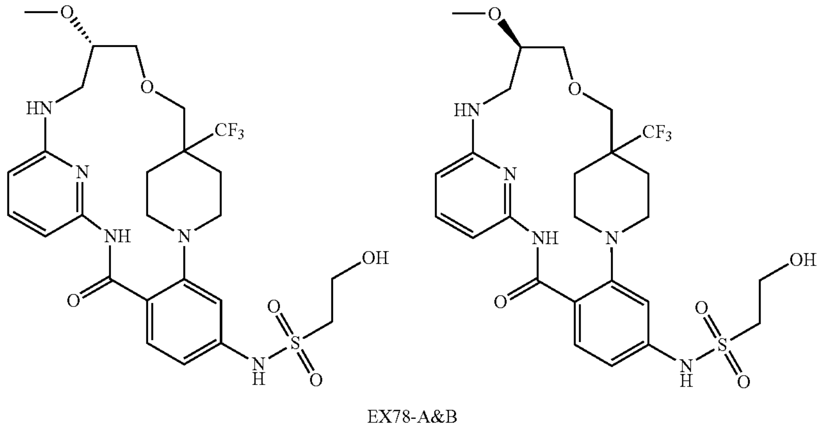

EX78-A&B

Step 1:

EX78-1 was prepared as described in Example 31 (EX31) Steps 1-3, except EX48-1 was used instead of EX02-1 in Step 1.

Step 2:

EX78 was prepared as described in Example 66 Step 2, except EX78-1 was used instead of EX66-1. LCMS $[M+H]^+$: 588.3.

Step 3:

EX78-A and EX78-B were separated from EX78 by SFC. SFC analytic condition: column: Cellulose-2, 100*4.6 mm, 3.0 m; mobile phase A: supercritical $CO_2$, mobile phase B: ethanol (0.05% DEA), 40% mobile phase B, 5 min; flow rate: 2.8 mL/min; column temp: 35° C.

EX78-A: $^1$H NMR (400 MHz, $CD_3OD$) δ 8.08 (d, J=8.6 Hz, 1H), 7.50 (d, J=7.6 Hz, 1H), 7.38 (t, J=7.9 Hz, 1H), 7.26 (d, J=2.0 Hz, 1H), 7.16 (dd, J=8.6, 2.1 Hz, 1H), 6.28 (d, J=8.0 Hz, 1H), 4.22 (d, J=12.1 Hz, 1H), 3.96 (t, J=6.2 Hz, 2H), 3.62 (d, J=5.2 Hz, 1H), 3.48 (t, J=5.6 Hz, 2H), 3.45 (s, 3H), 3.38 (t, J=6.2 Hz, 5H), 3.15 (d, J=8.9 Hz, 3H), 3.07 (d, J=13.0 Hz, 1H), 2.67 (d, J=9.4 Hz, 2H), 1.93 (t, J=15.3 Hz, 2H). LCMS $[M+H]^+$: 588.3. Retention time @SFC: 1.793 min.

EX78-B: $^1$H NMR (400 MHz, $CD_3OD$) δ 8.08 (d, J=8.6 Hz, 1H), 7.50 (d, J=7.4 Hz, 1H), 7.38 (t, J=7.9 Hz, 1H), 7.26 (d, J=2.1 Hz, 1H), 7.16 (dd, J=8.6, 2.1 Hz, 1H), 6.28 (d, J=8.0 Hz, 1H), 4.22 (d, J=11.2 Hz, 1H), 3.96 (t, J=6.2 Hz, 2H), 3.62 (d, J=5.4 Hz, 1H), 3.48 (t, J=5.7 Hz, 2H), 3.45 (s, 3H), 3.38 (t, J=6.2 Hz, 5H), 3.15 (d, J=8.8 Hz, 3H), 3.06 (t, J=12.7 Hz, 1H), 2.67 (d, J=10.4 Hz, 2H), 1.93 (t, J=15.1 Hz, 2H). LCMS $[M+H]^+$: 588.3. Retention time @SFC: 2.350 min.

Example 79 (EX79-A&B)

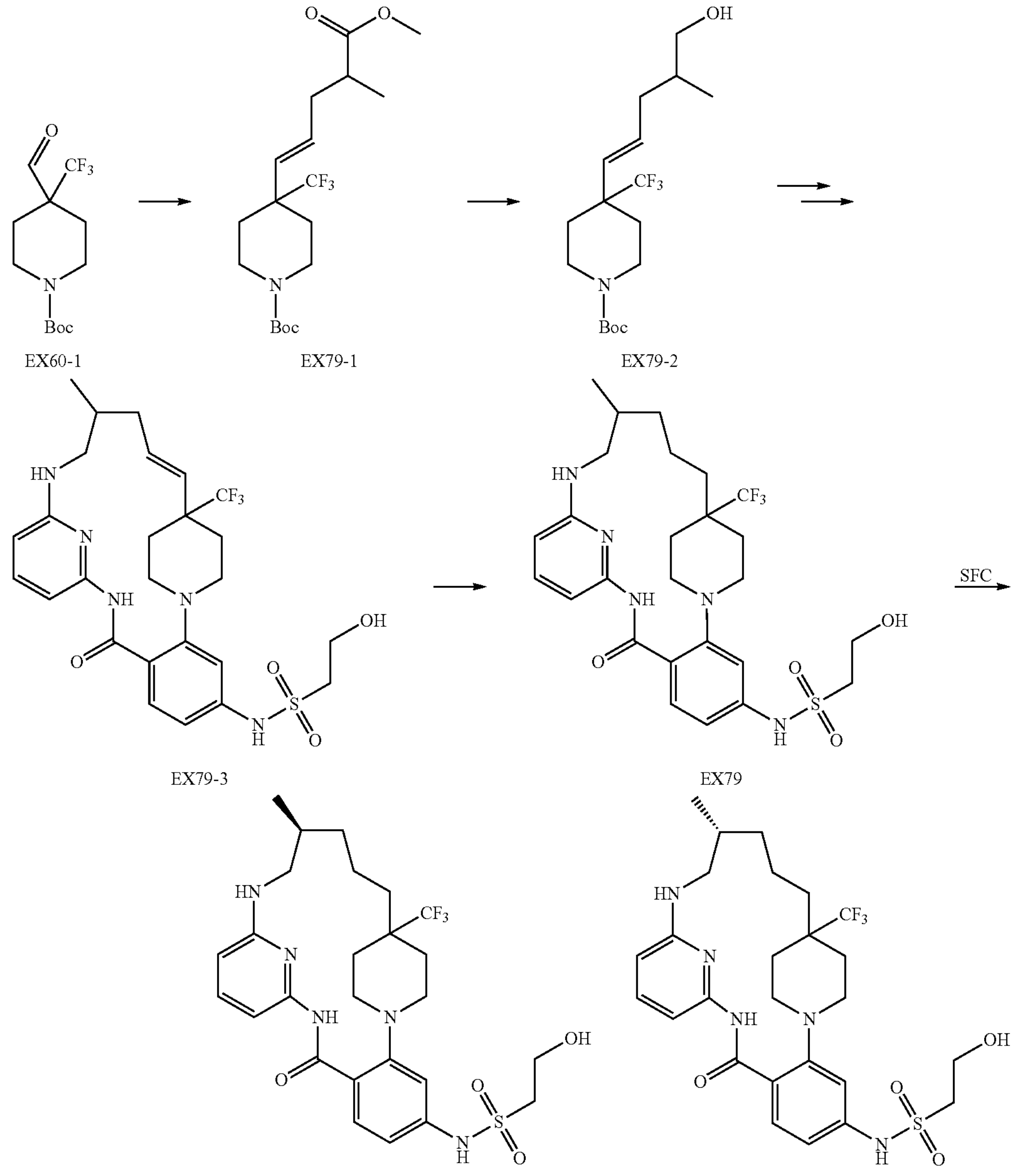

EX60-1 EX79-1 EX79-2

EX79-3 EX79

EX79-A&B

Step 1:

EX79-1 was prepared as described in Example 34 (EX34) Step 2, except EX60-1 was used instead of EX34-1 and (4-methoxy-3-methyl-4-oxobutyl)triphenylphosphonium bromide was used instead of (4-(benzyloxy)butyl)triphenylphosphonium bromide. LCMS [M-$^t$Bu+H]$^+$: 296.1.

Step 2:

To a solution of EX79-1 (6.9 g, 18.2 mmol) in THF (200 mL) was added $LiBHEt_3$ (1 M, 55 mL, 55 mmol) under $N_2$ atmosphere at 0° C. The mixture was stirred at 25° C. for 2 hrs. The mixture was quenched with MeOH (300 mL) and concentrated under reduced pressure. The residue was diluted with saturated aq. $NH_4Cl$ (300 mL) and extracted with EtOAc (300 mL×3). The combined organic layer was dried over $MgSO_4$, concentrated under reduced pressure and purified by silica gel chromatography to afford EX79-2. LCMS [M-$^t$Bu+H]$^+$: 296.1

Step 3:

EX79-3 was prepared as described in Example 76 (EX76) Steps 1-3, except EX79-1 was used instead of EX35-1 in Step 1 and 6-bromo-2-fluoropyridine was used instead of 6-bromo-2,3-difluoropyridine in Step 2. LCMS [M+H]$^+$: 568.2.

Step 4:

EX79 was prepared as described in Example 59 (EX59), except EX79-3 was used instead of EX52. LCMS [M+H]$^+$: 570.3.

Step 5:

EX79-A (12.03 mg) and EX79-B (12.10 mg) were separated from EX79 by SFC. SFC analytic condition: column:

Chiralpak AD-3, 150*4.6 mm, 3.0 m; mobile phase A: supercritical $CO_2$, mobile phase B: ethanol (0.05% DEA), 40% mobile phase B, 5 min; flow rate: 2.5 mL/min; column temp: 35° C.

EX79-A: $^1$H NMR (400 MHz, $CD_3OD$) δ 7.86 (d, J=8.5 Hz, 1H), 7.38 (d, J=7.7 Hz, 1H), 7.24 (t, J=8.0 Hz, 1H), 7.03-6.96 (m, 2H), 6.16 (d, J=8.0 Hz, 1H), 3.84 (t, J=6.2 Hz, 2H), 3.38 (d, J=5.0 Hz, 2H), 3.26 (t, J=6.2 Hz, 2H), 3.10-3.01 (m, 2H), 2.97-2.80 (m, 2H), 2.25-2.09 (m, 2H), 1.89-1.78 (m, 2H), 1.78-1.67 (m, 1H), 1.67-1.58 (m, 1H), 1.54-1.43 (m, 2H), 1.36-1.25 (m, 2H), 1.16-1.09 (m, 1H), 0.92 (d, J=6.9 Hz, 3H). LCMS $[M+H]^+$: 570.1. Retention time @SFC: 1.300 min.

EX79-B: $^1$H NMR (400 MHz, $CD_3OD$) δ 7.98 (d, J=8.5 Hz, 1H), 7.50 (d, J=7.6 Hz, 1H), 7.36 (t, J=8.0 Hz, 1H), 7.15-7.08 (m, 2H), 6.28 (d, J=8.1 Hz, 1H), 3.96 (t, J=6.2 Hz, 2H), 3.50 (d, J=4.9 Hz, 2H), 3.38 (t, J=6.3 Hz, 2H), 3.23-3.14 (m, 2H), 3.09-2.94 (m, 2H), 2.37-2.21 (m, 2H), 2.02-1.90 (m, 2H), 1.89-1.70 (m, 2H), 1.68-1.54 (m, 2H), 1.50-1.42 (m, 1H), 1.40-1.32 (m, 1H), 1.29-1.18 (m, 1H), 1.04 (d, J=6.9 Hz, 3H). LCMS $[M+H]^+$: 570.5. Retention time @SFC: 1.446 min.

Example 80 (EX80)

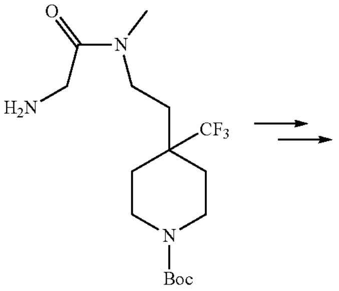

EX80-1

-continued

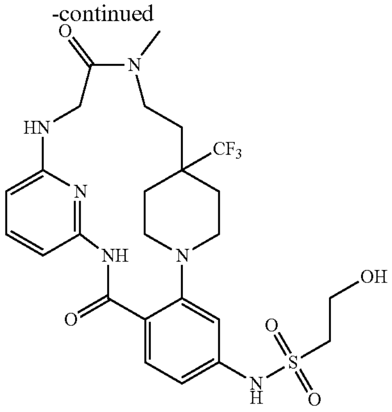

EX80

Step 1:

EX80 was prepared as described in Example 76 (EX76) Steps 2-3, except EX80-1 was used instead of EX76-2 and 6-bromo-2-fluoropyridine was used instead of 6-bromo-2,3-difluoropyridine in Step 2. $^1$H NMR (400 MHz, $CD_3OD$) δ 8.20 (d, J=8.7 Hz, 1H), 7.49-7.43 (m, 2H), 7.32 (d, J=2.1 Hz, 1H), 7.22 (dd, J=8.7, 2.2 Hz, 1H), 6.38 (dd, J=7.2, 1.6 Hz, 1H), 4.44 (s, 2H), 3.96 (t, J=6.2 Hz, 2H), 3.74-3.67 (m, 2H), 3.38 (t, J=6.2 Hz, 2H), 3.14 (d, J=12.9 Hz, 4H), 2.98 (s, 3H), 2.51 (s, 2H), 2.27 (d, J=14.5 Hz, 2H), 2.10-2.01 (m, 2H). LCMS $[M+H]^+$: 585.3.

Example 81 (EX81-A&B)

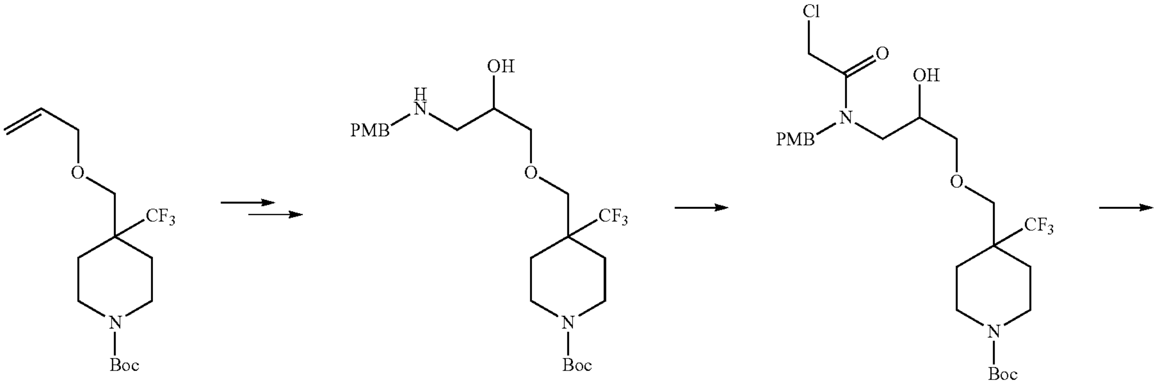

EX46-1 EX81-1 EX81-2

-continued

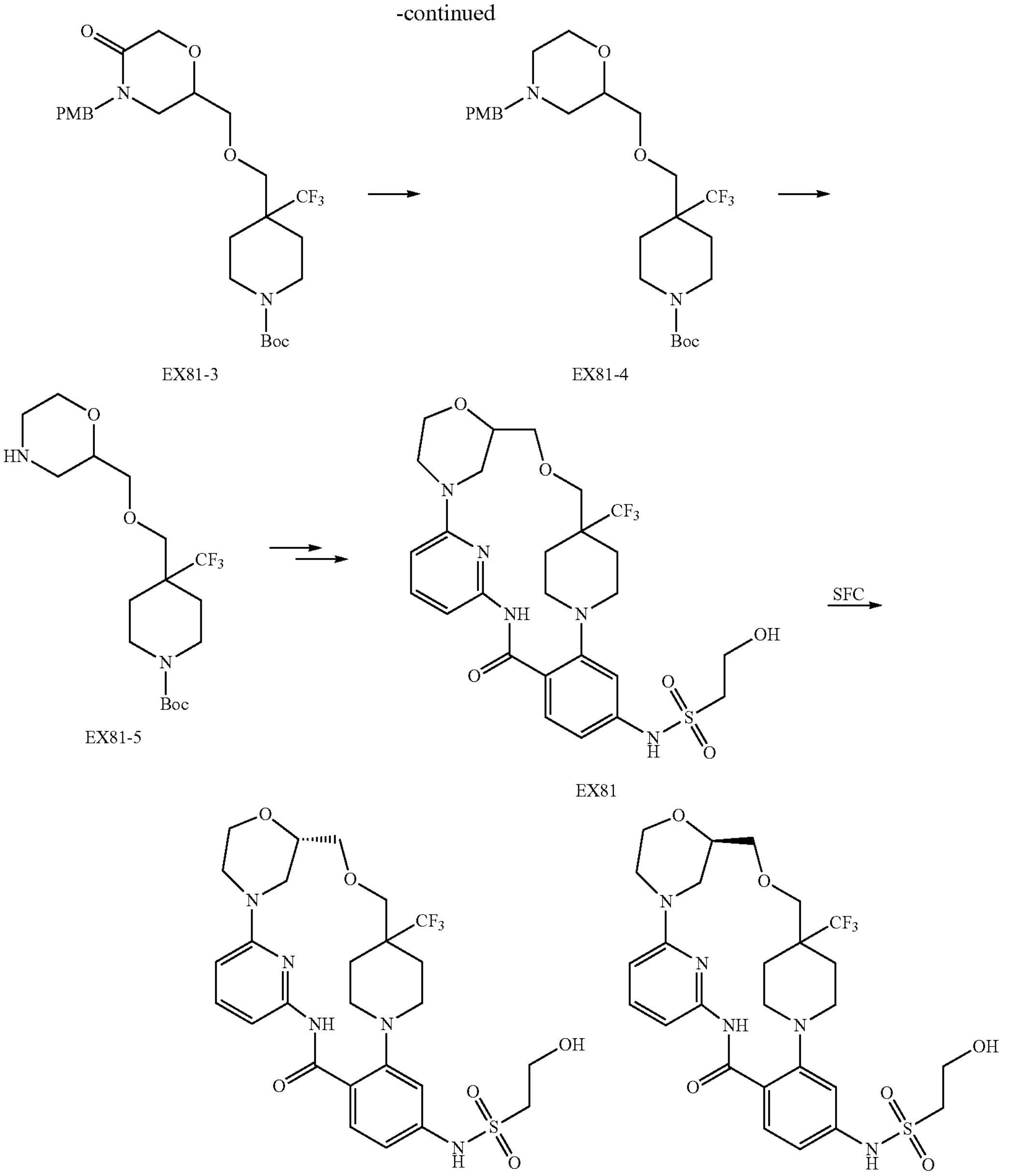

EX81-3

EX81-4

EX81-5

EX81

EX81-A&B

Step 1:

EX81-1 was prepared as described in Example 31 (EX31) Steps 1-2, except EX46-1 was used instead of EX02-1 in Step 1.

Step 2:

To a mixture of EX81-1 (5 g, 10.49 mmol) and TEA (2.9 mL, 20.99 mmol) in DCM (85 mL) was added dropwise chloroacetyl chloride (1.8 g, 15.74 mmol) at 0° C. The mixture was stirred at 0° C. for 2 hrs. The mixture was quenched with water (50 mL) and extracted with DCM (50 mL×3). The combined organic layer was dried over $MgSO_4$ and concentrated to afford EX81-2. LCMS $[M\text{-}Boc+H]^+$: 453.2.

Step 3:

To a solution of EX81-2 (5 g, 9.04 mmol) in MeOH (85 mL) and $H_2O$ (8.5 mL) was added $K_2CO_3$ (1.9 g, 13.56 mmol). The mixture was stirred at 80° C. for 18 hrs. The resulting mixture was concentrated, quenched with water (100 mL) and extracted with EtOAc (100 mL×3). The combined organic layer was dried over $MgSO_4$, concentrated and purified by silica gel chromatography to afford EX81-3. LCMS $[M\text{-}Boc+H]^+$: 417.3.

Step 4:

To a solution of EX81-3 (2.9 g, 5.61 mmol) in THF (145 mL) was added borane tetrahydrofuran (11 mL, 11.23 mmol) at 0° C. under $N_2$ atmosphere, and the reaction was stirred at 70° C. for 18 hrs. The reaction was quenched with MeOH (50 mL), and the mixture was stirred at 40° C. for 2 hrs. The mixture was concentrated under reduced pressure, diluted with water and extracted with DCM (50 mL×3). The combined organic layer was dried over $MgSO_4$, concentrated and purified by silica gel chromatography to afford EX81-4. LCMS $[M+H]^+$: 503.4.

Step 5:

To a solution of EX81-4 (2.65 g, 5.27 mmol) in EtOAc (30 mL) was added Pd/C (10%, 2.8 g, 2.64 mmol). The mixture was purged with $H_2$ for 3 times. The mixture was stirred at 25° C. for 18 hrs under $H_2$ (15 Psi) atmosphere. The reaction mixture was filtrated, washed with EtOAc (50 mL) and the filtrate was concentrated to afford EX81-5. LCMS $[M+H]^+$: 383.2.

Step 6:

EX81 was prepared as described in Example 62 Step 2, except EX81-5 was used instead of EX62-1. LCMS $[M+H]^+$: 600.3.

Step 7:

EX81-A (18.72 mg) and EX81-B (19.56 mg) were separated from EX81 by SFC. SFC analytic condition: column: Cellulose-4, 100*4.6 mm, 3.0 m; mobile phase A: supercritical $CO_2$, mobile phase B: Methanol (0.05% DEA), 60% mobile phase B, 5 min; flow rate: 2.8 mL/min; column temp: 40° C.

EX81-A: $^1$H NMR (400 MHz, $CD_3OD$) δ 8.09 (d, J=8.6 Hz, 1H), 7.64-7.53 (m, 2H), 7.27 (d, J=2.1 Hz, 1H), 7.16 (dd, J=8.6, 2.1 Hz, 1H), 6.52 (d, J=7.5 Hz, 1H), 4.16 (d, J=13.2 Hz, 1H), 3.99-3.91 (m, 3H), 3.88-3.76 (m, 2H), 3.73-3.65 (m, 2H), 3.57 (dd, J=12.3, 7.0 Hz, 3H), 3.52-3.44 (m, 2H), 3.38 (t, J=6.2 Hz, 2H), 3.24-3.05 (m, 4H), 2.67-2.53 (m, 2H), 1.97 (dd, J=26.4, 13.8 Hz, 2H). LCMS $[M+H]^+$: 600.3. Retention time @SFC: 1.675 min.

EX81-B: $^1$H NMR (400 MHz, $CD_3OD$) δ 8.09 (d, J=8.6 Hz, 1H), 7.64-7.53 (m, 2H), 7.27 (d, J=2.1 Hz, 1H), 7.16 (dd, J=8.6, 2.1 Hz, 1H), 6.52 (d, J=7.6 Hz, 1H), 4.17 (d, J=10.7 Hz, 1H), 3.99-3.91 (m, 3H), 3.88-3.77 (m, 2H), 3.74-3.64 (m, 2H), 3.57 (dd, J=12.2, 7.0 Hz, 3H), 3.51-3.45 (m, 2H), 3.38 (t, J=6.2 Hz, 2H), 3.24-3.05 (m, 4H), 2.67-2.51 (m, 2H), 1.97 (dd, J=25.7, 14.5 Hz, 2H). LCMS $[M+H]^+$: 600.3. Retention time @SFC: 1.810 min.

Example 82 (EX82)

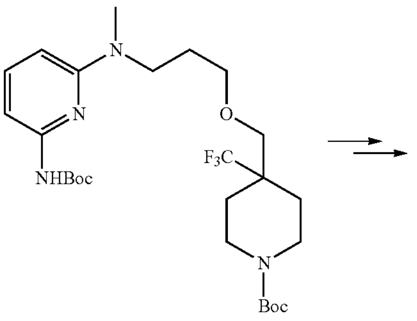

EX72-1

-continued

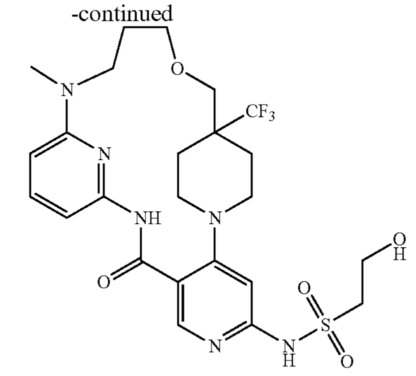

EX82

Step 1:

EX82 was prepared as described in Example 1 (EX01) Steps 4-8, except EX72-1 was used instead of EX01-3 in Step 4 and 6-bromo-4-chloropyridine-3-carboxylate was used instead of methyl 2-fluoro-4-iodobenzoate in Step 5. $^1$H NMR (400 MHz, $CD_3OD$) δ 8.25 (s, 1H), 7.41-7.58 (m, 2H), 6.76 (s, 1H), 6.36 (d, J=8.14 Hz, 1H), 3.87-4.03 (m, 4H) 3.35-3.48 (m, 8H), 3.08 (t, J=12.21 Hz, 2H), 2.90 (s, 3H), 2.42-2.62 (m, 2H), 1.75-1.95 (m, 4H). LCMS $[M+H]^+$: 573.3.

Example 83 (EX83)

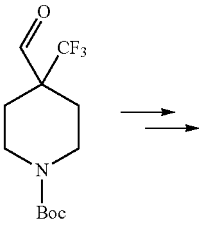

EX60-1

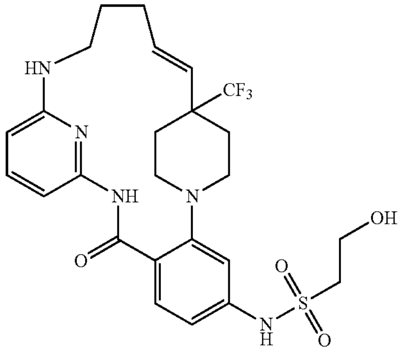

EX83

Step 1:

EX83 was prepared as described in Example 79 (EX79) Steps 1-3, except (4-ethoxy-4-oxobutyl)triphenylphosphonium bromide was used instead of (4-methoxy-3-methyl-4-oxobutyl)triphenylphosphonium bromide in Step 1. $^1$H NMR (400 MHz, $CD_3OD$) δ 7.99 (d, J=8.5 Hz, 1H), 7.46 (d, J=7.7 Hz, 1H), 7.37 (t, J=7.9 Hz, 1H), 7.26 (d, J=1.8 Hz, 1H), 7.14 (dd, J=8.6, 1.9 Hz, 1H), 6.24 (d, J=8.0 Hz, 1H), 5.59-5.44 (m, 2H), 3.96 (t, J=6.2 Hz, 2H), 3.48 (t, J=6.1 Hz, 2H), 3.38 (t, J=6.2 Hz, 2H), 3.19 (s, 2H), 3.08 (t, J=12.1 Hz, 2H), 2.59 (t, J=12.1 Hz, 4H), 2.19 (d, J=14.8 Hz, 2H), 1.64 (d, J=8.1 Hz, 2H). LCMS $[M+H]^+$: 554.3.

Example 84 (EX84-A&B)

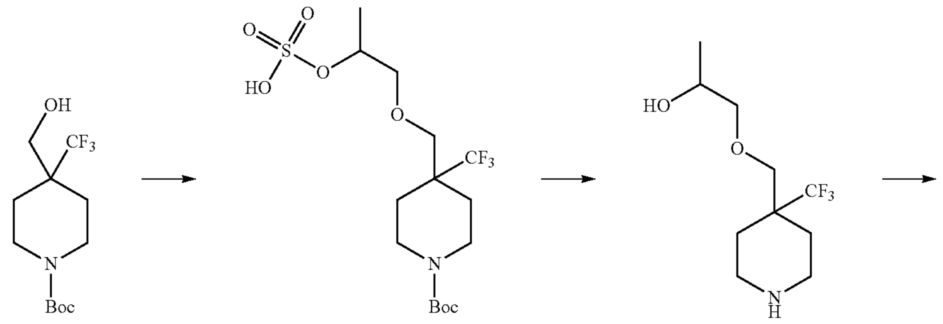

EX17-2 EX84-1 EX84-2

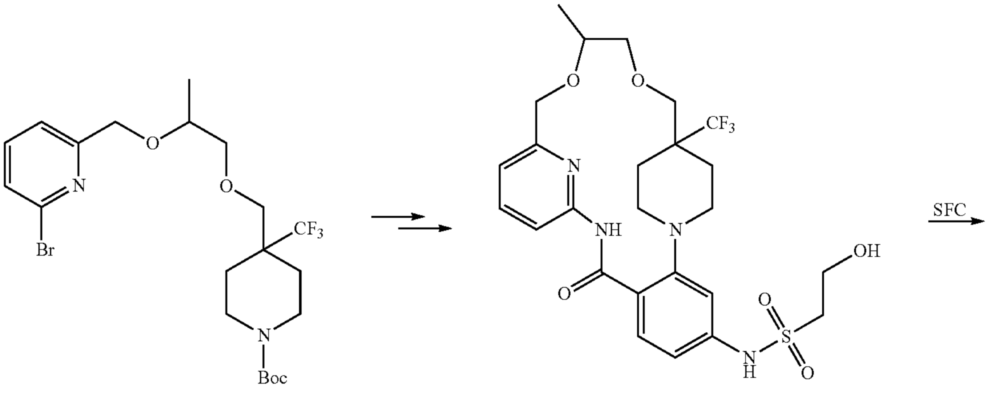

EX84-3 EX84

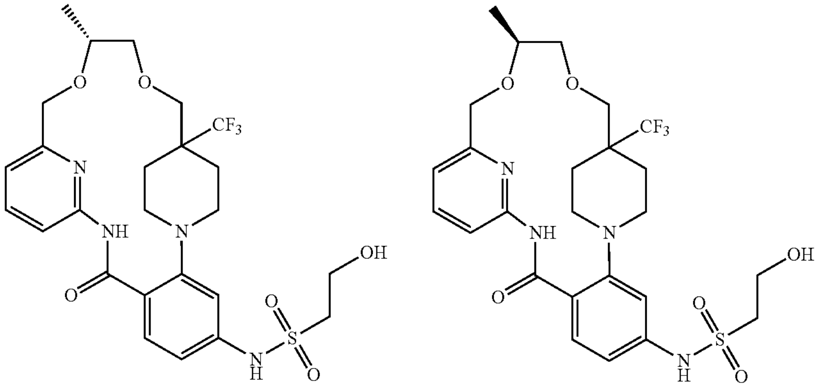

EX84-A&B

Step 1:

To a solution of EX17-2 (2 g, 7.06 mmol) in DMF (20 mL) was added NaH (1.4 g, 35.3 mmol) at 0° C. under $N_2$. The resulting mixture was stirred at 0° C. for 30 min. Then 4-methyl-1,3,2-dioxathiolane 2,2-dioxide (2.9 g, 21.18 mmol) was added to the reaction mixture. The resulting mixture was stirred at 25° C. for 2 hrs. The reaction mixture was quenched with water (10 mL) at 0° C., and the reaction mixture was concentrated under reduced pressure to give EX84-1. LCMS $[M\text{-}^tBu+H]^+$: 366.1.

Step 2:

To a solution of EX84-1 (2.7 g, 6.41 mmol) in MeOH (30 mL) was added HCl/dioxane (4M, 32 mL, 128.14 mmol). The reaction was stirred at 25° C. for 2 hrs. The reaction mixture was concentrated under reduced pressure to give EX84-2. LCMS $[M+H]^+$: 242.1.

Step 3:

To a solution of EX84-2 (1.4 g, 5.8 mmol) and $Boc_2O$ (4 mL, 17.41 mmol) in THF (20 mL) were added $Na_2CO_3$ (20. mL, 40.61 mmol). The resulting mixture was stirred at 25° C. for 3 hrs. The reaction was diluted with water (50 mL), and extracted with EtOAc (50 mL×3). The combined organic layer was dried over $MgSO_4$, and concentrated under reduced pressure and purified by silica gel chromatography to give EX84-3. LCMS $[M\text{-}^tBu+H]^+$: 286.1.

Step 4:

To a solution of EX84-3 (1.3 g, 3.81 mmol) in DMF (20 mL) was added NaH (0.5 g, 11.42 mmol) at 0° C. under $N_2$. The resulting mixture was stirred at 0° C. for 30 min. Then 2-bromo-6-(chloromethyl)pyridine (0.9 g, 4.569 mmol) was added to the reaction mixture. The resulting mixture was stirred at 25° C. for 2 hrs. The reaction mixture was quenched with water (50 mL) at 0° C., and then extracted with EtOAc (50 mL×3). The combined organic layer was dried over $MgSO_4$, concentrated under reduced pressure and purified by silica gel chromatography to afford EX84-4. LCMS $[M\text{-}Boc+H]^+$: 411.2, 413.2.

Step 5:

EX84 was prepared as described in Example 61 (EX61) Steps 2-3, except EX84-4 was used instead of EX61-1 in Step 2. LCMS $[M+H]^+$: 573.1.

Step 6:

EX84-A (34.58 mg) and EX84-B (34.99 mg) were separated from EX84 by SFC. SFC analytic condition: column: Cellulose-2, 100*4.6 mm, 3.0 m; mobile phase A: supercritical $CO_2$, mobile phase B: ethanol (0.05% DEA), 60% mobile phase B, 5 min; flow rate: 2.5 mL/min; column temp: 35° C.

EX84-A: $^1H$ NMR (400 MHz, $CD_3OD$) δ 8.30 (d, J=7.9 Hz, 1H), 8.08 (d, J=8.6 Hz, 1H), 7.85-7.78 (m, 1H), 7.26 (d, J=2.0 Hz, 1H), 7.18 (dd, J=8.6, 2.1 Hz, 1H), 7.14 (d, J=7.2 Hz, 1H), 4.72 (d, J=12.2 Hz, 1H), 4.52 (d, J=12.2 Hz, 1H), 3.97 (t, J=6.2 Hz, 2H), 3.77 (s, 1H), 3.57-3.36 (m, 6H), 3.13 (dd, J=28.7, 15.0 Hz, 4H), 2.78 (s, 1H), 2.55 (s, 1H), 1.94 (dd, J=29.3, 14.3 Hz, 2H), 1.17 (d, J=6.3 Hz, 3H). LCMS $[M+H]^+$: 573.2. Retention time @SFC: 1.012 min.

EX84-2: $^1H$ NMR (400 MHz, $CD_3OD$) δ 8.30 (d, J=8.1 Hz, 1H), 8.09 (d, J=8.6 Hz, 1H), 7.82 (dd, J=7.4, 8.3 Hz, 1H), 7.26 (d, J=2.0 Hz, 1H), 7.21-7.12 (m, 2H), 4.72 (d, J=12.3 Hz, 1H), 4.52 (d, J=12.1 Hz, 1H), 3.96 (t, J=6.3 Hz, 2H), 3.77 (s, 1H), 3.55-3.35 (m, 6H), 3.20-3.05 (m, 4H), 2.83-2.47 (m, 2H), 2.02-1.85 (m, 2H), 1.17 (d, J=6.4 Hz, 3H). LCMS $[M+H]^+$: 573.2. Retention time @SFC: 1.708 min.

Example 85 (EX85-A&B)

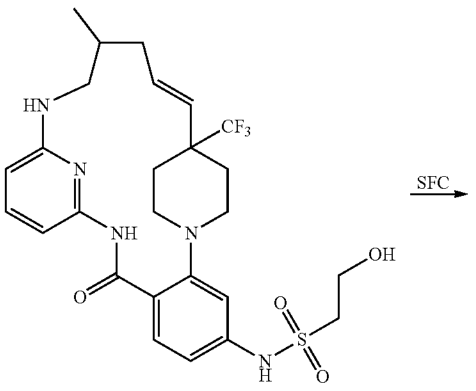

EX79-3

-continued

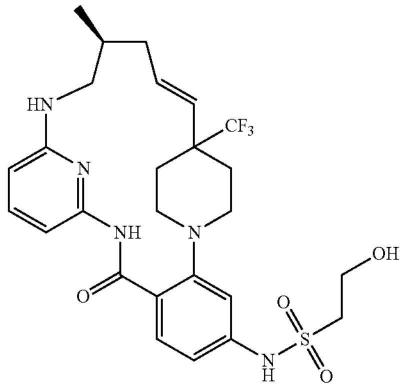

EX85-A&B

+

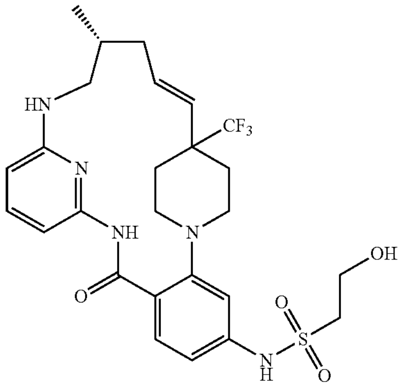

EX85-A&B

Step 1:

EX85-A (13.17 mg) and EX85-B (13.50 mg) were separated from EX79-3 by SFC. SFC analytic condition: column: (S,S)Whelk-01, 100*4.6 mm, 5.0 m; mobile phase A: supercritical $CO_2$, mobile phase B: ethanol (0.05% DEA), 40% mobile phase B, 5 min; flow rate: 2.5 mL/min; column temp: 40° C.

EX85-A: $^1H$ NMR (400 MHz, $CD_3OD$) δ 7.96 (d, J=8.7 Hz, 1H), 7.29-7.52 (m, 2H), 7.23 (s, 1H), 7.12 (d, J=8.4 Hz, 1H), 6.23 (d, J=8.1 Hz, 1H), 5.55 (s, 2H), 3.94 (t, J=5.7 Hz, 2H), 3.32-3.46 (m, 4H), 2.92-3.23 (m, 4H), 2.59-2.73 (m, 2H), 2.34-2.55 (m, 2H), 2.04-2.25 (m, 2H), 1.78 (d, J=1.9 Hz, 1H), 0.96 (d, J=6.1 Hz, 3H). LCMS $[M+H]^+$: 568.3. Retention time @SFC: 2.722 min.

EX85-B: $^1H$ NMR (400 MHz, $CD_3OD$) S 7.98 (d, J=8.6 Hz, 1H), 7.46 (d, J=7.6 Hz, 1H), 7.37 (t, J=7.9 Hz, 1H), 7.25 (d, J=2.0 Hz, 1H), 7.14 (dd, J=8.6, 2.0 Hz, 1H), 6.25 (d, J=8.0 Hz, 1H), 5.62-5.52 (m, 2H), 3.96 (t, J=6.2 Hz, 2H), 3.41 (dt, J=12.6, 6.9 Hz, 3H), 3.31-3.08 (m, 4H), 3.01 (t, J=12.6 Hz, 1H), 2.75-2.60 (m, 2H), 2.56-2.36 (m, 2H), 2.22 (d, J=13.6 Hz, 1H), 2.11 (d, J=14.8 Hz, 1H), 1.86-1.75 (m, 1H), 0.98 (d, J=6.7 Hz, 3H). LCMS $[M+H]^+$: 568.3. Retention time @SFC: 3.150 min.

Example 86 (EX86)

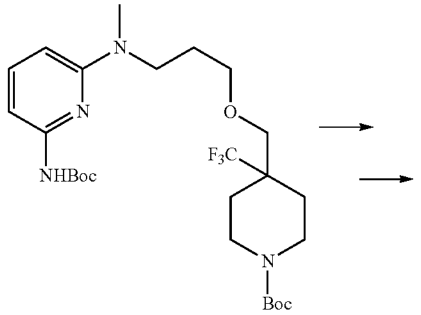

EX72-1

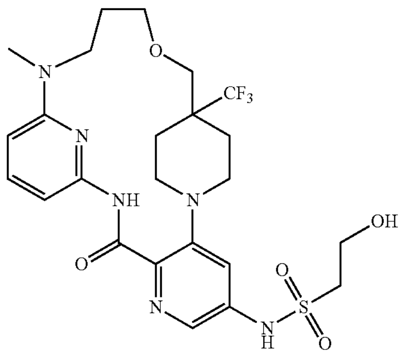

EX86

Step 1:

EX86 was prepared as described in Example 1 (EX01) Steps 4-8, except EX72-1 was used instead of EX01-3 in Step 4 and methyl 5-bromo-3-fluoropyridine-2-carboxylate was used instead of methyl 2-fluoro-4-iodobenzoate in Step 5. $^1$H NMR (400 MHz, $CD_3OD$) δ 8.54-8.14 (m, 1H), 7.70 (s, 1H), 7.62 (d, J=7.5 Hz, 1H), 7.57-7.50 (m, 1H), 6.37 (d, J=8.3 Hz, 1H), 3.96 (t, J=5.9 Hz, 4H), 3.45 (t, J=5.2 Hz, 2H), 3.42-3.37 (m, 4H), 3.24-3.17 (m, 2H), 3.15-3.05 (m, 2H), 2.92 (s, 3H), 2.72-2.62 (m, 2H), 1.92 (br d, J=14.8 Hz, 2H), 1.85-1.78 (m, 2H). LCMS $[M+H]^+$: 573.3.

Example 87 (EX87)

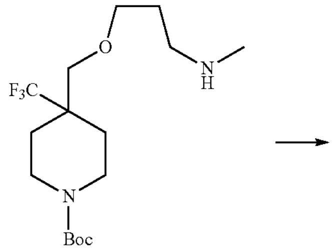

EX62-1

-continued

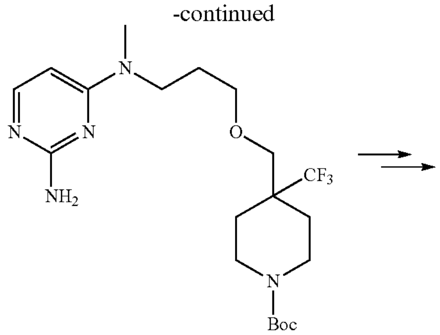

EX87-1

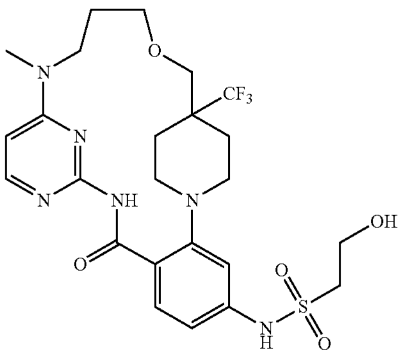

EX87

Step 1:

To a solution of EX62-1 (1 g, 1.69 mmol) and 4-chloropyrimidin-2-amine (439 mg, 3.39 mmol) in NMP (15 mL) were added DIEA (0.84 mL, 5.08 mmol) and CsF (514 mg, 3.39 mmol) under $N_2$ atmosphere. The mixture was stirred at 140° C. for 12 hrs. The mixture was diluted with water (50 mL) and extracted with EtOAc (50 mL×3). The combined organic layer was dried over $MgSO_4$, concentrated under reduced pressure and purified by flash silica gel chromatography to afford EX87-1. LCMS $[M+H]^+$: 448.3.

Step 2:

EX87 was prepared as described in Example 1 (EX01) Steps 4-8, except EX87-1 was used instead of EX01-3. $^1$H NMR (400 MHz, $CD_3OD$) δ 8.16 (d, J=8.5 Hz, 1H), 8.07 (d, J=6.0 Hz, 1H), 7.30 (d, J=1.5 Hz, 1H), 7.20-7.14 (m, 1H), 6.46 (d, J=6.3 Hz, 1H), 4.60 (s, 1H), 3.98 (t, J=7.2 Hz, 2H), 3.94 (t, J=6.1 Hz, 2H), 3.48 (t, J=5.0 Hz, 2H), 3.43 (s, 2H), 3.36 (t, J=6.1 Hz, 2H), 3.12 (d, J=9.3 Hz, 4H), 3.06 (s, 3H), 2.73-2.61 (m, 2H), 1.95 (d, J=15.1 Hz, 2H), 1.90-1.82 (m, 2H). LCMS $[M+H]^+$: 573.2.

Example 88 (EX88-A&B)

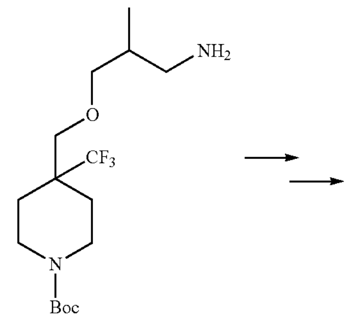

EX76-1

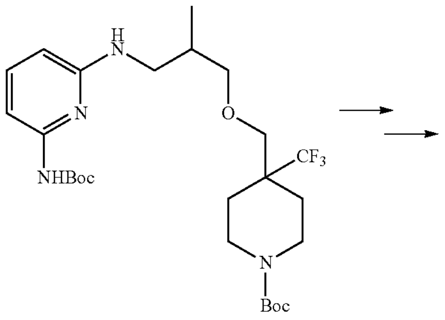

EX88-1

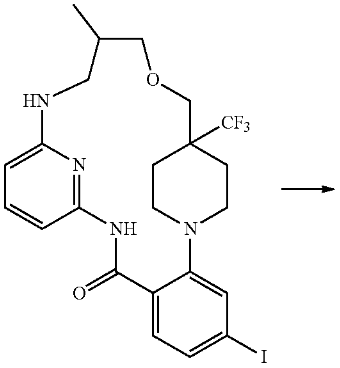

EX88-2

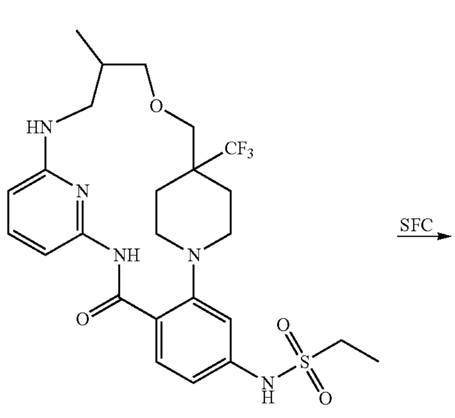

EX88

-continued

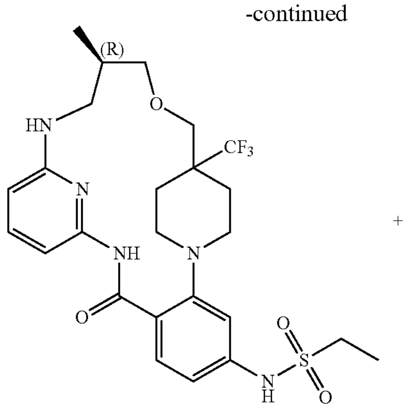

EX88-A&B

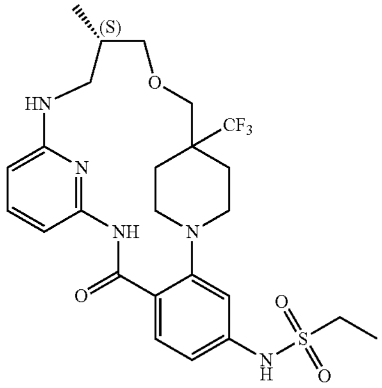

EX88-A&B

Step 1:

EX88-1 was prepared as described in Example 61 (EX61) Steps 1-2, except EX76-1 was used instead of EX44-2 and 6-bromo-2-fluoropyridine was used instead of 6-bromo-2,3-difluoropyridine in Step 1. LCMS $[M+H]^+$: 347.2.

Step 2:

EX88-2 was prepared as described in Example 1 (EX01) Steps 4-7, except EX88-1 was used instead of EX01-3 in Step 4. LCMS $[M+H]^+$: 575.2.

Step 3:

To a solution of EX88-2 (170 mg, 0.30 mmol) and ethanesulfonamide (161 mg, 1.48 mmol) in DMF (5 mL) were added CuI (56 mg, 0.30 mmol), $K_3PO_4$ (189 mg, 0.89 mmol) and DMDACH (41 mg, 0.30 mmol). The reaction was stirred at 145° C. for 2 hrs. The reaction was quenched with saturated aq. $NH_4Cl$ (10 mL) and extracted with EtOAc (10 mL×3). The combined organic layer was dried over $MgSO_4$, concentrated under reduced pressure and purified by prep-HPLC to afford EX88. LCMS $[M+H]^+$: 556.3

Step 4:

EX88-A (48.23 mg) and EX88-B (47.04 mg) were separated from EX88 by SFC. SFC analytic condition: column: Chiralpak IC-3, 100*4.6 mm, 3.0 m; mobile phase A: supercritical $CO_2$, mobile phase B: iso-propanol (0.05% DEA), 50% mobile phase B, 5 min; flow rate: 2.8 mL/min; column temp: 35° C.

EX88-A: $^1H$ NMR (400 MHz, $CD_3OD$) δ 8.07 (d, J=8.6 Hz, 1H), 7.44 (d, J=7.6 Hz, 1H), 7.37-7.30 (m, 1H), 7.25 (s, 1H), 7.13 (d, J=8.5 Hz, 1H), 6.23 (d, J=8.0 Hz, 1H), 4.17 (dd, J=4.5, 13.4 Hz, 1H), 3.44-3.36 (m, 3H), 3.22-3.08 (m, 6H), 3.06-2.95 (m, 2H), 2.82-2.59 (m, 2H), 1.99-1.78 (m, 3H), 1.32 (t, J=7.3 Hz, 3H), 0.96 (d, J=6.9 Hz, 3H). LCMS $[M+H]^+$: 556.3. Retention time @SFC: 1.395 min.

EX88-B: $^1$H NMR (400 MHz, $CD_3OD$) δ 8.07 (d, J=8.6 Hz, 1H), 7.44 (d, J=7.6 Hz, 1H), 7.38-7.31 (m, 1H), 7.26 (s, 1H), 7.13 (d, J=8.5 Hz, 1H), 6.23 (d, J=8.0 Hz, 1H), 4.17 (dd, J=4.5, 13.4 Hz, 1H), 3.46-3.37 (m, 3H), 3.21-3.10 (m, 6H), 3.07-2.97 (m, 2H), 2.83-2.58 (m, 2H), 1.99-1.79 (m, 3H), 1.32 (t, J=7.3 Hz, 3H), 0.96 (d, J=6.9 Hz, 3H). LCMS $[M+H]^+$: 556.2. Retention time @SFC: 1.792 min.

Example 89 (EX89)

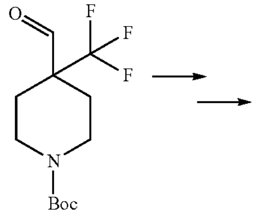

EX60-1

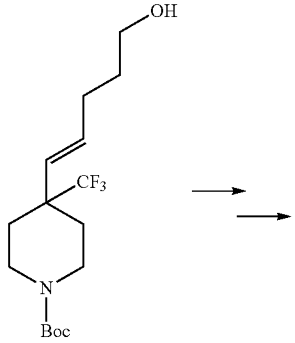

EX89-1

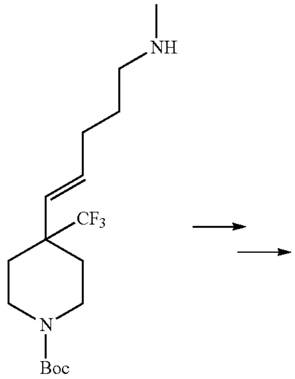

EX89-2

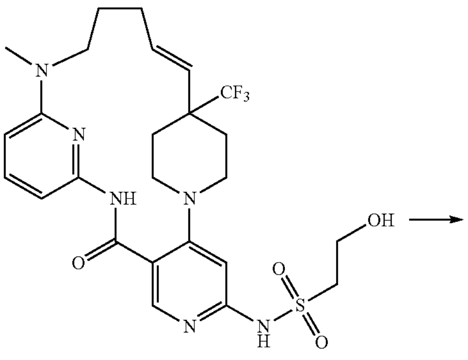

EX89-3

-continued

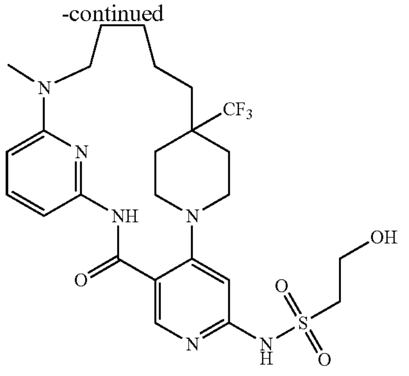

EX89

Step 1:

EX89-1 was prepared as described in Example 79 (EX79) Steps 1-2, except (4-ethoxy-4-oxobutyl)triphenylphosphonium bromide was used instead of (4-methoxy-3-methyl-4-oxobutyl)triphenylphosphonium bromide in Step 1. LCMS $[M\text{-}^tBu+H]^+$: 282.1.

Step 2:

EX89-2 was prepared as described in Example 4 (EX04) Steps 1-2, except EX89-1 was used instead of EX01-2 in Step 1. LCMS $[M+H]^+$: 351.1.

Step 3:

EX89-3 was prepared as described in Example 72 Steps 1-2, except EX89-2 was used instead of EX62-1 in Step 1 and 6-bromo-4-chloropyridine-3-carboxylate was used instead of methyl 6-bromo-2-fluoronicotinate in Step 2. LCMS $[M+H]^+$: 569.3.

Step 4:

EX89 was prepared as described in Example 59 (EX59), except EX89-3 was used instead of EX89. $^1$H NMR (400 MHz, $CD_3OD$) δ 8.06 (s, 1H), 7.60 (d, J=7.7 Hz, 1H), 7.54 (t, J=8.0 Hz, 1H), 6.67 (s, 1H), 6.38 (d, J=8.1 Hz, 1H), 4.00 (t, J=6.4 Hz, 2H), 3.86 (t, J=6.0 Hz, 2H), 3.55-3.45 (m, 2H), 3.38 (s, 2H), 3.13-3.03 (m, 2H), 2.90 (s, 3H), 2.20-2.04 (m, 2H), 1.85-1.61 (m, 6H), 1.45-1.38 (m, 2H), 1.30-1.18 (m, 2H). LCMS $[M+H]^+$: 571.3.

Example 90 (EX90) & Example 91 (EX91)

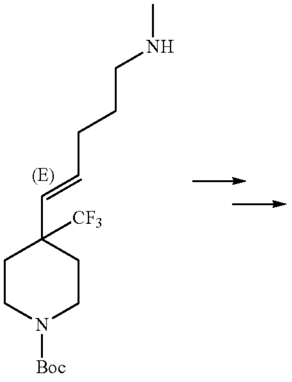

EX89-2

-continued

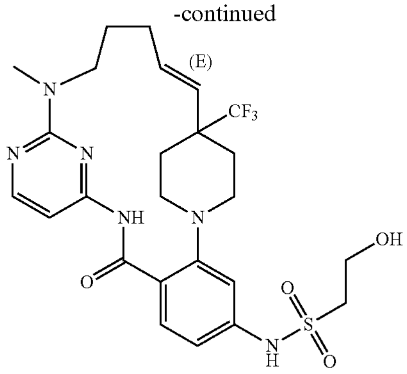

EX91

+

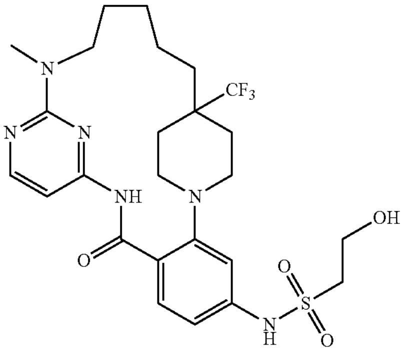

EX90

Step 1:

EX91 was prepared as described in Example 74 (EX74) Steps 1-2, except EX89-2 was used instead of EX62-1 in Step 1. $^1$H NMR (400 MHz, $CD_3OD$) δ 8.25 (d, J=5.7 Hz, 1H), 7.98 (d, J=8.6 Hz, 1H), 7.54 (d, J=5.7 Hz, 1H), 7.27 (d, J=2.1 Hz, 1H), 7.20-7.12 (m, 1H), 5.62-5.48 (m, 2H), 3.96 (t, J=6.2 Hz, 2H), 3.75 (t, J=6.1 Hz, 2H), 3.38 (t, J=6.2 Hz, 2H), 3.24-3.15 (m, 5H), 3.13-3.04 (m, 2H), 2.55 (d, J=11.6, 7.1 Hz, 4H), 2.20 (d, J=14.9 Hz, 2H), 1.81-1.70 (m, 2H). LCMS $[M+H]^+$: 569.3.

Step 2:

EX90 was prepared as described in Example 59 (EX59), except EX91 was used instead of EX52. $^1$H NMR (400 MHz, $CD_3OD$) δ 8.24 (d, J=5.7 Hz, 1H), 7.97 (d, J=8.5 Hz, 1H), 7.60 (d, J=5.7 Hz, 1H), 7.16-7.08 (m, 2H), 3.96 (t, J=6.2 Hz, 2H), 3.80 (t, J=6.6 Hz, 2H), 3.38 (t, J=6.2 Hz, 2H), 3.22-3.12 (m, 2H), 3.08-3.00 (m, 5H), 2.28-2.15 (m, 2H), 2.02-1.92 (m, 2H), 1.83-1.74 (m, 2H), 1.74-1.67 (m, 2H), 1.57-1.48 (m, 2H), 1.42-1.31 (m, 2H). LCMS $[M+H]^+$: 571.3.

Example 92 (EX92-A&B)

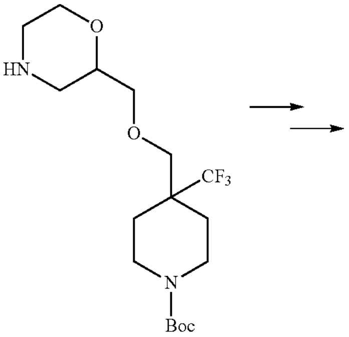

EX81-5

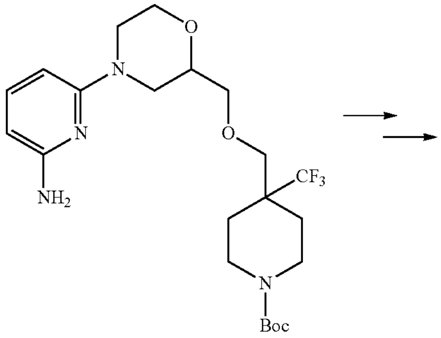

EX92-1

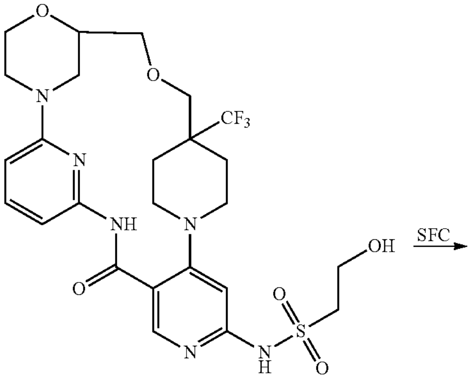

EX92

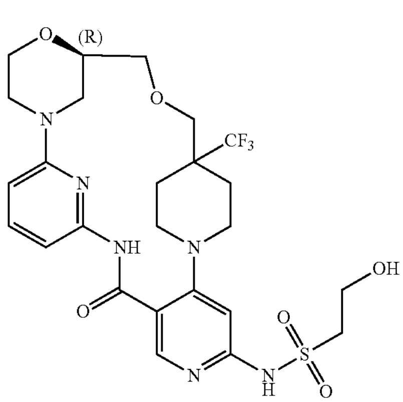

+

EX92-A&B

-continued

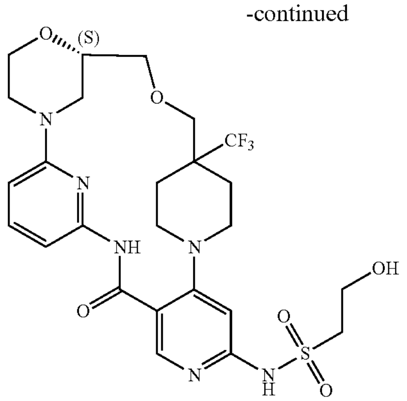

EX92-A&B

Step 1:

EX92-1 was prepared as described in Example 48 (EX48) Steps 1-2, except EX81-5 was used instead of EX44-2 in Step 1.

Step 2:

EX92 was prepared as described in Example 82 (EX82), except EX92-1 was used instead of EX72-1. LCMS $[M+H]^+$: 601.3.

Step 4:

EX92-A (8.65 mg) and EX92-B (9.60 mg) were separated from EX92 by SFC. SFC analytic condition: column: Chiralcel OD-3, 50*4.6 mm, 3.0 μm; mobile phase A: supercritical $CO_2$, mobile phase B: ethanol (0.05% DEA), 40% mobile phase B, 5 min; flow rate: 4 mL/min; column temp: 35° C.

EX92-A: $^1$H NMR (400 MHz, $CD_3OD$) δ 8.32 (s, 1H), 7.58 (t, J=8.0 Hz, 1H), 7.46 (d, J=7.8 Hz, 1H), 6.80 (s, 1H), 6.54 (d, J=8.3 Hz, 1H), 4.21-4.14 (m, 1H), 4.06-3.96 (m, 3H), 3.88-3.78 (m, 2H), 3.76-3.67 (m, 2H), 3.65-3.58 (m, 2H), 3.56-3.38 (m, 7H), 3.19-3.09 (m, 2H), 2.57-2.44 (m, 2H), 2.07-1.98 (m, 1H), 1.95-1.86 (m, 1H). LCMS $[M+H]^+$: 601.2. Retention time @SFC: 0.939 min.

EX92-B: $^1$H NMR (400 MHz, $CD_3OD$) S 8.32 (s, 1H), 7.58 (t, J=8.0 Hz, 1H), 7.46 (d, J=7.7 Hz, 1H), 6.79 (s, 1H), 6.53 (d, J=8.3 Hz, 1H), 4.21-4.12 (m, 1H), 4.04-3.95 (m, 3H), 3.87-3.78 (m, 2H), 3.76-3.66 (m, 2H), 3.65-3.57 (m, 2H), 3.56-3.36 (m, 7H), 3.19-3.07 (m, 2H), 2.58-2.44 (m, 2H), 2.01 (d, J=15.0 Hz, 1H), 1.91 (d, J=14.7 Hz, 1H). LCMS $[M+H]^+$: 601.2. Retention time @SFC: 1.240 min.

Example 93 (EX93-A&B)

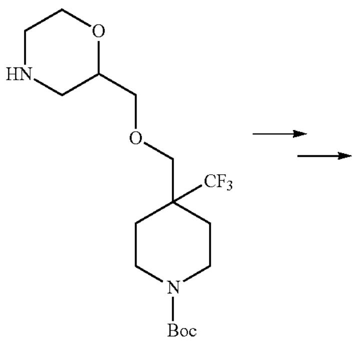

EX81-5

-continued

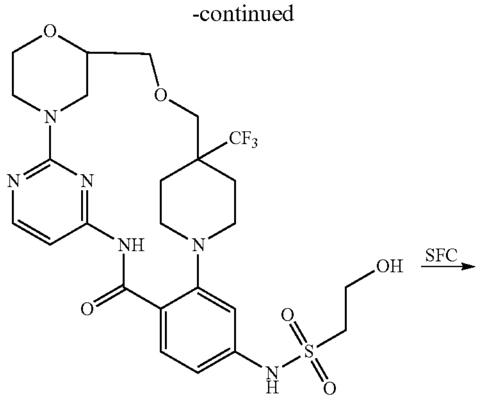

EX93

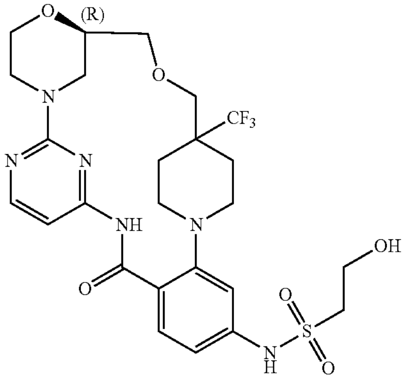

+

EX93-A&B

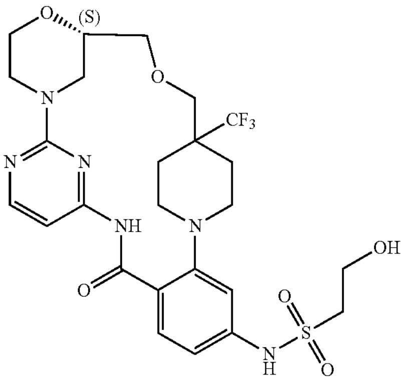

EX93-A&B

Step 1:

EX93 was prepared as described in Example 74 (EX74) Steps 1-2, except EX81-5 was used instead of EX62-1 in Step 1. LCMS $[M+H]^+$: 601.1.

Step 2:

EX93-A (8.65 mg) and EX93-B (9.60 mg) were separated from EX93 by SFC. SFC analytic condition: column: Cellulose-2, 100*4.6 mm, 3.0 m; mobile phase A: supercritical $CO_2$, mobile phase B: Methanol (0.05% DEA), 40% mobile phase B, 5 min; flow rate: 2.8 mL/min; column temp: 35° C.

EX93-A: $^1$H NMR (400 MHz, $CD_3OD$) δ 8.27 (d, J=5.6 Hz, 1H), 8.08 (d, J=8.6 Hz, 1H), 7.54 (d, J=5.6 Hz, 1H), 7.28 (d, J=2.1 Hz, 1H), 7.20-7.14 (m, 1H), 4.18-4.10 (m, 1H), 4.00-3.94 (m, 3H), 3.92-3.81 (m, 3H), 3.81-3.74 (m, 1H), 3.73-3.63 (m, 2H), 3.59 (d, J=9.1 Hz, 1H), 3.51-3.45 (m, 2H), 3.39 (t, J=6.3 Hz, 2H), 3.20-3.08 (m, 4H), 2.64-2.44 (m, 2H), 2.05-1.90 (m, 2H). LCMS $[M+H]^+$: 601.3. Retention time @SFC: 2.993 min.

EX93-B: $^{1}H$ NMR (400 MHz, $CD_3OD$) δ 8.27 (d, J=5.6 Hz, 1H), 8.07 (d, J=8.6 Hz, 1H), 7.54 (d, J=5.6 Hz, 1H), 7.27 (d, J=2.1 Hz, 1H), 7.17 (dd, J=8.6, 2.1 Hz, 1H), 4.19-4.11 (m, 1H), 4.00-3.93 (m, 3H), 3.91-3.82 (m, 3H), 3.80-3.74 (m, 1H), 3.73-3.63 (m, 2H), 3.62-3.56 (m, 1H), 3.51-3.45 (m, 2H), 3.38 (t, J=6.3 Hz, 2H), 3.18-3.08 (m, 4H), 2.65-2.42 (m, 2H), 2.05-1.90 (m, 2H). LCMS $[M+H]^+$: 601.2. Retention time @SFC: 3.599 min.

Example 94 (EX94)

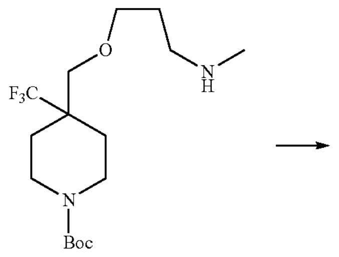

EX62-1

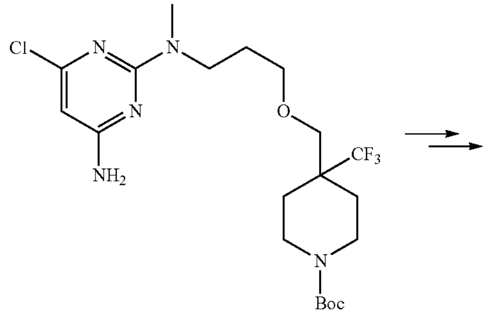

EX94-1

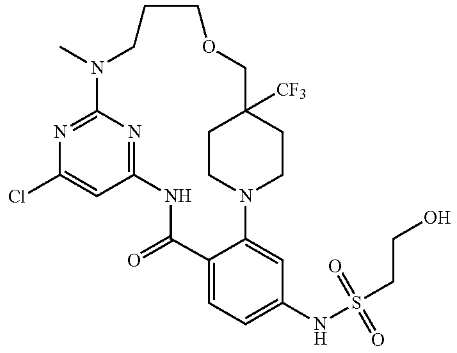

EX94

Step 1:

To a solution of EX62-1 (2 g, 5.64 mmol) and 2,6-dichloropyrimidin-4-amine (1.85 g, 11.29 mmol) in n-BuOH (100 mL) was added DIEA (2.8 mL, 16.93 mmol) under $N_2$ atmosphere. The mixture was stirred at 120° C. for 2 hrs. The mixture was diluted with water (100 mL) and extracted with EtOAc (100 mL×3). The combined organic layer was dried over $MgSO_4$, concentrated under reduced pressure and purified by silica gel chromatography to afford EX94-1. LCMS $[M+H]^+$: 482.2, 484.1.

Step 2:

EX94 was prepared as described in Example 74 (EX74) Step 2, except EX94-1 was used instead of EX74-1. $^{1}H$ NMR (400 MHz, $CD_3OD$) δ 8.12 (dd, J=8.7, 1.7 Hz, 1H), 7.56 (s, 1H), 7.31 (t, J=2.1 Hz, 1H), 7.22-7.15 (m, 1H), 3.96 (t, J=6.2 Hz, 2H), 3.90 (t, J=7.3 Hz, 2H), 3.49 (t, J=5.2 Hz, 2H), 3.44 (s, 2H), 3.39 (t, J=6.2 Hz, 2H), 3.10 (s, 7H), 2.72-2.58 (m, 2H), 1.95 (d, J=14.6 Hz, 2H), 1.90-1.80 (m, 2H). LCMS $[M+H]^+$: 607.2.

Example 95 (EX95)

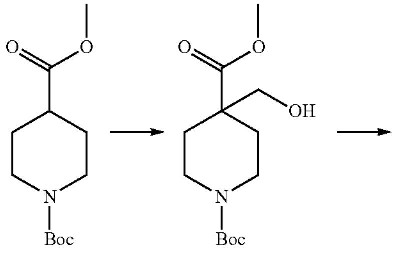

EX95-1

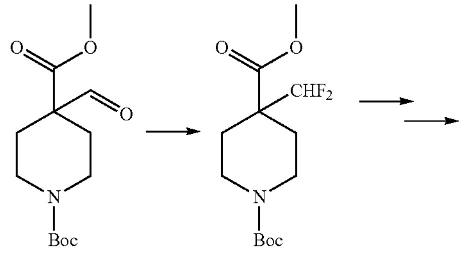

EX95-2 EX95-3

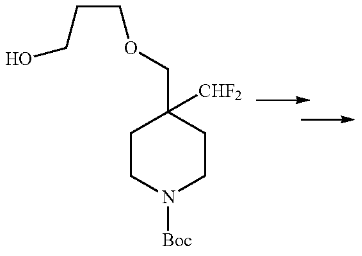

EX95-4

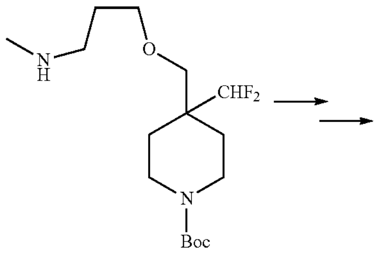

EX95-5

-continued

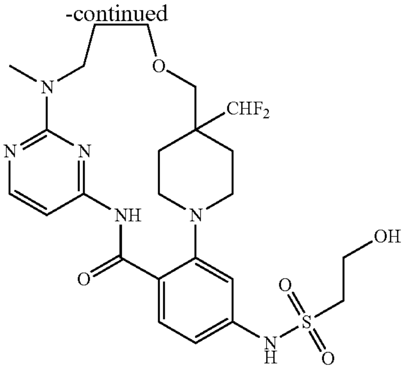

EX95

Step 1:

To a solution of 1-(tert-butyl) 4-methyl piperidine-1,4-dicarboxylate (50 g, 205.51 mmol) in THF (800 mL) was added LDA (123.3 mL, 246.61 mmol) under $N_2$ protection at −78° C. The mixture was stirred at −78° C. for 1 hr. And then formaldehyde (11.3 mL, 411 mmol) was added at −78° C. The mixture was stirred at 25° C. for 3 hrs. The mixture was quenched by saturated aq. $NH_4Cl$ (500 mL) and extracted with EtOAc (500 mL×3). The combined organic layer was dried over $MgSO_4$, concentrated under reduced pressure and purified by silica gel chromatography to afford EX95-1.

Step 2:

To a solution of DMSO (26.0 mL, 365.9 mmol) in DCM (170 mL) was added $(COCl)_2$ (15.5 mL, 182.9 mmol) in DCM (170 mL) at −78° C. over 20 min and the reaction was warmed to −60° C. over 25 min. Then EX95-1 (25 g, 91.5 mmol) in DCM (300 mL) was slowly added and the resulting mixture was warmed to −45° C. After stirring at −45° C. for 1 h, TEA (101.4 mL, 731.8 mmol) was added and the reaction was warmed to 0° C. over 1 h. The reaction was quenched with saturated aq. $NaHCO_3$ (100 mL) and extracted with DCM (50 mL×3). The combined organic layer was washed with brine, dried over $MgSO_4$, concentrated under reduced pressure and purified by silica gel chromatography to give EX95-2. LCMS $[M\text{-}Boc+H]^+$: 172.1.

Step 3:

To a solution of EX95-2 (18 g, 66.34 mmol) in DCM (400 mL) was added DAST (21.4 g, 132.7 mmol) at 0° C. and the reaction was stirred at 25° C. for 16 hrs. The reaction was quenched with saturated aq. $NaHCO_3$ (200 mL) and extracted with DCM (200 mL×3). The combined organic layer was dried over $MgSO_4$, concentrated under reduced pressure and purified by silica gel chromatography to give EX95-3.

Step 4:

EX95-4 was prepared as described in Example 17 (EX17) Steps 2-3, except EX95-3 was used instead of EX17-1 in Step 2. LCMS $[M\text{-}^tBu+H]^+$: 268.1.

Step 5:

EX95-5 was prepared as described in Example 4 (EX04) Steps 1-2, except EX95-4 was used instead of EX01-2 in Step 1. LCMS $[M+H]^+$: 337.1.

Step 6:

EX95 was prepared as described in Example 74 (EX74), except EX95-5 was used instead of EX62-1 in Step 1. $^1H$ NMR (400 MHz, DMSO-$d_6$) δ 12.11 (s, 1H), 8.22 (d, J=5.6 Hz, 1H), 8.03-7.96 (m, 1H), 7.41 (d, J=5.6 Hz, 1H), 7.20 (s, 1H), 7.13-7.06 (m, 1H), 6.31 (t, J=55.1 Hz, 1H), 3.82-3.72 (m, 4H), 3.39-3.33 (m, 4H), 3.30-3.26 (m, 2H), 3.00-2.97 (m, 7H), 2.43-2.33 (m, 2H), 1.74-1.68 (m, 4H). LCMS $[M+H]^+$: 555.3.

Example 96 (EX96-A&B)

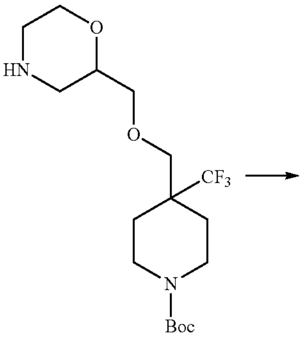

EX81-5

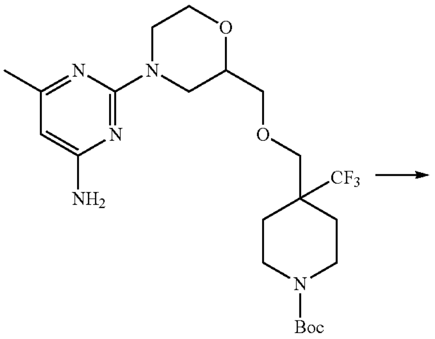

EX96-1

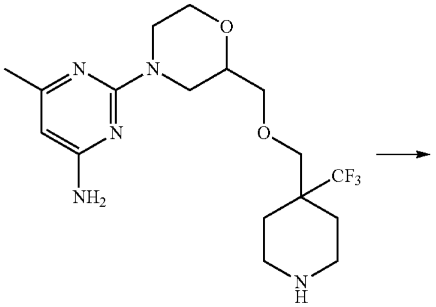

EX96-2

-continued

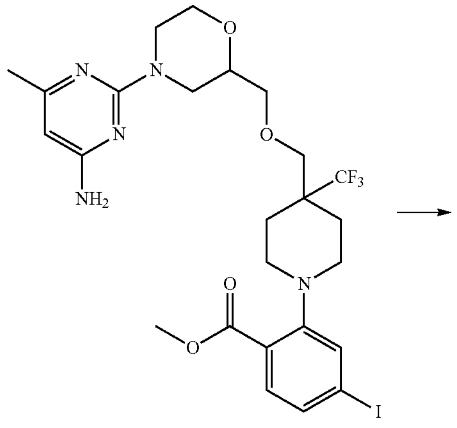

EX96-3

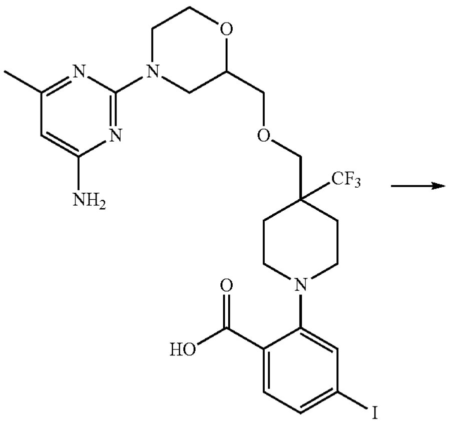

EX96-4

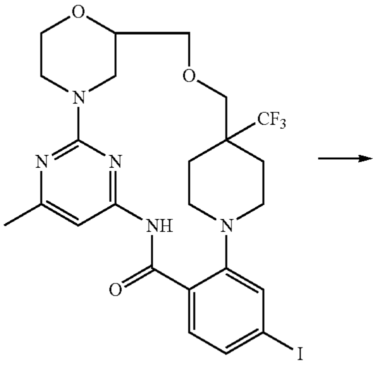

EX96-5

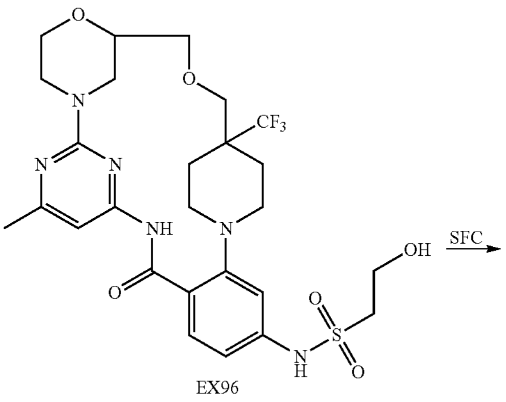

EX96

-continued

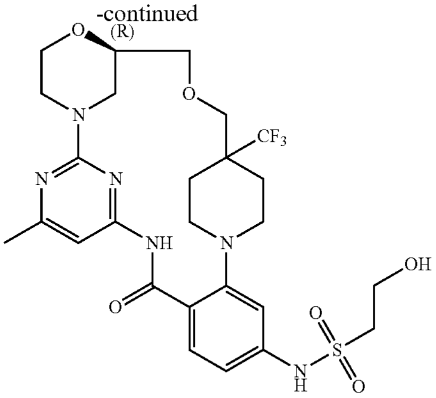

EX96-A&B

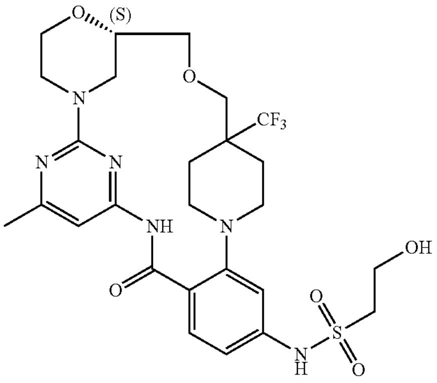

EX96-A&B

Step 1:

To a solution of EX81-5 (1.8 g, 4.71 mmol) and 2-chloro-6-methylpyrimidin-4-amine (1.0 g, 7.06 mmol) in NMP (18 mL) was added DIEA (2.3 mL, 14.1 mmol) under $N_2$ atmosphere. The mixture was stirred at 140° C. for 2 hrs. The reaction was quenched with water (100 mL) and extracted with EtOAc (100 mL×3). The combined organic layer was dried over $MgSO_4$, concentrated under reduced pressure and purified by silica gel chromatography to afford EX96-1. LCMS $[M+H]^+$: 490.3.

Step 2:

EX96-2 was prepared as described in Example 1 (EX01) Step 4, except EX96-1 was used instead of EX01-3.

Step 3:

To a solution of EX96-2 (1.4 g, 3.60 mmol) and methyl 2-fluoro-4-iodobenzoate (1.5 g, 5.39 mmol) in DMF (15 mL) was added $K_2CO_3$ (1.5 g, 10.8 mmol) under $N_2$ atmosphere. The resulting mixture was stirred at 120° C. for 18 hrs. The reaction was quenched with water (50 mL) and extracted with EtOAc (50 mL×3). The combined organic layer was dried over $MgSO_4$, concentrated under reduced pressure and purified by silica gel chromatography to afford EX96-3. LCMS $[M+H]^+$: 650.2.

Step 4:

To a solution of EX96-3 (640 mg, 0.99 mmol) in MeOH (20 mL) was added NaOH (1 M, 9.9 mL, 9.85 mmol). The resulting mixture was stirred at 50° C. for 3 hrs. The reaction was concentrated under reduced pressure, followed by the neutralization (pH=7) with aq. HCl (1 M). The mixture was extracted with EtOAc (50 mL×3). The combined organic layer was dried over $MgSO_4$ and concentrated under reduced pressure to afford EX96-4. LCMS $[M+H]^+$: 636.2.

Step 5:

To a solution of EX96-4 (260 mg, 0.41 mmol) in DCM (30 mL) were added $POCl_3$ (114 μL, 1.23 mmol) and pyridine (1981 μL, 24.5 mmol), and the reaction was stirred at 40° C. for 3 hrs. The reaction was quenched with water (50 mL) and extracted with DCM (50 mL×3). The combined organic layer was dried over $MgSO_4$, concentrated under reduced pressure and purified by silica gel chromatography to afford EX96-5. LCMS $[M+H]^+$: 618.2.

Step 6:

To a solution of EX96-5 (165 mg, 0.27 mmol) and 2-hydroxyethane-1-sulfonamide (167 mg, 1.34 mmol) in DMF (5 mL) were added $Cs_2CO_3$ (435 mg, 1.34 mmol), DMEDA (18 mg, 0.13 mmol) and CuI (10.2 mg, 0.053 mmol) under $N_2$ atmosphere. The reaction was stirred at 100° C. for 18 hrs. The reaction was quenched with saturated aq. $NH_4Cl$ (30 mL). The mixture was extracted with EtOAc (20 mL×3). The combined organic layer was dried over $MgSO_4$, and concentrated under reduced pressure. The residue was purified by prep-HPLC to afford EX96. LCMS $[M+H]^+$: 615.4.

Step 7:

EX96-A (8.59 mg) and EX96-B (10.09 mg) were separated from EX96 by SFC. SFC analytic condition: column: Cellulose-4, 100*4.6 mm, 3.0 m; mobile phase A: supercritical $CO_2$, mobile phase B: Methanol (0.05% DEA), 40% mobile phase B, 5 min; flow rate: 2.8 mL/min; column temp: 40° C.

EX96-A: $^1$H NMR (400 MHz, $CD_3OD$) δ 8.07 (d, J=8.7 Hz, 1H), 7.44 (s, 1H), 7.27 (d, J=2.2 Hz, 1H), 7.17 (dd, J=8.6, 2.1 Hz, 1H), 4.18-4.10 (m, 1H), 3.98-3.90 (m, 5H), 3.87-3.80 (m, 1H), 3.79-3.69 (m, 2H), 3.68-3.61 (m, 1H), 3.59 (d, J=9.1 Hz, 1H), 3.50-3.44 (m, 2H), 3.38 (t, J=6.2 Hz, 2H), 3.19-3.08 (m, 4H), 2.63-2.46 (m, 2H), 2.37 (s, 3H), 2.03-1.90 (m, 2H). LCMS $[M+H]^+$: 615.3. Retention time @SFC: 2.252 min.

EX96-B: $^1$H NMR (400 MHz, $CD_3OD$) δ 8.07 (d, J=8.6 Hz, 1H), 7.44 (s, 1H), 7.26 (d, J=2.2 Hz, 1H), 7.16 (dd, J=8.6, 2.2 Hz, 1H), 4.14 (d, J=12.2 Hz, 1H), 4.00-3.89 (m, 5H), 3.87-3.80 (m, 1H), 3.79-3.73 (m, 1H), 3.73-3.69 (m, 1H), 3.68-3.62 (m, 1H), 3.59 (d, J=9.1 Hz, 1H), 3.51-3.45 (m, 2H), 3.40-3.37 (m, 2H), 3.21-3.08 (m, 4H), 2.62-2.47 (m, 2H), 2.37 (s, 3H), 2.06-1.88 (m, 2H). LCMS $[M+H]^+$: 615.3. Retention time @SFC: 2.480 min.

Example 97 (EX97)

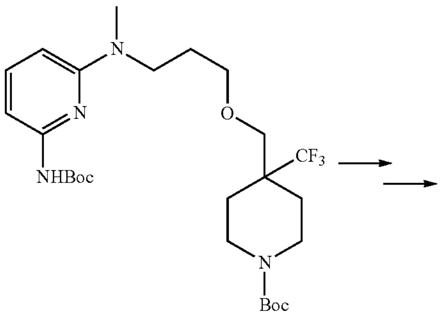

EX82-1

-continued

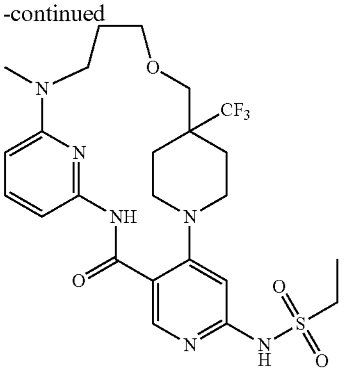

EX97

Step 1:

EX97 was prepared as described in Example 1 (EX01) Steps 4-8, except EX82-1 was used instead of EX01-3 in Step 4 and ethanesulfonamide was used instead of 2-hydroxyethane-1-sulfonamide in Step 8. $^1$H NMR (400 MHz, DMSO-$d_6$) δ 8.29 (s, 1H) 7.47-7.56 (m, 1H) 7.37 (d, J=7.92 Hz, 1H) 6.63 (s, 1H) 6.32 (d, J=8.14 Hz, 1H) 3.80-3.86 (m, 2H) 3.20-3.37 (m, 8H) 2.90 (t, J=11.66 Hz, 2H) 2.81 (s, 3H) 2.31-2.41 (m, 2H) 1.81 (d, J=14.09 Hz, 2H) 1.65-1.74 (m, 2H) 1.20 (t, J=7.37 Hz, 3H). LCMS $[M+H]^+$: 557.3.

Example 98 (EX98)

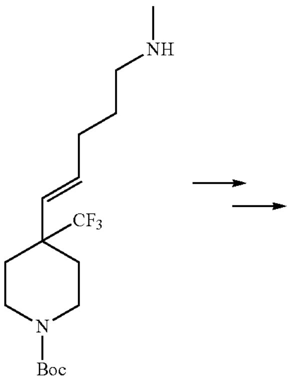

EX89-2

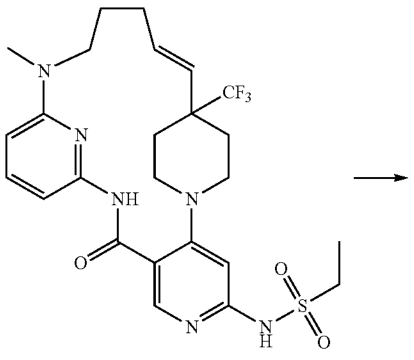

EX98-1

-continued

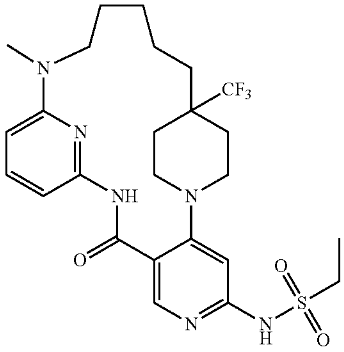

EX98

-continued

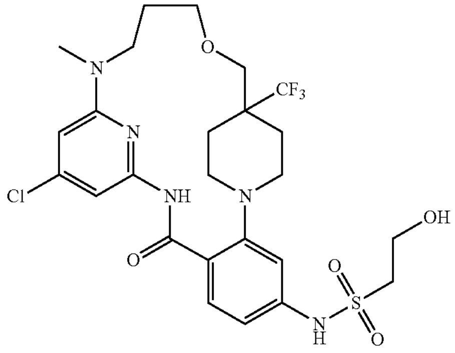

EX99

Step 1:

EX98-1 was prepared as described in Example 89 Step 3, except ethanesulfonamide was used instead of 2-hydroxy-ethane-1-sulfonamide. LCMS $[M+H]^+$: 553.1.

Step 2:

EX98 was prepared as described in Example 59 (EX59), except EX98-1 was used instead of EX52. $^1$H NMR (400 MHz, $CD_3OD$) δ 8.18-8.00 (m, 1H), 7.61 (d, J=7.8 Hz, 1H), 7.54 (t, J=8.0 Hz, 1H), 6.64 (s, 1H), 6.38 (d, J=8.2 Hz, 1H), 3.89-3.83 (m, 2H), 3.52-3.43 (m, 2H), 3.10-3.03 (m, 2H), 2.89 (s, 3H), 2.15-2.07 (m, 2H), 1.79-1.62 (m, 6H), 1.42-1.30 (m, 9H). LCMS $[M+H]^+$: 555.1.

Example 99 (EX99)

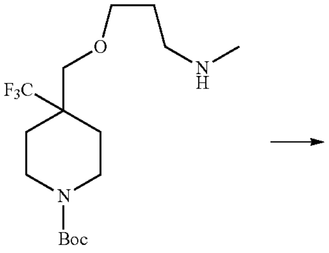

EX62-1

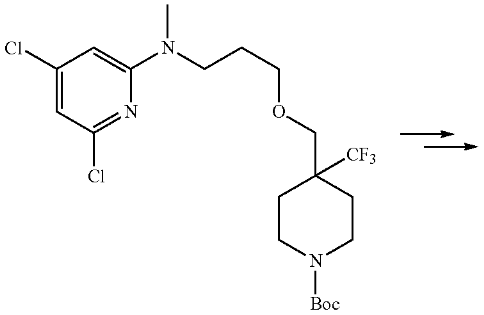

EX99-1

Step 1:

To a solution of EX62-1 (1.6 g, 4.5 mmol) and 4,6-dichloro-2-fluoropyridine (0.8 g, 5 mmol) in NMP (20 mL) was added DIEA (3.7 mL, 22.6 mmol) under $N_2$ atmosphere. The reaction mixture was stirred at 140° C. for 3 hrs. The reaction mixture was diluted with water (100 mL) and extracted with EtOAc (100 mL×3). The combined organic layer was dried over $MgSO_4$, concentrated under reduced pressure and purified by silica gel chromatography to afford EX99-1. LCMS $[M+H]^+$: 500.2, 502.1.

Step 2:

EX99 was prepared as described in Example 61 (EX61) Steps 2-3, except EX99-1 was used instead of EX61-1 in Step 2. $^1$H NMR (400 MHz, $CD_3OD$) δ 8.10 (d, J=8.7 Hz, 1H), 7.68 (d, J=1.5 Hz, 1H), 7.27 (d, J=2.2 Hz, 1H), 7.16 (dd, J=8.6, 2.2 Hz, 1H), 6.36 (d, J=1.4 Hz, 1H), 3.99-3.93 (m, 4H), 3.49-3.45 (m, 2H), 3.43-3.36 (m, 4H), 3.16-3.06 (m, 4H), 2.93 (s, 3H), 2.72-2.61 (m, 2H), 1.98-1.90 (m, 2H), 1.87-1.77 (m, 2H). LCMS $[M+H]^+$: 606.3.

Example 100 (EX100-A&B)

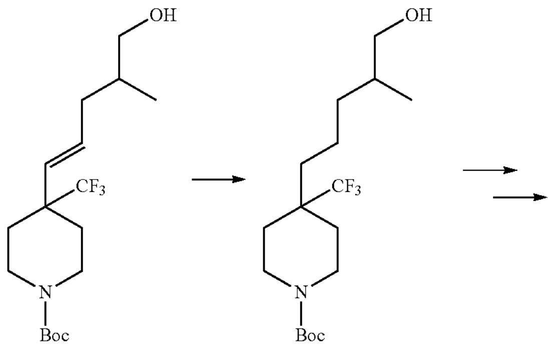

EX79-2 EX100-1

-continued

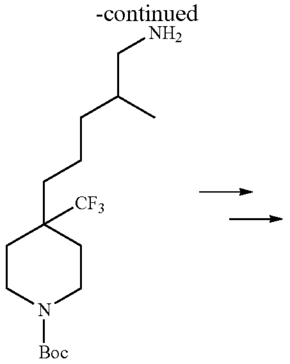

EX100-2

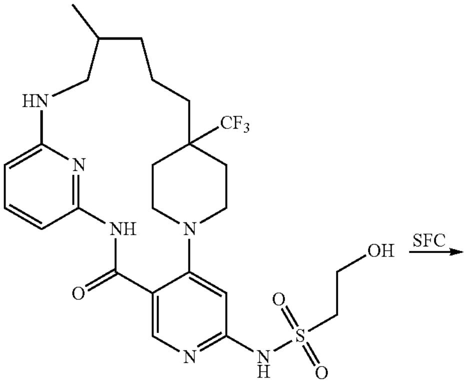

EX100

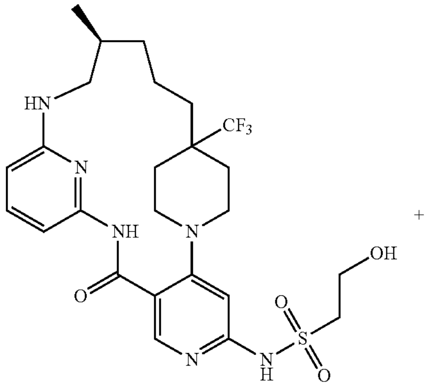

EX100-A&B

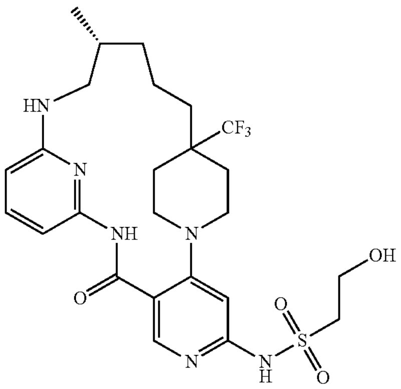

EX100-A&B

Step 1:

EX100-1 was prepared as described in Example 34 (EX34) Step 3, except EX79-2 was used instead of EX34-2. LCMS [M-$^t$Bu+H]$^+$: 298.0.

Step 2:

EX100-2 was prepared as described in Example 20 (EX20) Steps 3-4, except EX100-1 was used instead of EX20-2 in Step 3. LCMS [M+H]$^+$: 353.1.

Step 3:

EX100 was prepared as described in Example 92 (EX92) Steps 1-2, except EX100-2 was used instead of EX81-5. LCMS [M+H]$^+$: 571.4.

Step 4:

EX100-A (25.53 mg) and EX100-B (24.54 mg) were separated from EX100 by SFC. SFC analytic condition: column: Chiralcel OD-3, 150*4.6 mm, 3.0 μm; mobile phase A: supercritical $CO_2$, mobile phase B: Methanol (0.05% DEA), 40% mobile phase B, 5 min; flow rate: 2.5 mL/min; column temp: 35° C.

EX100-A: $^1$H NMR (400 MHz, $CD_3OD$) δ 8.07 (s, 1H), 7.48 (d, J=7.7 Hz, 1H), 7.36 (t, J=8.0 Hz, 1H), 6.68 (s, 1H), 6.27 (d, J=8.1 Hz, 1H), 4.00 (t, J=6.4 Hz, 2H), 3.74-3.66 (m, 1H), 3.50-3.38 (m, 5H), 3.12-3.02 (m, 2H), 2.20-2.07 (m, 2H), 1.89-1.70 (m, 4H), 1.56-1.46 (m, 2H), 1.36-1.28 (m, 2H), 1.25-1.16 (m, 1H), 1.06-1.00 (m, 3H). LCMS [M+H]$^+$: 571.3. Retention time @SFC: 2.980 min.

EX100-B: $^1$H NMR (400 MHz, $CD_3OD$) δ 8.07 (s, 1H), 7.48 (d, J=7.7 Hz, 1H), 7.36 (t, J=8.0 Hz, 1H), 6.68 (s, 1H), 6.27 (d, J=8.2 Hz, 1H), 4.00 (t, J=6.4 Hz, 2H), 3.77-3.65 (m, 1H), 3.50-3.38 (m, 5H), 3.07 (t, J=12.7 Hz, 2H), 2.14 (t, J=14.6 Hz, 2H), 1.92-1.69 (m, 4H), 1.57-1.45 (m, 2H), 1.35-1.28 (m, 2H), 1.26-1.16 (m, 1H), 1.02 (d, J=6.9 Hz, 3H). LCMS [M+H]$^+$: 571.3. Retention time @SFC: 4.530 min.

Example 101 (EX101-A&B)

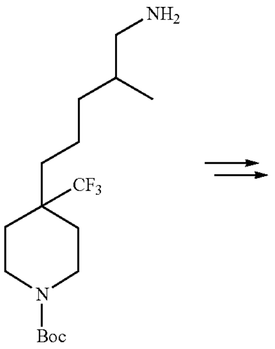

EX100-2

-continued

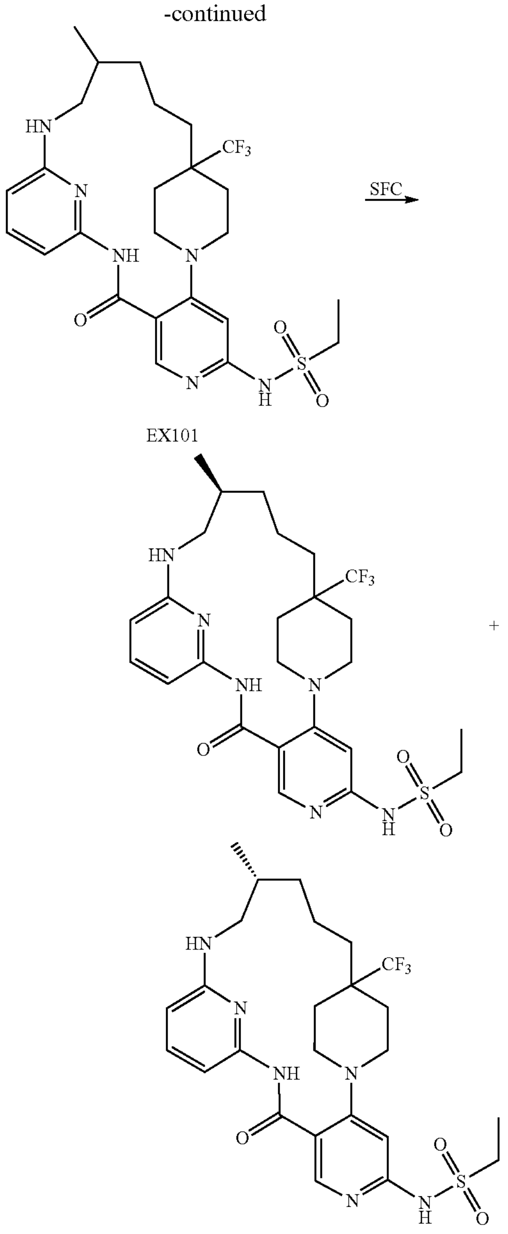

EX101

EX101-A&B

Step 1:

EX101 was prepared as described in Example 100 (EX100) Step 3, except ethanesulfonamide was used instead of 2-hydroxyethane-1-sulfonamide. LCMS $[M+H]^+$: 555.3.

Step 2:

EX101-A (14.34 mg) and EX101-B (15.39 mg) were separated from EX101 by SFC. SFC analytic condition: column: Chiralcel OD-3, 150*4.6 mm, 3.0 μm; mobile phase A: supercritical $CO_2$, mobile phase B: Methanol (0.05% DEA), 40% mobile phase B, 5 min; flow rate: 2.5 mL/min; column temp: 35° C.

EX101-A: $^1$H NMR (400 MHz, $CD_3OD$) δ 8.07 (s, 1H), 7.39-7.30 (m, 2H), 6.50 (s, 1H), 6.25 (dd, J=7.7, 1.2 Hz, 1H), 3.33-3.21 (m, 6H), 2.94-2.83 (m, 2H), 2.05-1.95 (m, 2H), 1.76-1.59 (m, 4H), 1.44-1.33 (m, 2H), 1.25-1.16 (m, 5H), 1.11-1.00 (m, 1H), 0.91 (d, J=6.9 Hz, 3H). LCMS $[M+H]^+$: 555.3. Retention time @SFC: 2.448 min.

EX101-B: $^1$H NMR (400 MHz, $CD_3OD$) δ 8.15-7.95 (m, 1H), 7.40-7.30 (m, 2H), 6.50 (s, 1H), 6.25 (d, J=7.8 Hz, 1H), 3.35-3.20 (m, 6H), 2.94-2.84 (m, 2H), 2.04-1.95 (m, 2H), 1.75-1.61 (m, 4H), 1.46-1.33 (m, 2H), 1.25-1.18 (m, 5H), 1.11-1.03 (m, 1H), 0.92 (d, J=6.9 Hz, 3H). LCMS $[M+H]^+$: 555.3. Retention time @SFC: 3.717 min.

Example 102 (EX102-A&B)

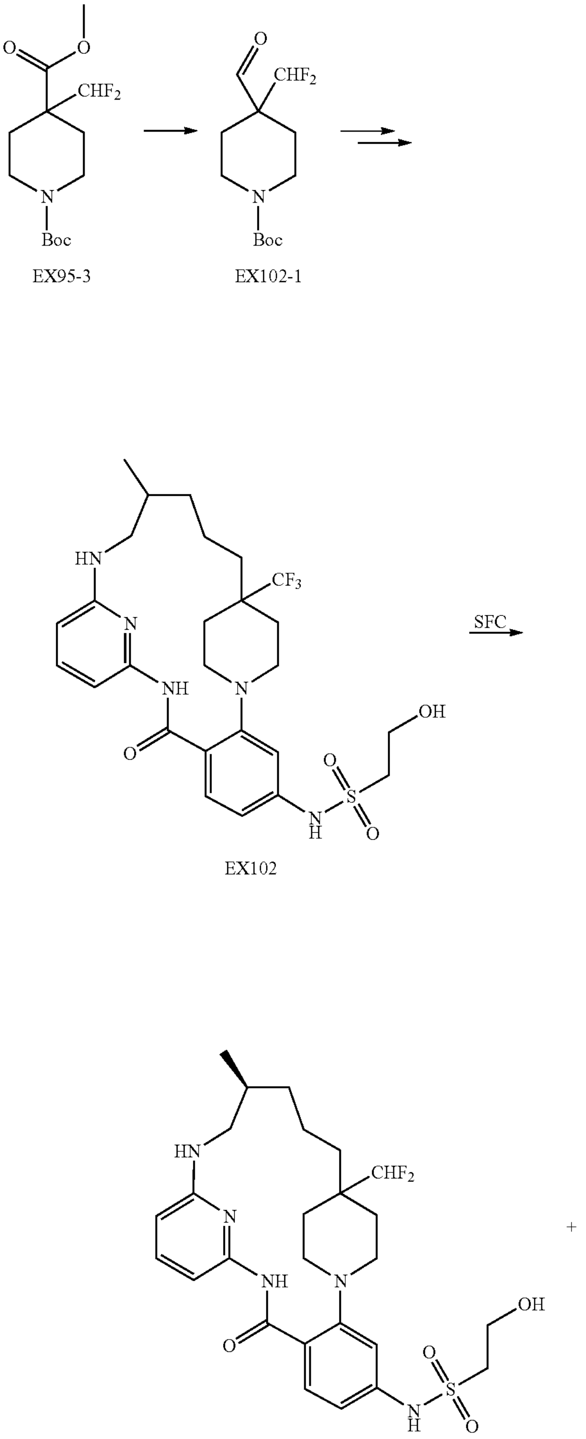

EX95-3

EX102-1

EX102

-continued

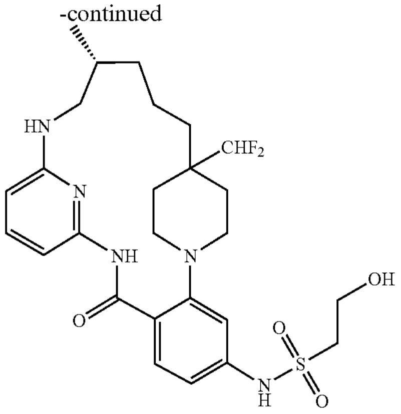

EX102-A&B

Step 1:

To a solution of EX95-3 (3 g, 10.23 mmol) in DCM (150 mL) was added DIBAL-H (1 M, 20.5 mL, 20.46 mmol) at −78° C. under $N_2$ atmosphere. The mixture was stirred at −78° C. for 3 hrs. MeOH (80 mL) was added to the mixture at −78° C. followed by aq. saturated potassium sodium tartrate. The resulting mixture was stirred until the mixture became a clear solution. The mixture was extracted with DCM (300 mL×3). The combined organic layer was dried over $MgSO_4$, concentrated under reduced pressure and purified by flash silica gel chromatography to afford EX102-1.

Step 2:

EX102 was prepared as described in Example 79 (EX79) Steps 1-4, except EX102-1 was used instead of EX60-1 in Step 1. LCMS $[M+H]^+$: 552.4.

Step 3:

EX102-A (40.79 mg) and EX102-B (40.40 mg) were separated from EX102 by SFC. SFC analytic condition: column: ChiralCel OJ-H, 150*4.6 mm, 5.0 m; mobile phase A: supercritical $CO_2$, mobile phase B: Methanol (0.05% DEA), 5%-40% mobile phase B, 8 min; flow rate: 2.5 mL/min; column temp: 40° C.

EX102-A: $^1H$ NMR (400 MHz, $CD_3OD$) δ 7.98 (d, J=8.6 Hz, 1H), 7.50 (d, J=7.7 Hz, 1H), 7.36 (t, J=8.0 Hz, 1H), 7.14 (d, J=2.1 Hz, 1H), 7.09 (dd, J=8.6, 2.2 Hz, 1H), 6.28 (d, J=8.1 Hz, 1H), 5.94 (t, J=56.4 Hz, 1H), 3.96 (t, J=6.3 Hz, 2H), 3.51-3.47 (m, 2H), 3.39-3.36 (m, 2H), 3.19-3.12 (m, 2H), 3.09-2.97 (m, 2H), 2.33-2.14 (m, 2H), 1.86-1.70 (m, 4H), 1.64-1.53 (m, 1H), 1.49-1.42 (m, 1H), 1.38-1.24 (m, 3H), 1.03 (d, J=6.9 Hz, 3H). LCMS $[M+H]^+$: 552.4. Retention time @SFC: 4.678 min.

EX102-B: $^1H$ NMR (400 MHz, $CD_3OD$) δ 7.98 (d, J=8.6 Hz, 1H), 7.50 (dd, J=7.8, 0.8 Hz, 1H), 7.36 (t, J=8.0 Hz, 1H), 7.14 (d, J=2.2 Hz, 1H), 7.09 (dd, J=8.6, 2.1 Hz, 1H), 6.28 (dd, J=8.2, 0.8 Hz, 1H), 5.94 (t, J=56.5 Hz, 1H), 3.96 (t, J=6.3 Hz, 2H), 3.49 (t, J=4.5 Hz, 2H), 3.38 (t, J=6.3 Hz, 2H), 3.19-3.10 (m, 2H), 3.10-2.95 (m, 2H), 2.32-2.13 (m, 2H), 1.87-1.71 (m, 4H), 1.64-1.53 (m, 1H), 1.50-1.40 (m, 1H), 1.37-1.21 (m, 3H), 1.03 (d, J=6.9 Hz, 3H). LCMS $[M+H]^+$: 552.3. Retention time @SFC: 5.011 min.

Example 103 (EX103)

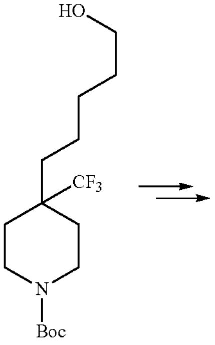

EX60-3

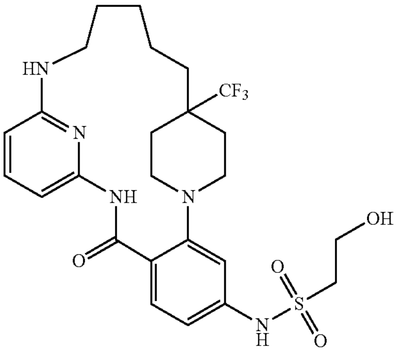

EX103

Step 1:

EX103 was prepared as described in Example 56 (EX56) Steps 1-3, except EX60-3 was used instead of EX55-1 in Step 1. $^1H$ NMR (400 MHz, $CD_3OD$) δ 7.98 (d, J=8.5 Hz, 1H), 7.46 (d, J=7.7 Hz, 1H), 7.36 (t, J=7.9 Hz, 1H), 7.16-7.08 (m, 2H), 6.22 (d, J=8.1 Hz, 1H), 3.96 (t, J=6.2 Hz, 2H), 3.59 (t, J=6.5 Hz, 2H), 3.38 (t, J=6.2 Hz, 2H), 3.17 (d, J=7.9 Hz, 2H), 3.02 (t, J=12.2 Hz, 2H), 2.35-2.21 (m, 2H), 1.98 (d, J=15.1 Hz, 2H), 1.75-1.59 (m, 4H), 1.53 (dd, J=10.7, 5.4 Hz, 2H), 1.44 (dd, J=12.7, 5.9 Hz, 2H). LCMS $[M+H]^+$: 556.3.

Example 104. (EX104)

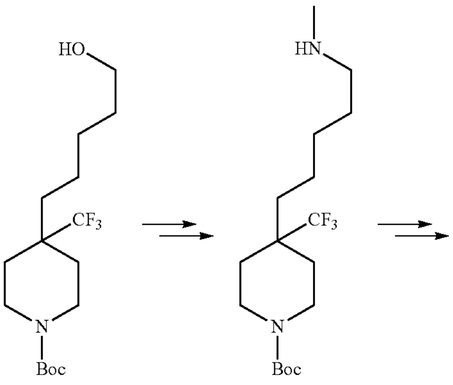

EX60-3 EX104-1

-continued

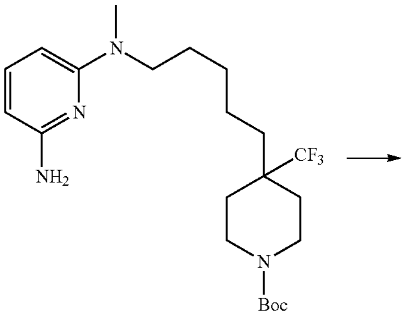

EX104-2

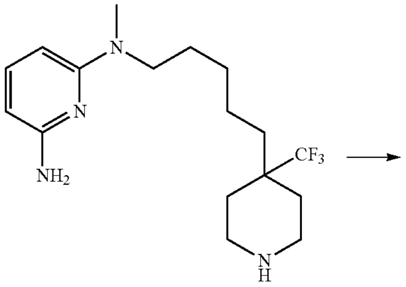

EX104-3

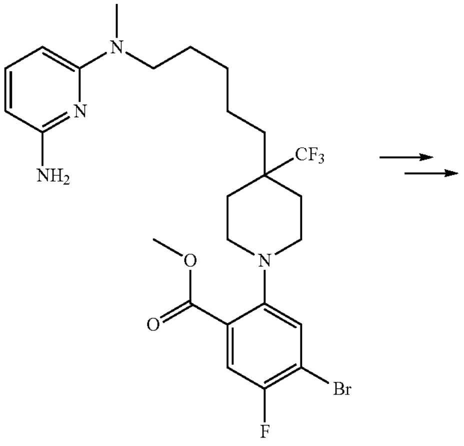

EX104-4

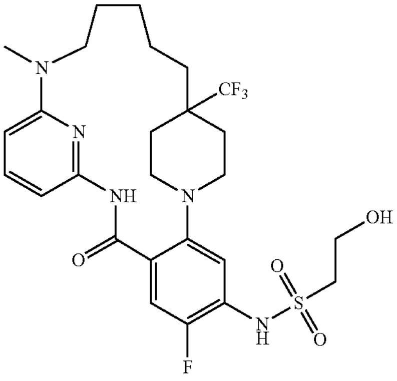

EX104

Step 1:

EX104-1 was prepared as described in Example 4 (EX04) Steps 1-2, except EX60-3 was used instead of EX01-2 in Step 1.

Step 2:

EX104-2 was prepared as described in Example 48 (EX48) Steps 1-2, except EX104-1 was used instead of EX44-2 in Step 1.

Step 3:

EX104-2 was prepared as described in Example 1 (EX01) Step 4, except EX104-2 was used instead of EX01-3.

Step 4:

To a solution of EX104-3 (500 mg, 1.45 mmol) and methyl 4-bromo-2,5-difluorobenzoate (547 mg, 2.18 mmol) in CAN (5 mL) was added DIEA (3.6 mL, 21.8 mmol). The reaction was stirred at 90° C. for 48 hrs. The mixture was diluted with $H_2O$ (10 mL) and extracted with EtOAc (10 mL×3). The combined organic layer was dried over $MgSO_4$ and concentrated under vacuum. The residue was purified by silica gel chromatography to afford EX104-4. LCMS $[M+H]^+$: 575.2, 577.2.

Step 5:

EX104 was prepared as described in Example 1 (EX01) Steps 6-8, except EX104-4 was used instead of EX01-5. $^1H$ NMR (400 MHz, DMSO-$d_6$) δ 11.52 (s, 1H), 7.76 (d, J=11.7 Hz, 1H), 7.57-7.47 (m, 2H), 7.36 (d, J=7.1 Hz, 1H), 6.35 (d, J=8.0 Hz, 1H), 3.81-3.75 (m, 4H), 3.35 (t, J=6.3 Hz, 2H), 3.09-3.00 (m, 2H), 2.90-2.79 (m, 5H), 2.21-2.10 (m, 2H), 1.98-1.89 (m, 2H), 1.69-1.51 (m, 4H), 1.47-1.38 (m, 2H), 1.32-1.23 (m, 2H). LCMS $[M+H]^+$: 588.3.

Example 105. (EX105-A&B)

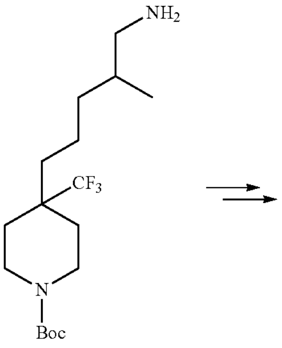

EX100-2

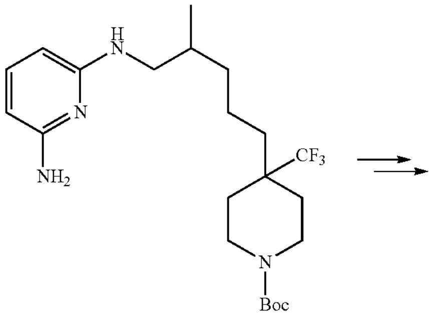

EX105-1

-continued

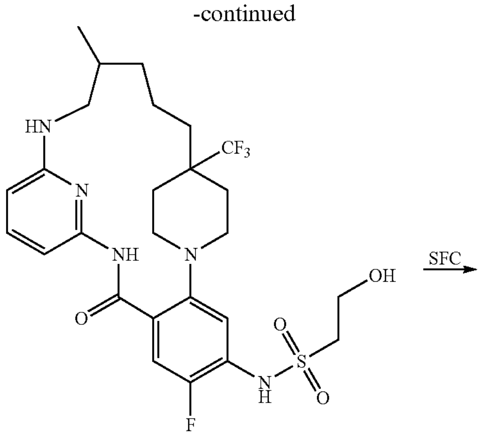

EX105

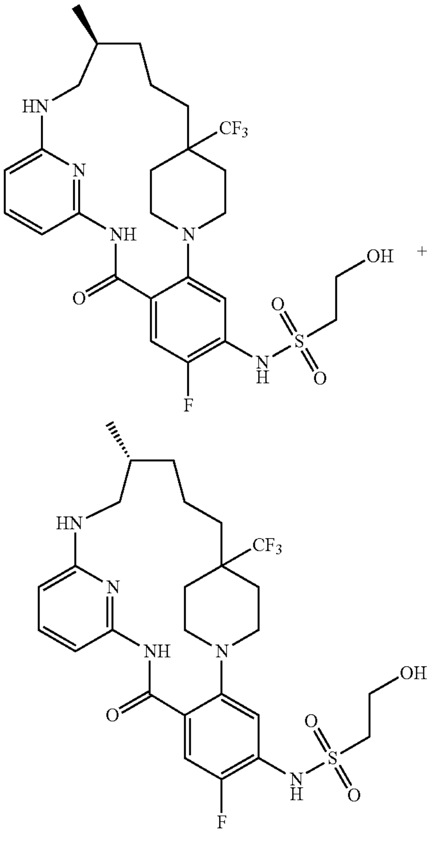

EX105-A&B

Step 1:

EX105-1 was prepared as described in Example 48 (EX48) Steps 1-2, except EX100-2 was used instead of EX44-2 in Step 1.

Step 2:

EX105 was prepared as described in Example 104 (EX104) Steps 3-5, except EX105-1 was used instead of EX104-2 in Step 3.

Step 3:

EX105-A (13.67 mg) and EX105-B (24.45 mg) were separated from EX105 by SFC. SFC analytic condition: column: ChiralPak AY-3 100×4.6 mm I.D., 3 um; mobile phase A: supercritical $CO_2$, mobile phase B: IPA (0.05% DEA), 40% mobile phase B, 8 min; flow rate: 2.5 mL/min; column temp: 40° C.

EX105-A: $^1$H NMR (400 MHz, $CD_3OD$) δ 7.84 (d, J=11.8 Hz, 1H), 7.54 (d, J=7.2 Hz, 1H), 7.48 (d, J=7.7 Hz, 1H), 7.37 (t, J=8.0 Hz, 1H), 6.30 (d, J=8.1 Hz, 1H), 3.98 (t, J=6.2 Hz, 2H), 3.60-3.52 (m, 1H), 3.41 (t, J=6.3 Hz, 2H), 3.17-3.10 (m, 2H), 3.09-2.97 (m, 2H), 2.42-2.22 (m, 2H), 2.06-1.94 (m, 2H), 1.84-1.71 (m, 2H), 1.71-1.56 (m, 2H), 1.54-1.43 (m, 1H), 1.43-1.23 (m, 3H), 1.04 (d, J=6.8 Hz, 3H). LCMS $[M+H]^+$: 588.3. Retention time @SFC: 1.877 min.

EX105-B: $^1$H NMR (400 MHz, $CD_3OD$) δ 7.84 (d, J=11.8 Hz, 1H), 7.54 (d, J=7.1 Hz, 1H), 7.48 (d, J=7.7 Hz, 1H), 7.37 (t, J=8.0 Hz, 1H), 6.30 (d, J=8.1 Hz, 1H), 4.00-3.97 (m, 2H), 3.59-3.53 (m, 1H), 3.42-3.40 (m, 2H), 3.16-3.11 (m, 2H), 3.08-2.97 (m, 2H), 2.41-2.23 (m, 2H), 2.04-1.98 (m, 2H), 1.83-1.73 (m, 2H), 1.67-1.57 (m, 2H), 1.55-1.47 (m, 1H), 1.41-1.36 (m, 3H), 1.06-1.03 (m, 3H). LCMS $[M+H]^+$: 588.3. Retention time @SFC: 5.983.

Example 106 (EX106)

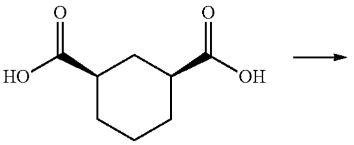

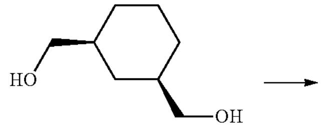

EX106-1

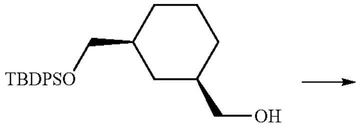

EX106-2

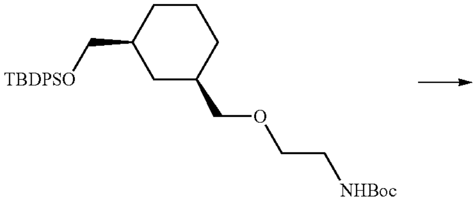

EX106-3

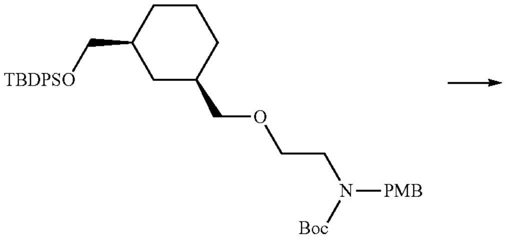

EX106-4

-continued

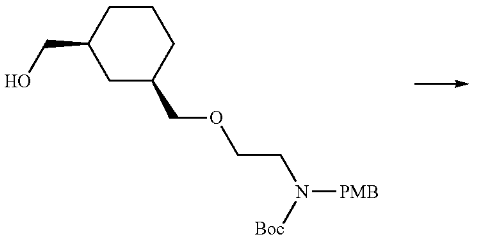

EX106-5

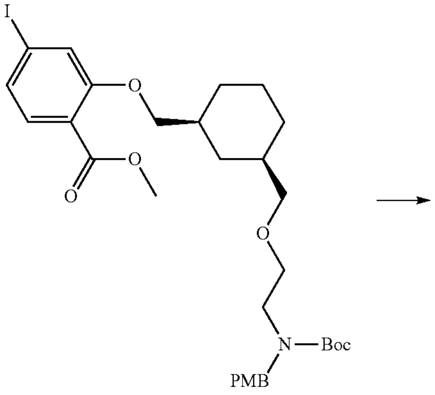

EX106-6

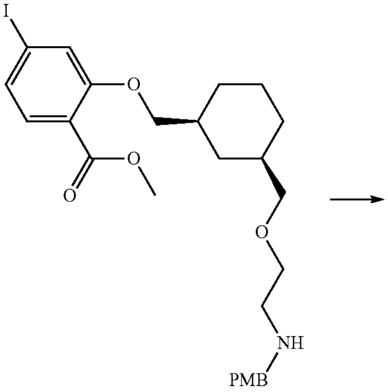

EX106-7

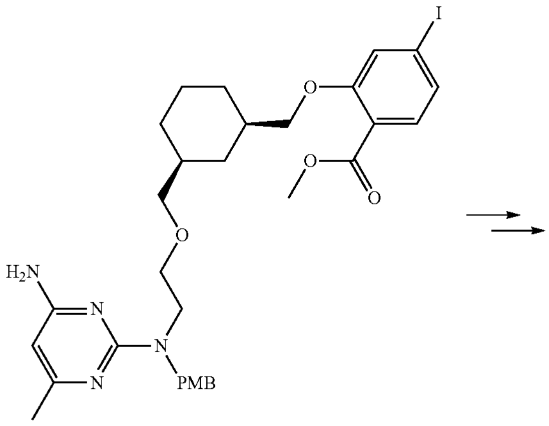

EX106-8

-continued

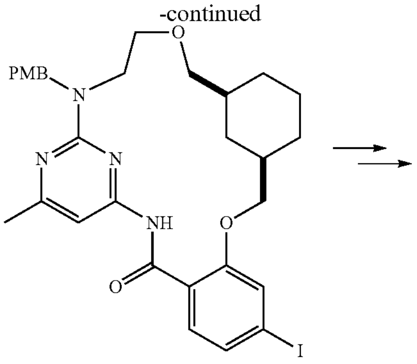

EX106-9

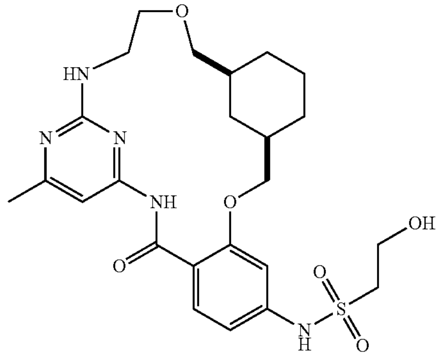

EX106

Step 1:

To a solution of cis-cyclohexane-1,3-dicarboxylic acid (15 g, 87.1 mmol) in THF (45 mL) was added $BH_3$ (1 M in THF, 192 mL, 191.6 mmol) at 0° C. under $N_2$ atmosphere, and the reaction was stirred at 25° C. for 18 hrs. The reaction was quenched with water (60 mL) and MeOH (210 mL). The mixture was concentrated under reduced pressure. The residue was extracted with EtOAc (200 mL×3). The combined organic layer was dried over $MgSO_4$, concentrated under vacuum and purified by silica gel chromatography to afford EX106-1.

Step 2:

To a solution of EX106-1 (8.4 g, 58.25 mmol) in DMF (80 mL) were added imidazole (7.9 g, 116.5 mmol) and TBDPSCl (15.11 mL, 58.25 mmol). The reaction was stirred at 25° C. for 2 hrs. The reaction was extracted with brine and EtOAc. The combined organic layer was dried over $MgSO_4$, concentrated under vacuum and purified by silica gel chromatography to afford EX106-2. LCMS $[M+H]^+$: 383.2.

Step 3:

To a solution of EX106-2 (90 mg, 0.235 mmol) in DMF was added NaH (8.5 mg, 0.353 mmol) at 0° C., and the resulting mixture was stirred for 1 h, followed by the addition of 2-methylpropan-2-yl 2,2-dioxo-2,6-1,2,3-oxathiazolidine-3-carboxylate (78.8 mg, 0.353 mmol). The reaction was stirred at 25° C. for 2 hrs. The reaction mixture was diluted with water (100 mL) and extracted with EtOAc (100 mL×3). The organic layer was washed with saturated brine, dried over $Na_2SO_4$, and concentrated under vacuum. The residue was purified by silica gel chromatography to afford EX106-3. LCMS $[M+H]^+$: 526.5.

Step 4:

To a solution of EX106-3 (3500 mg, 6.657 mmol) in DMF (30 mL) was added NaH (239.6 mg, 9.985 mmol) at 0° C., and the resulting mixture was stirred for 1 h, followed by the addition of 4-(chloromethyl)-1-methoxybenzene (2084.8 mg, 13.313 mmol). The reaction was stirred at 25° C. for 2 hrs. The reaction was quenched by aqueous $NH_4Cl$ and extracted with EtOAc. The organic layer was washed with brine and concentrated in vacuo. The residue was purified by silica gel chromatography to afford EX106-4. LCMS $[M+H]^+$: 646.7.

Step 5:

To a solution of EX106-4 (2700 mg, 4.180 mmol) in THF (30 mL) was added TBAF (3278.9 mg, 12.539 mmol). The reaction was stirred at 25° C. for 2 hrs, quenched by aqueous $NH_4Cl$, and extracted with EtOAc. The organic layer was washed with brine and concentrated in vacuo. The residue was purified by silica gel chromatography to afford EX106-5. LCMS $[M+H]^+$: 246.9.

Step 6:

To a solution of EX106-5 (1300 mg, 3.189 mmol) and $PPh_3$ (1673.2 mg, 6.379 mmol) in THF (2 mL) were added methyl 2-hydroxy-4-iodobenzoate (34.2 mg, 0.123 mmol) and DIAD (1289.8 mg, 6.379 mmol). The reaction was stirred at 25° C. overnight. The reaction mixture was quenched by water and extracted with EtOAc. The organic phase was washed with brine, dried over $Na_2SO_4$ and evaporated under reduced pressure. The residue was purified by silica gel chromatography to afford EX106-6. LCMS $[M+H]^+$: 668.2.

Step 7:

To a solution of EX106-6 (1100 mg, 1.648 mmol) in DCM (10 mL) was added TFA (3 mL). The reaction was stirred at 25° C. for 2 hs. The reaction mixture was evaporated under reduced pressure to afford EX106-7. LCMS $[M+H]^+$: 568.2.

Step 8:

To a solution of EX106-7 (800 mg, 1.41 mmol) in DMSO (10 mL) were added DIEA (0.70 mL, 4.229 mmol) and 2-chloro-6-methylpyrimidin-4-amine (404.9 mg, 2.81 mmol). The reaction was stirred at 120° C. for 48 hs. The reaction was extracted with EtOAc and the organic phase was washed with brine, dried over $Na_2SO_4$ and evaporated under reduced pressure. The residue was purified by silica gel chromatography to afford EX106-8. LCMS $[M+H]^+$: 675.3.

Step 9:

EX106-9 was prepared as described in Example 1 (EX01) Steps 6-7, except EX106-8 was used instead of EX01-5 in Step 6.

Step 10:

EX106 was prepared as described in Example 12 (EX12) Steps 5-6, except EX106-9 was used instead of EX12-4 in Step 5. $^1H$ NMR (400 MHz, $CD_3OD$) δ 7.88 (d, J=8.6 Hz, 1H), 7.42 (s, 1H), 7.06 (d, J=1.9 Hz, 1H), 6.96 (dd, J=8.5, 1.9 Hz, 1H), 4.05-3.92 (m, 4H), 3.70 (dt, J=12.1, 5.3 Hz, 2H), 3.51 (dd, J=10.4, 4.1 Hz, 1H), 3.40 (t, J=6.2 Hz, 3H), 3.24 (t, J=10.1 Hz, 1H), 2.63 (d, J=12.6 Hz, 1H), 2.33 (s, 3H), 1.86 (d, J=12.8 Hz, 3H), 1.72 (d, J=13.5 Hz, 1H), 1.57 (d, J=13.1 Hz, 1H), 1.49-1.40 (m, 1H), 1.31 (s, 1H), 1.17-1.05 (m, 1H), 0.91 (q, J=12.0 Hz, 2H). LCMS $[M+H]^+$: 520.3.

Example 107. (EX107-A&B)

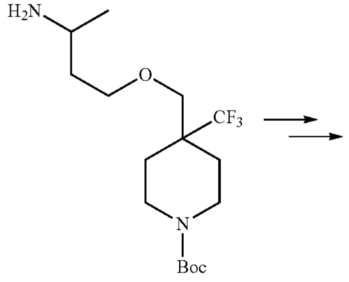

EX107-1

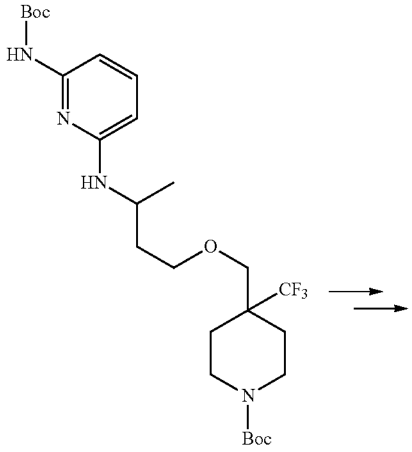

EX107-2

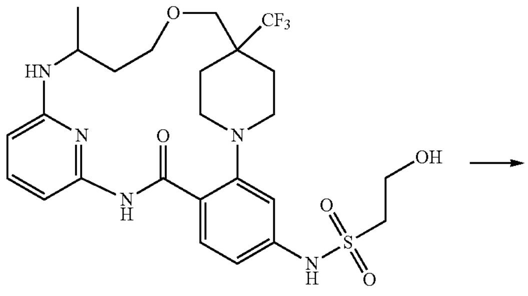

EX107

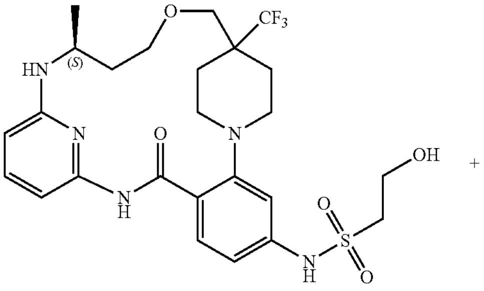

-continued

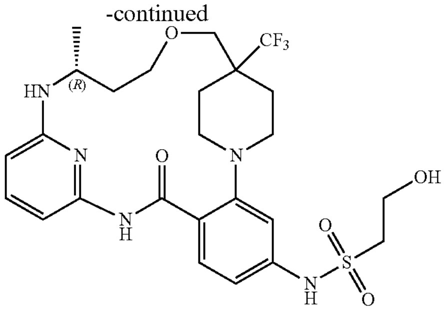

EX107-A&B

Step 1:

EX107-2 was prepared as described in Example 61 (EX61) Steps 1-2, except EX107-1 was used instead of EX44-2 and 2-bromo-6-fluoropyridine was used instead of 2-bromo-3,6-difluoropyridine in Step 1.

Step 2:

EX107 was prepared as described in Example 20 (EX20) Steps 6-8, except EX107-2 was used instead of EX20-5 in Step 6.

Step 3:

EX107-A (16.89 mg) and EX107-B (23.56 mg) were separated from EX105 by SFC. SFC analytic condition: column: Column: (S,S)Whelk-01 100×4.6 mm I.D., 5.0 um; mobile phase A: supercritical $CO_2$, mobile phase B: ethanol (0.05% DEA), 50% mobile phase B, 8 min; flow rate: 2.5 mL/min; column temp: 40° C.

EX107-A: $^1$H NMR (400 MHz, $CD_3OD$) δ 8.05 (d, J=8.6 Hz, 1H), 7.46 (d, J=7.7 Hz, 1H), 7.36 (t, J=7.9 Hz, 1H), 7.24 (d, J=2.2 Hz, 1H), 7.15 (dd, J=8.6, 2.1 Hz, 1H), 6.22 (d, J=8.0 Hz, 1H), 4.84-4.73 (m, 2H), 3.96 (t, J=6.2 Hz, 2H), 3.63-3.53 (m, 2H), 3.49-3.41 (m, 1H), 3.38 (t, J=6.3 Hz, 2H), 3.29-3.18 (m, 3H), 3.10 (d, J=11.9 Hz, 1H), 2.91 (t, J=12.8 Hz, 1H), 2.85-2.74 (m, 1H), 2.61-2.49 (m, 1H), 2.05 (dd, J=14.7, 2.6 Hz, 1H), 1.77 (dd, J=14.6, 2.6 Hz, 1H), 1.72-1.62 (m, 2H), 1.17 (d, J=6.8 Hz, 3H). LCMS $[M+H]^+$: 572.1. Retention time @SFC: 1.665 min.

EX107-B: $^1$H NMR (400 MHz, $CD_3OD$) δ 8.03 (d, J=8.5 Hz, 1H), 7.47-7.41 (m, 1H), 7.38-7.31 (m, 1H), 7.22 (d, J=1.4 Hz, 1H), 7.13 (d, J=8.6 Hz, 1H), 6.20 (d, J=8.0 Hz, 1H), 4.81-4.73 (m, 2H), 3.94 (t, J=6.2 Hz, 2H), 3.54 (d, J=8.5 Hz, 2H), 3.46-3.40 (m, 1H), 3.36 (t, J=6.2 Hz, 2H), 3.27-3.18 (m, 3H), 3.08 (d, J=10.4 Hz, 1H), 2.89 (t, J=12.8 Hz, 1H), 2.82-2.72 (m, 1H), 2.60-2.47 (m, 1H), 2.03 (d, J=14.6 Hz, 1H), 1.75 (d, J=14.5 Hz, 1H), 1.66 (s, 2H), 1.15 (d, J=6.8 Hz, 3H). LCMS $[M+H]^+$: 572.3. Retention time @SFC: 1.970 min.

Example 108 (EX108)

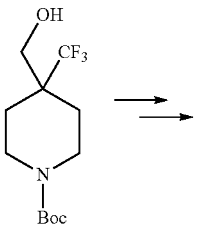

EX117-2

-continued

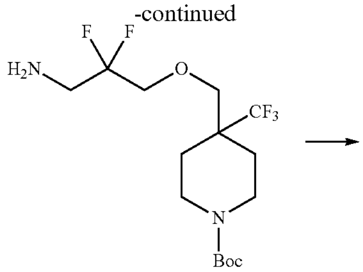

EX108-1

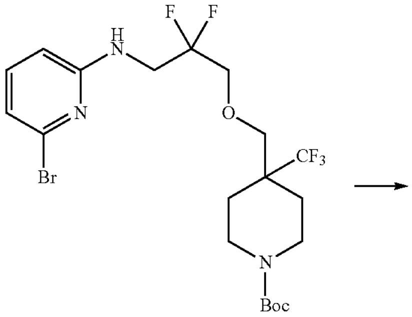

EX108-2

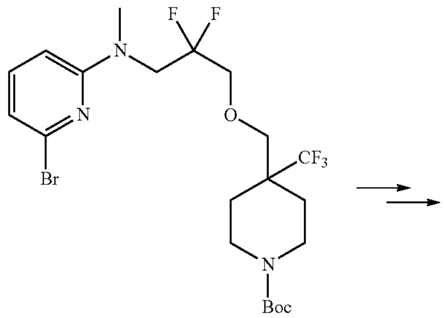

EX108-3

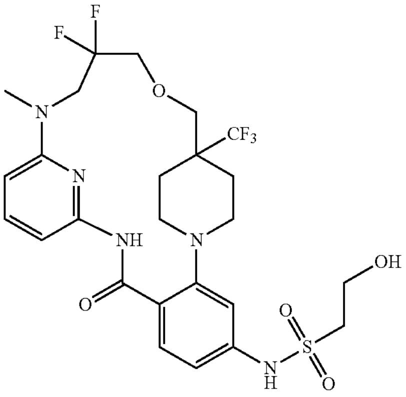

EX108

Step 1:

EX108-1 was prepared as described in Example 28 (EX28) Steps 1-5, except EX17-2 was used instead of tert-butyl 4-(hydroxymethyl)-4-methylpiperidine-1-carboxylate in Step 1.

Step 2:

EX108-2 was prepared as described in Example 61 (EX61) Step 1, except EX108-1 was used instead of EX44-2 and 2-bromo-6-fluoropyridine was used instead of 2-bromo-3,6-difluoropyridine.

Step 3:

To a solution of EX108-2 (700 mg, 1.32 mmol) in THF (20 mL) was added NaH (263.0 mg, 6.57 mmol) under $N_2$ protection. The mixture was stirred at 25° C. for 0.5 h, followed by the addition of iodomethane (559.7 mg, 3.94 mmol). The resulting mixture was stirred at 60° C. for 1.5 hrs. The reaction was quenched with water (20 mL) and extracted with EtOAc (20 mL×3). The combined organic layer was dried over $MgSO_4$, concentrated under vacuum and purified by silica gel chromatography to afford EX108-3. LCMS $[M+H]^+$: 546.0.

Step 4:

EX108 was prepared as described in Example 61 (EX61) Steps 2-3, except EX108-3 was used instead of EX61-1 in Step 2. $^1H$ NMR (400 MHz, DMSO-$d_6$) δ 11.63 (s, 1H), 8.00 (d, J=8.6 Hz, 1H), 7.67-7.55 (m, 2H), 7.19 (s, 1H), 7.13-7.06 (m, 1H), 6.43 (d, J=7.9 Hz, 1H), 4.35 (t, J=15.7 Hz, 2H), 3.73 (dd, J=12.5, 6.1 Hz, 4H), 3.49 (s, 2H), 3.33 (t, J=6.4 Hz, 2H), 3.07 (s, 2H), 2.99 (s, 3H), 2.93 (d, J=12.7 Hz, 2H), 2.44 (s, 2H), 1.89 (d, J=14.0 Hz, 2H). LCMS $[M+H]^+$: 608.2.

Example 109 (EX109)

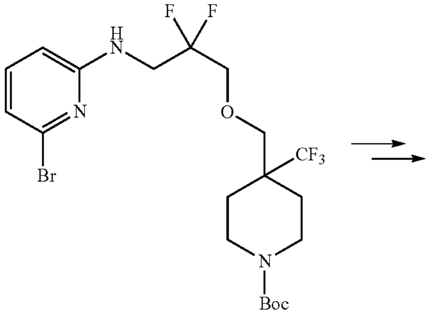

EX108-2

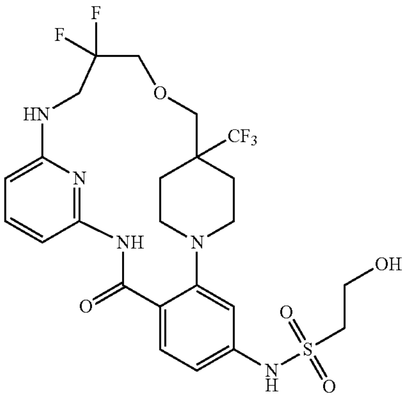

EX109

Step 1:

EX109 was prepared as described in Example 61 (EX61) Steps 2-3, except EX108-2 was used instead of EX61-1 in Step 2. $^1H$ NMR (400 MHz, $CD_3OD$) δ 8.02 (d, J=8.6 Hz, 1H), 7.56 (d, J=7.7 Hz, 1H), 7.44 (t, J=8.0 Hz, 1H), 7.21 (d, J=2.1 Hz, 1H), 7.14 (dd, J=8.6, 2.1 Hz, 1H), 6.33 (d, J=8.1 Hz, 1H), 4.11 (t, J=14.0 Hz, 2H), 3.96 (t, J=6.2 Hz, 2H), 3.71 (t, J=11.7 Hz, 2H), 3.53 (s, 2H), 3.39 (t, J=6.2 Hz, 2H), 3.18 (t, J=8.2 Hz, 2H), 3.09 (t, J=12.7 Hz, 2H), 2.64 (t, J=12.8 Hz, 2H), 1.93 (d, J=14.6 Hz, 2H). LCMS $[M+H]^+$: 594.2.

Example 110 (EX110)

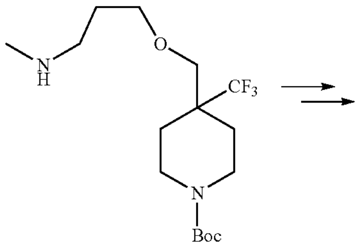

EX95-5

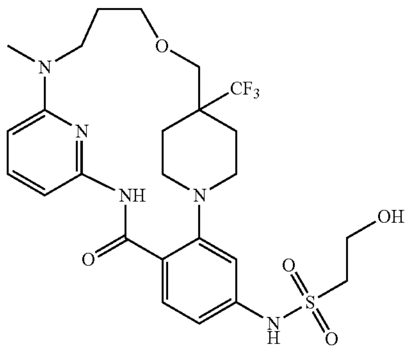

EX110

Step 1:

EX110 was prepared as described in Example 72 (EX72), except EX95-5 was used instead of EX62-1 in Step 1. $^1H$ NMR (400 MHz, $CD_3OD$) δ 8.08 (d, J=8.6 Hz, 1H), 7.59 (d, J=7.7 Hz, 1H), 7.52 (t, J=8.0 Hz, 1H), 7.26 (d, J=2.2 Hz, 1H), 7.13 (dd, J=8.6, 2.2 Hz, 1H), 6.34 (d, J=8.1 Hz, 1H), 6.15 (t, J=55.6 Hz, 1H), 4.01-3.90 (m, 4H), 3.48-3.42 (m, 2H), 3.42-3.37 (m, 2H), 3.36-3.34 (m, 2H), 3.14-3.05 (m, 4H), 2.96-2.89 (m, 3H), 2.68-2.55 (m, 2H), 1.83-1.74 (m, 4H). LCMS $[M+H]^+$: 554.3.

Example 111 (EX111-A&B)

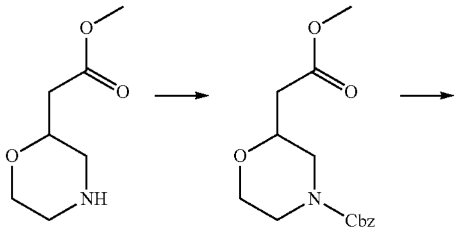

EX111-1

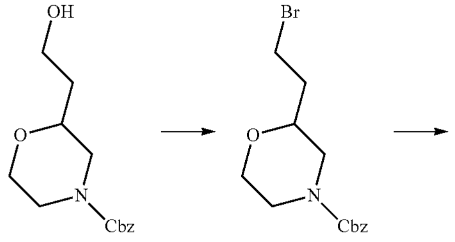

EX111-2 EX111-3

-continued

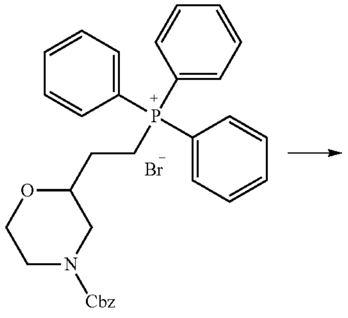

EX111-4

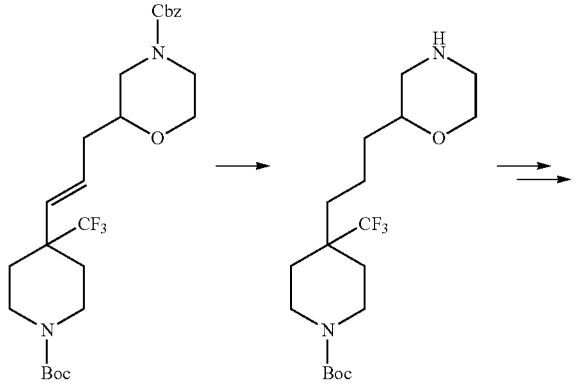

EX111-5 EX111-6

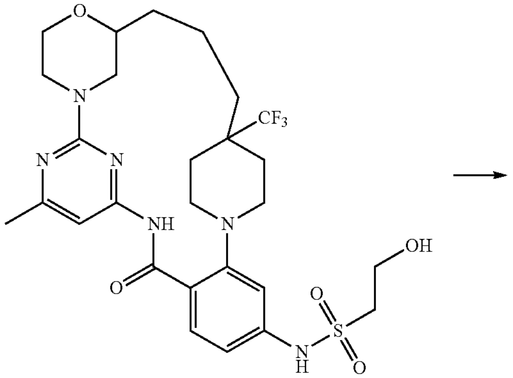

EX111

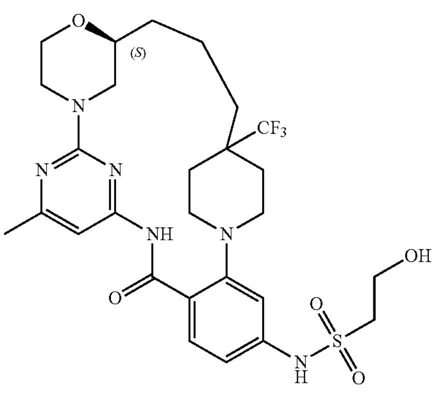

EX111

+

-continued

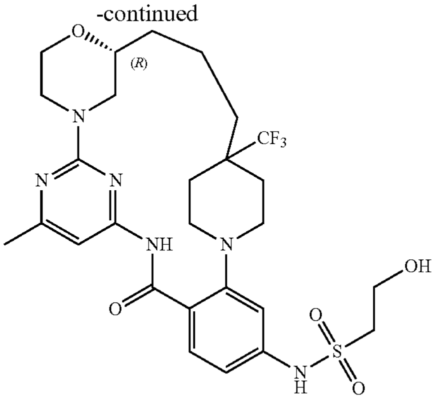

EX111-A&B

Step 1:

To a solution of methyl 2-(morpholin-2-yl)acetate (HCl salt, 50 g, 255.62 mmol) in DCM (500 mL) were added TEA (177.2 mL, 1278.12 mmol) and CbzCl (43.2 mL, 306.75 mmol) at 0° C. The mixture was stirred at 25° C. for 12 hrs. The reaction was diluted with water (300 mL) and extracted with DCM (300 mL×3). The combined organic layer was dried over $MgSO_4$ and purified by silica gel chromatography to afford EX111-1. LCMS $[M-44+H]^+$: 250.1.

Step 2:

To a solution of EX111-1 (20 g, 68.19 mmol) in THF (600 mL) was added Super-H (1 M, 200 mL, 200 mmol) under $N_2$ atmosphere at 0° C. The mixture was stirred at 25° C. for 2 hrs. The mixture was quenched with MeOH (500 mL) and concentrated under reduced pressure. Saturated $NH_4Cl$ (500 mL) was added and the mixture was extracted with EtOAc (500 mL×3). The combined organic layer was dried over $MgSO_4$, concentrated under reduced pressure and purified by silica gel chromatography to afford EX111-2. LCMS $[M-44+H]^+$: 222.2.

Step 3:

To a solution of EX111-2 (40 g, 150.77 mmol) and $PPh_3$ (47.5 g, 180.93 mmol) in DCM (800 mL) was added a solution of $CBr_4$ (75 g, 226.16 mmol) in DCM (400 mL) at 0° C. The mixture was stirred at 25° C. for 2 hrs. The mixture was concentrated under reduced pressure and purified by silica gel chromatography to afford EX111-3. LCMS $[M-44+H]^+$: 284.0, 286.0.

Step 4:

A solution of EX111-3 (43 g, 131.02 mmol) and $PPh_3$ (34.4 g, 131.02 mmol) in toluene (600 mL) was stirred at 120° C. for 12 hrs. The mixture was concentrated under reduced pressure and purified by silica gel chromatography to afford EX111-4. LCMS $[M+H]^+$: 510.3.

Step 5:

To a solution of EX111-4 (12 g, 23.5 mmol) in THF (125 mL) was added NaHMDS (1 M, 32 mL, 32.05 mmol) at −78° C. under $N_2$ atmosphere. The mixture was stirred at −78° C. for 1 hr, followed by the addition of a solution of EX60-1 (6 g, 21.37 mmol) in THF (25 mL) dropwise at −78° C. The mixture was stirred at 25° C. for 12 hrs. The reaction was quenched with aq. $NH_4Cl$ (100 mL) and extracted with EtOAc (100 mL×3). The combined organic layer was dried over $MgSO_4$, concentrated under reduced pressure and purified by silica gel chromatography to afford EX111-5. LCMS $[M-Boc+H]^+$: 413.1.

Step 6:

To a solution of EX111-5 (8.5 g, 16.58 mmol) in EtOAc (150 mL) was added Pd/C (6 g, 10% purity) under $N_2$ atmosphere. The mixture was stirred at 25° C. for 12 hrs under $H_2$ atmosphere. The reaction mixture was filtered through Celite, washed with EtOAc (200 mL) and concentrated under vacuum to give EX111-6. LCMS $[M+H]^+$: 381.1.

Step 7:

EX111 was prepared as described in Example 81 (EX81) Step 6, except EX111-6 was used instead of EX81-5.

Step 8:

EX111-A (16.44 mg) and EX111-B (18.05 mg) were separated from EX111 by SFC. SFC analytic condition: column: Column: Column: (S,S)Whelk-01 100×4.6 mm I.D., 5.0 um; mobile phase A: supercritical $CO_2$, mobile phase B: ethanol (0.05% DEA), 50% mobile phase B, 8 min; flow rate: 2.5 mL/min; column temp: 40° C.

EX111-A: $^1H$ NMR (400 MHz, $CD_3OD$) δ 8.16 (d, J=8.7 Hz, 1H), 7.42 (s, 1H), 7.27 (d, J=2.2 Hz, 1H), 7.20 (dd, J=8.7, 2.1 Hz, 1H), 4.74-4.69 (m, 1H), 4.46-4.39 (m, 1H), 3.96 (t, J=6.2 Hz, 2H), 3.93-3.88 (m, 1H), 3.64-3.54 (m, 2H), 3.38 (t, J=6.1 Hz, 3H), 3.18-3.00 (m, 5H), 2.47-2.39 (m, 1H), 2.36 (s, 3H), 2.32-2.20 (m, 2H), 2.16-2.07 (m, 1H), 1.78-1.55 (m, 6H). LCMS $[M+H]^+$: 613.2. Retention time @SFC: 2.713 min.

EX111-B: $^1H$ NMR (400 MHz, $CD_3OD$) δ 8.16 (d, J=8.7 Hz, 1H), 7.42 (s, 1H), 7.27 (d, J=2.2 Hz, 1H), 7.20 (dd, J=8.7, 2.2 Hz, 1H), 4.75-4.68 (m, 1H), 4.46-4.39 (m, 1H), 3.96 (t, J=6.2 Hz, 2H), 3.93-3.88 (m, 1H), 3.64-3.55 (m, 2H), 3.38 (t, J=6.2 Hz, 3H), 3.18-2.99 (m, 5H), 2.47-2.38 (m, 1H), 2.36 (s, 3H), 2.33-2.19 (m, 2H), 2.14-2.05 (m, 1H), 1.77-1.58 (m, 6H). LCMS $[M+H]^+$: 613.2. Retention time @SFC: 3.279 min:

Example 112 (EX112)

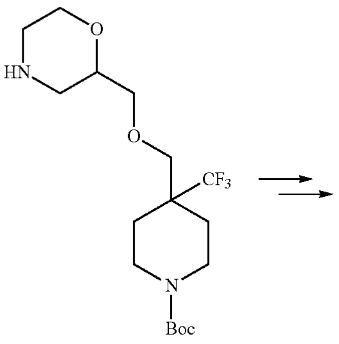

EX81-5

-continued

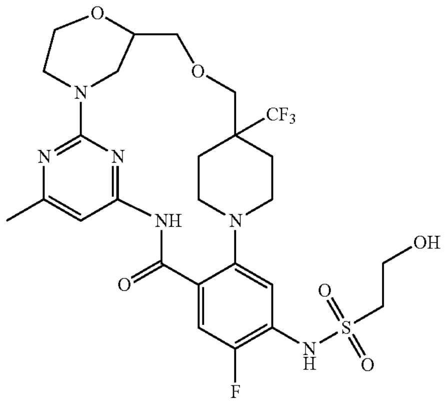

EX112

Step 1:

EX112 was prepared as described in Example 104 (EX104) Steps 2-5, except EX81-5 was used instead of EX104-1 in Step 2. $^1H$ NMR (400 MHz, $CD_3OD$) δ 7.90 (d, J=11.8 Hz, 1H), 7.70 (d, J=7.2 Hz, 1H), 7.43 (s, 1H), 4.32-4.23 (m, 1H), 4.03-3.95 (m, 3H), 3.88-3.81 (m, 2H), 3.79-3.70 (m, 2H), 3.69-3.62 (m, 2H), 3.59-3.50 (m, 2H), 3.49-3.45 (m, 1H), 3.42 (t, J=6.2 Hz, 2H), 3.15-3.08 (m, 4H), 2.60-2.48 (m, 2H), 2.37 (s, 3H), 2.03-1.93 (m, 2H). LCMS $[M+H]^+$: 633.2.

Example 113 (EX113-A&B)

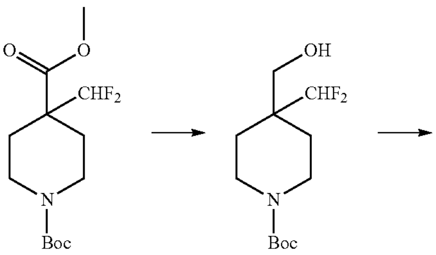

EX95-3 EX113-1

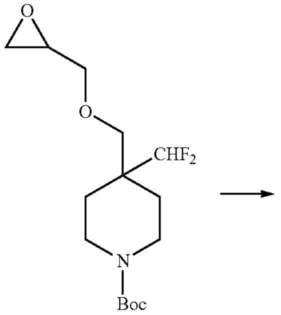

EX113-2

-continued

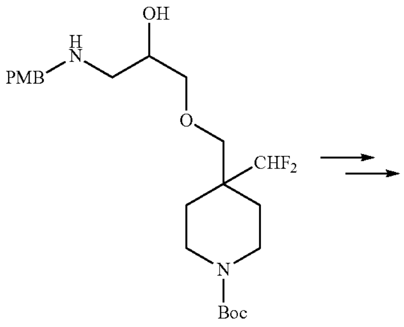

EX113-3

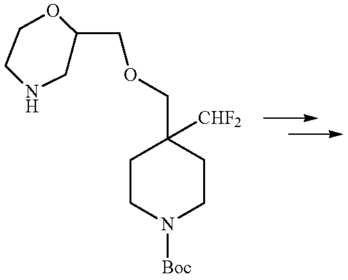

EX113-4

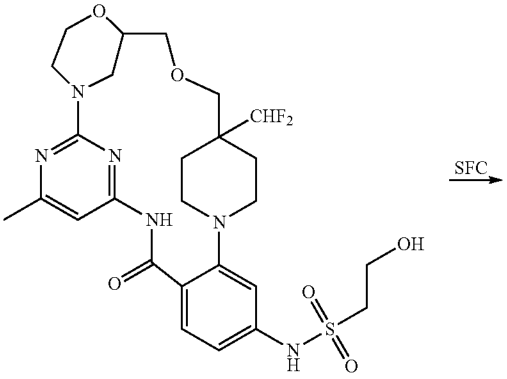

EX113

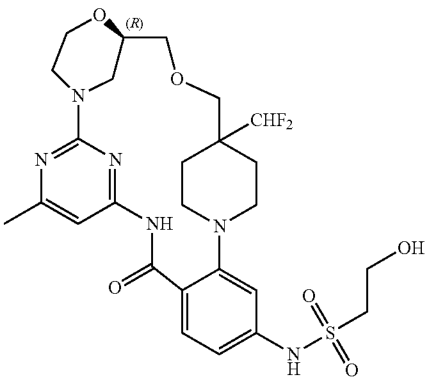

-continued

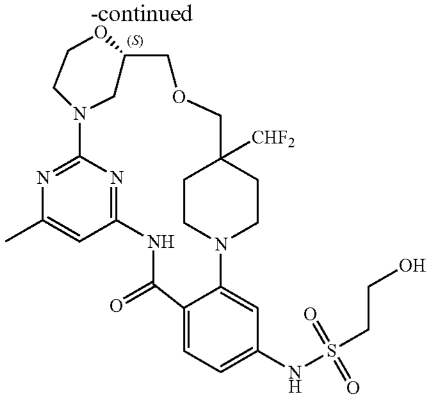

EX113-A&B

Step 1:

EX113-1 was prepared as described in Example 17 (EX17) Step 2, except EX95-3 was used instead of EX17-1.

Step 2:

To a solution of EX113-1 (8 g, 30.16 mmol) in THF (150 mL) was added NaH (60% in oil, 2.4 g, 60.31 mmol) under $N_2$ atmosphere at 0° C., followed by the addition of 2-(chloromethyl) oxirane (3.1 g, 33.17 mmol). The mixture was stirred at 80° C. for 6 hrs. The reaction was diluted with water (100 mL) and extracted with EtOAc (100 mL×3). The combined organic layer was dried over $MgSO_4$ and purified by silica gel chromatography to afford EX113-2. LCMS [M-$^t$Bu+H]$^+$: 266.0.

Step 3:

To a solution of EX113-2 (5 g, 15.56 mmol) in EtOH (100 ml) were added $PMBNH_2$ (4.27 g, 31.1 mmol) and DIEA (21.74 mL, 124 mmol) under $N_2$ atmosphere. The mixture was stirred at 80° C. for 2 hrs. The mixture was concentrated under reduced pressure, diluted with saturated $NH_4Cl$ (100 mL) and extracted with EtOAc (100 mL×3). The combined organic layer was dried with $MgSO_4$, concentrated under reduced pressure and purified by silica gel chromatography to afford EX113-3. LCMS [M+H]$^+$: 459.2.

Step 4:

EX113-4 was prepared as described in Example 81 (EX81) Steps 2-5, except EX113-3 was used instead of EX81-1 in Step 2.

Step 5:

EX113 was prepared as described in Example 96 (EX96) Step 1, except EX113-4 was used instead of EX81-5.

Step 6:

EX113-A (30.49 mg) and EX113-B (14.28 mg) were separated from EX111 by SFC. SFC analytic condition: column: Column: Column: Cellulose-2 100×4.6 mm I.D., 3 um; mobile phase A: supercritical $CO_2$, mobile phase B: methanol (0.05% DEA), 40% mobile phase B, 8 min; flow rate: 2.8 mL/min; column temp: 35° C.

EX113-A: $^1$H NMR (400 MHz, $CD_3OD$) δ 8.06 (d, J=8.6 Hz, 1H), 7.45 (s, 1H), 7.27 (d, J=2.1 Hz, 1H), 7.14 (dd, J=8.6, 2.1 Hz, 1H), 6.23 (t, J=55.3 Hz, 1H), 4.25-4.17 (m, 1H), 4.01-3.79 (m, 6H), 3.75-3.59 (m, 3H), 3.55-3.36 (m, 6H), 3.20-3.05 (m, 4H), 2.56-2.40 (m, 2H), 2.37 (s, 3H), 1.90-1.73 (m, 2H). LCMS [M+H]$^+$: 597.3. Retention time @SFC: 2.916 min.

EX113-B: $^1$H NMR (400 MHz, $CD_3OD$) δ 8.07 (d, J=8.6 Hz, 1H), 7.45 (s, 1H), 7.27 (d, J=2.2 Hz, 1H), 7.14 (dd, J=8.6, 2.1 Hz, 1H), 6.23 (t, J=55.3 Hz, 1H), 4.25-4.17 (m, 1H), 3.98-3.81 (m, 6H), 3.75-3.61 (m, 3H), 3.54-3.37 (m,

6H), 3.18-3.08 (m, 4H), 2.57-2.40 (m, 2H), 2.37 (s, 3H), 1.88-1.77 (m, 2H). LCMS $[M+H]^+$: 597.3. Retention time @SFC: 3.213 min.

Example 114 (EX114-A&B)

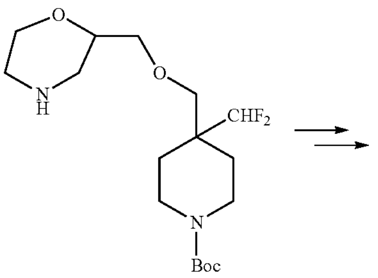

EX113-4

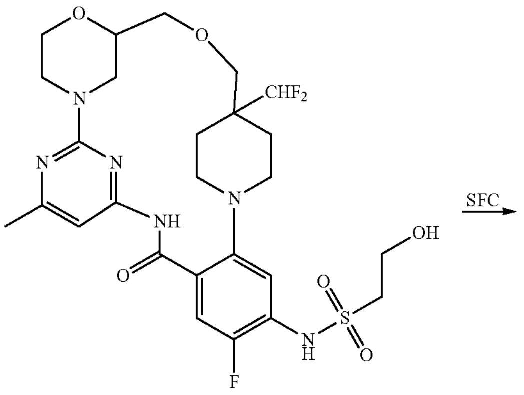

EX114

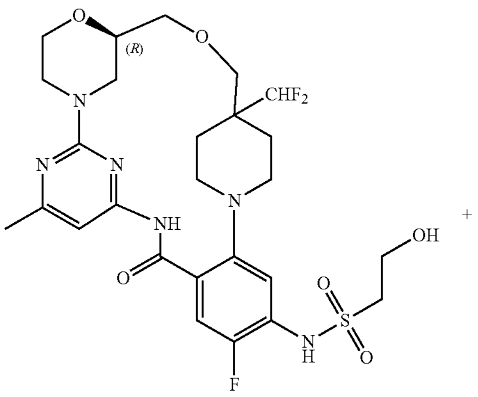

-continued

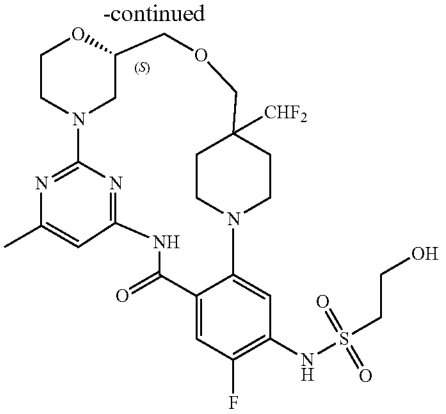

EX114-A&B

Step 1:

EX114 was prepared as described in Example 112 (EX112), except EX113-4 was used instead of EX81-5.

Step 2:

EX114-A (24.71 mg) and EX114-B (9.74 mg) were separated from EX111 by SFC. SFC analytic condition: column: Column: Column: Cellulose-2 100×4.6 mm I.D., 3 um; mobile phase A: supercritical $CO_2$, mobile phase B: methanol (0.05% DEA), 40% mobile phase B, 8 min; flow rate: 2.8 mL/min; column temp: 35° C.

EX114-A: $^1H$ NMR (400 MHz, DMSO-$d_6$) δ 12.07 (s, 1H), 7.77 (d, J=11.5 Hz, 1H), 7.51 (d, J=7.2 Hz, 1H), 7.32 (s, 1H), 6.44 (t, J=54.9 Hz, 1H), 4.23-4.14 (m, 1H), 3.96-3.87 (m, 1H), 3.78 (t, J=6.3 Hz, 2H), 3.70-3.46 (m, 6H), 3.43-3.33 (m, 5H), 3.10-2.90 (m, 4H), 2.31-2.18 (m, 5H), 1.76-1.66 (m, 2H). LCMS $[M+H]^+$: 615.3. Retention time @SFC: 2.419 min.

EX114-B: $^1H$ NMR (400 MHz, DMSO-$d_6$) δ 12.09 (s, 1H), 7.77 (d, J=11.5 Hz, 1H), 7.50 (d, J=7.1 Hz, 1H), 7.31 (s, 1H), 6.40 (t, J=54.9 Hz, 1H), 4.18 (d, J=10.9 Hz, 1H), 3.94-3.89 (m, 1H), 3.78 (t, J=6.2 Hz, 2H), 3.72-3.48 (m, 6H), 3.42-3.34 (m, 5H), 3.09-2.88 (m, 4H), 2.30-2.18 (m, 5H), 1.76-1.64 (m, 2H). LCMS $[M+H]^+$: 615.3. Retention time @SFC: 2.778 min.

Example 115 (EX115-A&B)

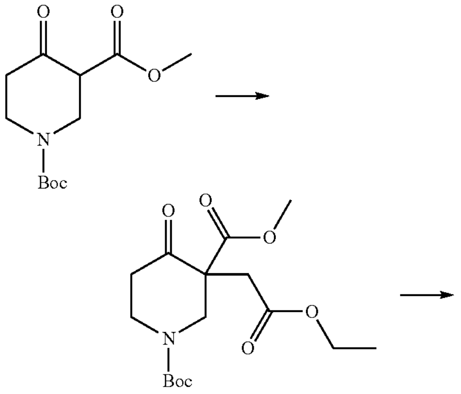

EX115-1

-continued

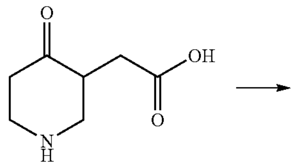

EX115-2

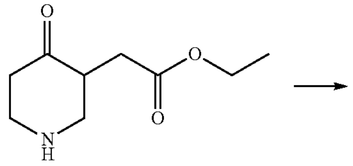

EX115-3

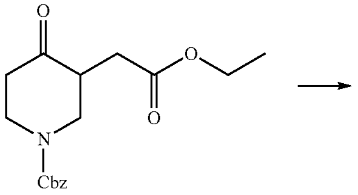

EX115-4

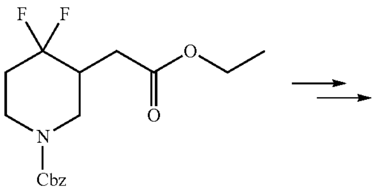

EX115-5

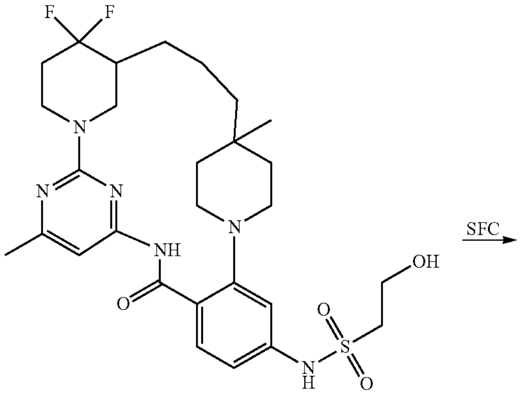

EX115

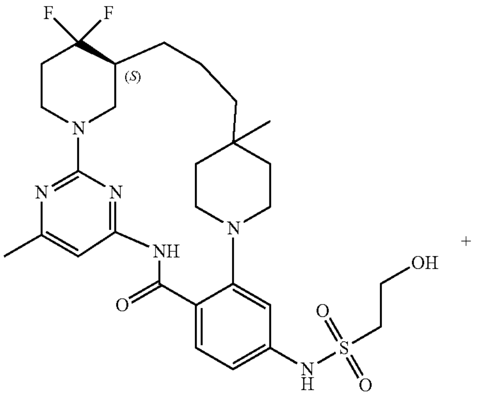

-continued

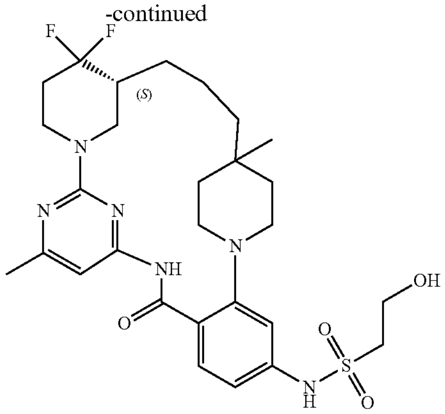

EX115-A&B

Step 1:

To a solution of 1-(tert-butyl) 3-methyl 4-oxopiperidine-1,3-dicarboxylate (80 g, 311 mmol) in DMF (500 mL) was added NaH (14.92 g, 373 mmol) at 0° C. The mixture was stirred at 25° C. for 1 hr, followed by the addition of ethyl 2-bromoacetate (51.9 g, 311 mmol). The resulting mixture was stirred at 25° C. for another 5 hrs. The mixture was quenched with water (500 mL) and extracted with EtOAc (500 mL×3). The combined organic layer was dried over $MgSO_4$, concentrated under reduced pressure and purified by silica gel chromatography to afford EX115-1. LCMS $[M\text{-}Boc+H]^+$: 244.1.

Step 2:

A solution of EX115-1 (210 g, 612 mmol) in concentrated HCl (510 mL, 6116 mmol) was stirred at 95° C. for 6 hrs and concentrated under vacuum to afford EX115-2. LCMS $[M+H]^+$: 158.0.

Step 3:

A solution of EX115-2 (210 g, 534 mmol) in EtOH (2100 mL) was stirred at 75° C. for 12 hrs. The reaction was concentrated under reduced pressure and the obtained residue was neutralized by DIEA (pH=7) to afford EX115-3. LCMS $[M+H]^+$: 186.1.

Step 4:

To a solution of EX115-3 (200 g, 432 mmol) in DCM (3000 mL) were added TEA (181 mL, 1296 mmol) and CbzCl (81 g, 475 mmol) at 0° C. The mixture was stirred at 25° C. for 2 hrs. The reaction was diluted with water (2000 mL) and extracted with DCM (1500 mL×2). The combined organic layer was dried over $MgSO_4$ and purified by silica gel chromatography to afford EX115-4. LCMS $[M+H]^+$: 320.1.

Step 5:

To a solution of EX115-4 (48 g, 150 mmol) in DCM (1000 mL) was added DAST (119 mL, 902 mmol) at 0° C. The reaction was stirred at 25° C. for 12 hrs. The reaction was quenched with saturated $NaHCO_3$ (1500 mL) and extracted with DCM (1000 mL×3). The combined organic layer was dried over $MgSO_4$, concentrated under reduced pressure and purified by silica gel chromatography to give EX115-5. LCMS $[M+H]^+$: 342.1.

Step 6:

EX115 was prepared as described in Example 111 (EX111) Steps 2-7, except EX115-5 was used instead of EX111-1 in Step 2 and EX34-1 was used instead of EX60-1 in Step 5.

Step 7:

EX115-A (24.71 mg) and EX115-B (9.74 mg) were separated from EX111 by SFC. SFC analytic condition: column: Column: Column: (S,S)Whelk-01 100×4.6 mm I.D., 5.0 um; mobile phase A: supercritical $CO_2$, mobile phase B: ethanol (0.05% DEA), 40% mobile phase B, 8 min; flow rate: 2.5 mL/min; column temp: 40° C.

EX115-A: $^1$H NMR (400 MHz, $CD_3OD$) δ 8.02 (d, J=8.6 Hz, 1H), 7.49 (s, 1H), 7.18 (s, 1H), 7.11-7.04 (m, 1H), 4.11-3.79 (m, 6H), 3.40-3.34 (m, 2H), 3.10-2.85 (m, 4H), 2.34 (s, 3H), 2.31-2.23 (m, 1H), 2.09-1.98 (m, 2H), 1.96-1.79 (m, 2H), 1.64-1.26 (m, 7H), 1.20-1.11 (m, 1H), 1.05 (s, 3H). LCMS $[M+H]^+$: 593.3. Retention time @SFC: 2.727 min.

EX115-B: $^1$H NMR (400 MHz, $CD_3OD$) δ 8.04 (d, J=8.6 Hz, 1H), 7.51 (s, 1H), 7.21 (d, J=2.2 Hz, 1H), 7.10 (dd, J=8.6, 2.1 Hz, 1H), 4.10-3.83 (m, 6H), 3.39 (t, J=6.3 Hz, 2H), 3.12-2.98 (m, 3H), 2.96-2.87 (m, 1H), 2.36 (s, 3H), 2.34-2.26 (m, 1H), 2.16-2.06 (m, 2H), 1.95-1.83 (m, 2H), 1.66-1.29 (m, 7H), 1.22-1.14 (m, 1H), 1.07 (s, 3H). LCMS $[M+H]^+$: 593.4. Retention time @SFC: 3.243 min.

II. Biological Evaluation

Example B1: KIF18A Assay

The KIF18A assay was performed as follows:

1.1. Prepared 1× Kinase Buffer 1.2. Compound Screening:

a) Added 40 μL test compound to 384-well dilution plate b) Diluted compound 1:3 in succession in DMSO for each column for 10 pts c) Transferred 0.1 μL diluted compound solution to 384 assay plate using Echo, each column containing 2 replicates d) Added 5 μL enzyme working solution to 384-well assay plate, centrifuge 1000 RPM for 1 min e) Incubated at 25° C. for 15 min f) Added 5 μL ATP working solution to initiate reaction g) Incubated at 25° C. for 60 min h) Added 10 μL ADP Glo reagent, centrifuge 1000 RPM for 1 min i) Incubated at 25° C. for 60 min j) Added 20 μL kinase detection reagent, centrifuge 1000 RPM for 1 min k) Incubated at 25° C. for 60 min l) Read Luminescence Signal on Envision 2104 plate reader.

1.3. Data Analysis—Calculated $IC_{50}$ and Plot Dose-Response Curve of Compounds:

Calculated $IC_{50}$ by fitting % Inhibition values and log of compound concentrations to nonlinear regression (dose response–variable slope) with GraphPad 6.0.

$$Y = \text{Bottom} + (\text{Top} - \text{Bottom})/(1 + 10\text{^}((\text{Log}IC50 - X) * HillSlope))$$

X: log of inhibitor concentration; Y: % Inhibition

The data for selected compounds disclosed herein is shown in Table 3.

TABLE 3

| No. | Kif18A $IC_{50}$ (μM) |
|---|---|
| EX01 | B |
| EX02 | A |
| EX03 | B |
| EX04 | B |
| EX05 | A |
| EX06 | A |
| EX07 | B |
| EX08 | A |
| EX09 | B |
| EX10 | B |
| EX11 | B |
| EX12 | B |
| EX13 | B |
| EX14 | B |
| EX15 | B |
| EX16 | B |
| EX17 | A |
| EX18 | B |
| EX19 | A |
| EX20 | B |
| EX21 | C |
| EX22 | C |
| EX23 | B |
| EX24 | A |
| EX25 | B |
| EX25-A | B |
| EX26 | B |
| EX27 | B |
| EX31 | B |
| EX33-A | B |
| EX33-B | B |
| EX34 | A |
| EX35 | B |
| EX36-A | B |
| EX36-B | B |
| EX37 | A |
| EX38 | B |
| EX40 | B |
| EX45 | B |
| EX48 | B |
| EX50 | B |
| EX55 | B |
| EX56-A | A |
| EX56-B | A |
| EX57 | B |
| EX58 | B |
| EX59 | B |
| EX67 | B |
| EX72 | A |
| E73 | B |
| EX74 | A |
| EX81-A | B |
| EX82 | B |
| EX100-B | A |
| EX102-A | A |
| EX106 | C |
| EX112 | A |
| EX113-A | B |
| EX115-B | B |

Note:

Biochemical assay $IC_{50}$ data are designated within the following ranges:

0 < A ≤ 0.010 μM 0.010 μM < B ≤ 0.100 μM 0.100 μM < C ≤ 1 μM 1.0 μM < D ≤ 10 μM

Example B2: OVCAR3 CTG Assay

Assay Condition

TABLE 4

| Vendor | Cat# | Lot. No | Description | Growth properties | Complete medium | Seeding Density | Incubation time |
|---|---|---|---|---|---|---|---|
| ATCC | HTB-161 | 4470175 | ovary, adenocarcinoma | adherent | RPMI 1640 + 0.01 mg/ml bovine insulin + 20% FBS | 2500 | 6 days |

Method

1) Cell Seeding:

a) Preparation of complete medium: Added FBS and appropriate additives according to the information sheet provided by the vendor. Mix gently.

b) Checked the cell name and complete medium and passage number marked on the flask. For adherent cell lines, refer to c to k. For suspension cell lines, refer to g to k.

c) Removed and discarded culture medium using a vacuum pump.

d) Briefly rinsed the cell layer with 0.25% (w/v) Trypsin-0.038% (w/v) EDTA solution to remove all traces of serum that contains trypsin inhibitor.

e) Added 3.0 ml of Trypsin-EDTA solution to flask and observed cells under an inverted microscope until cell layer is dispersed.

f) Added 9.0 ml of complete growth medium and aspirated cells by gently pipetting.

g) Transferred the cell suspension to a centrifuge tube and centrifuged at 1000 rpm for 4 minutes.

h) Discarded the supernatant using a vacuum pump.

i) Added appropriate volume of complete medium. Suspended the cell pellet by gently pipetting.

j) Counted the cell numbers with Vi-cell XR and adjusted cells to appropriate density.

k) Added 190 μL of cell suspension to 96-well opaque-walled clear bottom plates according to the planned plate layout and placed the plates in the $CO_2$ incubator overnight.

2) Compound Stock Preparation:

a) Plate preparation of testing articles:

The compounds were dissolved in DMSO to prepare 10 mM stock solution. The start working concentration (2 mM) was prepared with DMSO.

b) Staurosporine Plate Preparation:

0.4 mM Staurosporine was prepared in DMSO at working concentration.

c) Compound Addition:

The 20× compound containing medium was prepared according to the plate map. 10 μL of 20× compound containing medium was added into each well of the assay plates. Centrifuged at 1000 rpm for 1 minute. The total dilution was 200-fold.

3) Cells were Incubated with the Compounds for 6 Days at 5% CO2, 37° C.

Assay Measurement for CTG Assay

1) Preparation of Reagents a) Thawed the CellTiter-Glo buffer and equilibrated to room temperature prior to use.

b) Equilibrated the lyophilized CellTiter-Glo substrate to room temperature prior to use.

c) Transferred the appropriate volume of CellTiter-Glo buffer into the amber bottle containing CellTiter-Glo substrate to reconstitute the lyophilized enzyme/substrate mixture. This formed the CellTiter-Glo reagent.

d) Mixed by gently vortexing, swirling or by inverting the contents to obtain a homogeneous solution. The CellTiter-Glo substrate went into solution easily in less than one minute.

2) Assay Measurement a) Observed the cell morphology under an inverted microscope after corresponding treatment.

b) Equilibrated the plate and its contents to room temperature for approximately 30 minutes.

c) Added 100 μL of CellTiter-Glo reagent to the assay plate by Multidrop Combi instrument.

d) Mixed contents for 10 minutes on an orbital shaker to induce cell lysis.

e) Allowed the plate to incubate at room temperature for 10 minutes to stabilize luminescent signal.

f) Pasted the clear bottom with white back seal and record luminescence with Envision. The settings should be: Luminescence, measurement time 0.1 s.

Assay result: The data for selected compounds disclosed herein is shown in Table 5.

TABLE 5

| No. | OVCAR-3 $IC_{50}$ (μM) |
|---|---|
| EX01 | C |
| EX02 | B |
| EX03 | C |
| EX04 | B |
| EX05 | B |
| EX06 | C |
| EX07 | B |
| EX08 | C |
| EX09 | C |
| EX10 | C |
| EX11 | C |
| EX12 | B |
| EX13 | C |
| EX14 | B |
| EX15 | C |
| EX16 | C |
| EX17 | A |
| EX18 | C |
| EX19 | A |
| EX20 | B |
| EX21 | C |
| EX22 | C |
| EX23 | B |
| EX24 | B |
| EX25 | A |
| EX25-A | B |
| EX26 | D |
| EX27 | C |
| EX28 | B |
| EX29 | C |
| EX30 | B |
| EX31 | B |
| EX32-A | B |
| EX32-B | B |

TABLE 5-continued

| No. | OVCAR-3 $IC_{50}$ (μM) |
|---|---|
| EX33-A | C |
| EX33-B | D |
| EX34 | A |
| EX35 | C |
| EX36-A | B |
| EX36-B | A |
| EX37 | B |
| EX38 | B |
| EX39 | B |
| EX41 | C |
| EX42 | B |
| EX43 | A |
| EX44 | B |
| EX45 | C |
| EX46-A | B |
| EX46-B | B |
| EX47 | D |
| EX48 | B |
| EX49 | C |
| EX50 | B |
| EX51 | B |
| EX52 | D |
| EX53 | B |
| EX54 | B |
| EX55 | B |
| EX56 | B |
| EX56-A | B |
| EX56-B | A |
| EX57 | B |
| EX58 | B |
| EX59 | B |
| EX60 | B |
| EX61 | B |
| EX62 | B |
| EX63 | C |
| EX64 | B |
| EX65 | C |
| EX66 | B |
| EX67 | C |
| EX68 | B |
| EX69 | B |
| EX70 | B |
| EX71 | B |
| EX72 | C |
| EX73 | B |
| EX74 | B |
| EX75 | C |
| EX76-A | A |
| EX76-B | B |
| EX77 | C |
| EX78-A | B |
| EX78-B | A |
| EX79-A | B |
| EX79-B | A |
| EX80 | D |
| EX81-A | A |
| EX81-B | B |
| EX82 | B |
| EX83 | B |
| EX84-A | B |
| EX84-B | B |
| EX85-A | B |
| EX85-B | A |
| EX86 | B |
| EX87 | D |
| EX88-A | B |
| EX88-B | A |
| EX89 | B |
| EX90 | B |
| EX91 | B |
| EX92-A | B |
| EX92-B | A |
| EX93-A | A |
| EX93-B | B |
| EX94 | C |
| EX95 | B |
| EX96-A | A |

TABLE 5-continued

| No. | OVCAR-3 $IC_{50}$ (μM) |
|---|---|
| EX96-B | B |
| EX97 | B |
| EX98 | C |
| EX99 | C |
| EX100-A | B |
| EX100-B | A |
| EX101-A | B |
| EX101-B | A |
| EX102-A | B |
| EX102-B | A |
| EX103 | A |
| EX104 | B |
| EX105-A | A |
| EX106 | D |
| EX107-A | C |
| EX107-B | B |
| EX108 | C |
| EX109 | B |
| EX110 | B |
| EX111-A | C |
| EX111-B | B |
| EX112 | A |
| EX113-A | A |
| EX113-B | B |
| EX114-A | B |
| EX114-B | C |
| EX115-A | C |
| EX115-B | B |

Note:
Cellular assay $IC_{50}$ data are designated within the following ranges:
$0 < A \leq 0.010$ μM
0.010 μM $< B \leq 0.100$ μM
0.100 μM $< C \leq 1$ μM
1.0 μM $< D \leq 10$ μM.

We claim:

1. A compound of Formula (Ib), or a pharmaceutically acceptable salt thereof:

Formula (Ib)

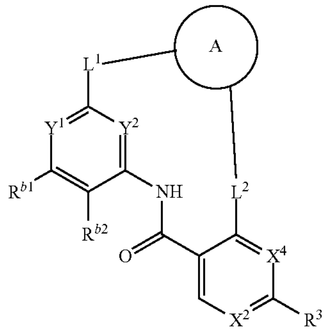

wherein, ring A is 4- to 6-membered heterocycloalkyl, which is optionally substituted with one or more $R^a$;

$L^1$ is $C_1$-$C_6$alkylene, $C_1$-$C_6$heteroalkylene, -heterocycloalkyl-$C_1$-$C_6$alkylene-, -heterocycloalkyl-$C_1$-$C_6$heteroalkylene-, -cycloalkyl-$C_1$-$C_6$alkylene-, -cycloalkyl-$C_1$-$C_6$heteroalkylene, —$C_1$-$C_6$alkylene-heterocycloalkyl-, —$C_1$-$C_6$heteroalkylene-heterocycloalkyl-, —$C_1$-$C_6$alkylene-cycloalkyl-, —$C_1$-$C_6$heteroalkylene-cycloalkyl-, —$C_1$-$C_6$heteroalkylene-cycloalkyl-$C_1$-$C_6$heteroalkylene, —$C_1$-$C_6$alkylene-cycloalkyl-$C_1$-$C_6$alkylene, $C_1$-$C_6$heteroalkylene-cycloalkyl-$C_1$-$C_6$alkylene, $C_1$-$C_6$alkylene-cycloalkyl-$C_1$-$C_6$heteroalkylene, —$C_1$-$C_6$heteroalkylene-heterocycloalkyl-$C_1$-$C_6$heteroalkylene, —$C_1$-$C_6$heteroalkylene-heterocycloalkyl-$C_1$-$C_6$alkylene, —$C_1$-$C_6$alkylene-heterocycloalkyl-$C_1$-$C_6$heteroalkylene, or —$C_1$-$C_6$alkylene-heterocycloalkyl-$C_1$-$C_6$alkylene, wherein each of the cycloalkyl, heterocycloalkyl, alkylene and heteroalkylene is optionally substituted with one or more $R^c$;

$L^2$ is a bond;

$X^2$ is N or $CR^2$;

$X^4$ is N or $CR^4$;

$Y^1$ is N or CH;

$Y^2$ is N or CH;

$R^{b1}$ is hydrogen, $C_1$-$C_6$alkyl or $C_1$-$C_6$haloalkyl;

$R^{b2}$ is hydrogen, $C_1$-$C_6$alkyl or $C_1$-$C_6$haloalkyl;

$R^2$ is hydrogen, halogen, or $C_1$-$C_3$alkyl;

$R^4$ is hydrogen or $C_1$-$C_3$alkyl;

$R^3$ is —Z—$R^5$, and Z—$R^5$ is selected from the group consisting of: —$NHSO_2CH_2CH_2OH$, —$NHSO_2CH_2CH_3$, —$NHSO_2CH_3$, —$NHC(CH_3)_2CH_2OH$, and

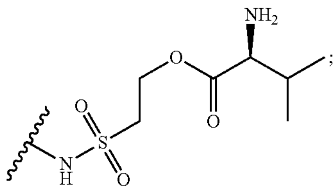 [SMILES: *NS(=O)(=O)CCOC(=O)[C@@H](N)C(C)C];

each of Ra is independently selected from halogen, —CN, —$NO_2$, $C_1$-$C_6$alkyl, $C_1$-$C_6$haloalkyl, and $C_3$-$C_6$ cycloalkyl;

each $R^c$ is independently selected from halogen, oxo, —OH, —$OR^7$, $C_1$-$C_6$haloalkyl, $C_1$-$C_6$alkyl, and cycloalkyl, wherein the alkyl or cycloalkyl is optionally substituted with one or more R;

$R^7$ is $C_1$-$C_3$alkyl; and each R is halogen, —CN, —OH, oxo, —$SF_5$, —SH, —$NH_2$, —$NHC_1$-$C_3$alkyl, —$N(C_1$-$C_3alkyl)_2$, $C_1$-$C_3$alkyl, $C_1$-$C_3$alkoxy, $C_1$-$C_3$haloalkyl, $C_1$-$C_3$haloalkoxy, $C_1$-$C_3$hydroxyalkyl, $C_1$-$C_3$aminoalkyl, $C_1$-$C_3$heteroalkyl, or $C_3$-$C_6$cycloalkyl.

2. The compound of claim 1, or a pharmaceutically acceptable salt thereof, wherein $L^1$ is selected from the group consisting of: —$OCH_2CH_2OCH_2$—, —$OCH_2CH_2CH_2OCH_2$—, —$OCH_2CH_2CH_2CH_2CH_2$—, —$OCH(CH_3)CH_2CH_2OCH_2$—, —$OCH_2CH(CH_3)CH_2OCH_2$—, —$OCH_2CH(CH_3)OCH_2CH_2$—, —$OCH(CH_3)CH_2OCH_2CH_2$—, —$CH_2OCH_2$—, —$CH_2CH_2OCH_2$—, —$CH_2CH_2CH_2CH_2OCH_2$—, —$CH_2OCH(CH_3)CH_2OCH_2$—, —$CH_2OCH_2CH_2$—, —$N(CH_3)CH_2CH_2OCH_2$—, —N(cyclopropyl)$CH_2CH_2CH_2OCH_2$—, —$N(CH_3)CH_2CH_2CH_2OCH_2$—, —$NHCH_2CH_2OCH_2$—, —$NHCH_2CH_2CH_2OCH_2$—, —$NHCH_2CH(CH_3)CH_2OCH_2$—, —$N(CH_3)CH_2CH_2OCH_2CH_2$—, —$NHCH_2CH_2OCH_2CH_2$—, —$NH(CH_2)_4$—, —$NH(CH_2)_5$—, —$NHCH_2CH(CH_3)(CH_2)_3$—, —$N(CH_3)(CH_2)_4$—, —$N(CH_3)(CH_2)_5$—, —$NHCH_2CH_2CH_2CH_2O$—, —$NHCH_2C(=O)N(CH_3)CH_2CH_2$—, —$NHCH_2CH_2CH_2NHCH_2$—, —$NHCH(CH_3)CH_2OCH_2CH_2$—, —$NHCH_2CH(CH_3)OCH_2CH_2$—, —$N(CH_3)CH_2CH(CH_3)OCH_2CH_2$—, —$NHCH_2CF_2CH_2OCH_2$—, —$N(CH_3)CH_2CF_2CH_2OCH_2$—, —$NHCH_2CH(CH_3)CH_2OCH_2$—, —$N(CH_3)CH_2CH(CH_3)CH_2OCH_2$—, —$NHCH(CH_3)CH_2CH_2OCH_2$—, —$NHCH_2CH_2CH(CH_3)OCH_2$—, —$NHCH_2CH(CH_3)CH_2OCH_2$—, —$NHCH_2CHFCH_2OCH_2$—, —$NHCH_2CH(OCH_3)CH_2OCH_2$—, —$NHCH_2CH(CF_3)CH_2OCH_2$—, —$NHCH_2CF_2CH_2OCH_2$—, —$NHCH_2CH(OH)CH_2OCH_2$—, —$N(CH_3)CH_2CH(CH_3)CH_2OCH_2$—, —$N(CH_3)CH_2CHFCH_2OCH_2$—, —$N(CH_3)CH_2CH(OCH_3)CH_2OCH_2$—, —$N(CH_3)CH_2CH(CF_3)CH_2OCH_2$—, —$N(CH_3)CH_2CF_2CH_2OCH_2$—, —$N(CH_3)CH_2CH(OH)CH_2OCH_2$—, —$C(=O)N(CH_3)CH_2CH_2OCH_2$—, —$C(=O)N(CH_3)CH_2CH_2CH_2OCH_2$—, and —$C(=O)N(CH_3)CH_2CH_2CH_2CH_2$—.

3. The compound of claim 1, or a pharmaceutically acceptable salt thereof, wherein the heterocycloalkyl of $L^1$ is

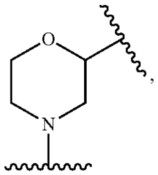, 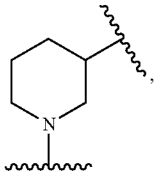, or

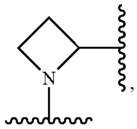, each of which is optionally substituted with one or more R.

4. The compound of claim 3, or a pharmaceutically acceptable salt thereof, wherein-$L^1$ is

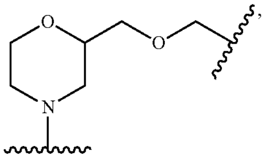,

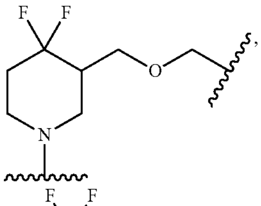, or

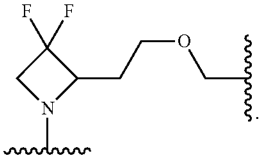.

5. The compound of claim 1, or a pharmaceutically acceptable salt thereof, wherein ring A is selected from the group consisting of:

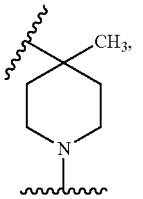
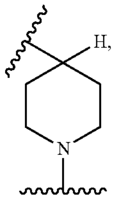
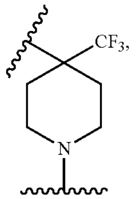
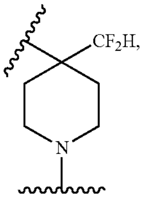
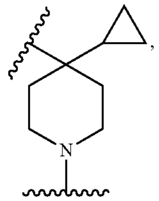
and
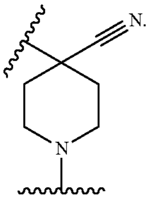
6. The compound of claim 1, or a pharmaceutically acceptable salt thereof, wherein
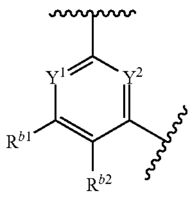
is selected from the group consisting of:
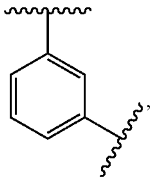
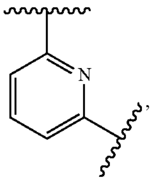
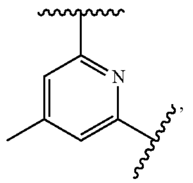
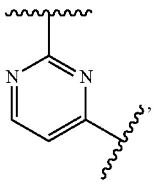
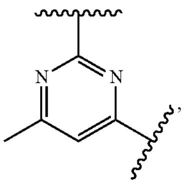
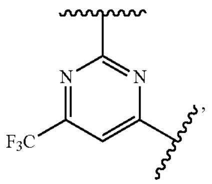
and
-continued
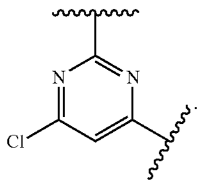
7. The compound of claim 1, or a pharmaceutically acceptable salt thereof, wherein $R^3$ is
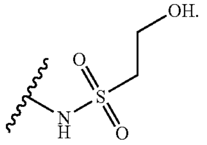 [SMILES: *NS(=O)(=O)CCO]
8. The compound of claim 1, or a pharmaceutically acceptable salt thereof, wherein the compound is
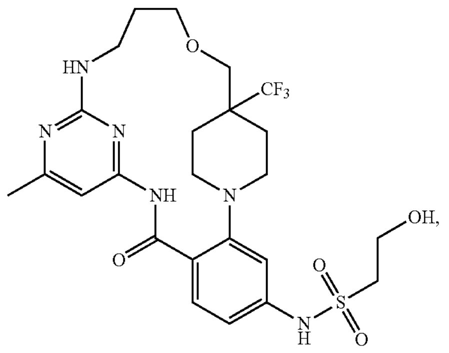
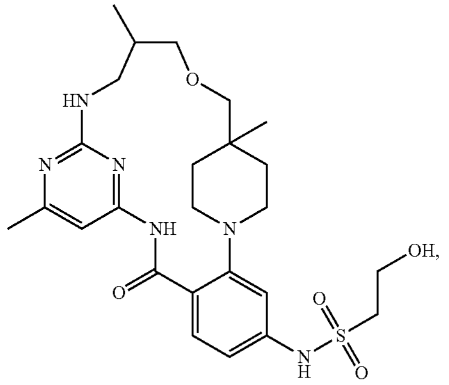
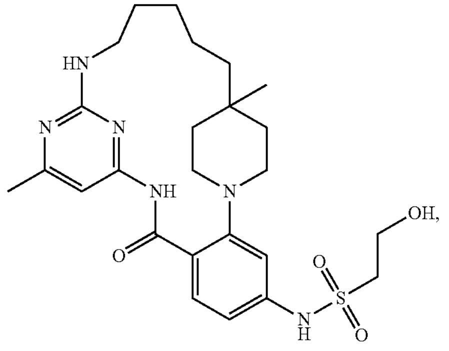

-continued
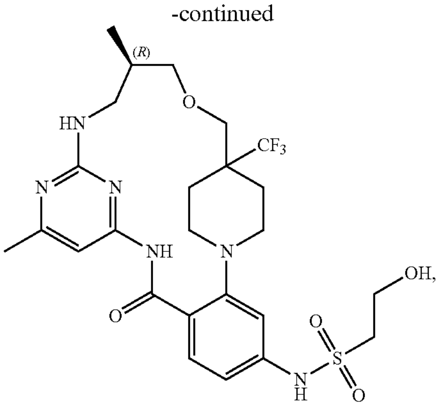
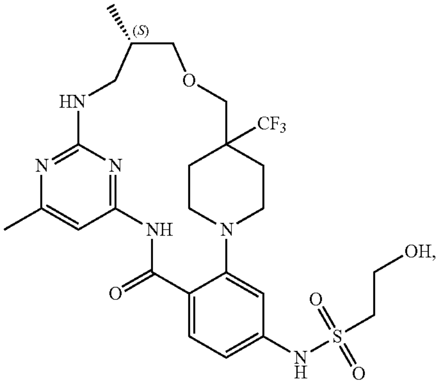
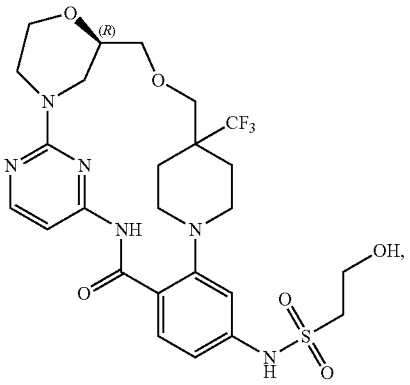
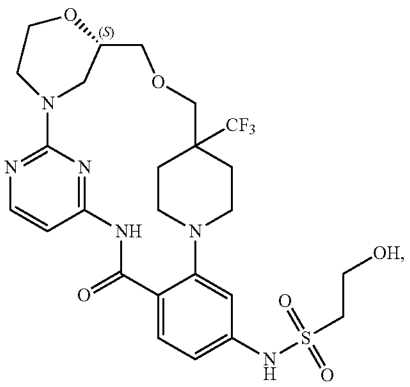
-continued
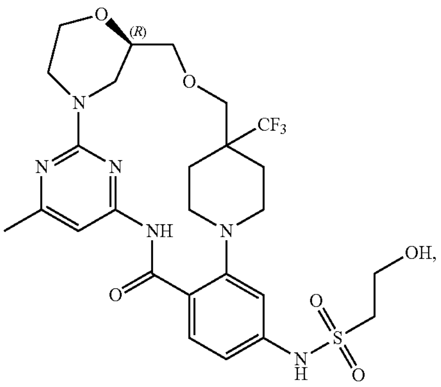
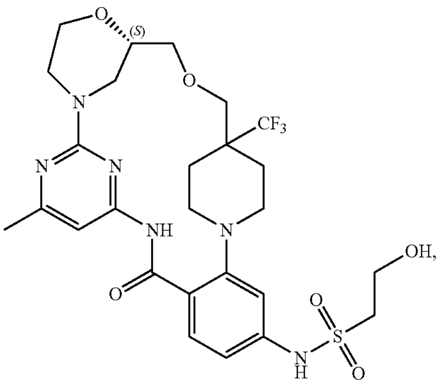
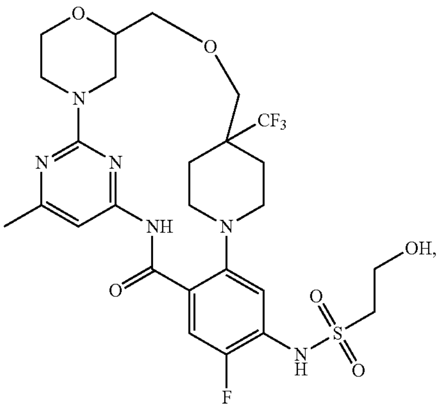
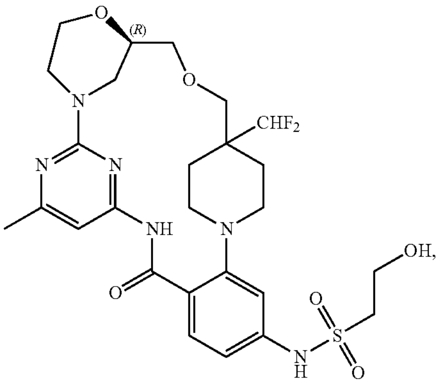
or -continued

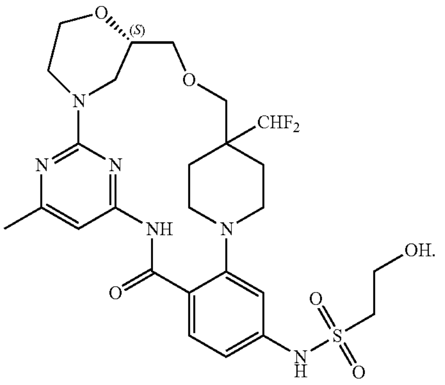

9. The compound of claim 1, or a pharmaceutically acceptable salt thereof, wherein the compound is

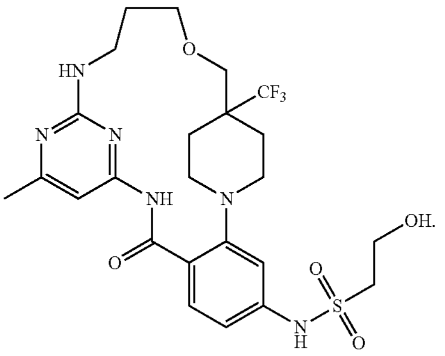 [SMILES: Cc1cc2nc(n1)NCCCOCC1(C(F)(F)F)CCN(CC1)c1cc(NS(=O)(=O)CCO)ccc1C(=O)N2]

10. The compound of claim 1, or a pharmaceutically acceptable salt thereof, wherein the compound is

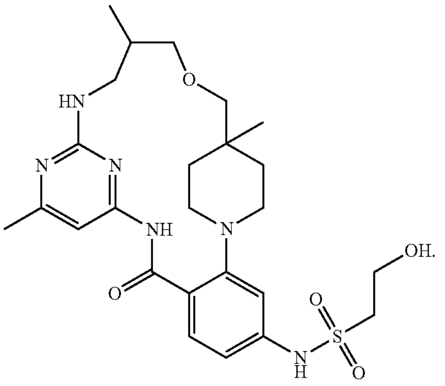 [SMILES: Cc1cc2nc(n1)NCC(C)COCC1(C)CCN(CC1)c1cc(NS(=O)(=O)CCO)ccc1C(=O)N2]

11. The compound of claim 1, or a pharmaceutically acceptable salt thereof, wherein the compound is

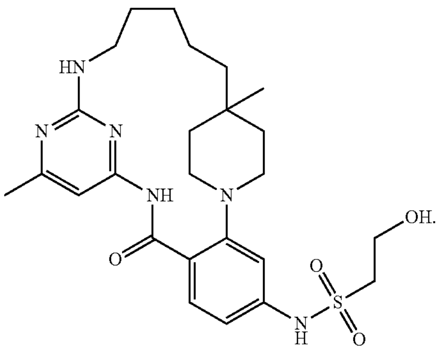 [SMILES: Cc1cc2nc(n1)NCCCCCC1(C)CCN(CC1)c1cc(NS(=O)(=O)CCO)ccc1C(=O)N2]

12. The compound of claim 1, or a pharmaceutically acceptable salt thereof, wherein the compound is

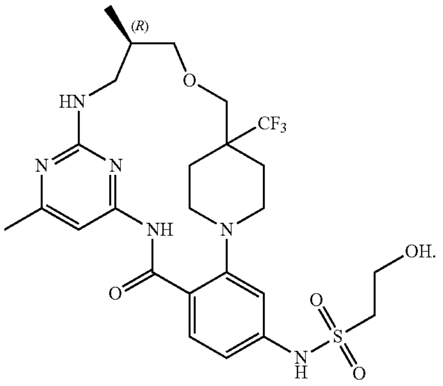

13. The compound of claim 1, or a pharmaceutically acceptable salt thereof, wherein the compound is

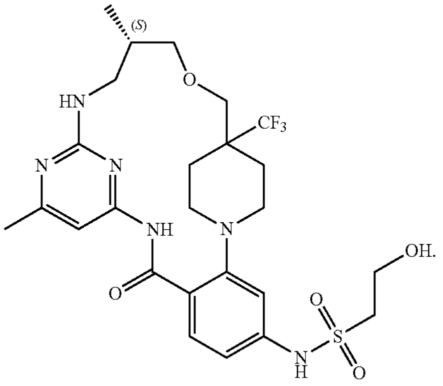

14. The compound of claim 1, or a pharmaceutically acceptable salt thereof, wherein the compound is

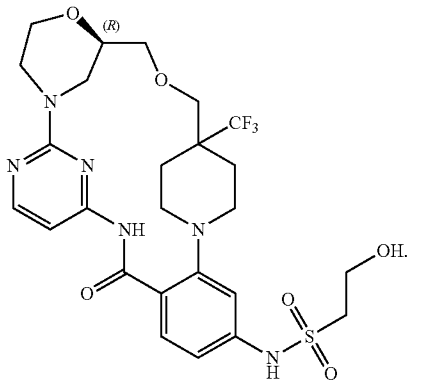

15. The compound of claim 1, or a pharmaceutically acceptable salt thereof, wherein the compound is

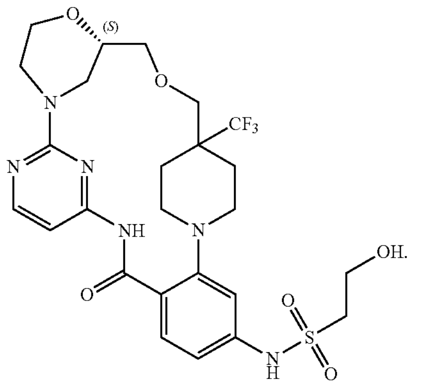

16. The compound of claim 1, or a pharmaceutically acceptable salt thereof, wherein the compound is

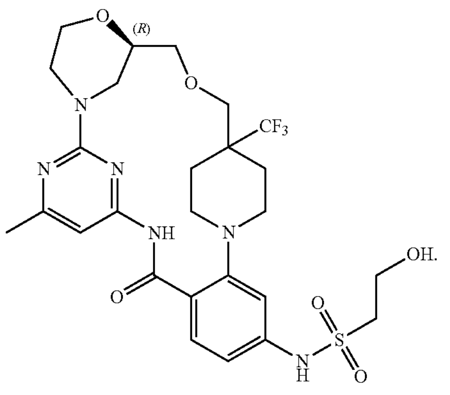

17. The compound of claim 1, or a pharmaceutically acceptable salt thereof, wherein the compound is

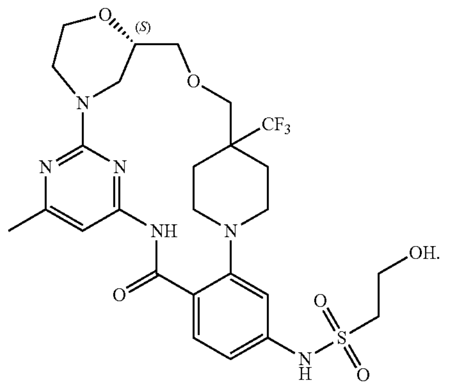

18. The compound of claim 1, or a pharmaceutically acceptable salt thereof, wherein the compound is

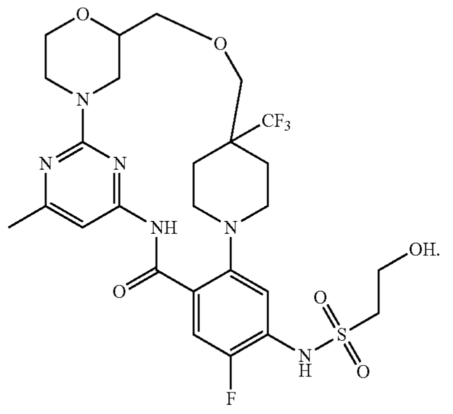 [SMILES: Cc1cc2nc(n1)N1CCOC(COCC3(C(F)(F)F)CCN(CC3)c3cc(NS(=O)(=O)CCO)c(F)cc3C(=O)N2)C1]

19. A pharmaceutical composition comprising a compound of claim 1, or a pharmaceutically acceptable salt thereof, and at least one pharmaceutically acceptable excipient.

20. The compound of claim 1, or a pharmaceutically acceptable salt thereof, wherein $L^1$ is-heterocycloalkyl-$C_1$-$C_6$alkylene-, -heterocycloalkyl-$C_1$-$C_6$heteroalkylene-, —$C_1$-$C_6$alkylene-heterocycloalkyl-, —$C_1$-$C_6$heteroalkylene-heterocycloalkyl-, —$C_1$-$C_6$heteroalkylene-heterocycloalkyl-$C_1$-$C_6$heteroalkylene, —$C_1$-$C_6$heteroalkylene-heterocycloalkyl-$C_1$-$C_6$alkylene, —$C_1$-$C_6$alkylene-heterocycloalkyl-$C_1$-$C_6$heteroalkylene, or —$C_1$-$C_6$alkylene-heterocycloalkyl-$C_1$-$C_6$alkylene, wherein each of the heterocycloalkyl, alkylene and heteroalkylene is optionally substituted with one or more $R^c$.

21. The compound of claim 20, wherein the heterocycloalkyl is a 4- to 6-membered heterocycloalkyl comprising 1 or 2 heteroatoms selected from N and O, which is optionally substituted with one or more R.

22. The pharmaceutical composition of claim 19, wherein the compound is
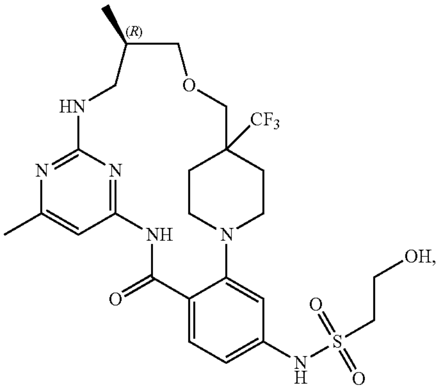
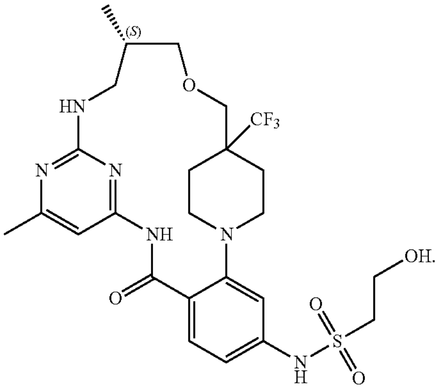
23. The pharmaceutical composition of claim 19, wherein the compound is
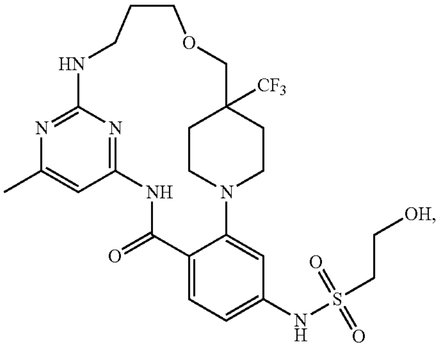
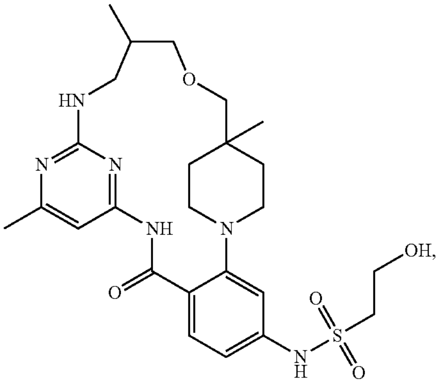
-continued
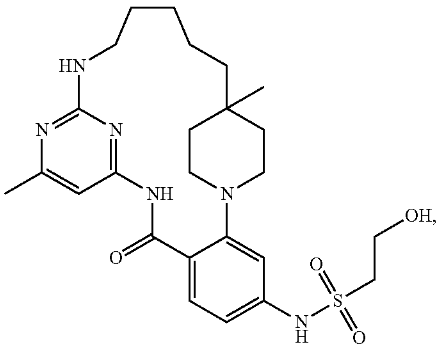
or
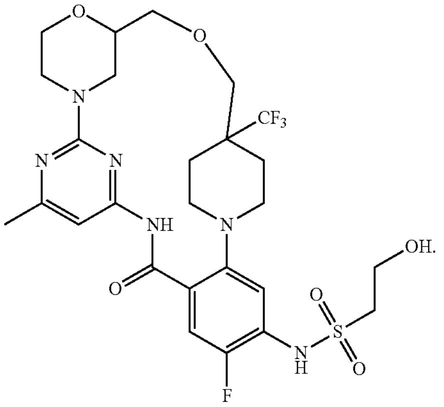
24. The pharmaceutical composition of claim 19, wherein the compound is
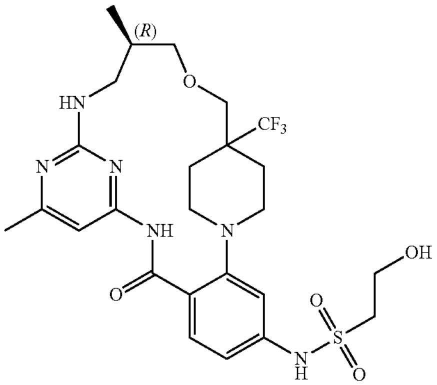
or

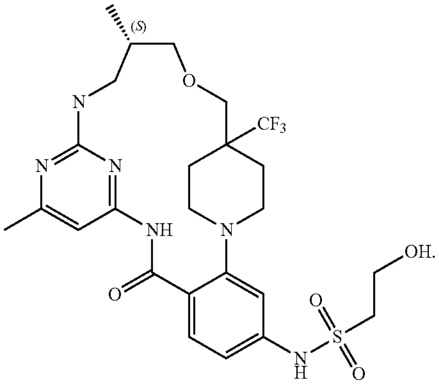
25. The pharmaceutical composition of claim 19, wherein the compound is
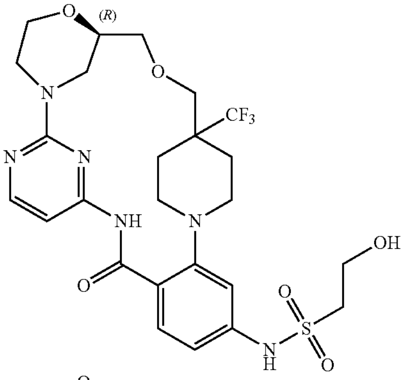
or
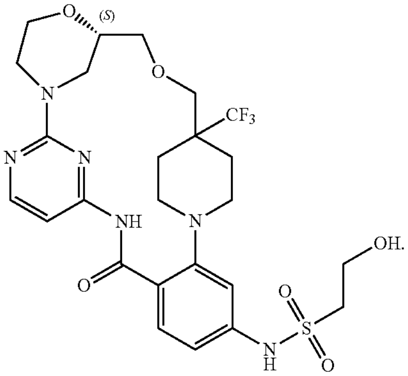
26. The pharmaceutical composition of claim 19, wherein the compound is
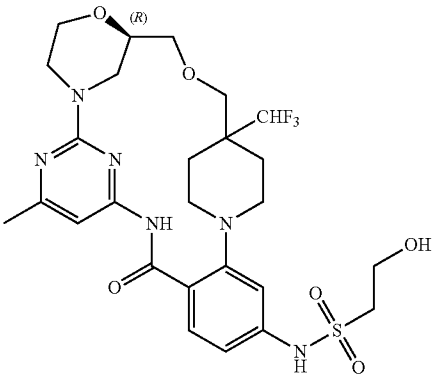
or
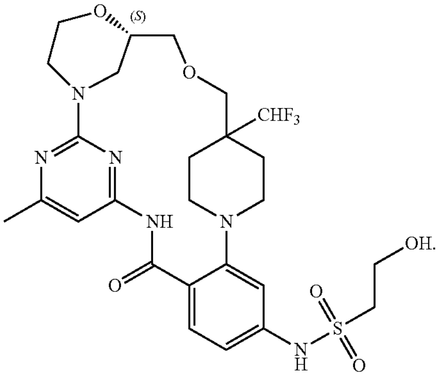
* * * * *